US012225815B2

(12) United States Patent
Ryu et al.

(10) Patent No.: US 12,225,815 B2
(45) Date of Patent: Feb. 11, 2025

(54) COMPOSITION FOR ORGANIC OPTOELECTRONIC DEVICE, ORGANIC OPTOELECTRONIC DEVICE, AND DISPLAY DEVICE

(71) Applicant: SAMSUNG SDI CO., LTD., Yongin-si (KR)

(72) Inventors: Dong Wan Ryu, Suwon-si (KR); Chang Ju Shin, Suwon-si (KR); Seungjae Lee, Suwon-si (KR); Hyung Sun Kim, Suwon-si (KR); Yuna Jang, Suwon-si (KR); Eun Sun Yu, Suwon-si (KR); Sung-Hyun Jung, Suwon-si (KR)

(73) Assignee: SAMSUNG SDI CO., LTD., Yongin-si (KR)

( * ) Notice: Subject to any disclaimer, the term of this patent is extended or adjusted under 35 U.S.C. 154(b) by 0 days.

(21) Appl. No.: 18/387,540

(22) Filed: Nov. 7, 2023

(65) Prior Publication Data

US 2024/0099129 A1 Mar. 21, 2024

Related U.S. Application Data

(63) Continuation of application No. 16/332,843, filed as application No. PCT/KR2017/005409 on May 24, 2017, now abandoned.

(30) Foreign Application Priority Data

Oct. 7, 2016 (KR) ........................ 10-2016-0129959

(51) Int. Cl.

*H10K 85/60* (2023.01)
*C07D 209/86* (2006.01)

(Continued)

(52) U.S. Cl.

CPC ......... *H10K 85/654* (2023.02); *C07D 209/86* (2013.01); *C07D 405/14* (2013.01);

(Continued)

(58) Field of Classification Search

CPC .... H10K 85/654; H10K 50/00; H10K 85/653; H10K 99/00; H10K 50/11;

(Continued)

(56) References Cited

U.S. PATENT DOCUMENTS 8,890,131 B2 * 11/2014 Lecloux ................ C07B 59/001 313/504
2007/0141387 A1 6/2007 Nakano et al.

(Continued)

FOREIGN PATENT DOCUMENTS

CN 101007942 A 8/2007
CN 103232843 A 8/2013

(Continued)

OTHER PUBLICATIONS

International Search Report for PCT/KR2017/005409 filed on May 24, 2017.

(Continued)

*Primary Examiner* — Michael Y Sun
(74) *Attorney, Agent, or Firm* — Lee IP Law, P.C.

(57) ABSTRACT

The present invention relates to a composition for an organic optoelectronic device, the composition comprising: a first host compound represented by Chemical Formula 1 below; and a second host compound represented by Chemical Formula 2 below, to an organic optoelectronic device using the composition and a display device. The details of Chemical Formulas 1 and 2 above are as defined in the specification.

8 Claims, 1 Drawing Sheet

(51) Int. Cl.

| | |
|---|---|
| ***C07D 405/14*** | (2006.01) |
| ***C07D 407/04*** | (2006.01) |
| ***C07D 407/10*** | (2006.01) |
| ***C07D 409/04*** | (2006.01) |
| ***C07D 409/10*** | (2006.01) |
| ***C09K 11/02*** | (2006.01) |
| ***H10K 50/00*** | (2023.01) |
| ***H10K 99/00*** | (2023.01) |
| *C09K 11/06* | (2006.01) |
| *H10K 50/11* | (2023.01) |
| *H10K 101/10* | (2023.01) |

(52) U.S. Cl.

CPC ......... *C07D 407/04* (2013.01); *C07D 407/10* (2013.01); *C07D 409/04* (2013.01); *C07D 409/10* (2013.01); *C09K 11/025* (2013.01); *H10K 50/00* (2023.02); *H10K 85/653* (2023.02); *H10K 99/00* (2023.02); *C09K 11/06* (2013.01); *H10K 50/11* (2023.02); *H10K 2101/10* (2023.02)

(58) Field of Classification Search

CPC ........... H10K 2101/10; H10K 2101/90; H10K 85/6572; H10K 85/6576; H10K 50/12; H10K 85/6574; C07D 209/86; C07D 405/14; C07D 407/04; C07D 407/10; C07D 409/04; C07D 409/10; C07D 307/91; C07D 333/76; C09K 11/025; C09K 11/06; C09K 2211/1088; C09K 2211/1092; Y02E 10/549

See application file for complete search history.

(56) References Cited

U.S. PATENT DOCUMENTS

| | | | | |
|---|---|---|---|---|
| 2007/0176541 | A1 | 8/2007 | Son et al. | |
| 2012/0085992 | A1 | 4/2012 | Beaujuge et al. | |
| 2014/0231769 | A1 | 8/2014 | Nishimura et al. | |
| 2015/0228909 | A1 | 8/2015 | Kim et al. | |
| 2016/0093808 | A1* | 3/2016 | Adamovich | H10K 85/626 252/301.16 |
| 2016/0126472 | A1 | 5/2016 | Oh et al. | |
| 2017/0237017 | A1 | 8/2017 | Parham et al. | |
| 2018/0175302 | A1* | 6/2018 | Jang | H10K 85/654 |
| 2018/0248126 | A1* | 8/2018 | Huh | C07F 9/58 |
| 2019/0221749 | A1 | 7/2019 | Yang et al. | |

FOREIGN PATENT DOCUMENTS

| | | | |
|---|---|---|---|
| CN | 105378028 | A | 3/2016 |
| JP | 2004-346082 | A | 12/2004 |
| JP | 2012-049518 | A | 3/2012 |
| JP | 2012-121883 | A | 6/2012 |
| JP | 2013-538440 | A | 10/2013 |
| JP | 2014-157947 | A | 8/2014 |
| KR | 10-0910150 | B1 | 7/2009 |
| KR | 10-2011-0128249 | A | 11/2011 |
| KR | 10-2012-0059377 | A | 6/2012 |
| KR | 10-2013-0117726 | A | 10/2013 |
| KR | 10-2013-0130788 | A | 12/2013 |
| KR | 10-2014-0074925 | A | 6/2014 |
| KR | 10-1423067 | B1 | 7/2014 |
| KR | 10-2014-0100447 | A | 8/2014 |
| KR | 10-2014-0132244 | A | 11/2014 |
| KR | 10-2015-0042335 | A | 4/2015 |
| KR | 10-2015-0074603 | A | 7/2015 |
| KR | 10-2015-0083385 | A | 7/2015 |
| KR | 10-2015-0097703 | A | 8/2015 |
| KR | 10-2015-0110101 | A | 10/2015 |
| KR | 10-2016-0028524 | A | 3/2016 |
| WO | WO 2012/127958 | A1 | 9/2012 |

OTHER PUBLICATIONS

Chinese Office Action and Search Report Dated Nov. 24, 2022.

U.S. Office action received in Co Pending related U.S. Appl. No. 18/210,280 dated Feb. 1, 2024.

Chinese Office Action (including a search report) dated Jun. 19, 2024, of the corresponding Chinese Patent Application No. 201780059494.2.

U.S. Office action received in co-pending U.S. Appl. No. 18/387,545, dated Jun. 6, 2024.

U.S. Office action received in co-pending U.S. Appl. No. 18/210,280, dated Jun. 6, 2024.

U.S. Office action received in co-pending U.S. Appl. No. 18/387,545, dated Sep. 24, 2024.

* cited by examiner

【Figure 1】
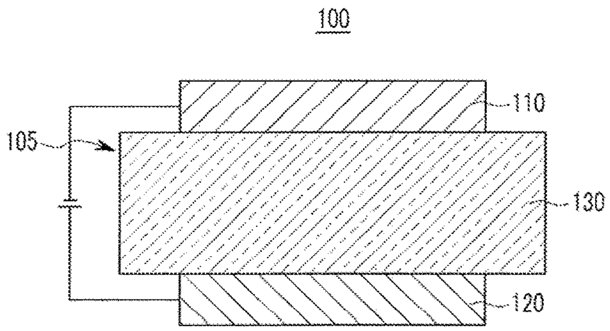
【Figure 2】
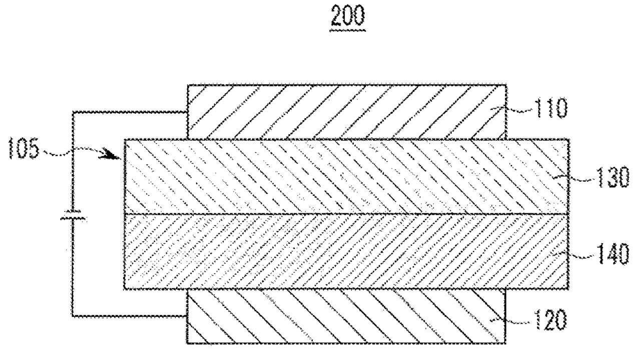

COMPOSITION FOR ORGANIC OPTOELECTRONIC DEVICE, ORGANIC OPTOELECTRONIC DEVICE, AND DISPLAY DEVICE

CROSS-REFERENCE TO RELATED APPLICATIONS

This is a continuation application based on pending application Ser. No. 16/332,843, filed Mar. 13, 2019, which is the U.S. national phase application based on PCT/KR2017/005409, filed May 24, 2017, which is based on Korean Patent Application No. 10-2016-0129959, filed Oct. 7, 2016, the entire contents of all being hereby incorporated by reference.

TECHNICAL FIELD

A composition for an organic optoelectronic device, an organic optoelectronic device, and a display device are disclosed.

BACKGROUND ART

An organic optoelectronic device is an element that converts electrical energy into photoenergy, and vice versa.

An organic optoelectronic device may be classified as follows in accordance with its driving principles. One is a photoelectric element where excitons are generated by photoenergy, separated into electrons and holes, and are transferred to different electrodes to generate electrical energy, and the other is a light emitting element where a voltage or a current is supplied to an electrode to generate photoenergy from electrical energy.

Examples of the organic optoelectronic device may be an organic photoelectric element, an organic light emitting diode, an organic solar cell, and an organic photo conductor drum.

Of these, an organic light emitting diode (OLED) has recently drawn attention due to an increase in demand for flat panel displays. The organic light emitting diode is an element converting electrical energy into light by applying a current to an organic light emitting material, and has a structure in which an organic layer is disposed between an anode and a cathode. Herein, the organic layer may include a light emitting layer and optionally an auxiliary layer, and the auxiliary layer may be for example at least one layer selected from a hole injection layer, a hole transport layer, an electron blocking layer, an electron transport layer, an electron injection layer, and a hole blocking layer.

Performance of an organic light emitting diode may be affected by characteristics of the organic layer, and among them, may be mainly affected by characteristics of an organic material of the organic layer.

Particularly, development for an organic material capable of increasing hole and electron mobility and simultaneously increasing electrochemical stability is needed so that the organic light emitting diode may be applied to a large-size flat panel display.

DISCLOSURE

Technical Problem

An embodiment provides a composition for an organic optoelectronic device capable of realizing high efficiency and long life-organic optoelectronic device.

Technical Solution

Another embodiment provides an organic optoelectronic device including the composition for an organic optoelectronic device.

Yet another embodiment provides a display device including the organic optoelectronic device.

According to an embodiment, a composition for an organic optoelectronic device includes a first host compound represented by Chemical Formula 1; and a second host compound represented by Chemical Formula 2.

[Chemical Formula 1]

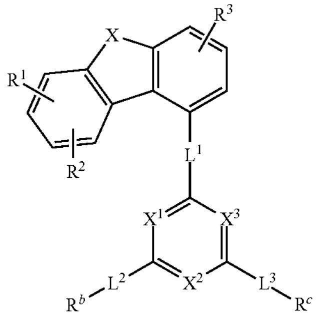

In Chemical Formula 1,

X is O or S, $L^1$ to $L^3$ are independently a single bond, or a substituted or unsubstituted C6 to C20 arylene group, $X^1$ to $X^3$ are independently N or $CR^a$, at least two of $X^1$ to $X^3$ are N, $R^1$ to $R^3$ are independently hydrogen, deuterium, a substituted or unsubstituted C1 to C10 alkyl group, a substituted or unsubstituted C6 to C12 aryl group, or a combination thereof, $R^a$ is hydrogen, deuterium, a substituted or unsubstituted C6 to C30 aryl group, a substituted or unsubstituted dibenzofuranyl group, a substituted or unsubstituted dibenzothiophenyl group, or a combination thereof, and $R^b$ and $R^c$ are independently a substituted or unsubstituted C6 to C30 aryl group, a substituted or unsubstituted dibenzofuranyl group, a substituted or unsubstituted dibenzothiophenyl group, or a combination thereof, wherein "substituted" of Chemical Formula 1 refers to replacement of at least one hydrogen by deuterium, a C6 to C30 aryl group, a dibenzofuranyl group, or a dibenzothiophenyl group;

[Chemical Formula 2]

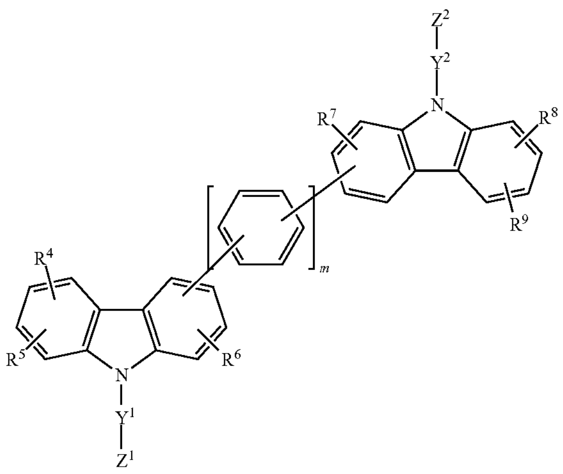

wherein, in Chemical Formula 2, $Y^1$ and $Y^2$ are independently a single bond, a substituted or unsubstituted C6 to C30 arylene group, a substituted or unsubstituted C2 to C30 heteroarylene group, or a combination thereof, $Z^1$ and $Z^2$ are independently a substituted or unsubstituted C6 to C30 aryl group, a substituted or unsubstituted C2 to C30 heterocyclic group, or a combination thereof, $R^4$ to $R^9$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, and m is one of integers of 0 to 2;

wherein "substituted" of Chemical Formula 2 refers to replacement of at least one hydrogen by deuterium, a C1 to C4 alkyl group, a C6 to C18 aryl group, or a C2 to C30 heteroaryl group.

According to another embodiment, an organic optoelectronic device includes an anode and a cathode facing each other and at least one organic layer disposed between the anode and the cathode, wherein the organic layer includes the composition for an organic optoelectronic device.

According to another embodiment, a display device including the organic optoelectronic device is provided.

Advantageous Effects

An organic optoelectronic device having high efficiency and a long life-span may be realized.

DESCRIPTION OF THE DRAWINGS

FIGS. 1 and 2 are cross-sectional views showing organic light emitting diodes according to embodiments.

MODE FOR INVENTION

Hereinafter, embodiments of the present invention are described in detail. However, these embodiments are exemplary, the present invention is not limited thereto and the present invention is defined by the scope of claims.

In the present specification, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a fluoro group, a C1 to C10 trifluoroalkyl group, a cyano group, or a combination thereof.

In one example of the present invention, the "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, or a C2 to C30 heteroaryl group. In addition, in specific examples of the present invention, "substituted" refers to replacement of at least one hydrogen of a substituent or a compound by deuterium, a C1 to C20 alkyl group, or a C6 to C30 aryl group. In addition, in specific examples of the present invention, "substituted" refers to replacement of at least one hydrogen of a substituent or a compound by deuterium, a C1 to C5 alkyl group, or a C6 to C18 aryl group. In addition, in specific examples of the present invention, the "substituted" refers to replacement of at least one hydrogen of a substituent or a compound by deuterium, a phenyl group, a biphenyl group, a terphenyl group, a naphthyl group, an anthracenyl group, a phenanthrenyl group, a triphenylene group, or a fluorenyl group.

In the present specification, when a definition is not otherwise provided, "hetero" refers to one including one to three heteroatoms selected from N, O, S, P, and Si, and remaining carbons in one functional group.

In the present specification, when a definition is not otherwise provided, "an alkyl group" refers to an aliphatic hydrocarbon group. The alkyl group may be "a saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group may have one to four carbon atoms in the alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

In the present specification, "aryl group" refers to a group including at least one hydrocarbon aromatic moiety, and may include

- a group in which all elements of the hydrocarbon aromatic moiety have p-orbitals which form conjugation, for example a phenyl group, a naphthyl group, and the like,
- a group in which two or more hydrocarbon aromatic moieties may be linked by a sigma bond, for example a biphenyl group, a terphenyl group, a quarterphenyl group, and the like, and
- a group in which two or more hydrocarbon aromatic moieties are fused directly or indirectly to provide a non-aromatic fused ring. For example, it may be a fluorenyl group.

The aryl group may include a monocyclic, polycyclic or fused ring polycyclic (i.e., rings sharing adjacent pairs of carbon atoms) functional group.

In the present specification, "a heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "a heteroaryl group" may refer to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

Specific examples of the heterocyclic group may include a pyridinyl group, a pyrimidinyl group, a pyrazinyl group, a pyridazinyl group, a triazinyl group, a quinolinyl group, an isoquinolinyl group, and the like.

More specifically, the substituted or unsubstituted C6 to C30 aryl group and/or the substituted or unsubstituted C2 to C30 heterocyclic group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylenyl group, a substituted or unsubstituted perylenyl group, a substituted or unsubstituted fluorenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted dibenzofuranyl group, or a substituted or unsubstituted dibenzothiophenyl group, or a combination thereof, but are not limited thereto.

In the present specification, hole characteristics refer to an ability to donate an electron to form a hole when an electric field is applied and that a hole formed in the anode may be easily injected into the light emitting layer and transported in the light emitting layer due to conductive characteristics according to a highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to a lowest unoccupied molecular orbital (LUMO) level.

Hereinafter, a composition for an organic optoelectronic device according to an embodiment is described.

The composition for an organic optoelectronic device according to an embodiment includes a first host compound and a second host compound.

The first host compound may be represented by Chemical Formula 1.

[Chemical Formula 1]

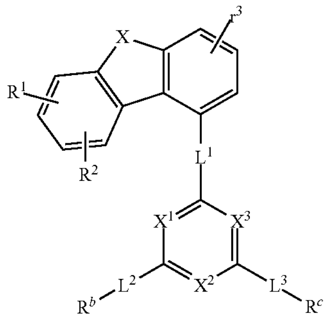

In Chemical Formula 1,

X is O or S, $L^1$ to $L^3$ are independently a single bond, or a substituted or unsubstituted C6 to C20 arylene group, $X^1$ to $X^3$ are independently N or $CR^a$, at least two of $X^1$ to $X^3$ are N, $R^1$ to $R^3$ are independently hydrogen, deuterium, a substituted or unsubstituted C1 to C10 alkyl group, a substituted or unsubstituted C6 to C12 aryl group, or a combination thereof, $R^a$ is hydrogen, deuterium, a substituted or unsubstituted C6 to C30 aryl group, a substituted or unsubstituted dibenzofuranyl group, a substituted or unsubstituted dibenzothiophenyl group, or a combination thereof, and $R^b$ and $R^c$ are independently a substituted or unsubstituted C6 to C30 aryl group, a substituted or unsubstituted dibenzofuranyl group, a substituted or unsubstituted dibenzothiophenyl group, or a combination thereof, wherein "substituted" of Chemical Formula 1 refers to replacement of at least one hydrogen by deuterium, a C6 to C30 aryl group, a dibenzofuranyl group, or a dibenzothiophenyl group.

Specifically, "substituted" of Chemical Formula 1 refers to replacement of at least one hydrogen by a C6 to C20 aryl group, a dibenzofuranyl group, or a dibenzothiophenyl group, more specifically "substituted" of Chemical Formula 1 refers to replacement of at least one hydrogen by a phenyl group, a biphenyl group, a terphenyl group, a naphthyl group, an anthracenyl group, a phenanthrenyl group, a triphenylene group, a fluorenyl group, a dibenzofuranyl group, or a dibenzothiophenyl group.

For example, in an embodiment of the present invention, the hexagonal ring including $X^1$ to $X^3$ may be a pyrimidinyl group that is substituted or unsubstituted with a phenyl group, a biphenyl group, a terphenyl group, a naphthyl group, an anthracenyl group, a phenanthrenyl group, a triphenylene group, a fluorenyl group, a dibenzofuranyl group, or a dibenzothiophenyl group; or a triazinyl group that is substituted or unsubstituted with a phenyl group, a biphenyl group, a terphenyl group, a naphthyl group, an anthracenyl group, a phenanthrenyl group, a triphenylene group, a fluorenyl group, a dibenzofuranyl group, or a dibenzothiophenyl group.

The first host compound includes the N-containing hexagonal ring having electron characteristics at the 1-position of dibenzofuran or dibenzothiophene, and thereby may have a lower LUMO energy level due to a strong interaction and may have excellent electron injection characteristics, and additionally a crystallization of a material in a molecular structure does not occur well, and when used in the light emitting layer together with the second host compound, a more uniform and stable thin film characteristics may be exhibited In particular, when a compound having a relatively high hole characteristics is used as a second host and used in the light emitting layer together with the first host compound, charge is balanced in the light emitting layer, thereby realizing a long life-span organic light emitting diode.

In a specific embodiment of the present invention, Chemical Formula 1 may be for example represented by one of Chemical Formula 1-A, Chemical Formula 1-B, and Chemical Formula 1-C according to specific structures of the hexagonal ring including $X^1$ to $X^3$.

[Chemical Formula 1-A]

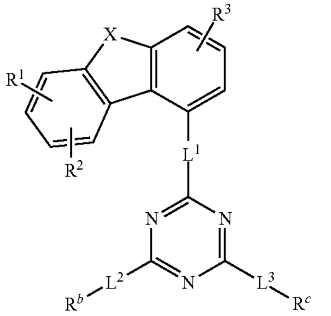

[Chemical Formula 1-B]

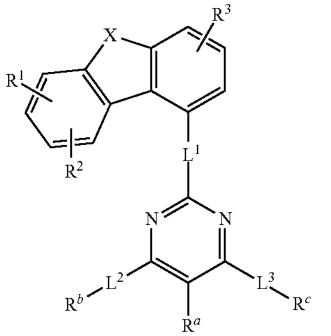

[Chemical Formula 1-C]

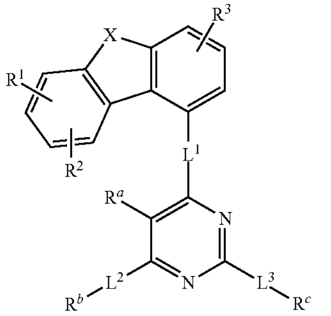

In Chemical Formula 1-A, Chemical Formula 1-B, and Chemical Formula 1-C, X, $R^1$ to $R^3$, $L^1$ to $L^3$, and $R^a$ to Rc are the same as described above.

In an embodiment of the present invention, $R^1$ to $R^3$ may independently be hydrogen, deuterium, a substituted or unsubstituted C1 to C4 alkyl group, a substituted or unsubstituted phenyl group, or a substituted or unsubstituted biphenyl group and in a specific embodiment of the present invention, $R^1$ to $R^3$ may be all hydrogen.

When $R^1$ to $R^3$ are all hydrogen, Chemical Formula 1 may be for example represented by one of Chemical Formula 1-A1, Chemical Formula 1-B1, and Chemical Formula 1-C1.

[Chemical Formula 1-A1]

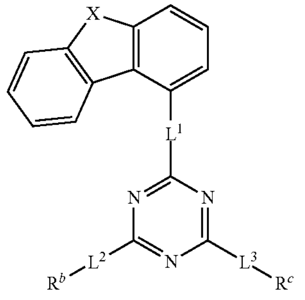

[Chemical Formula 1-B1]

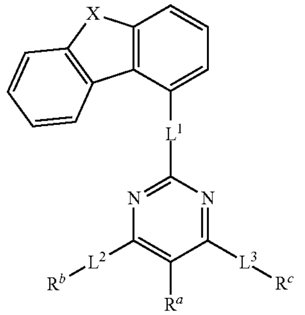

[Chemical Formula 1-C1]

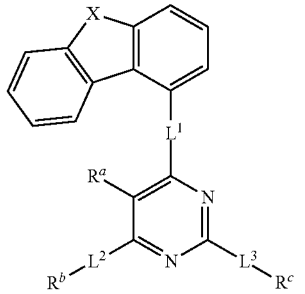

In Chemical Formula Chemical Formula 1-A1, Chemical Formula 1-B1, and Chemical Formula 1-C1, X, L1 to $L^3$, and $R^a$ to $R^c$ are the same as described above.

In an embodiment of the present invention, L1 to $L^3$ may independently a be selected from a single bond, or a substituted or unsubstituted C6 to C20 arylene group, specifically a single bond, a phenylene group, a biphenylene group, a naphthylenyl group, or a terphenylene group, and more specifically, a single bond or linking groups of Group I.

[Group I]
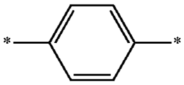
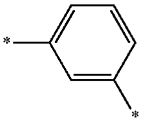
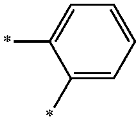
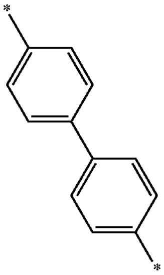
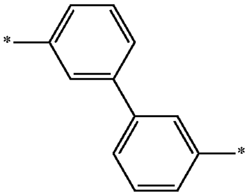
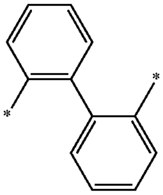
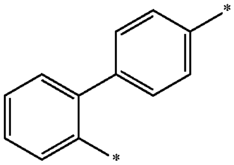
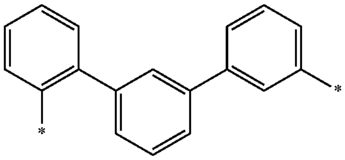
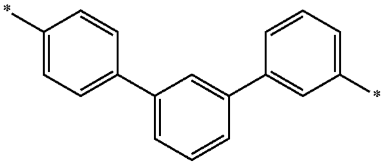
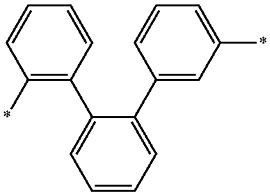
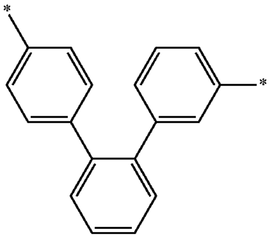
-continued
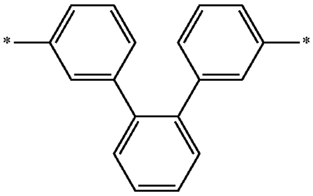
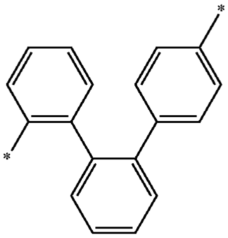
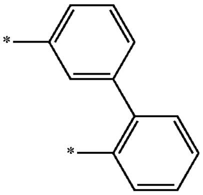
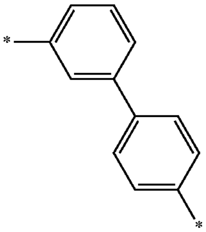
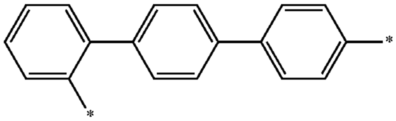
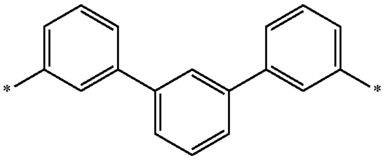
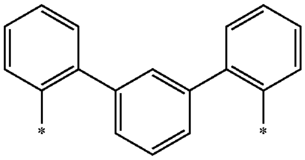
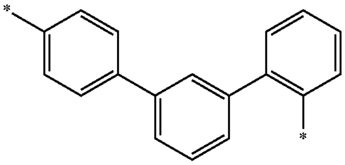
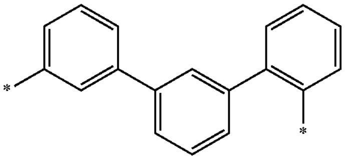
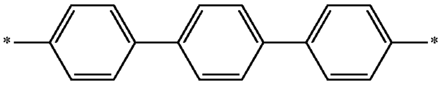
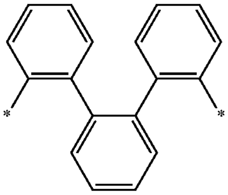
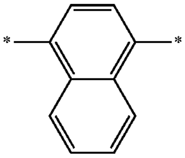

-continued

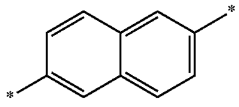

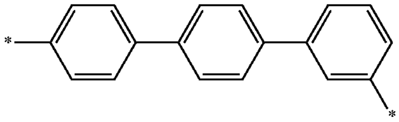

In Group I, * is a linking point with adjacent atoms.

For example, $L^1$ to $L^3$ may independently be a single bond, a para-phenylene group, a meta-phenylene group, or a biphenylene group.

In an embodiment of the present invention, $R^a$ may be hydrogen, a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylene group, a substituted or unsubstituted dibenzofuranyl group, or a substituted or unsubstituted dibenzothiophenyl group and $R^b$ and $R^c$ may independently be a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylene group, a substituted or unsubstituted dibenzofuranyl group, or a substituted or unsubstituted dibenzothiophenyl group, and specifically, $R^a$ may be hydrogen or may be selected from substituents of Group II and $R^b$ and $R^c$ may independently be selected from substituents of Group II.

[Group II]

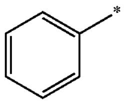

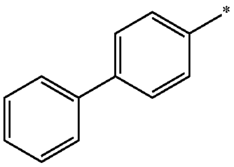

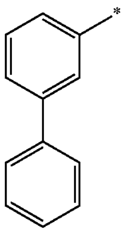

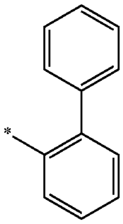

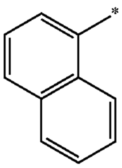

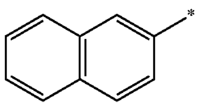

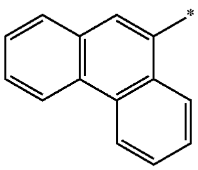

-continued

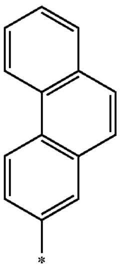

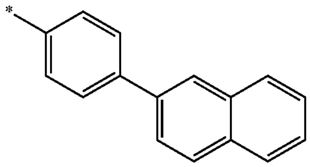

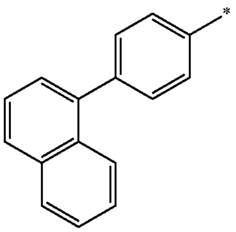

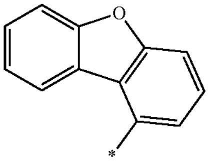

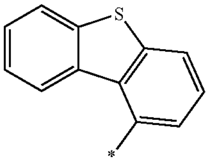

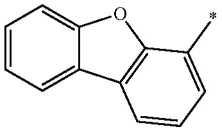

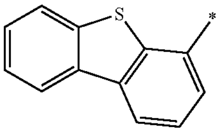

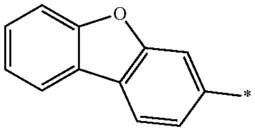

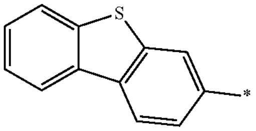

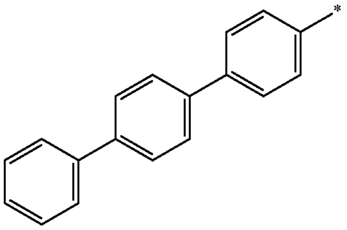

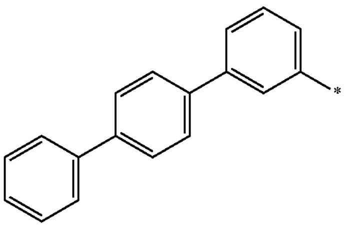

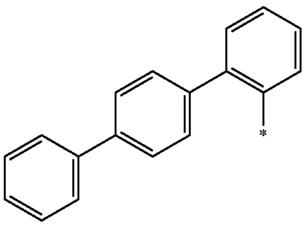

-continued
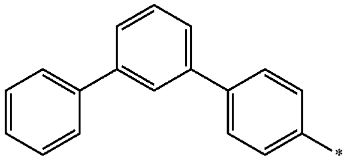
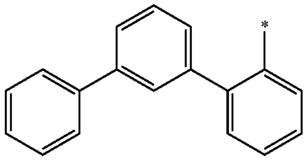
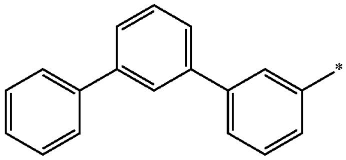
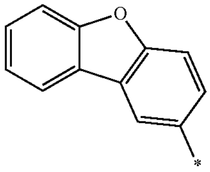
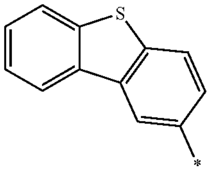
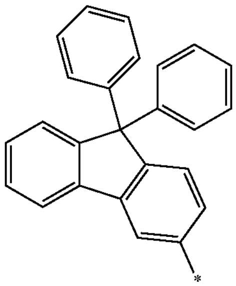
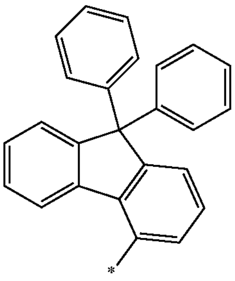
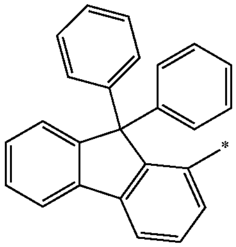
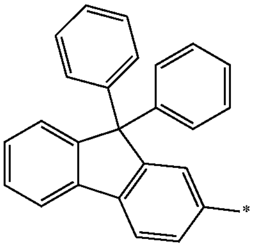
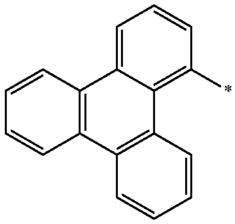
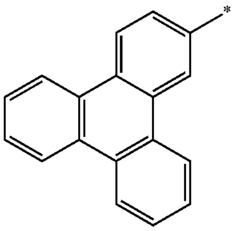
-continued
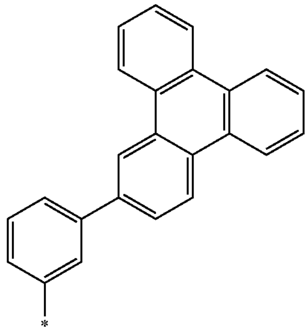
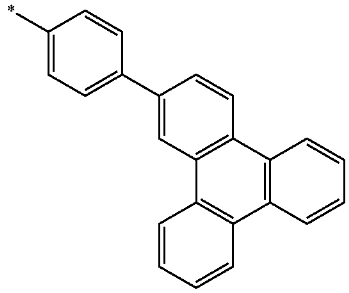
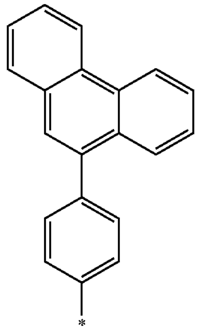
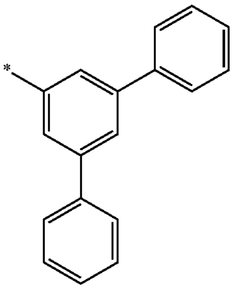
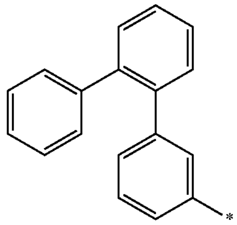
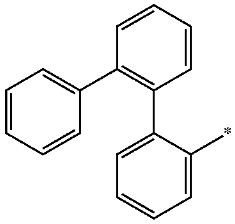
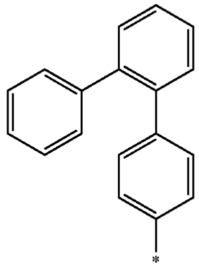
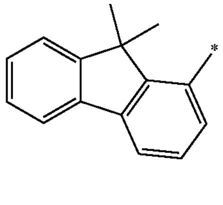
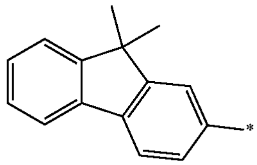
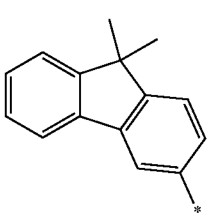

-continued

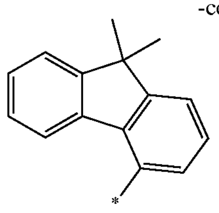

In Group II, * is a linking point with adjacent atoms.

In an example embodiment of the present invention, $R^a$ may be hydrogen, or a phenyl group and $R^b$ and $R^c$ may independently be a substituted or unsubstituted phenyl group, a substituted or unsubstituted biphenyl group, a substituted or unsubstituted terphenyl group, a substituted or unsubstituted triphenylene group, a substituted or unsubstituted dibenzofuranyl group, or a substituted or unsubstituted dibenzothiophenyl group. For example, $R^a$ may be hydrogen.

On the other hand, "substituted" of Chemical Formula 1 refers to replacement of at least one hydrogen by deuterium, a C6 to C20 aryl group, a dibenzofuranyl group, or a dibenzothiophenyl group, and specifically replacement of at least one hydrogen by deuterium, a phenyl group, a biphenyl group, a naphthyl group, an anthracenyl group, a phenanthrenyl group, a triphenylene group, a dibenzofuranyl group, or a dibenzothiophenyl group. Specifically, "substituted" of Chemical Formula 1 refers to replacement of at least one hydrogen by a phenyl group, a biphenyl group, a terphenyl group, naphthyl group, a triphenylene group, a dibenzofuranyl group, or a dibenzothiophenyl group.

In another specific embodiment of the present invention, at least one of RD and $R^c$ may be a substituted or unsubstituted C10 to C18 fused aryl group, for example, a naphthyl group, an anthracenyl group, a phenanthrenyl group, or a triphenylene group, and more specifically a triphenylene group. In the most specific embodiment of the present invention, $L^1$ to $L^3$ may independently be a single bond, a para-phenylene group, a meta-phenylene group, or a biphenylene group, $R^1$ to $R^3$ may independently be hydrogen, $R^a$ may be hydrogen or a phenyl group, $R^b$ and $R^c$ may independently be a substituted or unsubstituted phenyl group, a substituted or unsubstituted biphenyl group, a substituted or unsubstituted terphenyl group, a substituted or unsubstituted triphenylene group, a substituted or unsubstituted dibenzofuranyl group, or a substituted or unsubstituted dibenzothiophenyl group, and "substituted" refers to replacement of at least one hydrogen by a phenyl group, a biphenyl group, a terphenyl group, a naphthyl group, a triphenylene group, a substituted or unsubstituted dibenzofuranyl group, or a substituted or unsubstituted dibenzothiophenyl group.

The first host compound represented by Chemical Formula 1 may be for example selected from compounds of Group 1, but is not limited thereto.

[Group 1]

[A-1]

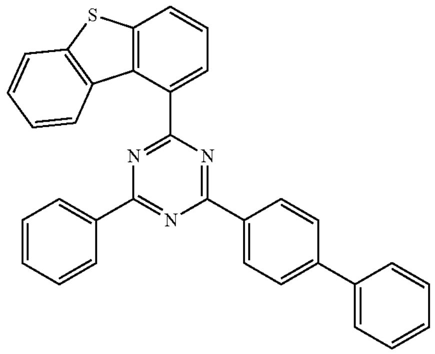

[A-2]

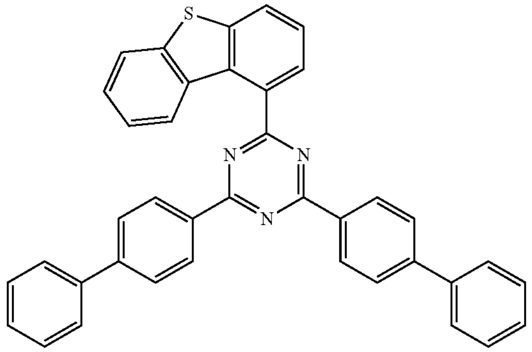

[A-3]

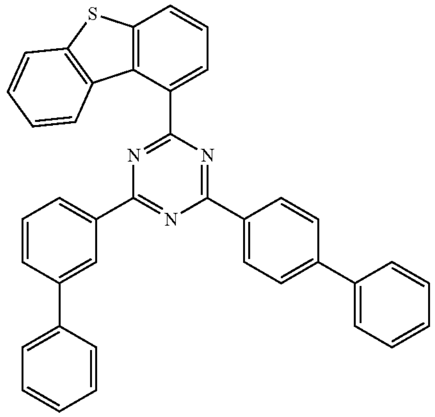

[A-4]

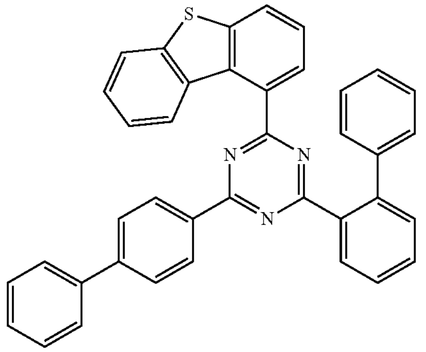

-continued
[A-5]
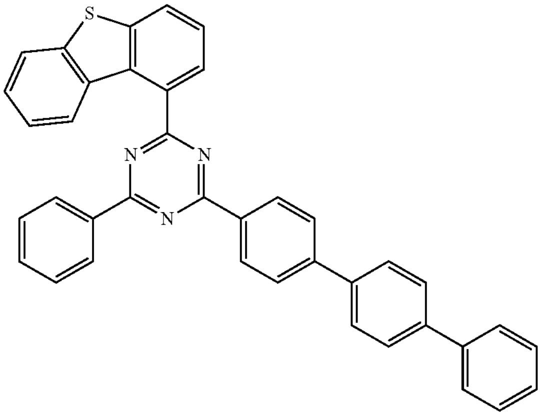
[A-6]
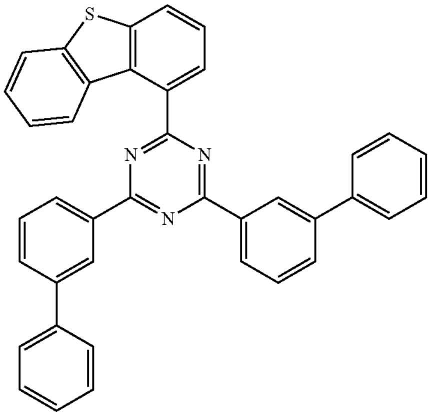
[A-7]
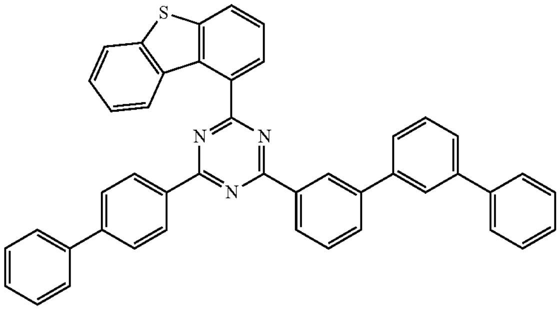
[A-8]
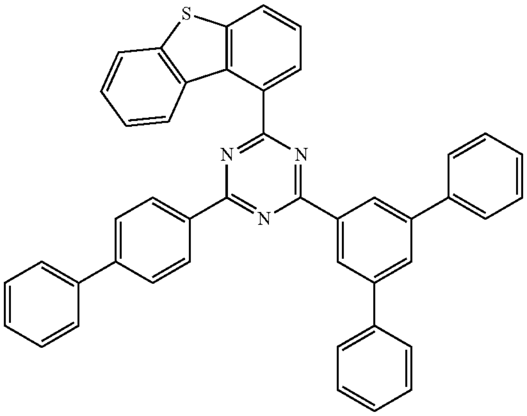
-continued
[A-9]
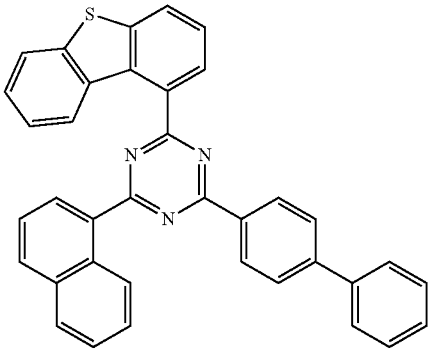
lp;2p
[A-10]
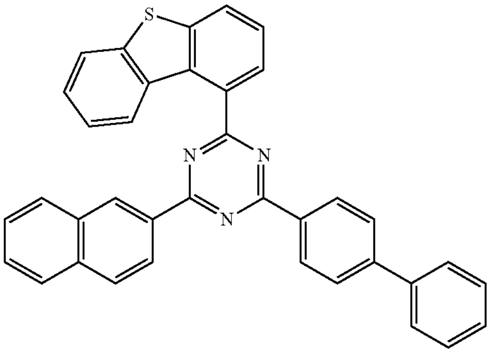
[A-11]
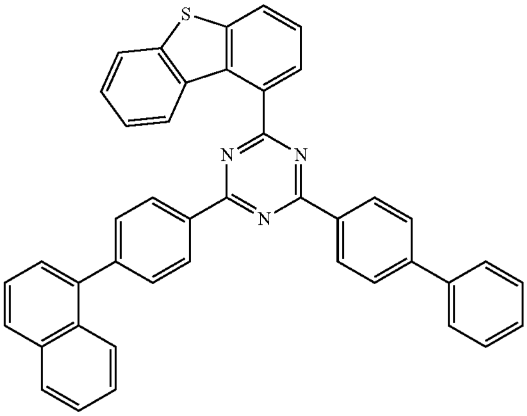
[A-12]
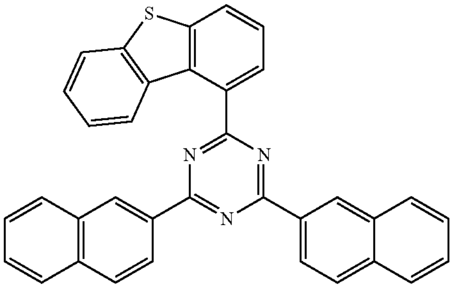

-continued
[A-13]
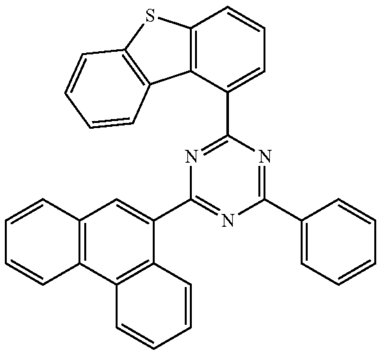
[A-14]
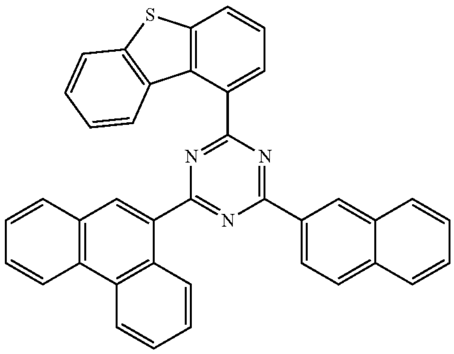
[A-15]
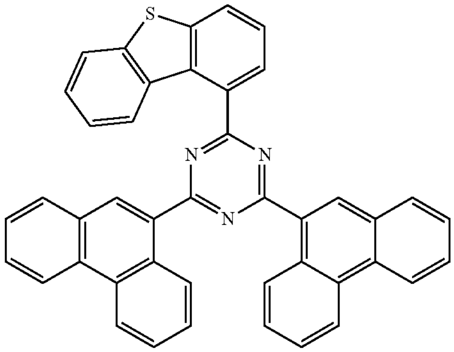
[A-16]
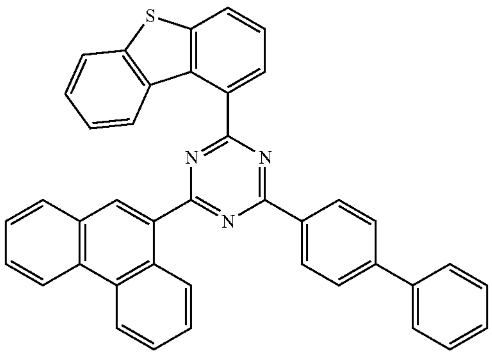
-continued
[A-17]
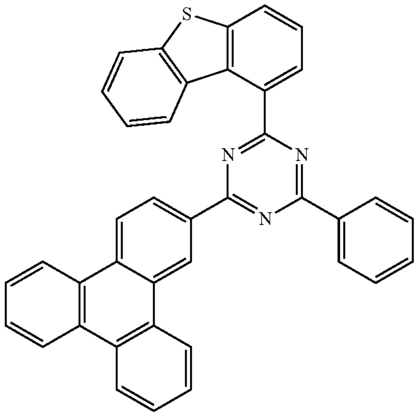
[A-18]
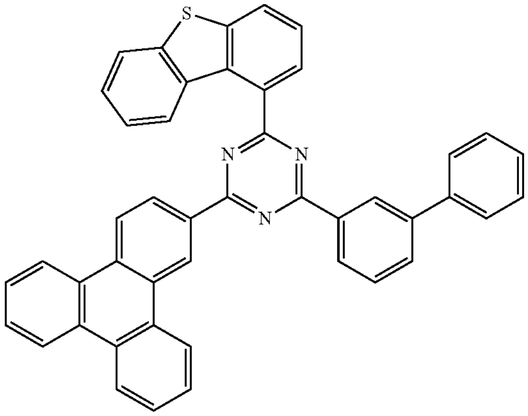
[A-19]
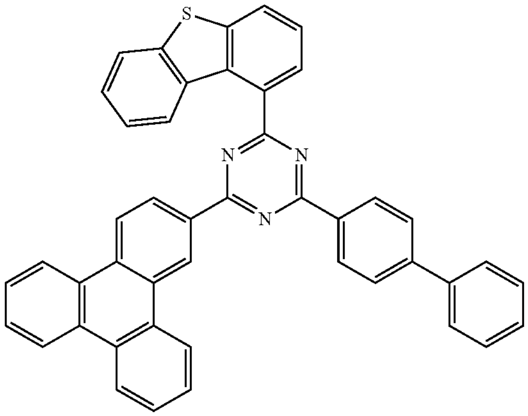

-continued
[A-20]
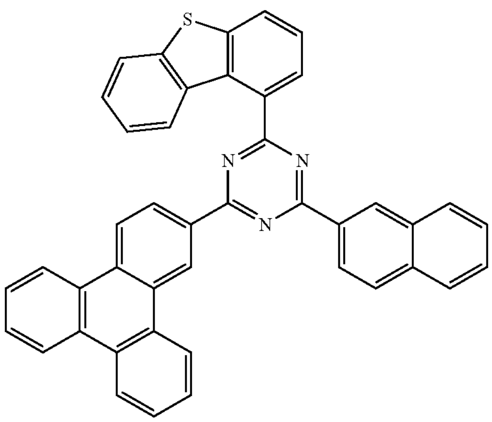
[A-21]
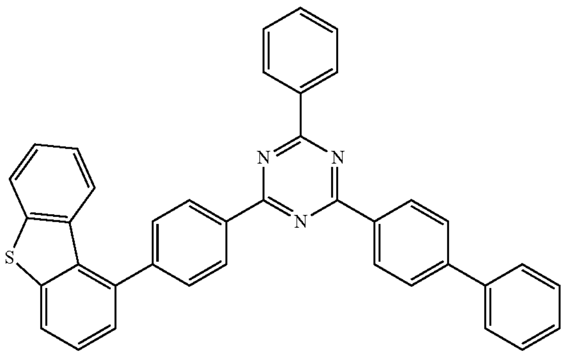
[A-22]
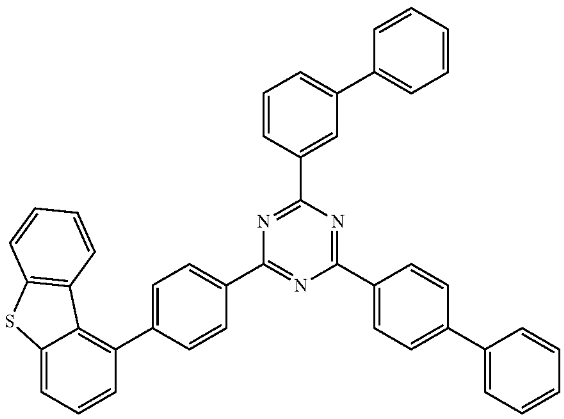
-continued
[A-23]
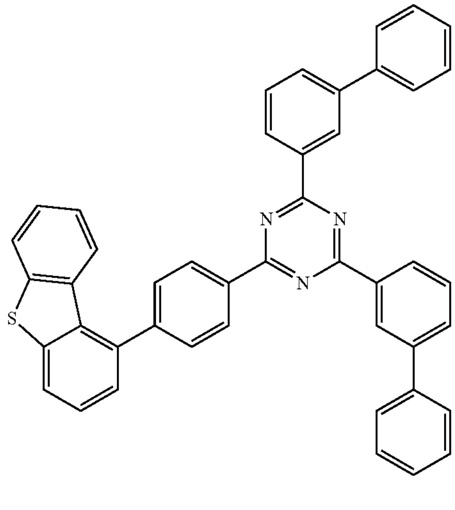
[A-24]
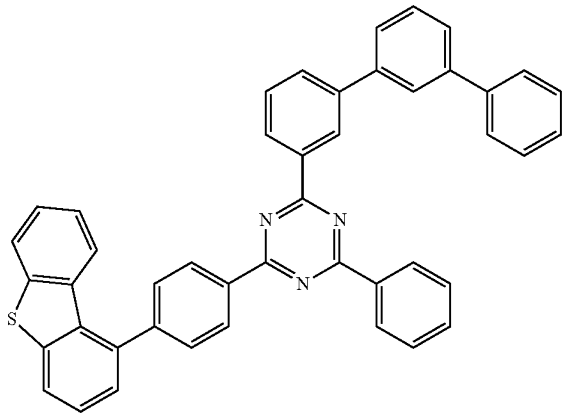
[A-25]
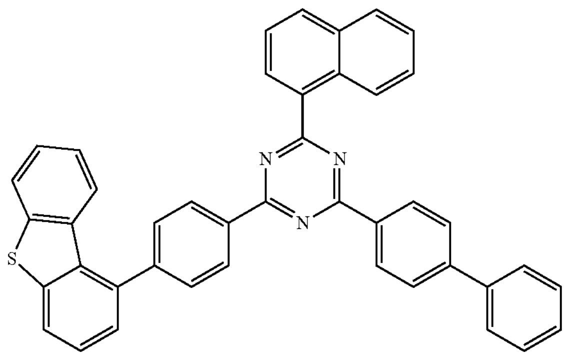

-continued
[A-26]
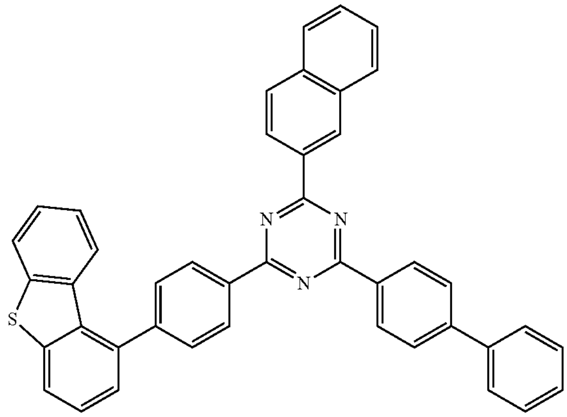
[A-27]
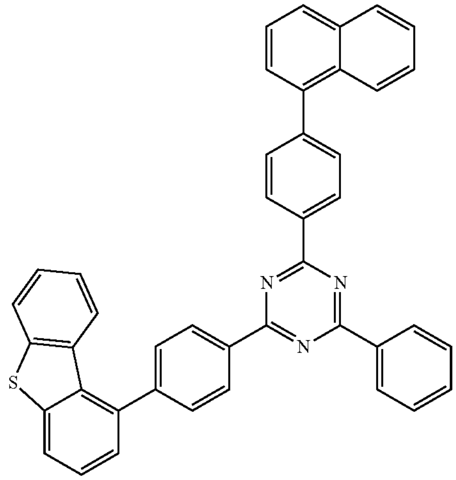
[A-28]
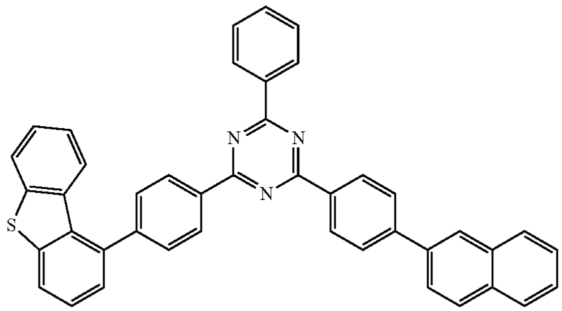
-continued
[A-29]
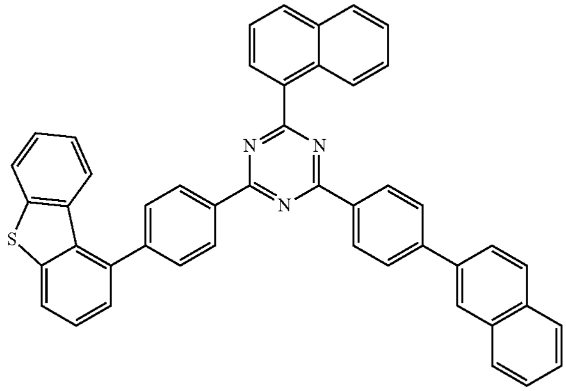
[A-30]
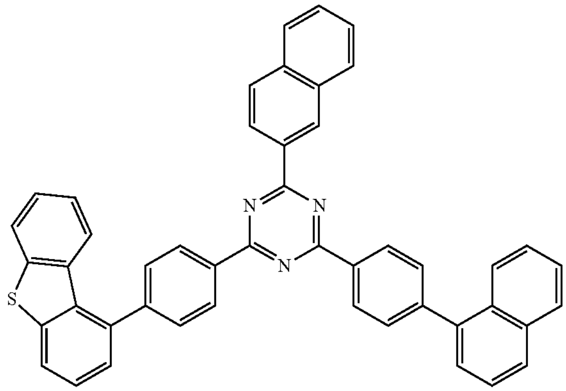
[A-31]
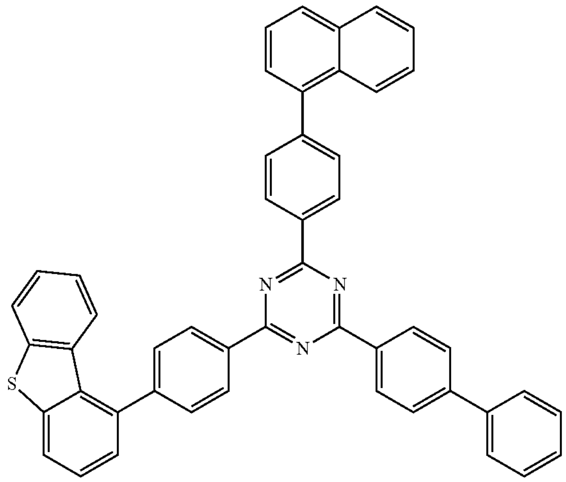

-continued
[A-32]
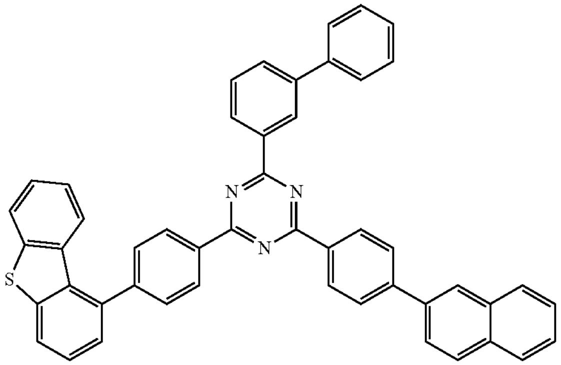
[A-33]
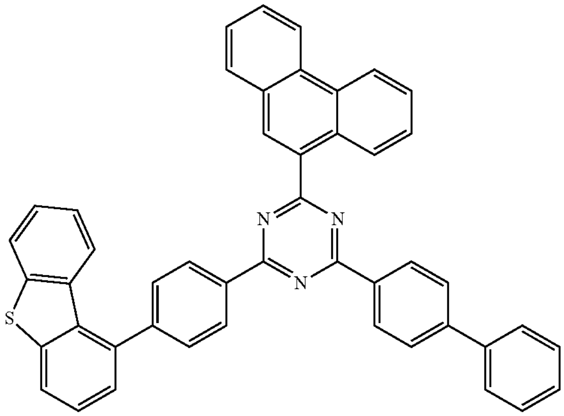
[A-34]
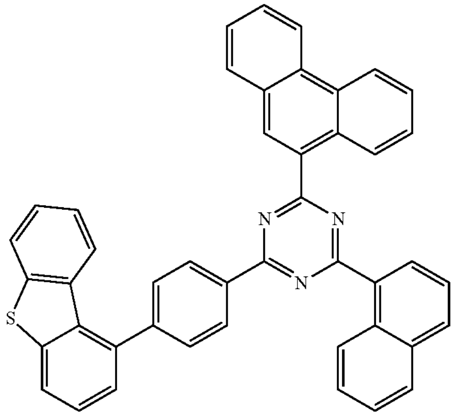
-continued
[A-35]
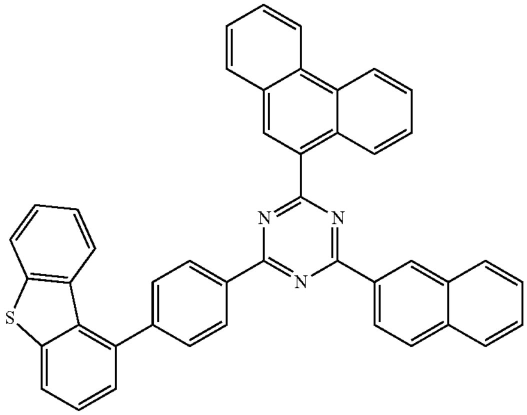
[A-36]
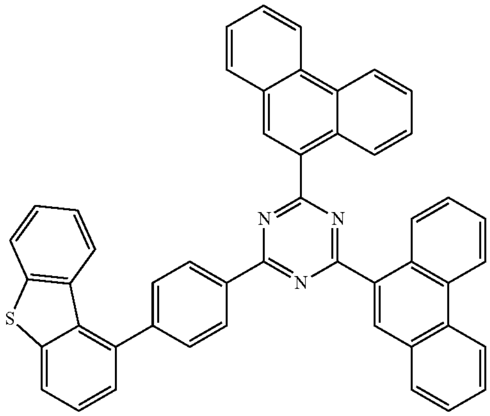
[A-37]
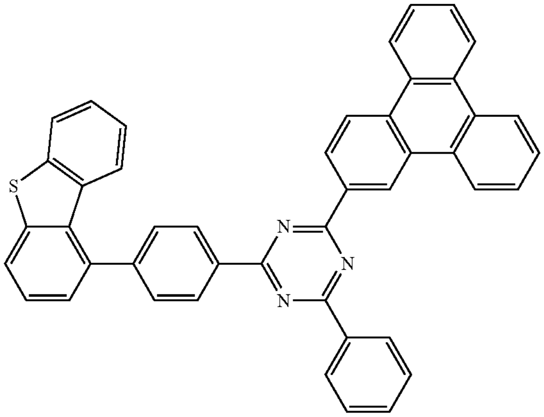

-continued
[A-38]
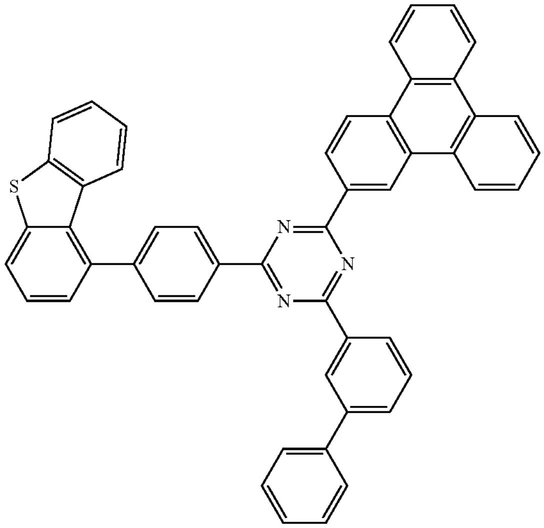
[A-39]
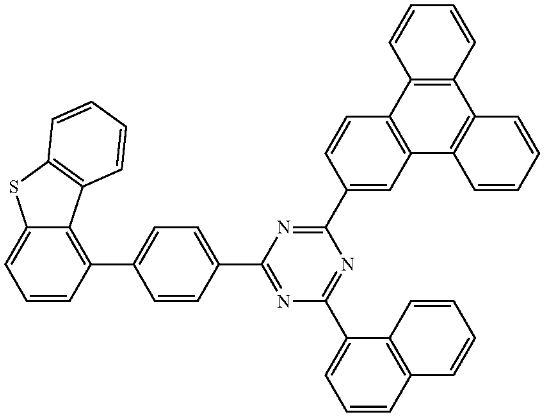
[A-40]
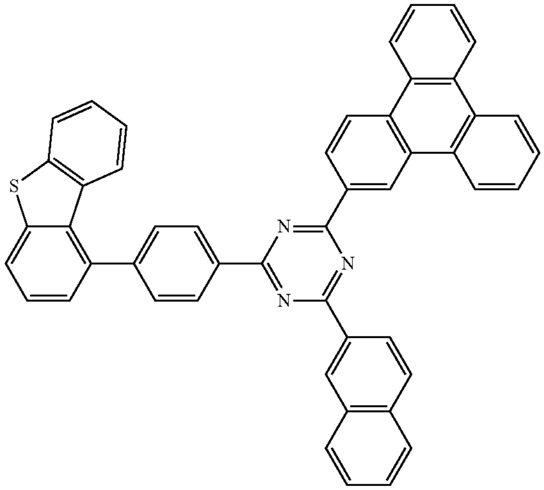
-continued
[A-41]
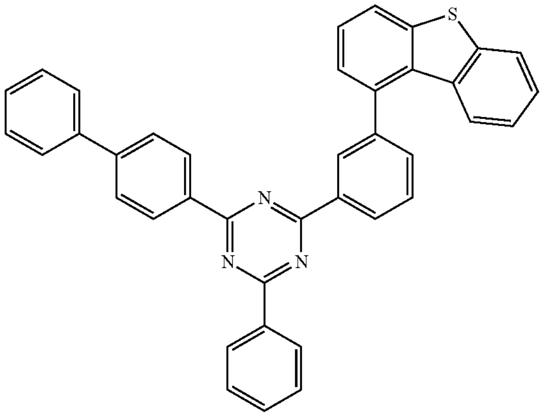
[A-42]
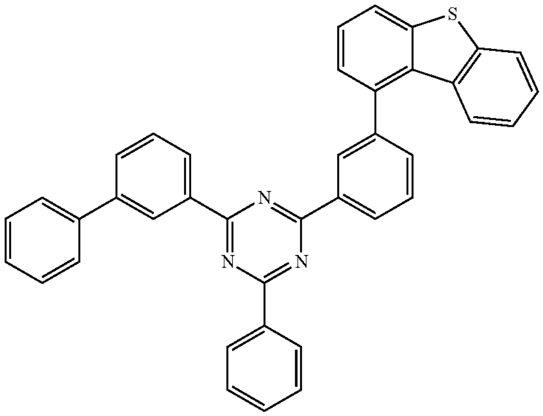
[A-43]
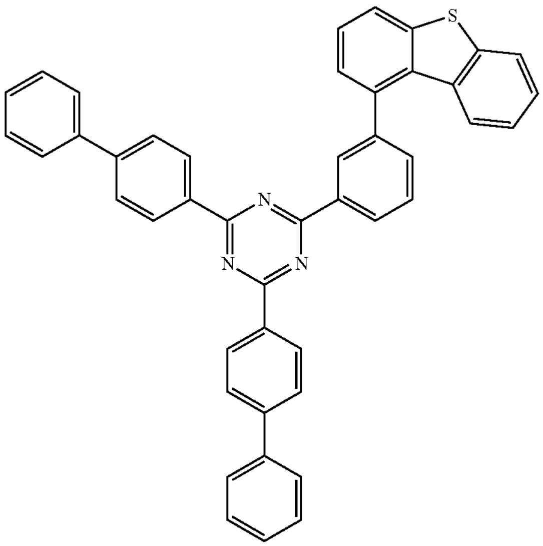

-continued
[A-44]
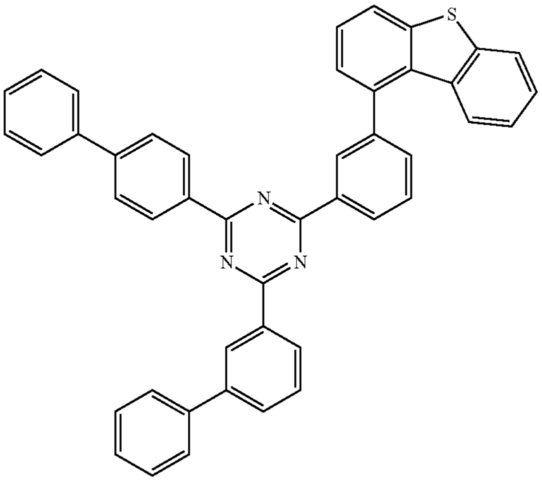
[A-45]
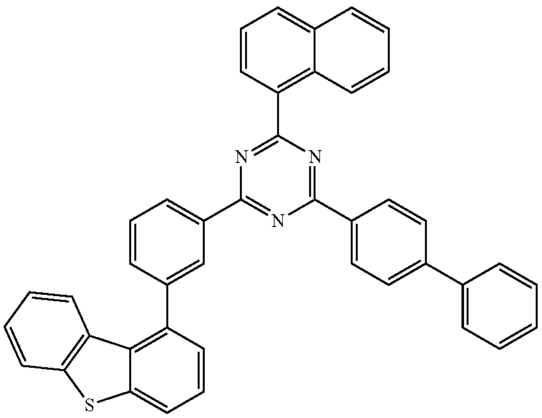
[A-46]
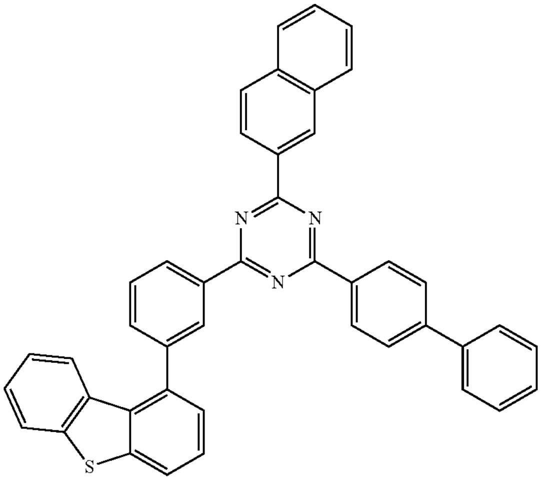
-continued
[A-47]
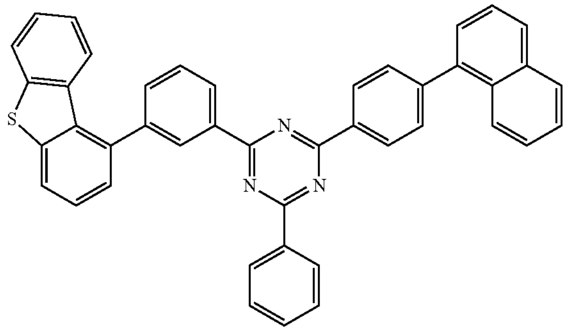
[A-48]
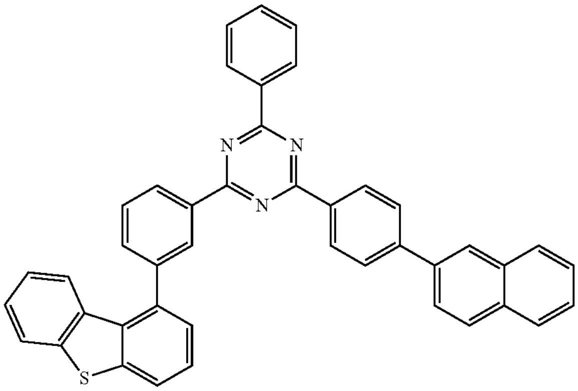
[A-49]
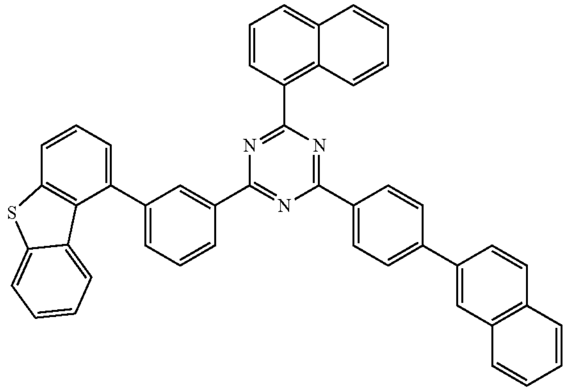
[A-50]
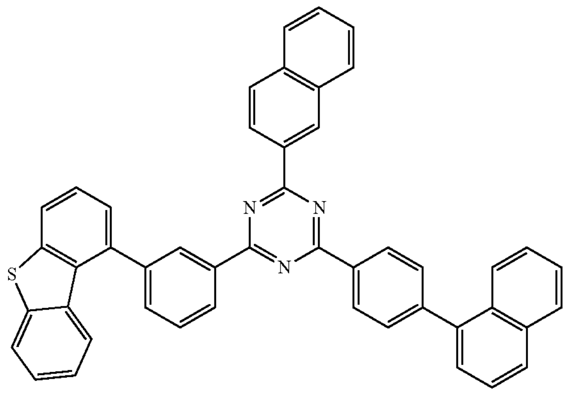

-continued
[A-51]
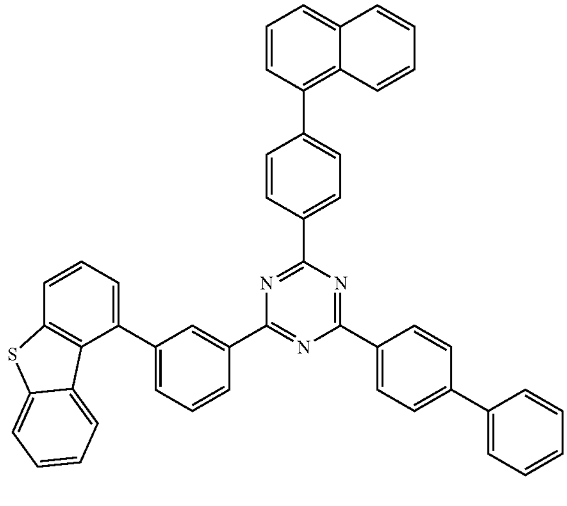
[A-52]
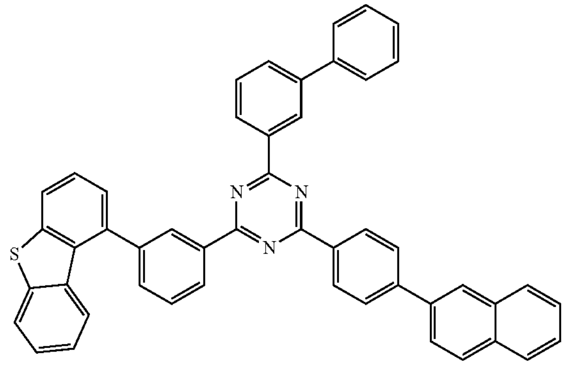
[A-53]
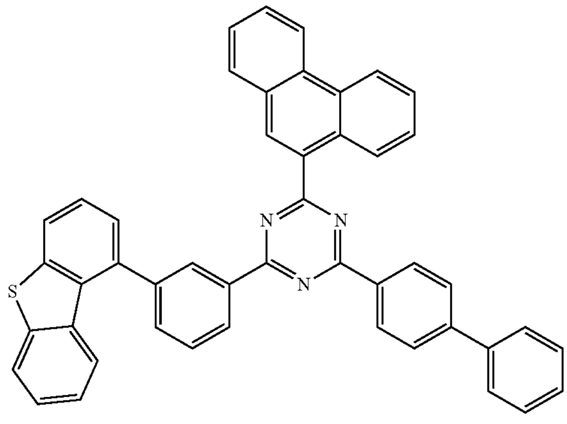
-continued
[A-54]
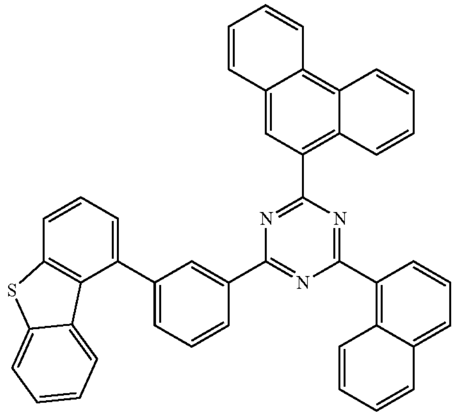
[A-55]
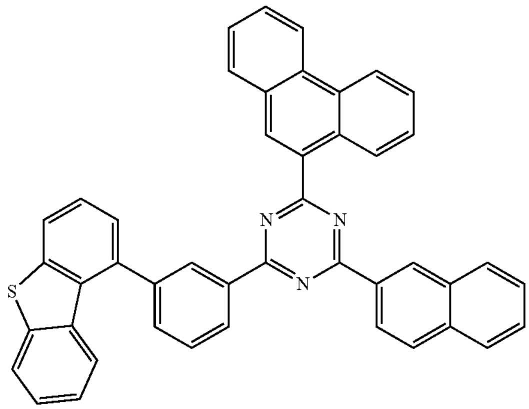
[A-56]
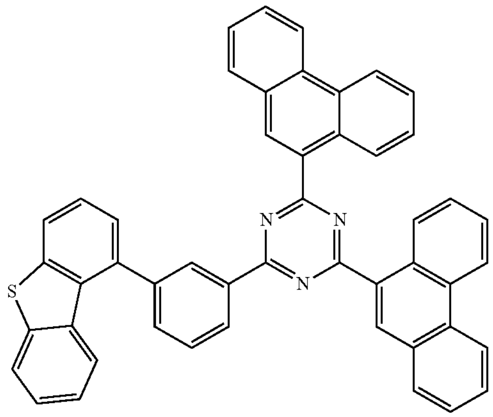

-continued
[A-57]
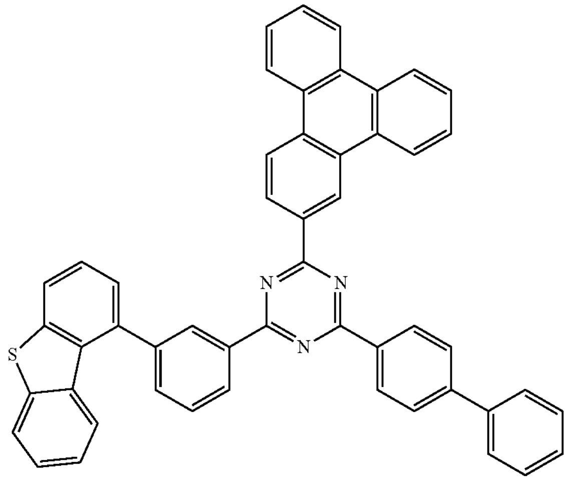
[A-58]
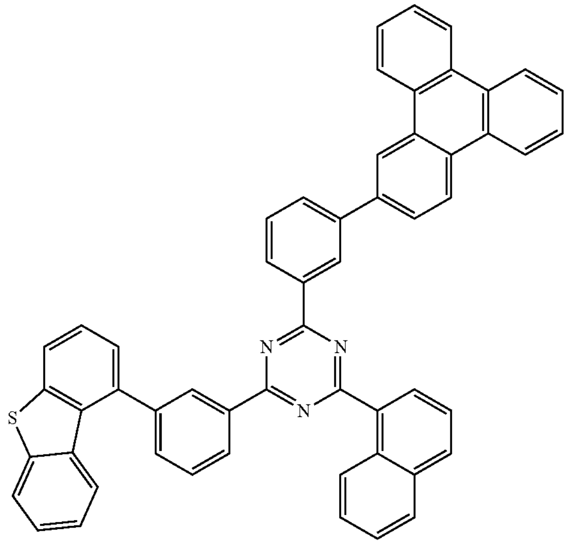
[A-59]
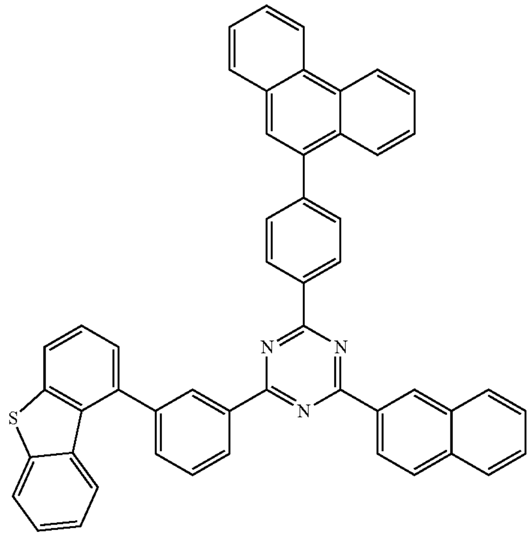
-continued
[A-60]
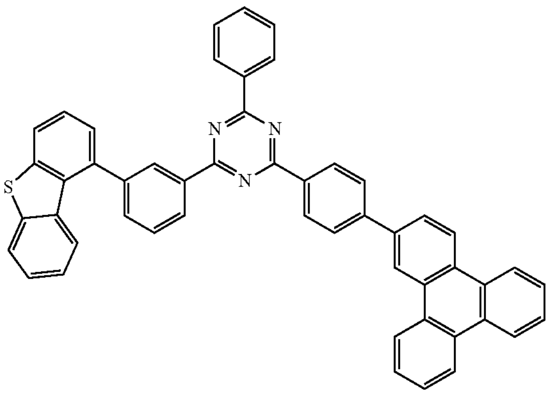
[A-61]
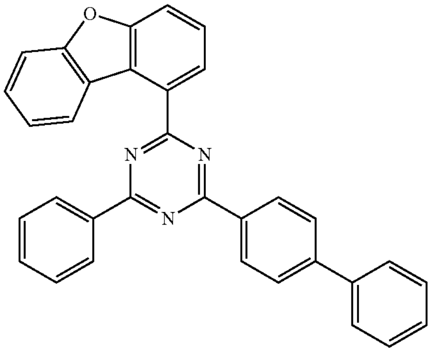
[A-62]
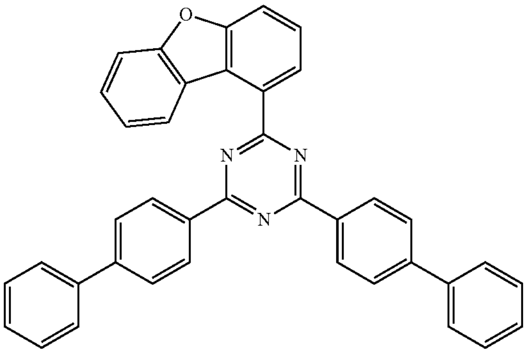
[A-63]
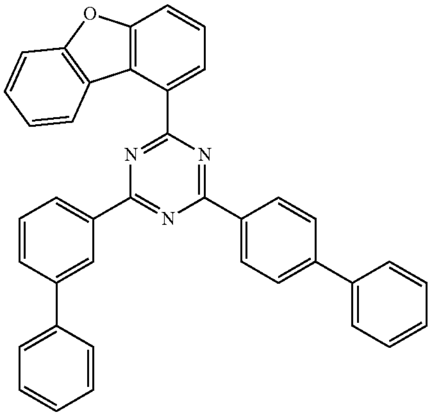

-continued
[A-64]
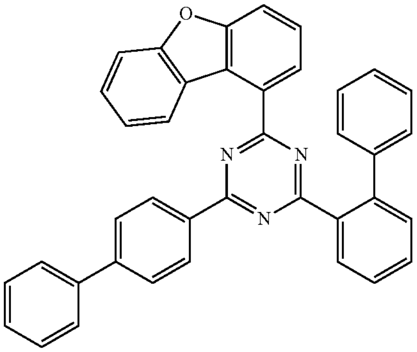
[A-65]
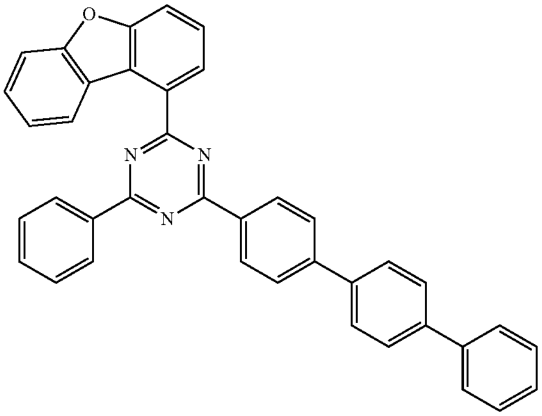
[A-66]
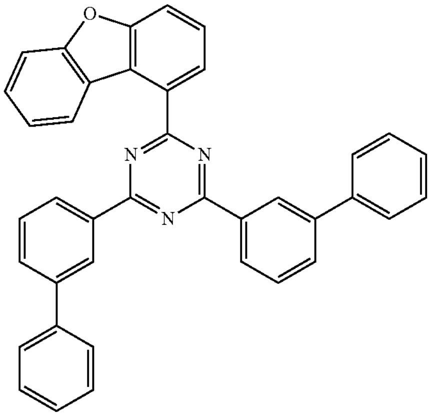
[A-67]
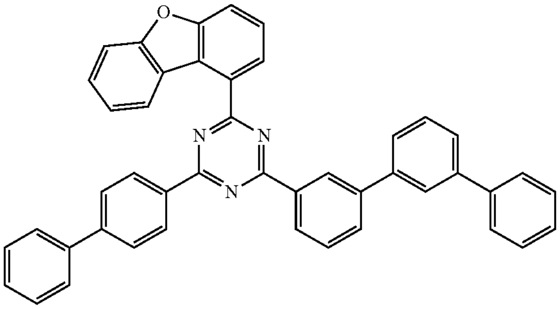
-continued
[A-68]
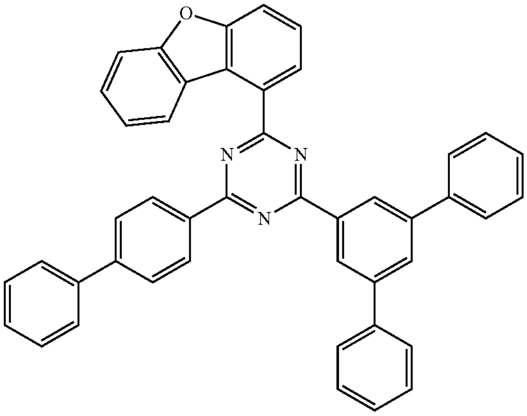
[A-69]
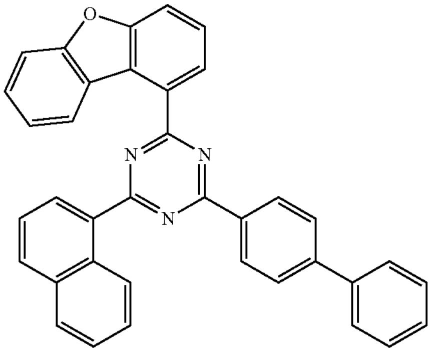
[A-70]
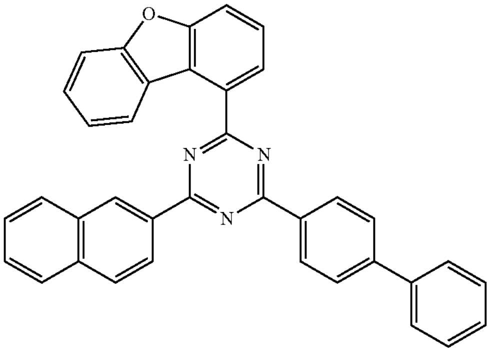
[A-71]
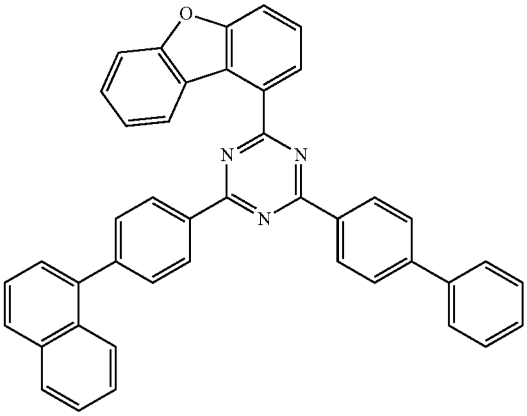

-continued
[A-72]
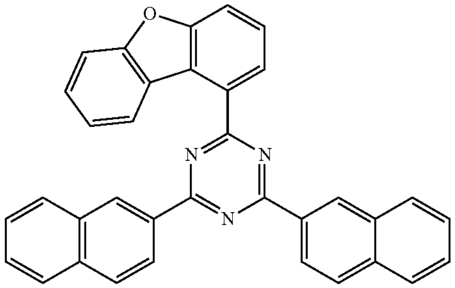
[A-73]
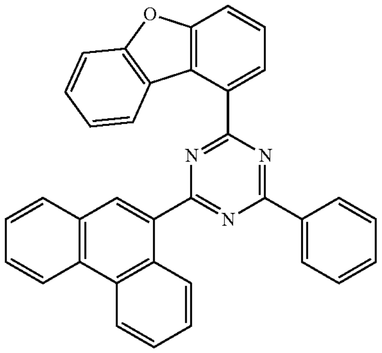
[A-74]
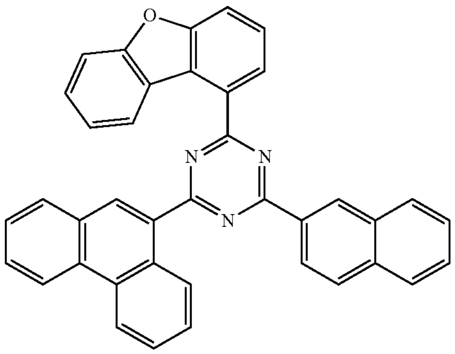
[A-75]
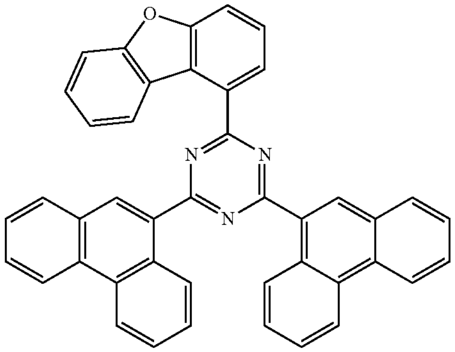
-continued
[A-76]
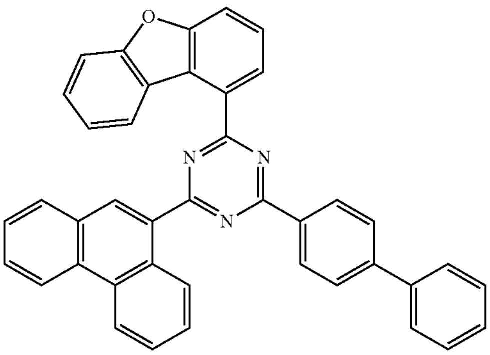
[A-77]
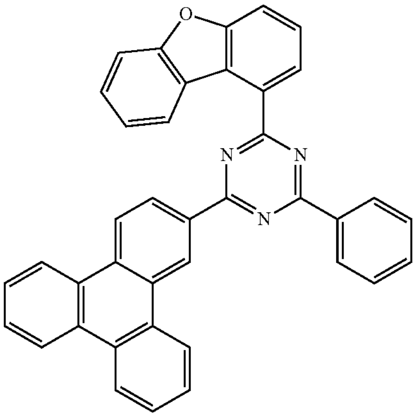
[A-78]
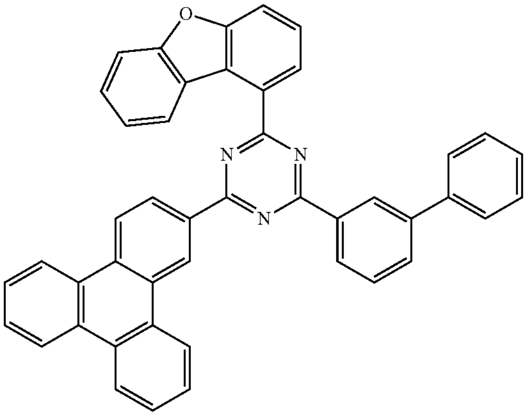

-continued
[A-79]
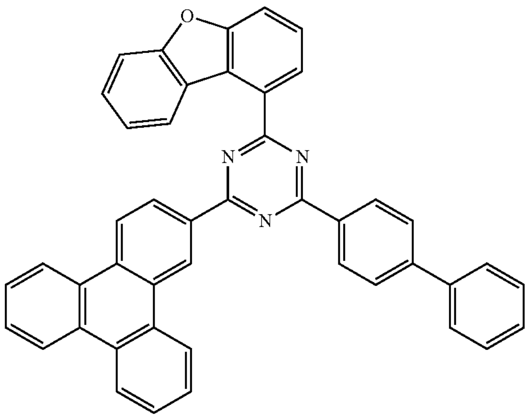
[A-80]
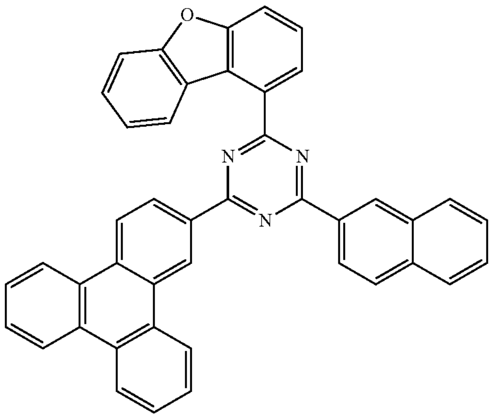
[A-81]
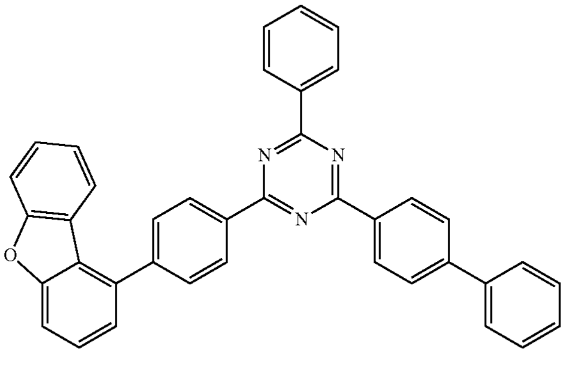
-continued
[A-82]
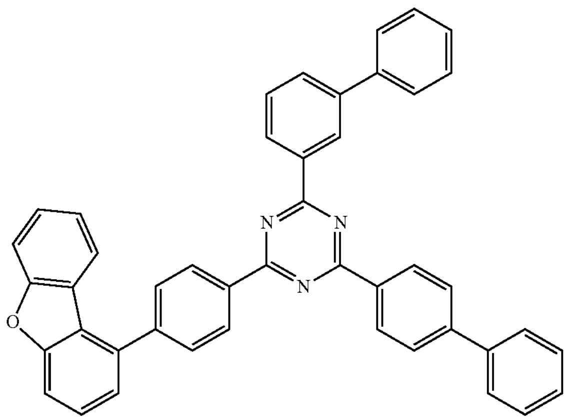
[A-83]
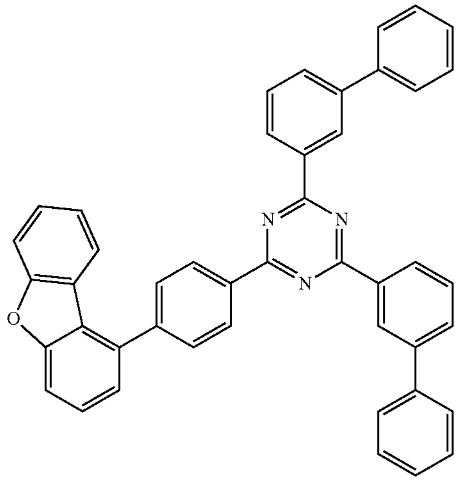
[A-84]
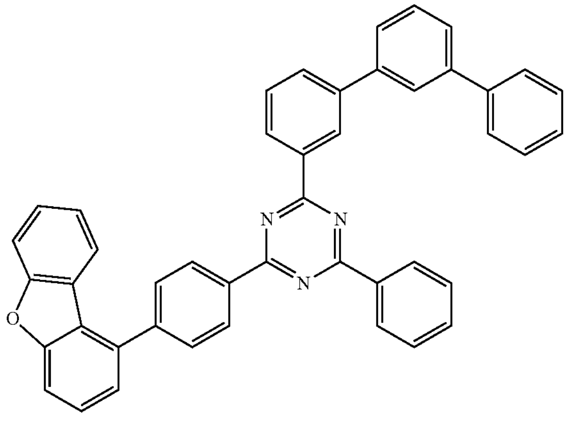

-continued
[A-85]
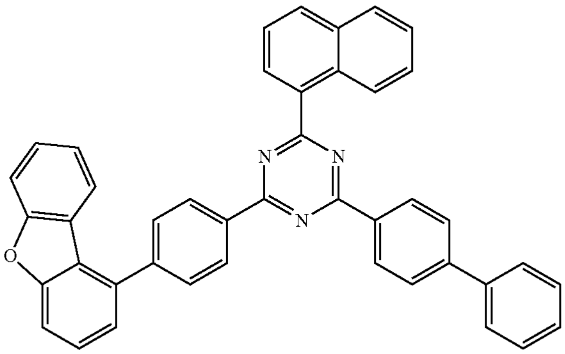
[A-86]
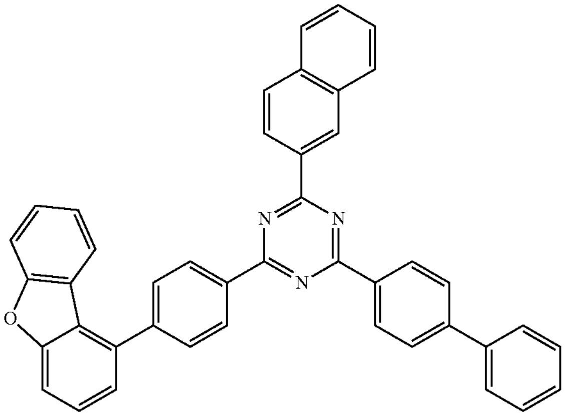
[A-87]
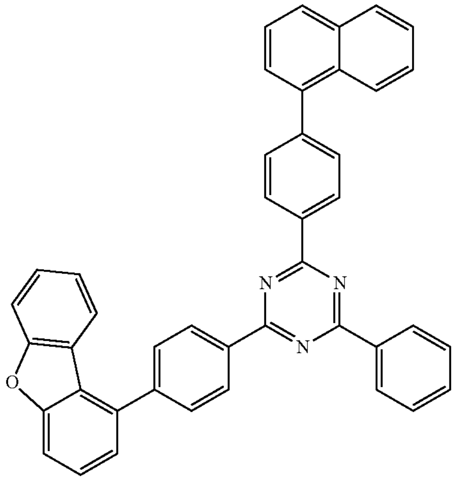
[A-88]
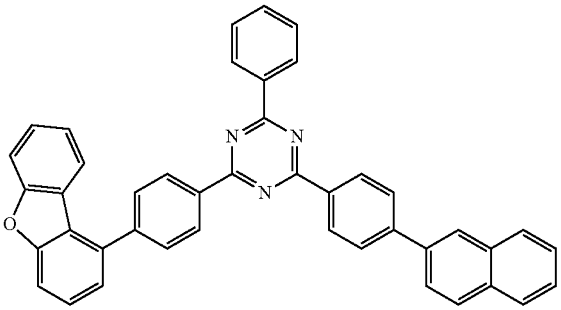
-continued
[A-89]
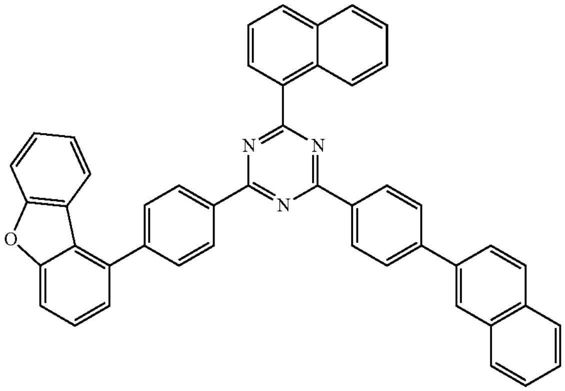
[A-90]
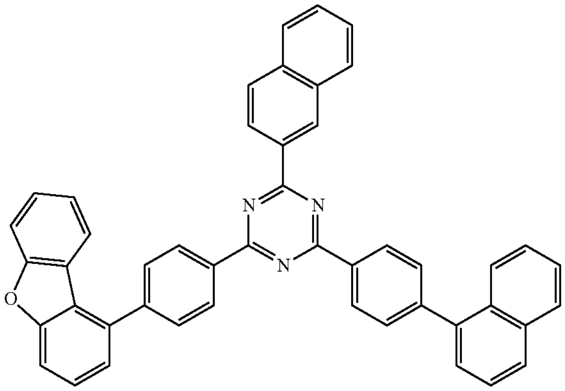
[A-91]
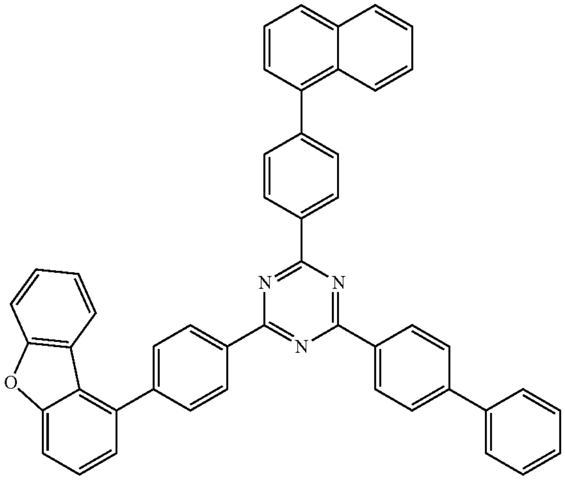

-continued
[A-92]
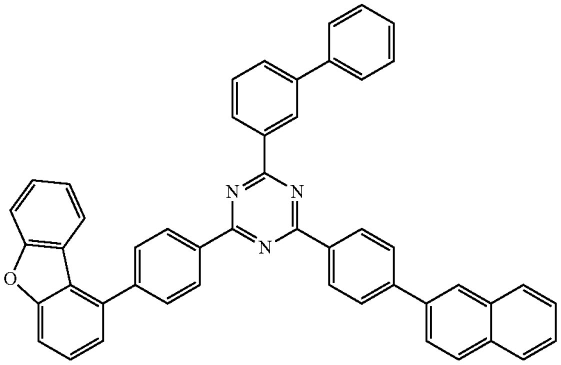
[A-93]
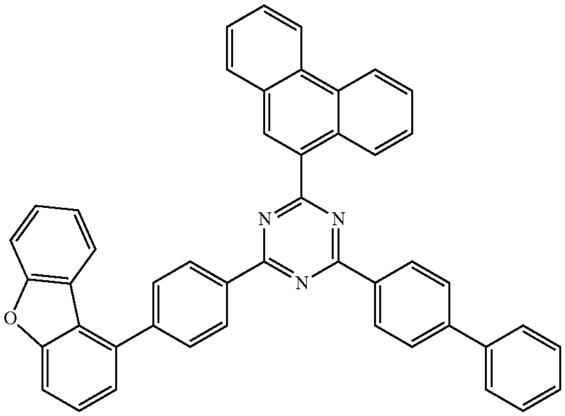
[A-94]
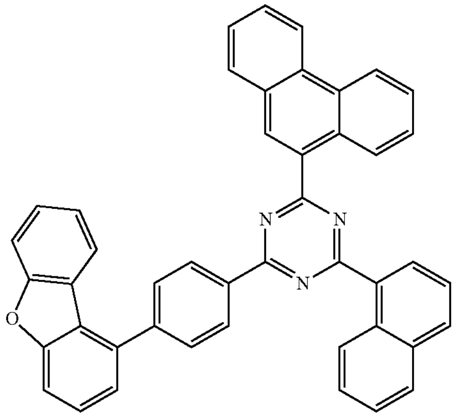
-continued
[A-95]
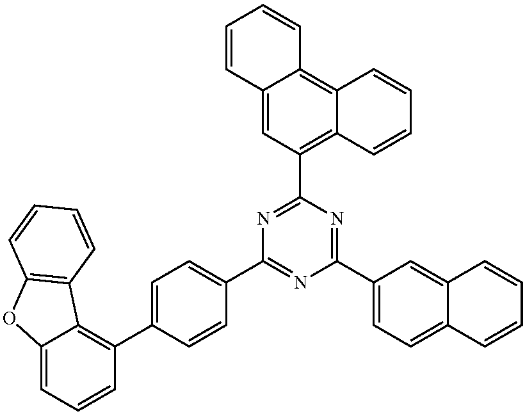
[A-96]
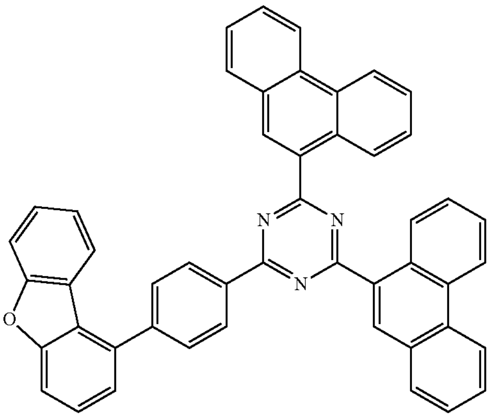
[A-97]
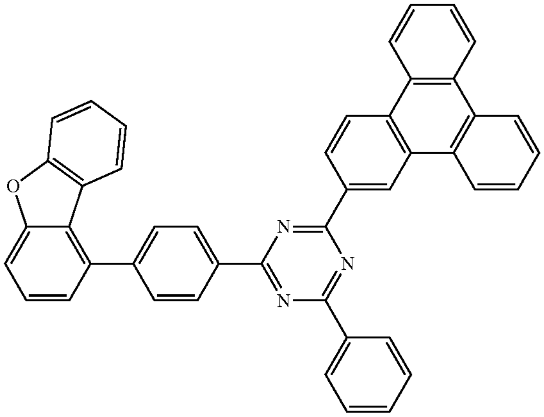

-continued
[A-98]
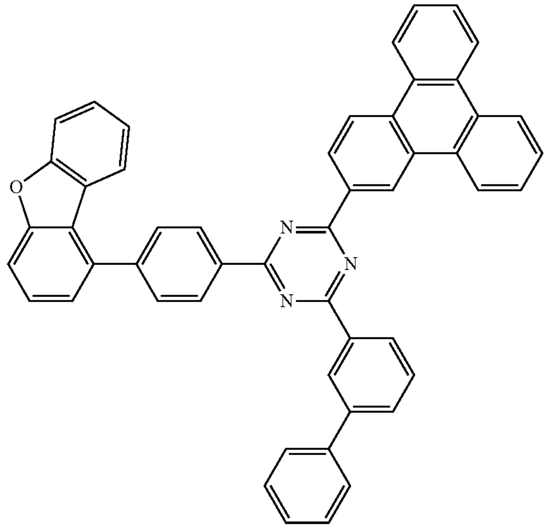
[A-99]
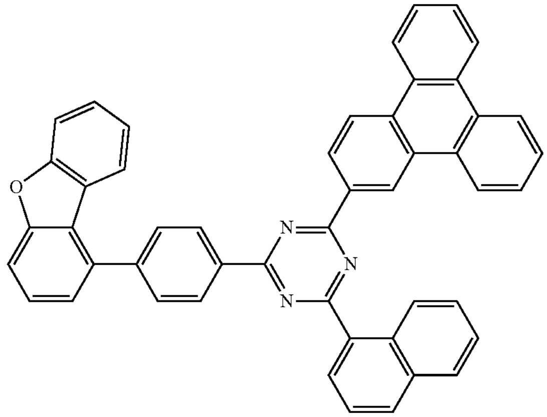
[A-100]
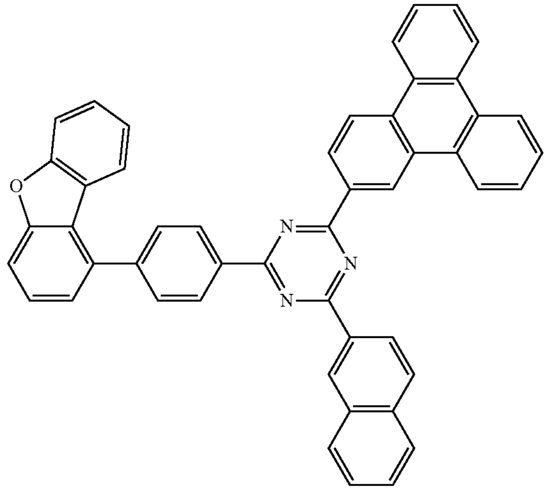
-continued
[A-101]
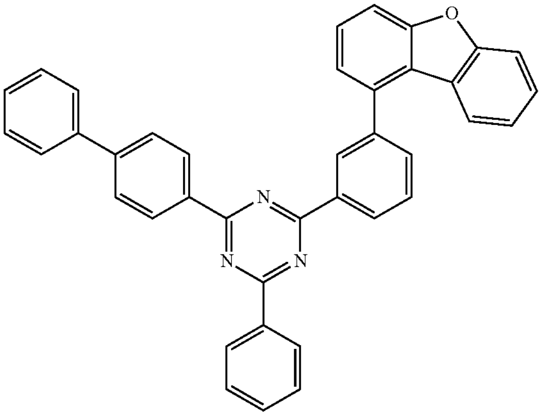
[A-102]
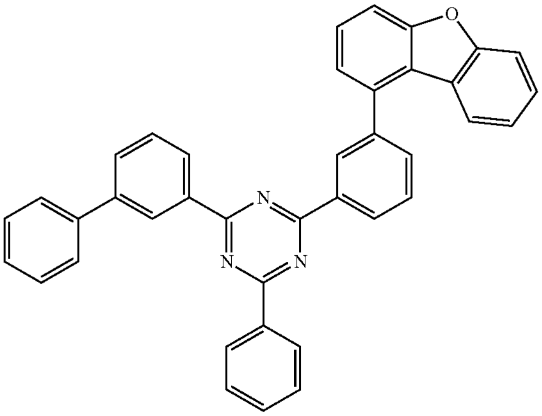
[A-103]
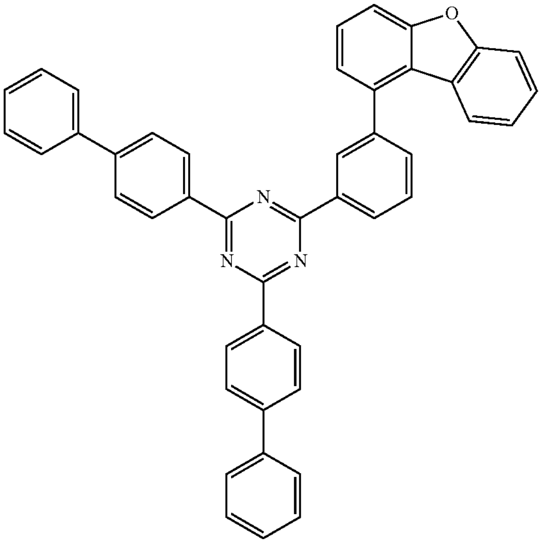

-continued
[A-104]
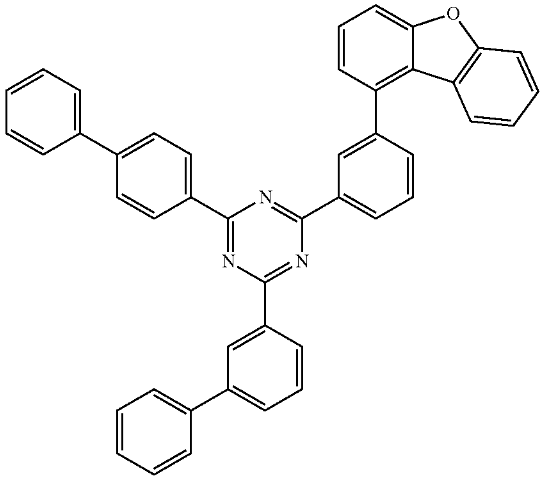
[A-105]
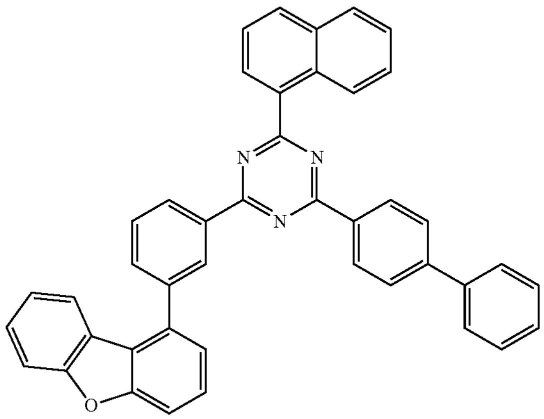
[A-106]
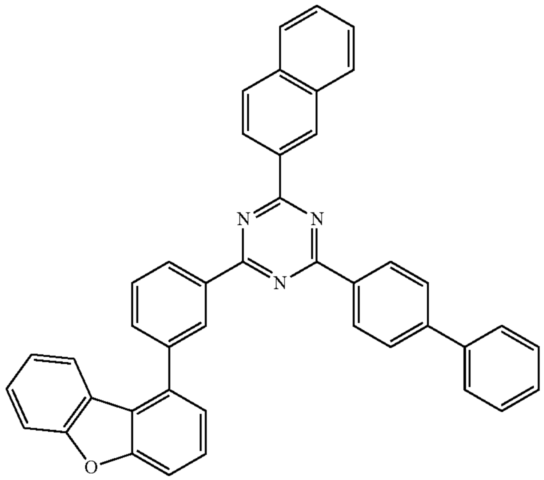
-continued
[A-107]
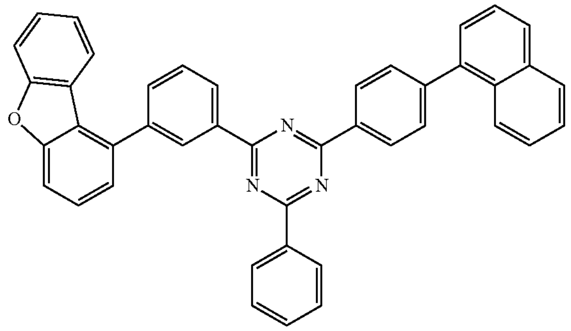
[A-108]
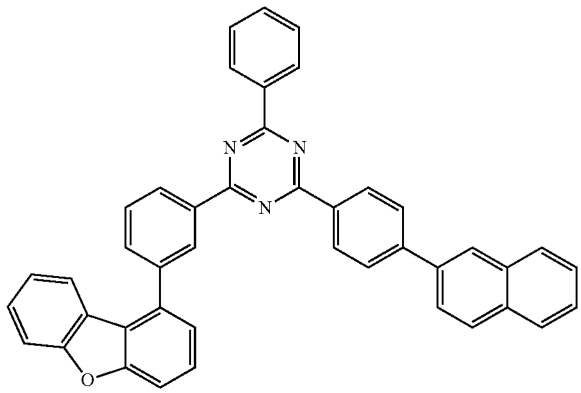
[A-109]
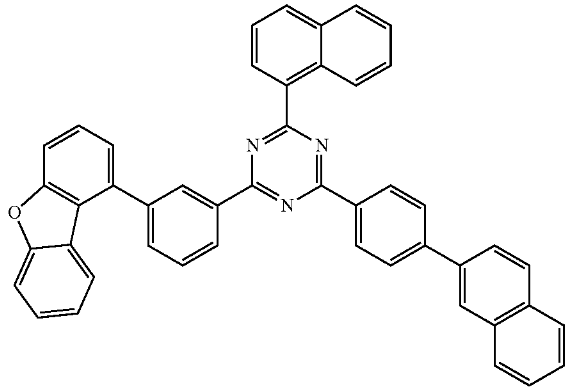
[A-110]
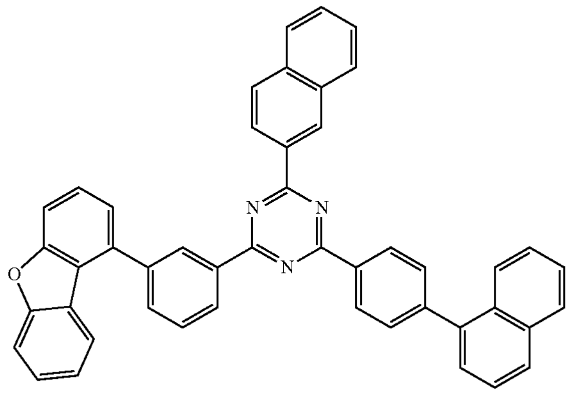

-continued
[A-111]
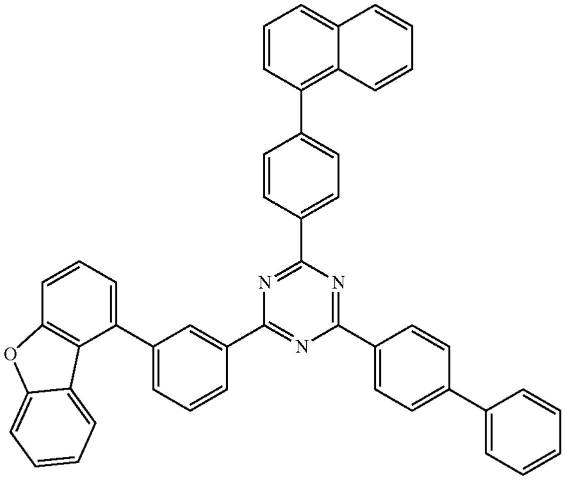
[A-112]
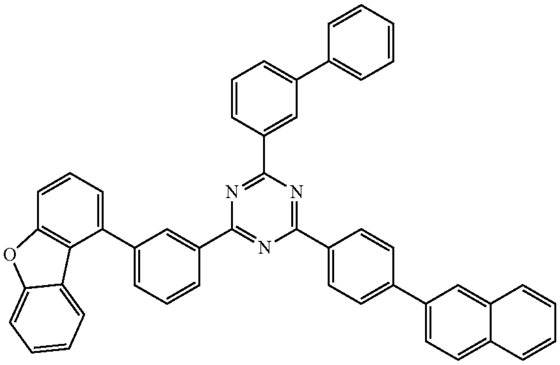
[A-113]
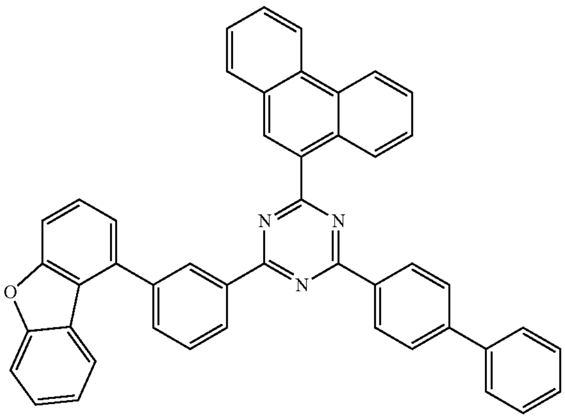
-continued
[A-114]
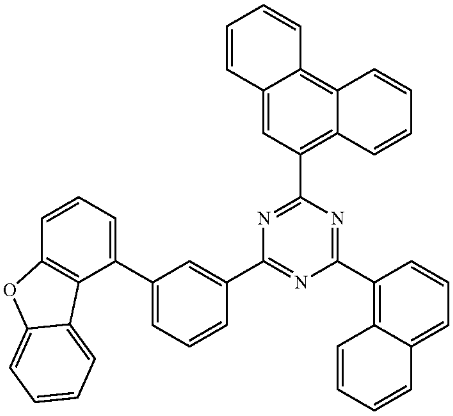
[A-115]
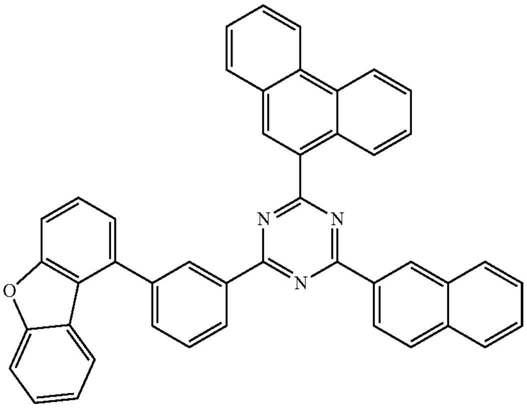
[A-116]
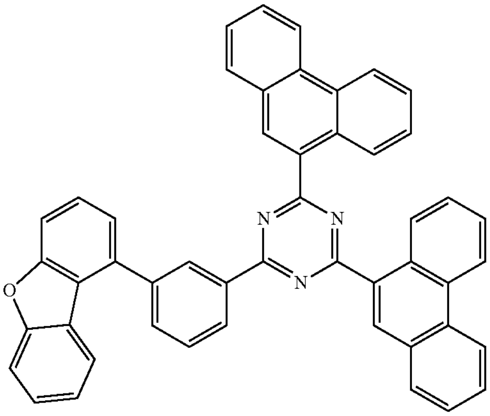

-continued
[A-117]
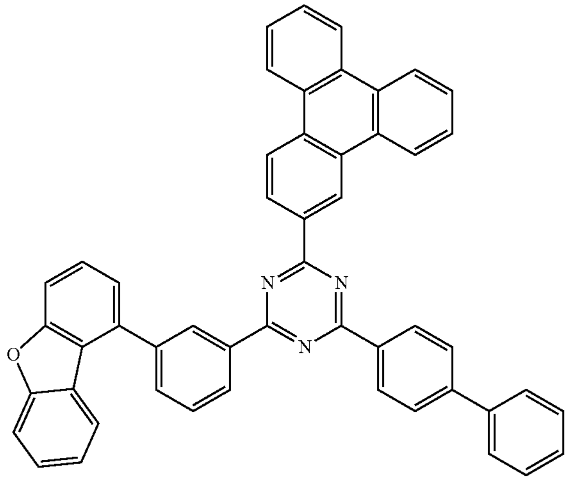
[A-118]
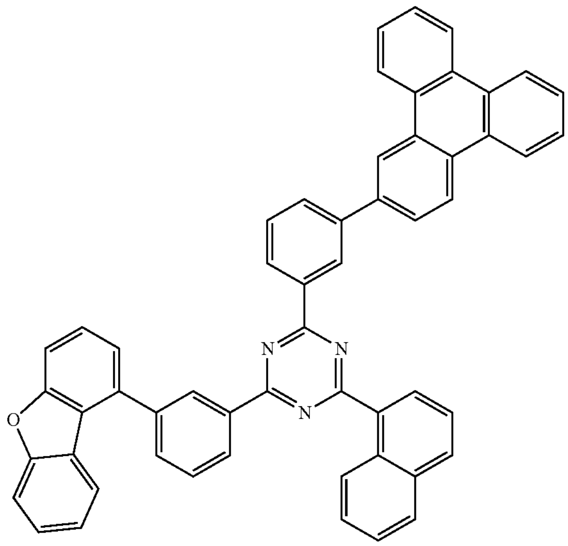
[A-119]
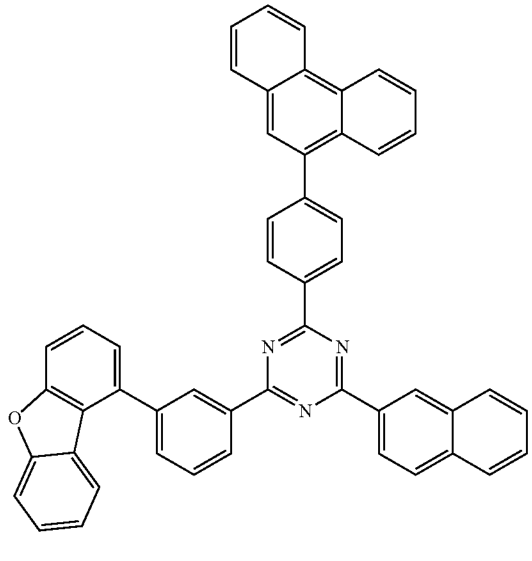
-continued
[A-120]
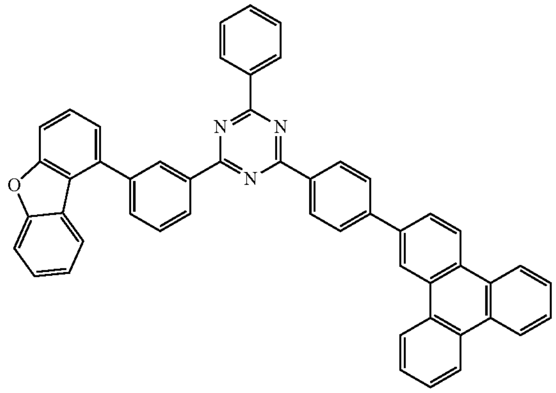
[B-1]
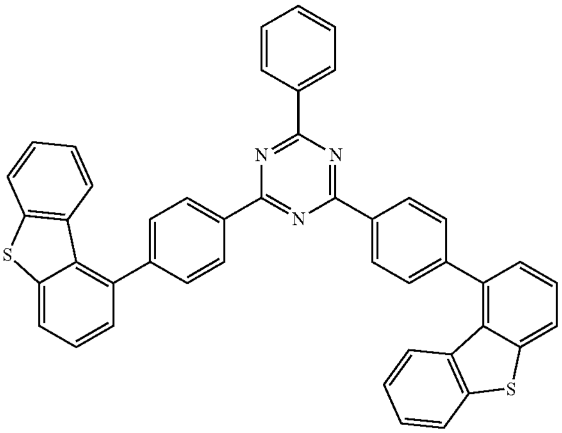
[B-2]
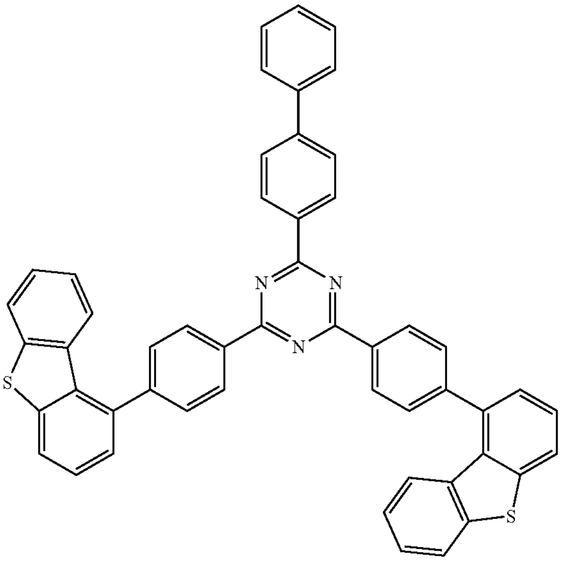

-continued
[B-3]
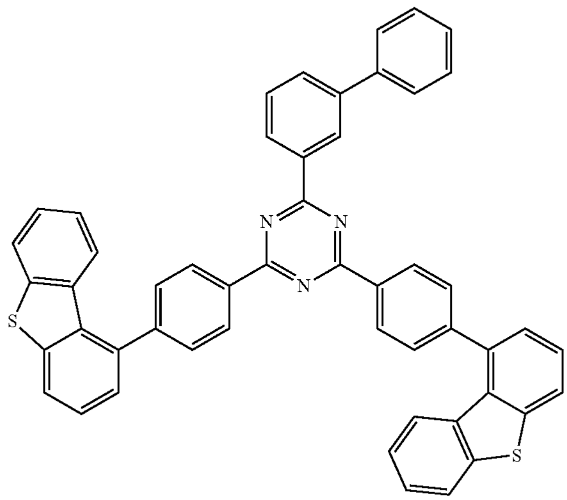
[B-4]
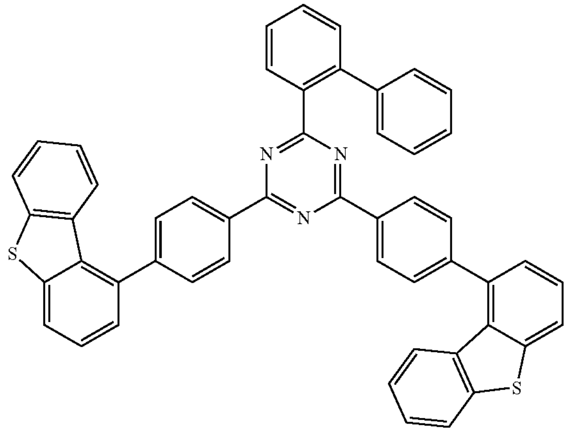
[B-5]
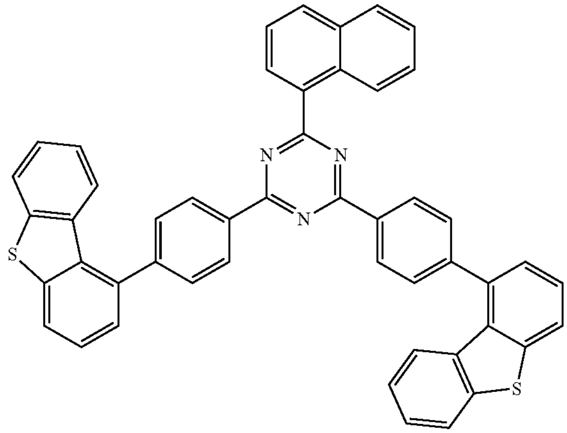
-continued
[B-6]
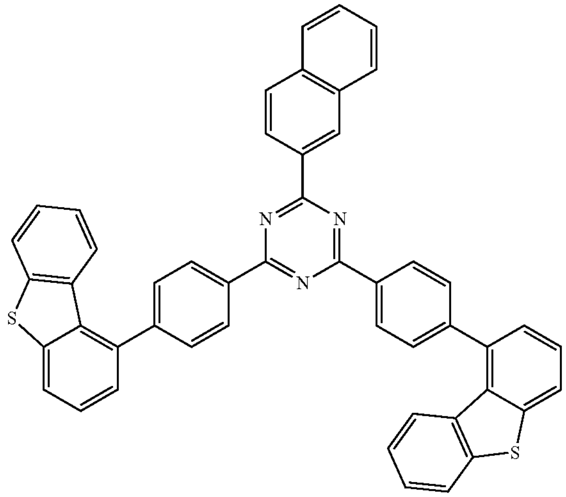
[B-7]
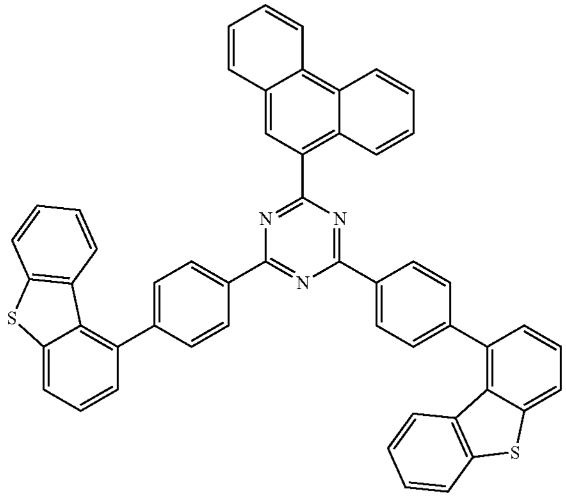
[B-8]
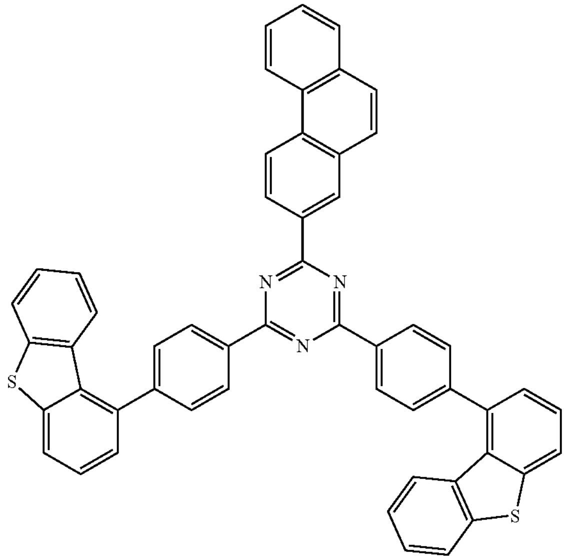

-continued
[B-9]
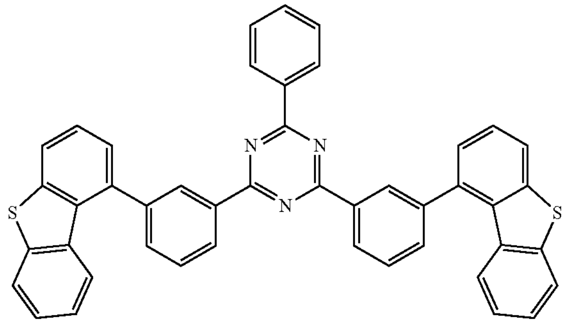
[B-10]
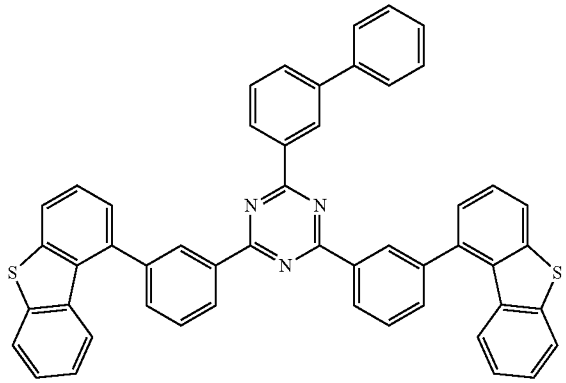
[B-11]
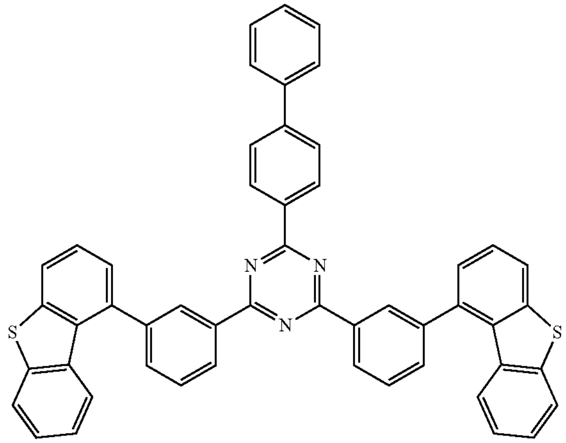
[B-12]
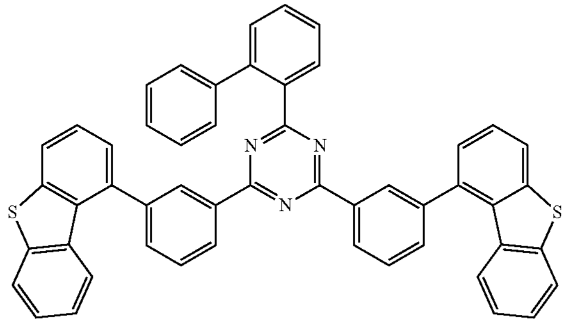
-continued
[B-13]
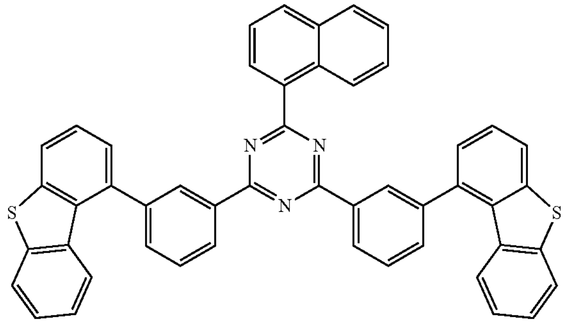
[B-14]
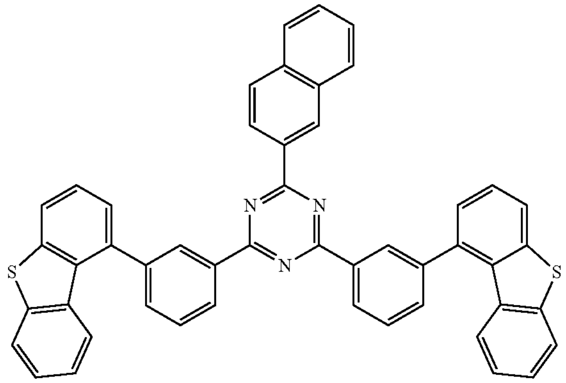
[B-15]
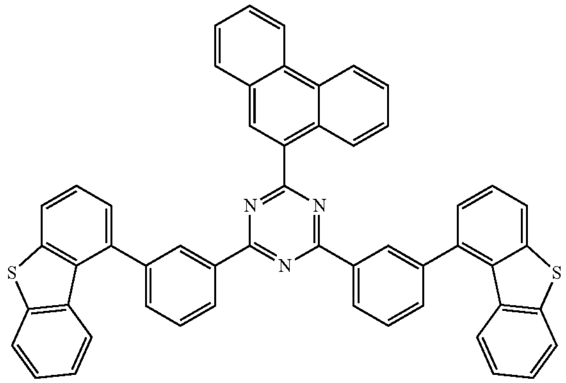
[B-16]
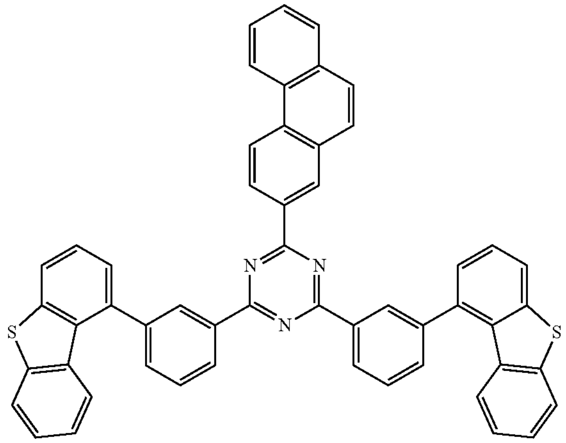

-continued
[B-17]
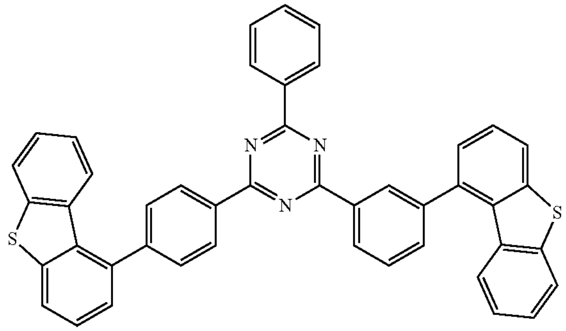
[B-18]
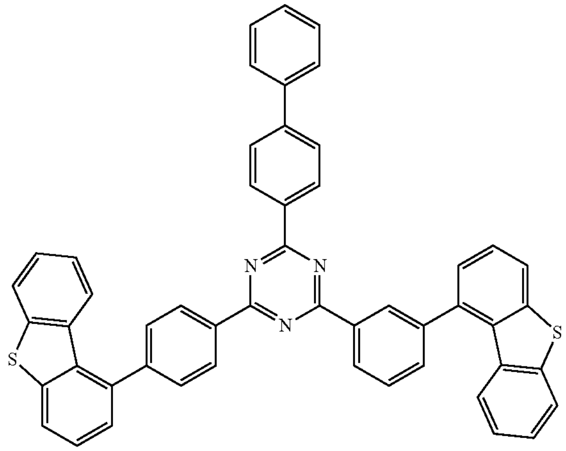
[B-19]
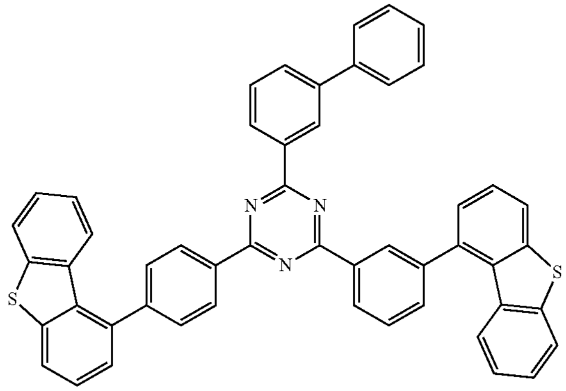
[B-20]
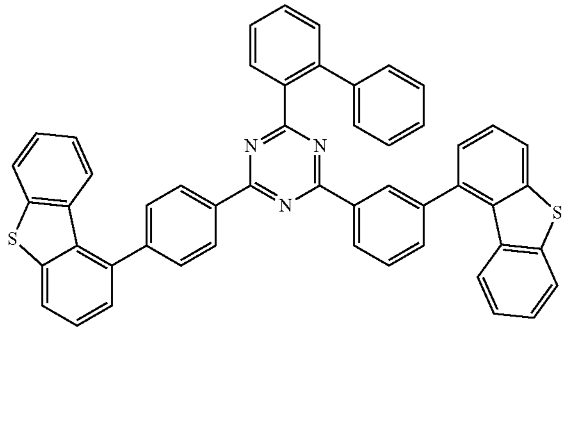
-continued
[B-21]
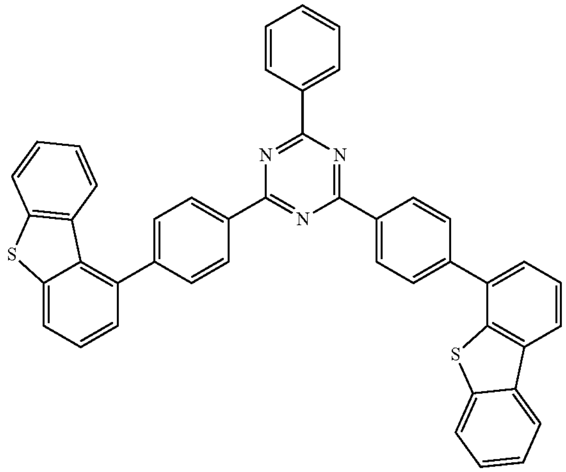
[B-22]
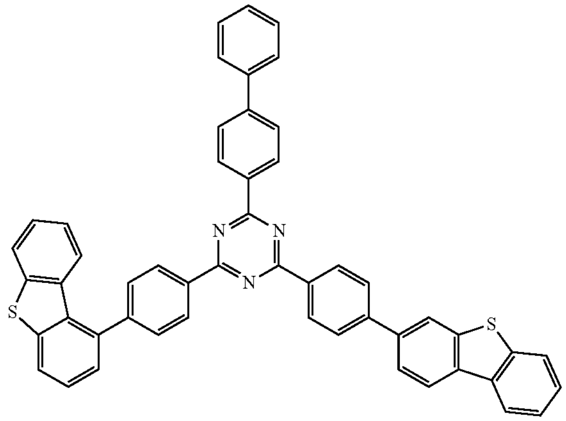
[B-23]
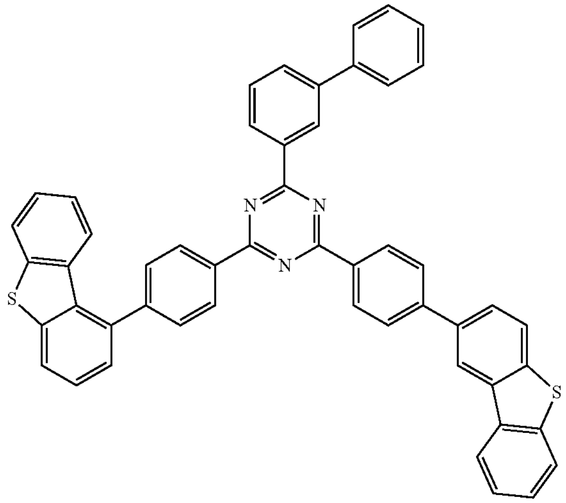

-continued
[B-24]
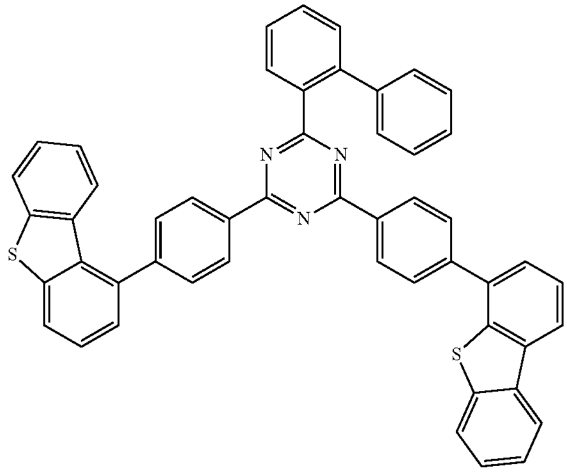
[B-25]
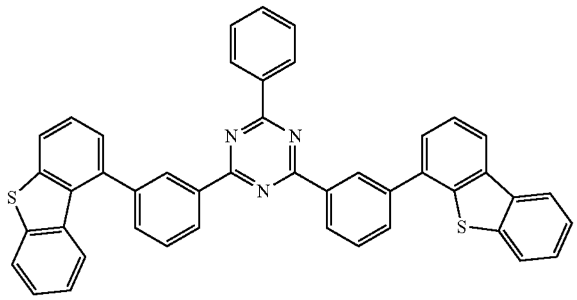
[B-26]
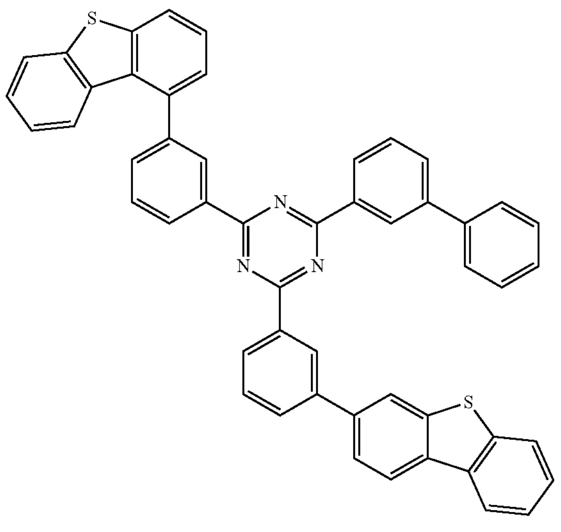
-continued
[B-27]
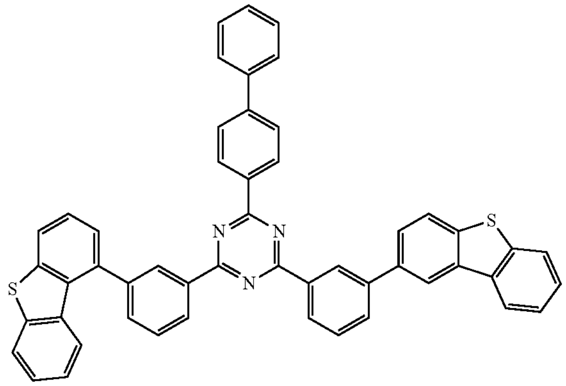
[B-28]
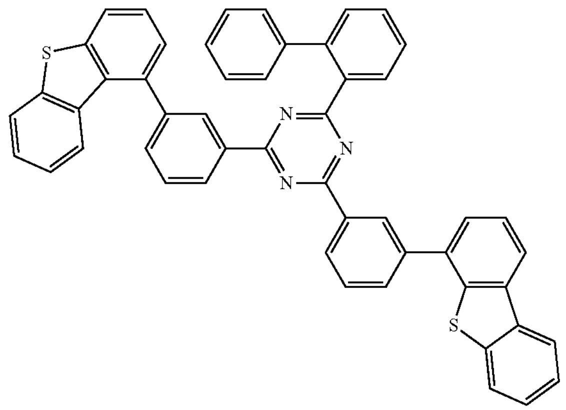
[B-29]
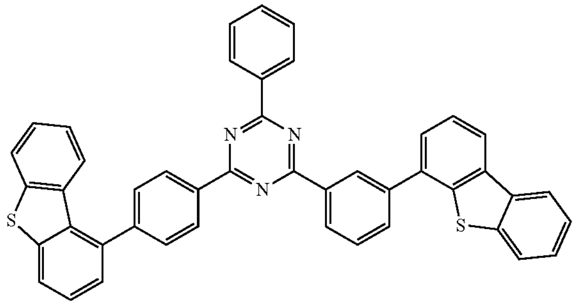

-continued
[B-30]
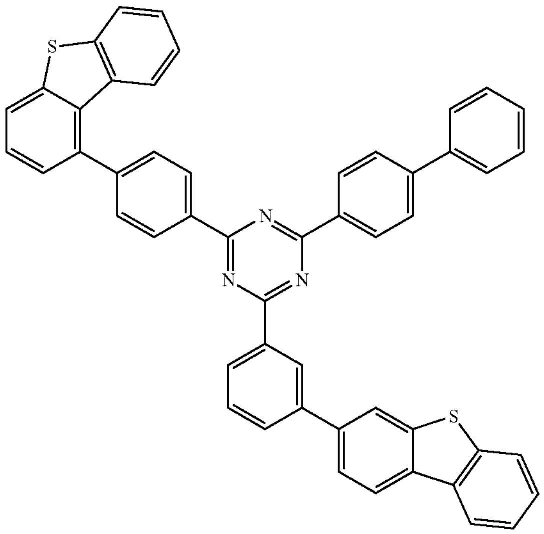
[B-31]
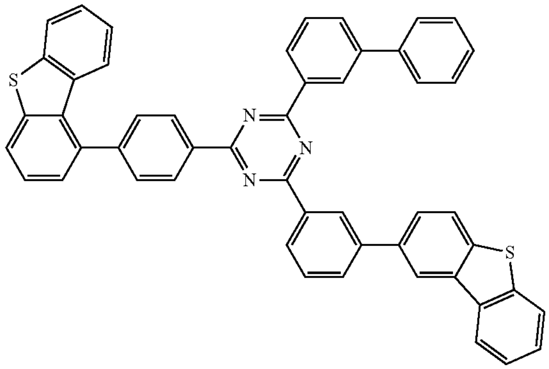
[B-32]
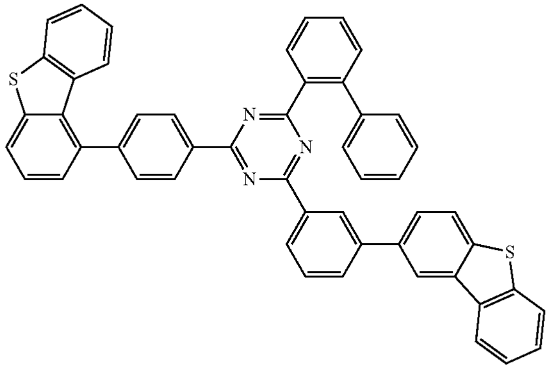
-continued
[B-33]
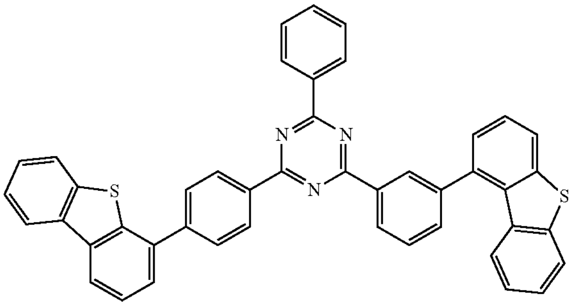
[B-34]
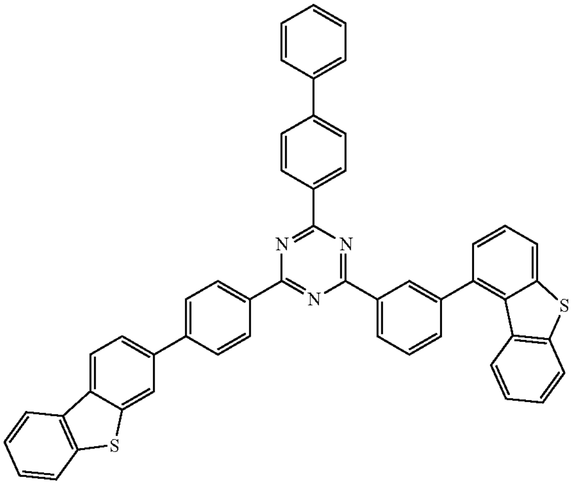
[B-35]
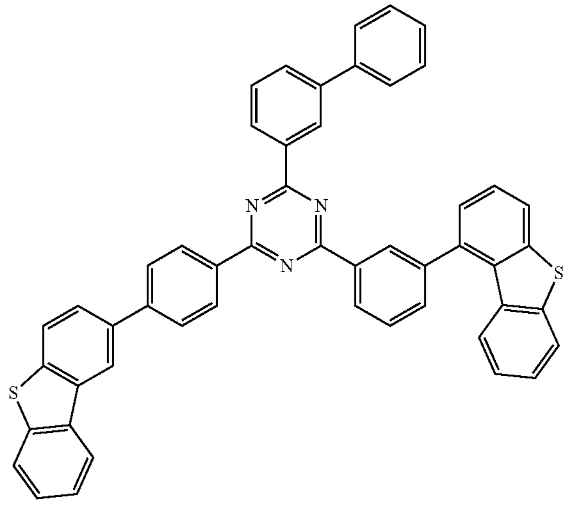

-continued
[B-36]
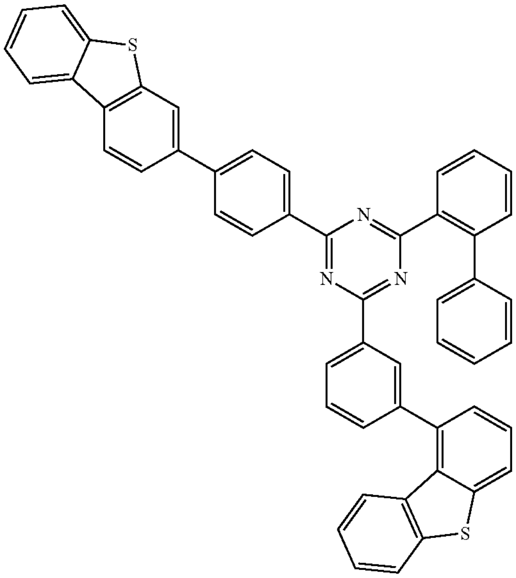
[B-37]
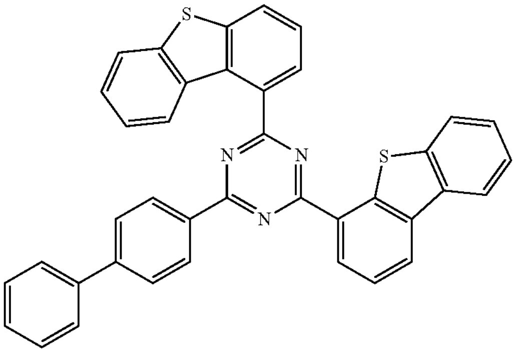
[B-38]
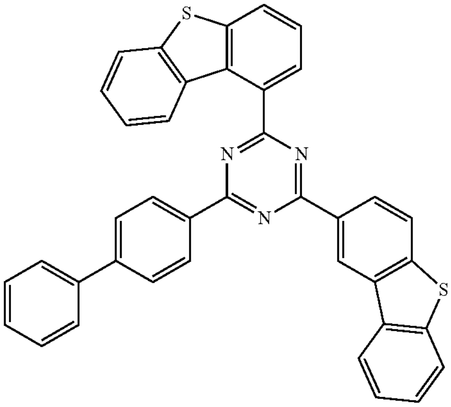
-continued
[B-39]
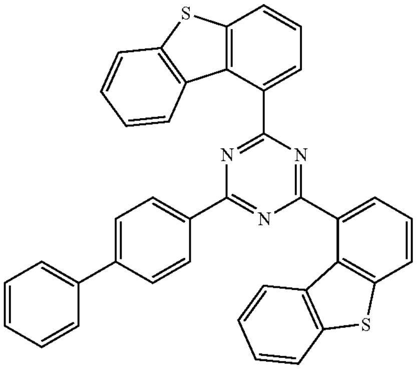
[B-40]
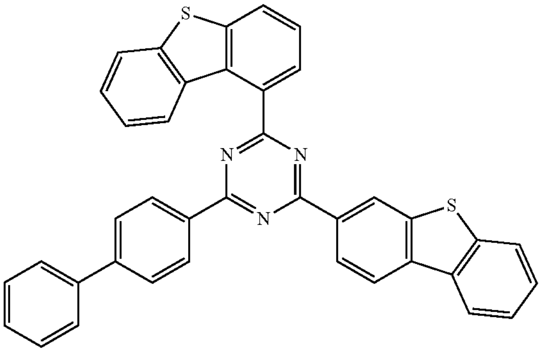
[B-41]
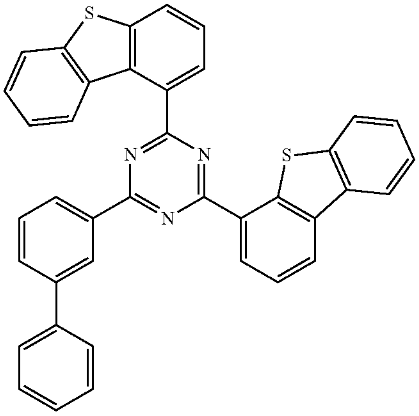
[B-42]
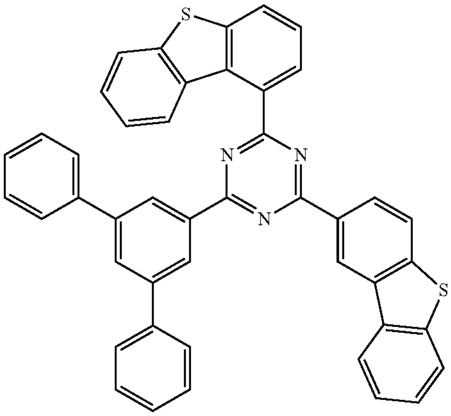

-continued
[B-43]
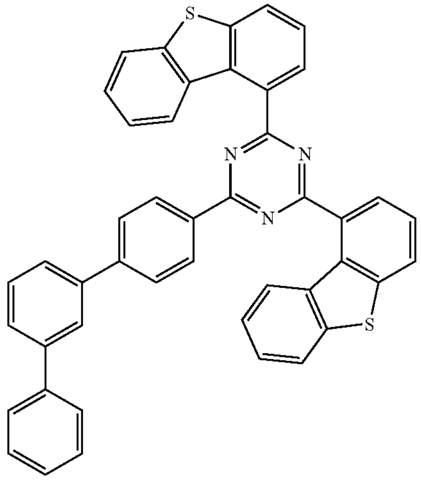
[B-44]
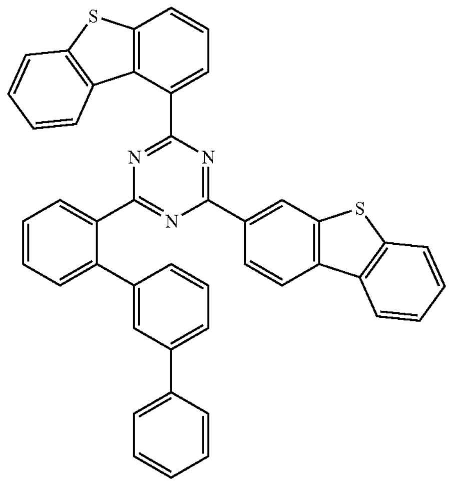
[B-45]
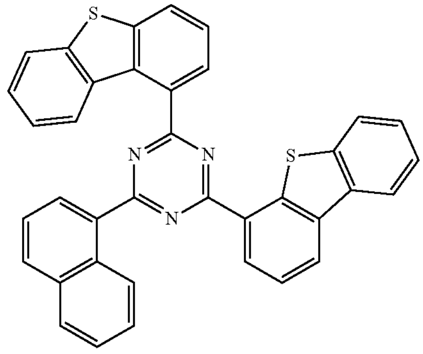
-continued
[B-46]
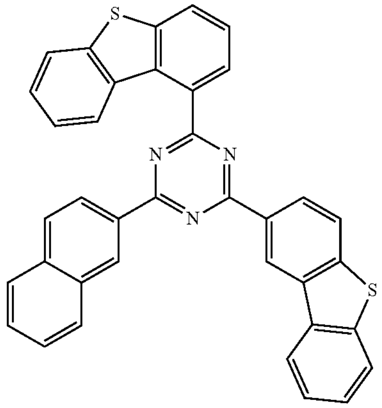
[B-47]
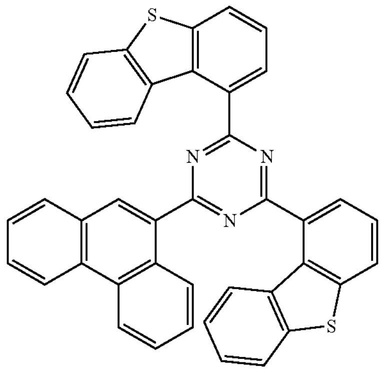
[B-48]
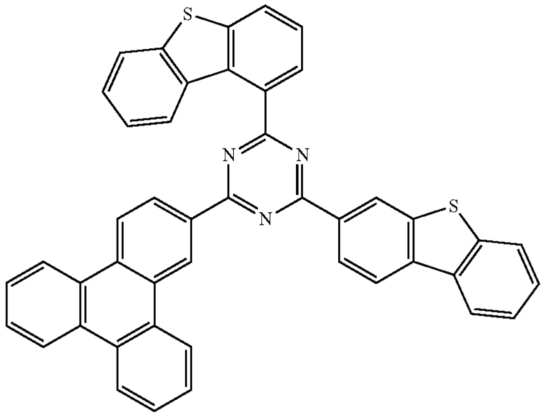
[B-49]
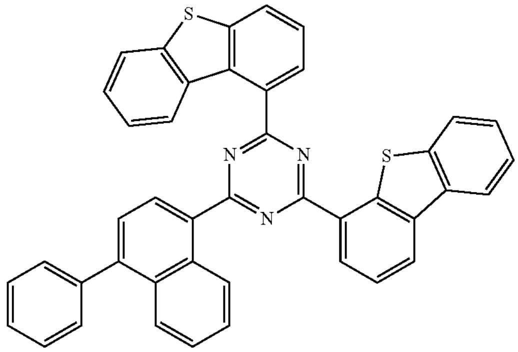

-continued
[B-50]
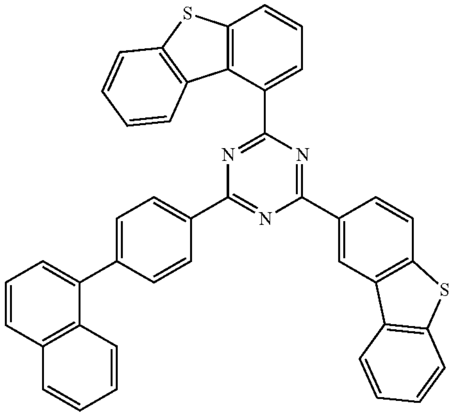
[B-51]
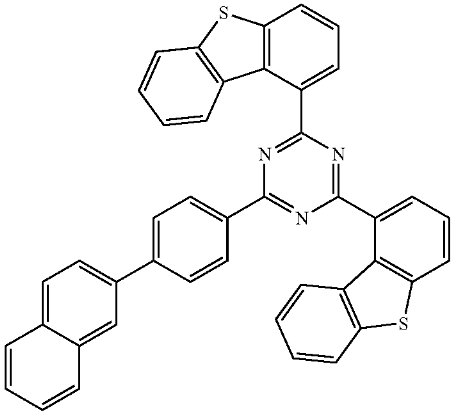
[B-52]
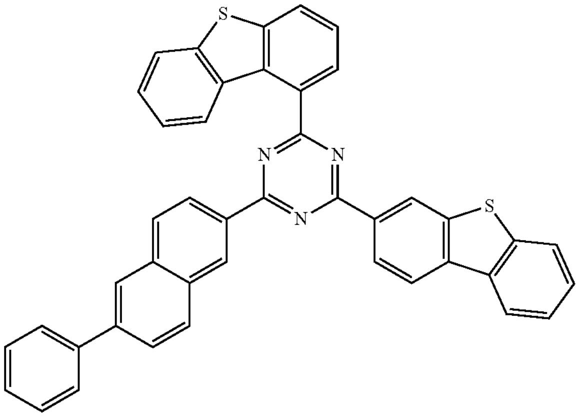
[B-53]
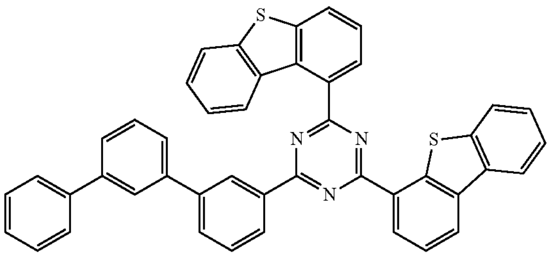
-continued
[B-54]
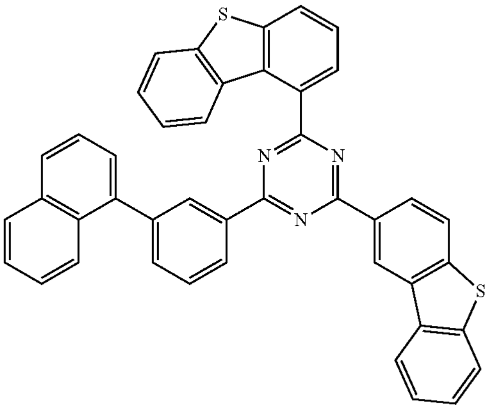
[B-55]
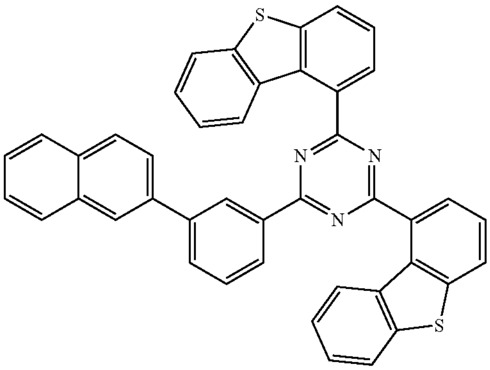
[B-56]
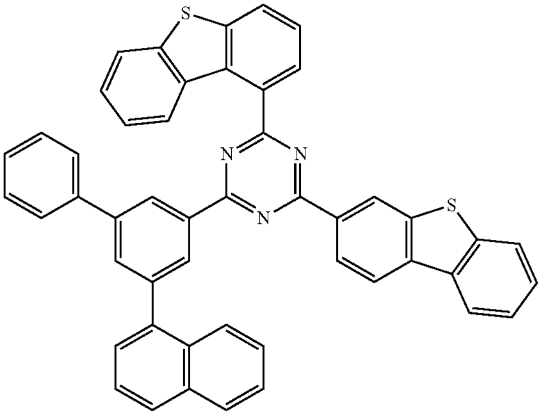

-continued
[B-57]
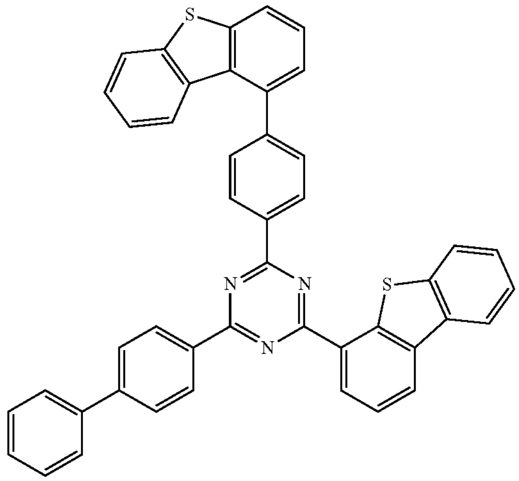
[B-58]
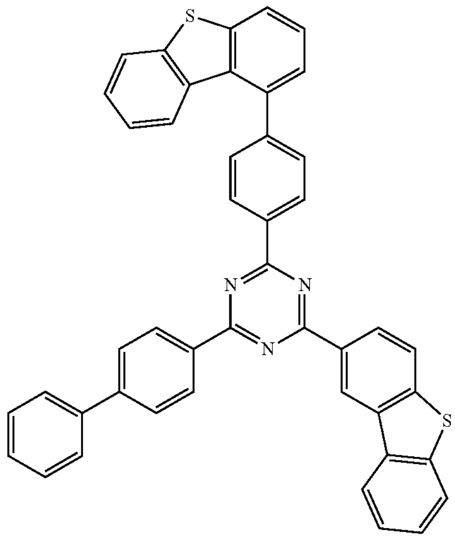
[B-59]
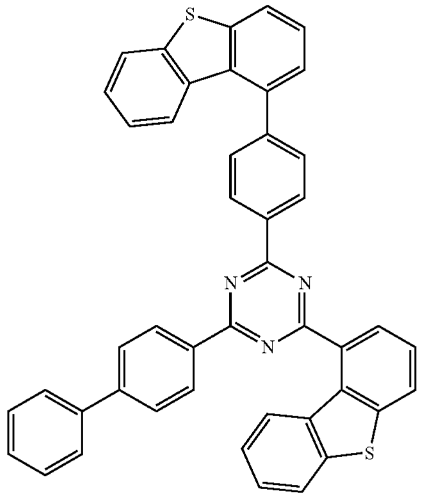
-continued
[B-60]
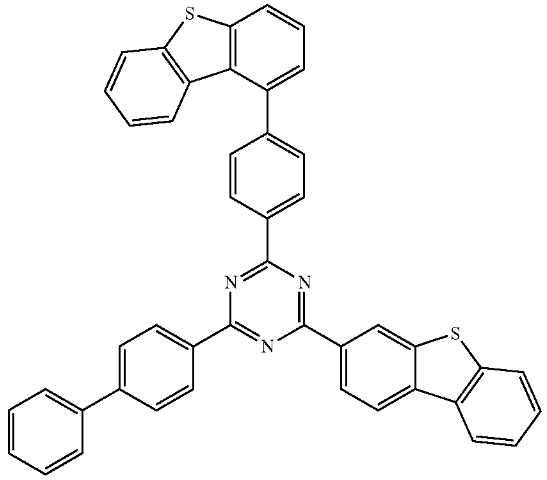
[B-61]
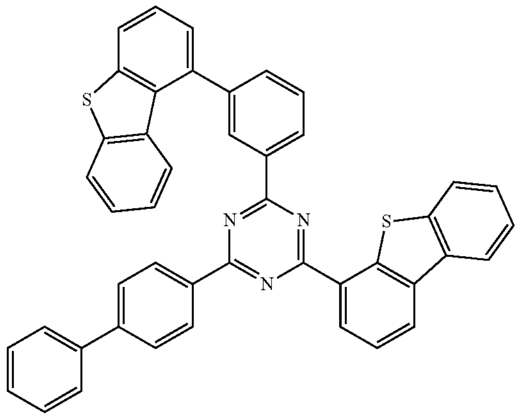
[B-62]
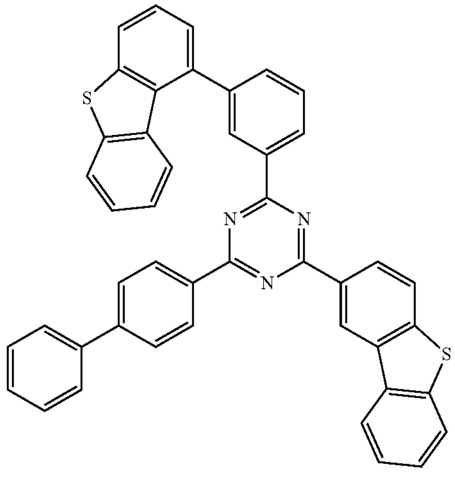

-continued
[B-63]
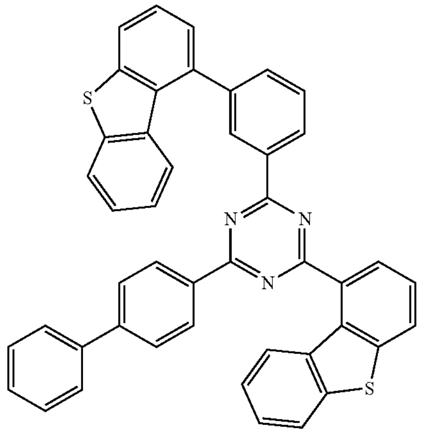
[B-64]
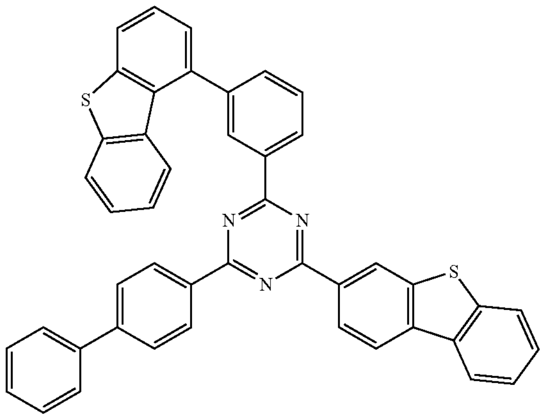
[B-65]
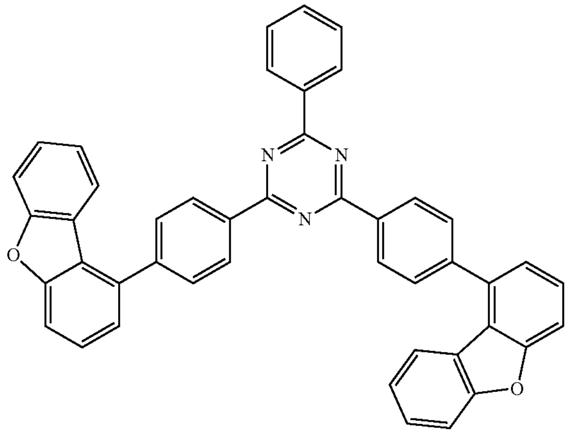
-continued
[B-66]
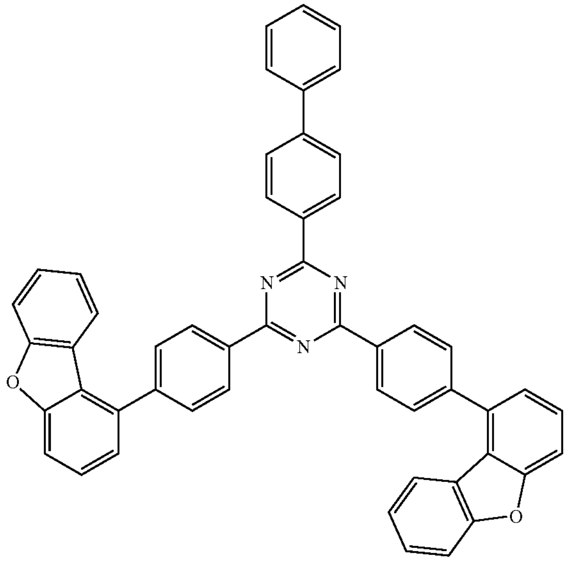
[B-67]
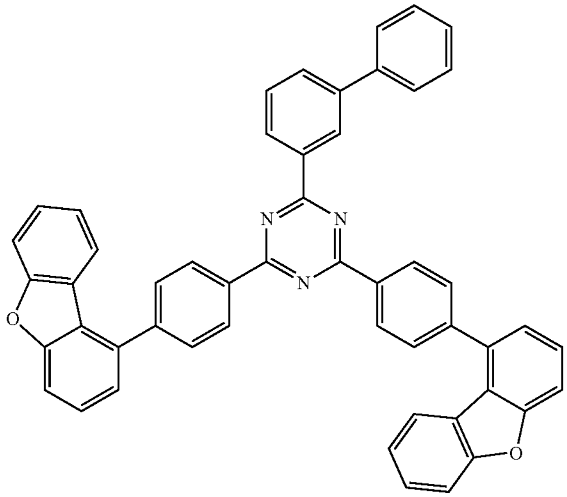
[B-68]
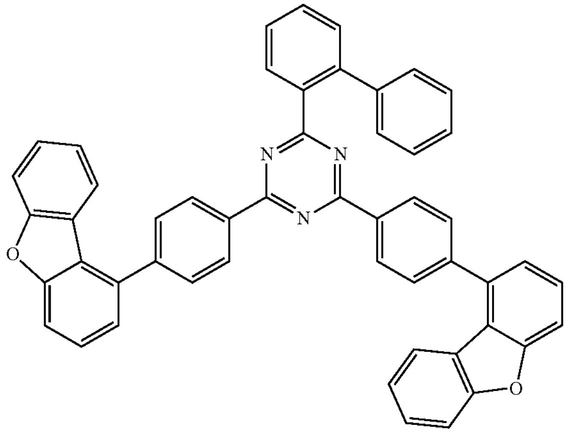

-continued
[B-69]
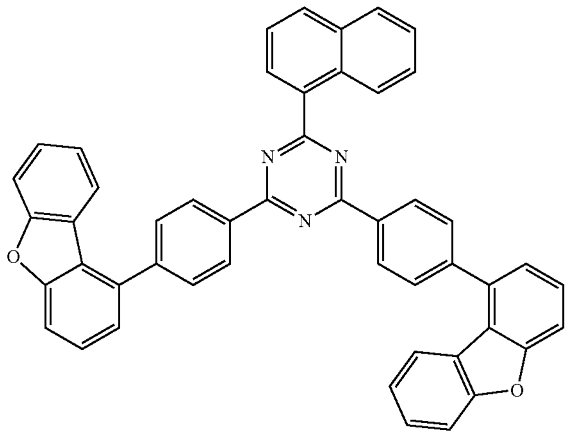
[B-70]
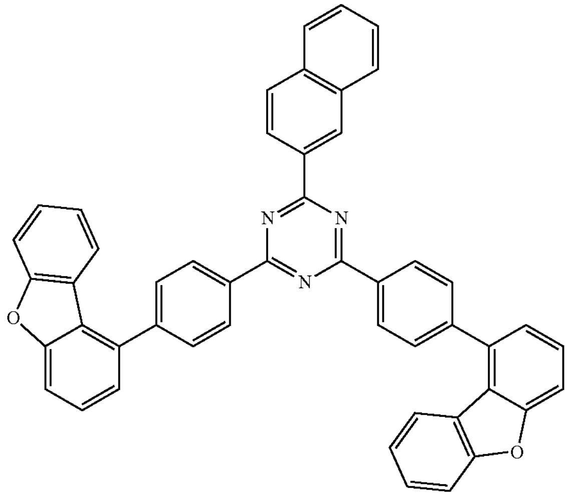
[B-71]
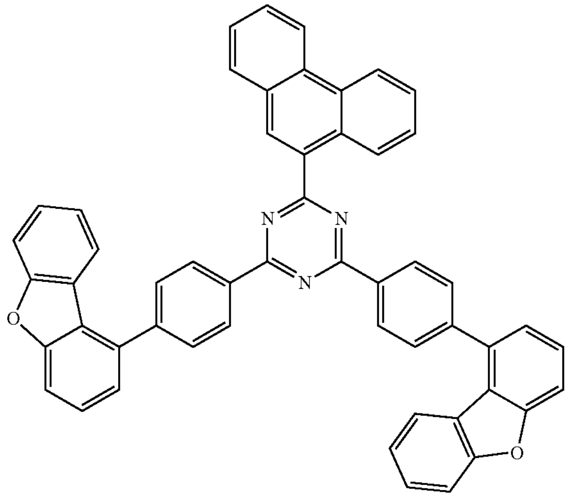
-continued
[B-72]
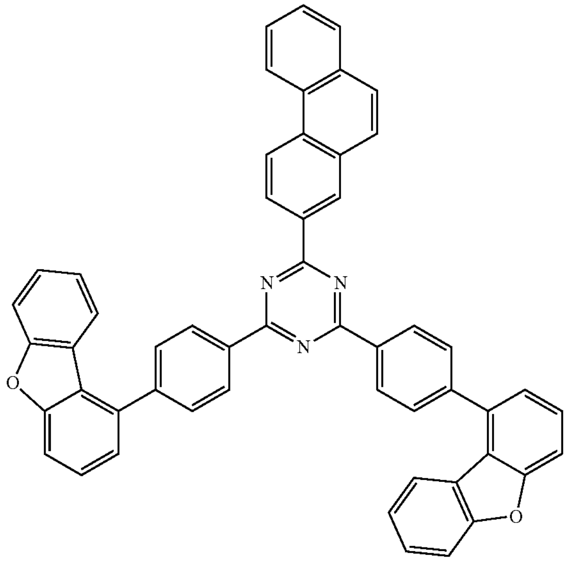
[B-73]
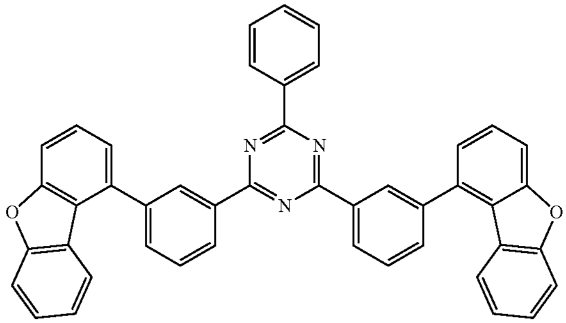
[B-74]
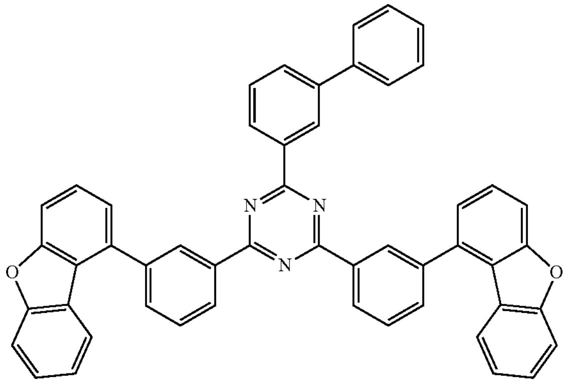

-continued
[B-75]
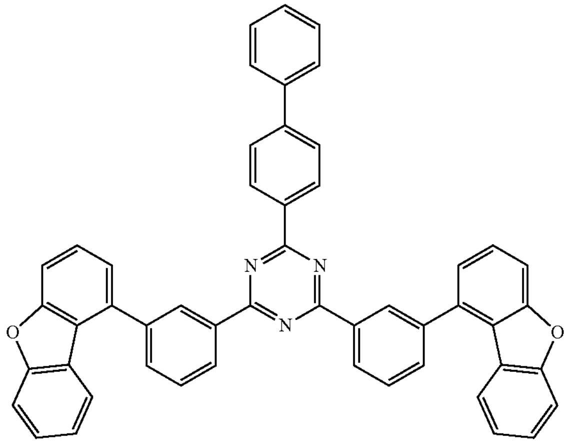
[B-76]
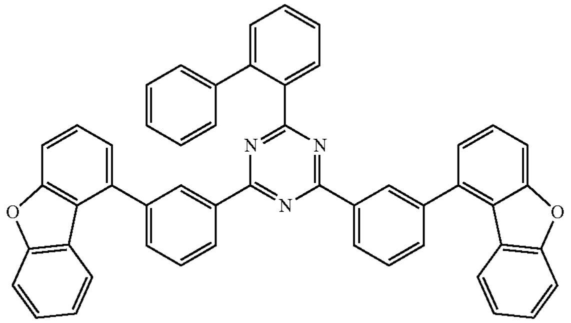
[B-77]
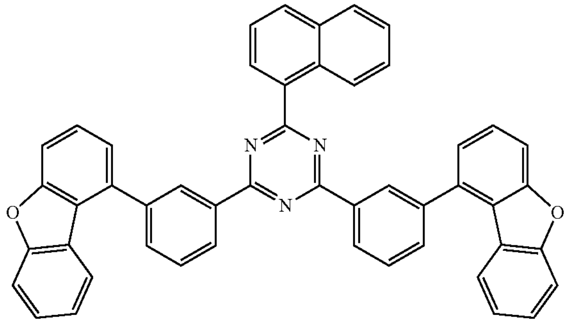
[B-78]
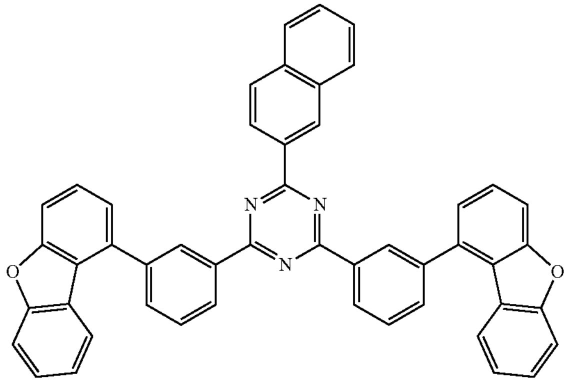
-continued
[B-79]
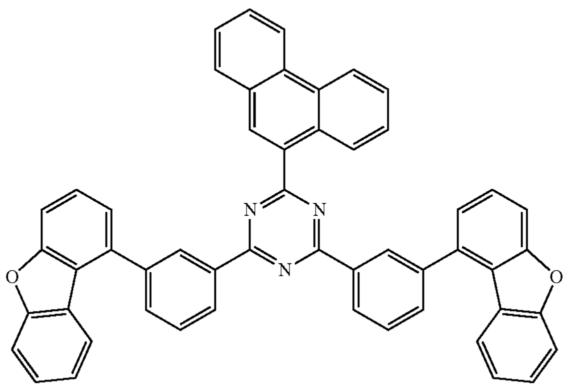
[B-80]
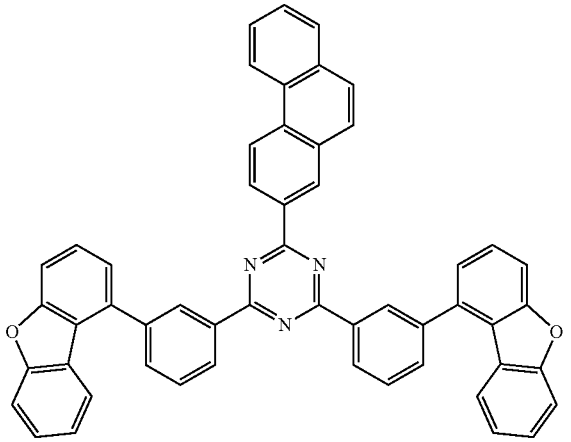
[B-81]
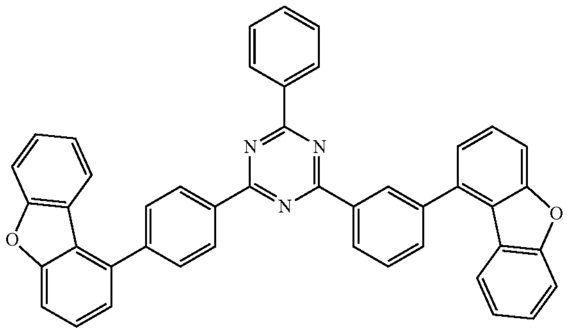

-continued
[B-82]
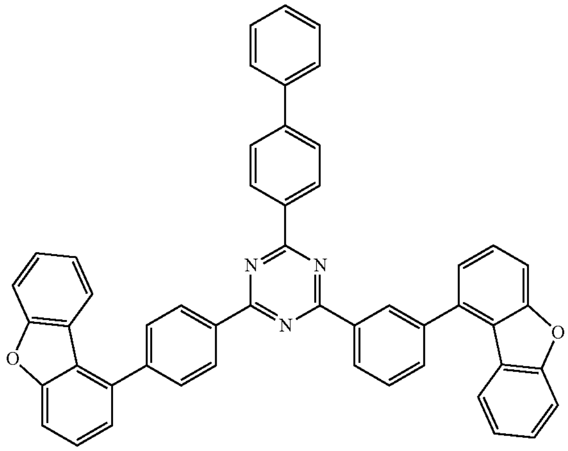
[B-83]
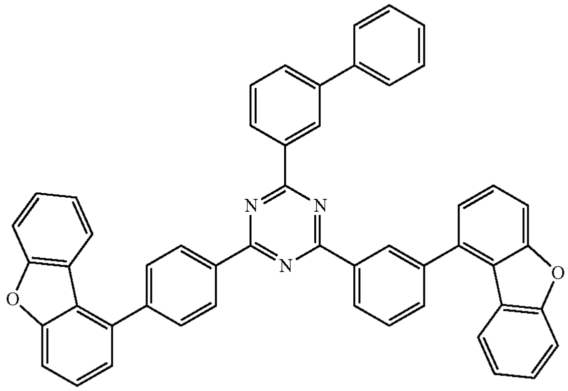
[B-84]
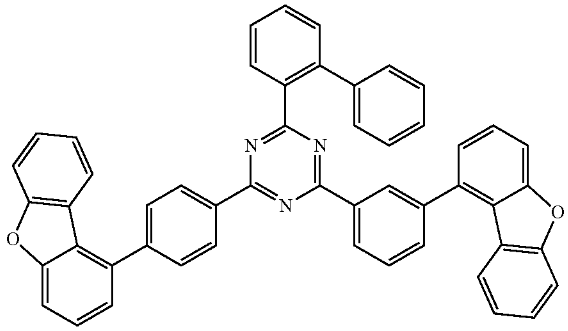
-continued
[B-85]
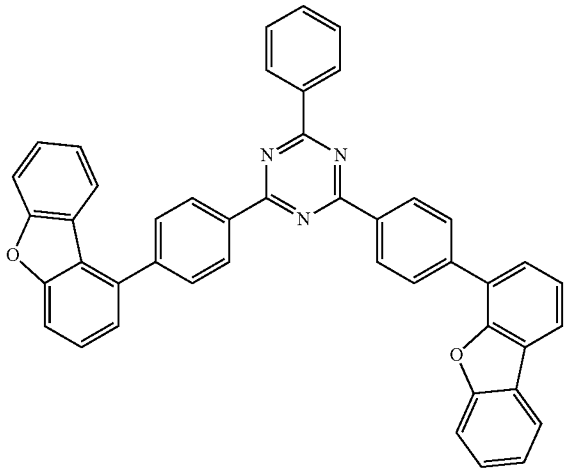
[B-86]
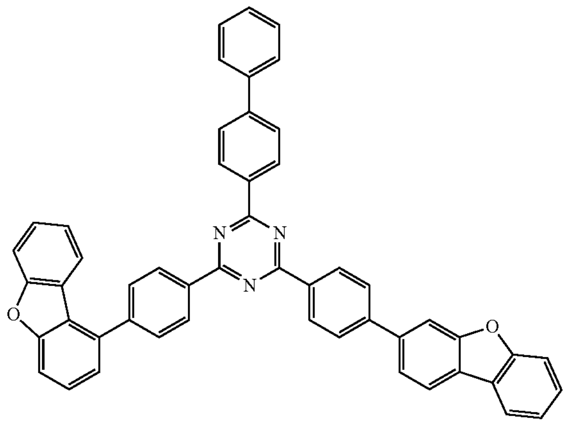
[B-87]
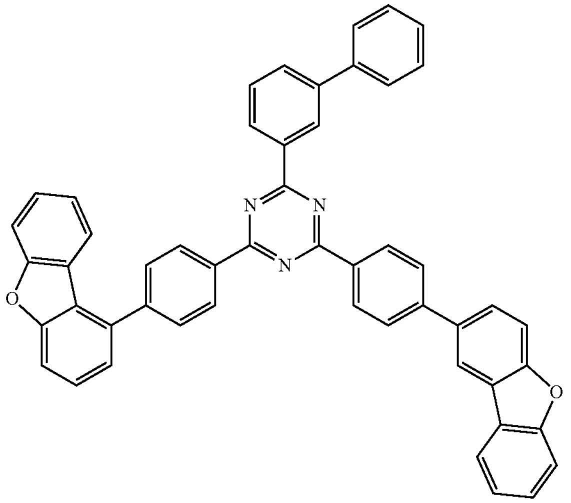

-continued
[B-88]
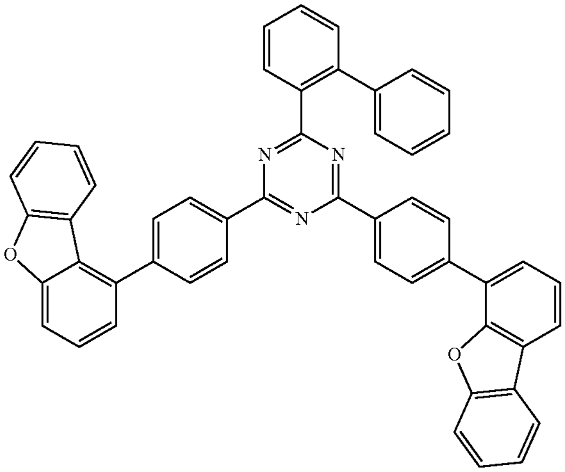
[B-89]
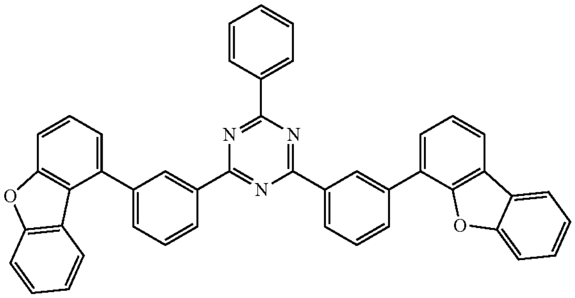
[B-90]
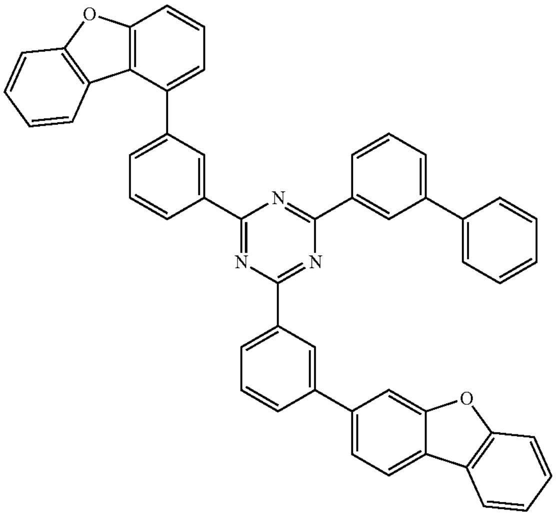
-continued
[B-91]
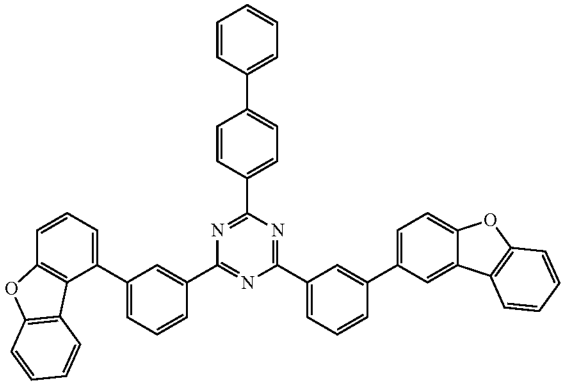
[B-92]
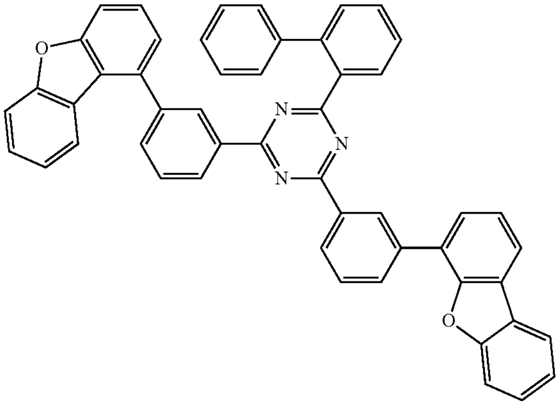
[B-93]
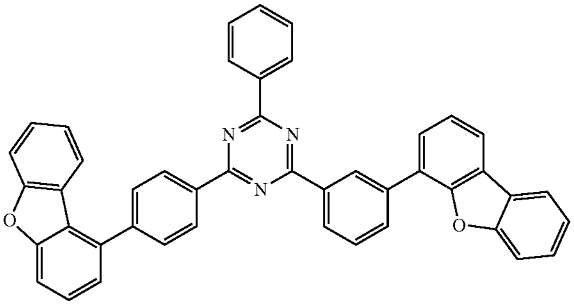

-continued
[B-94]
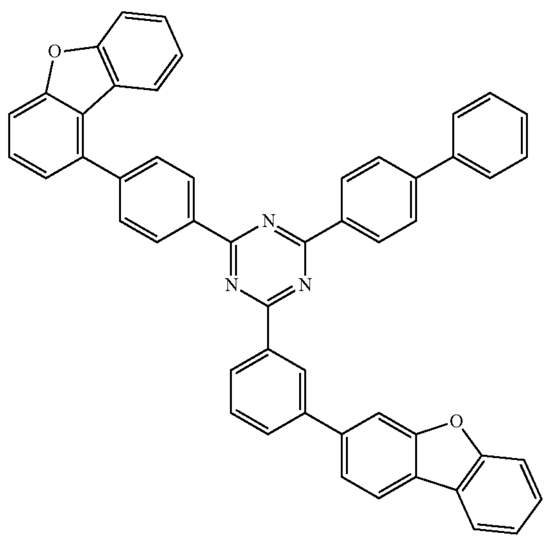
[B-95]
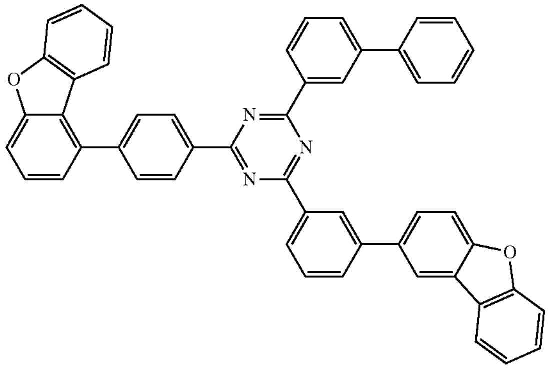
[B-96]
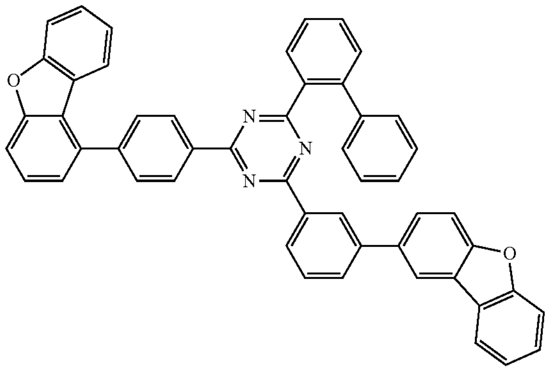
-continued
[B-97]
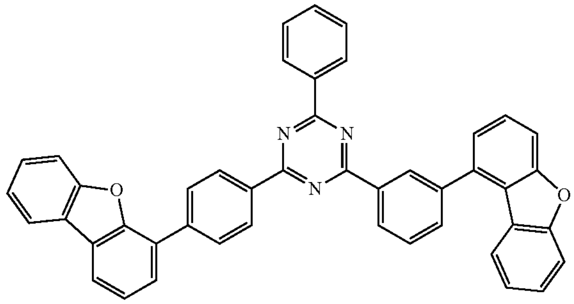
[B-98]
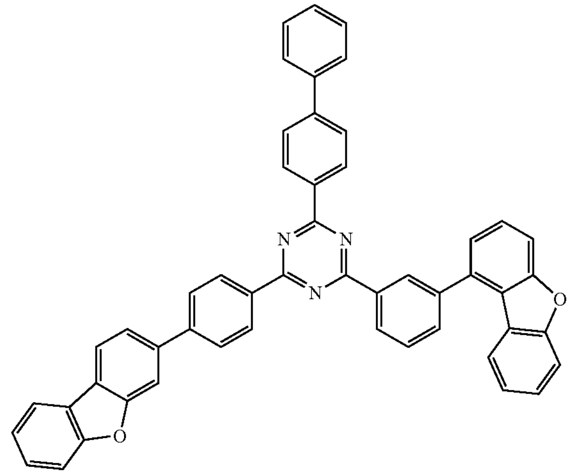
[B-99]
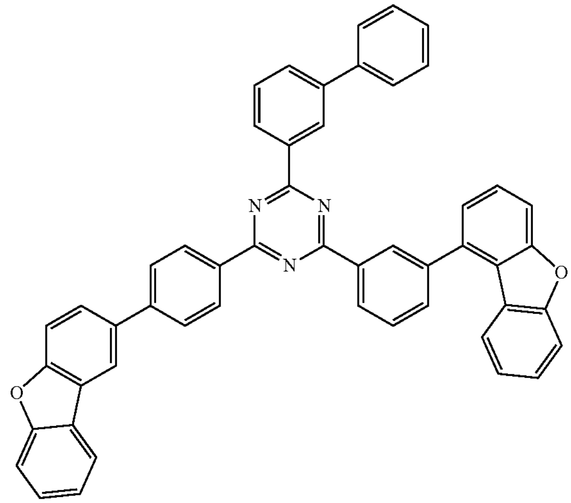

-continued
[B-100]
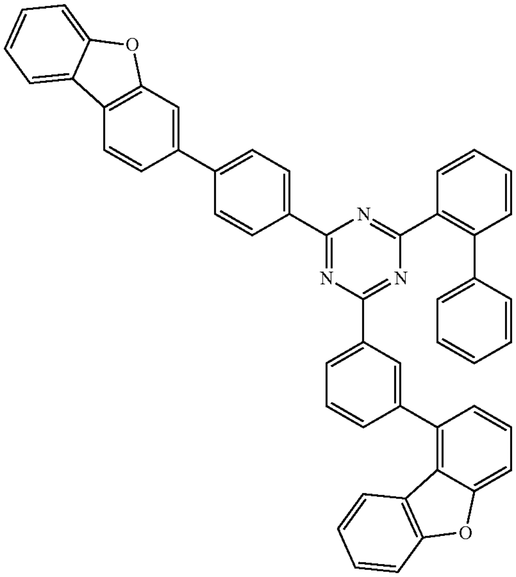
[B-101]
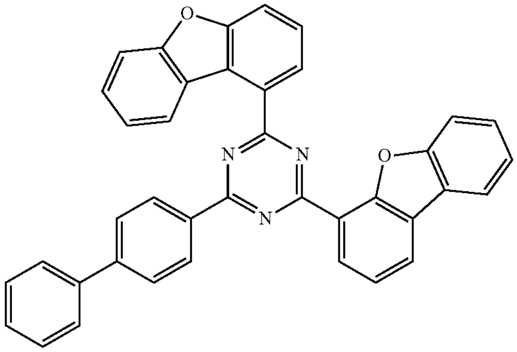
[B-102]
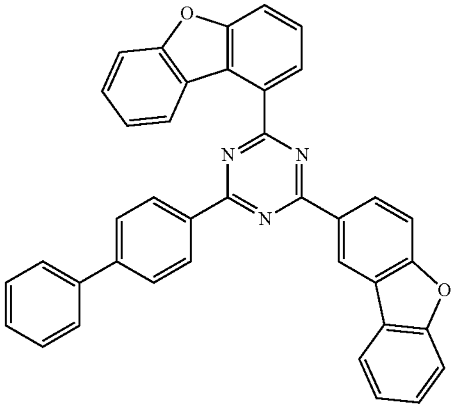
-continued
[B-103]
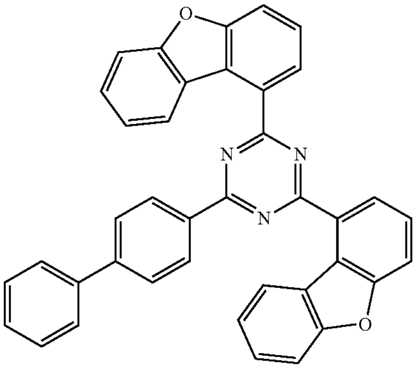
[B-104]
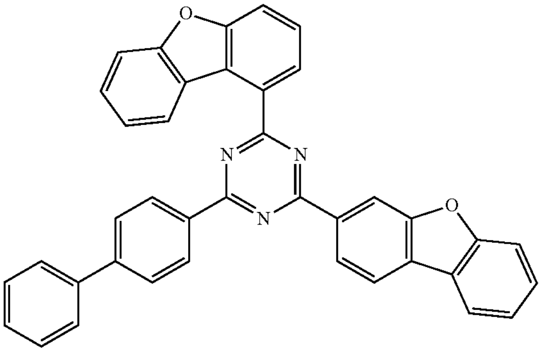
[B-105]
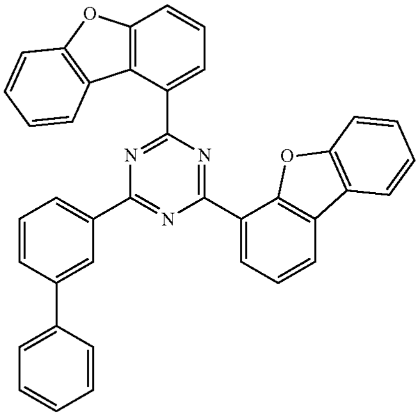
[B-106]
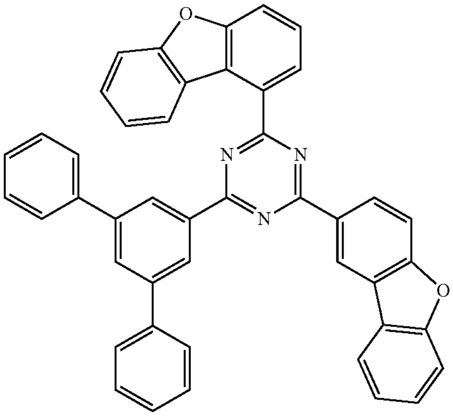

-continued
[B-107]
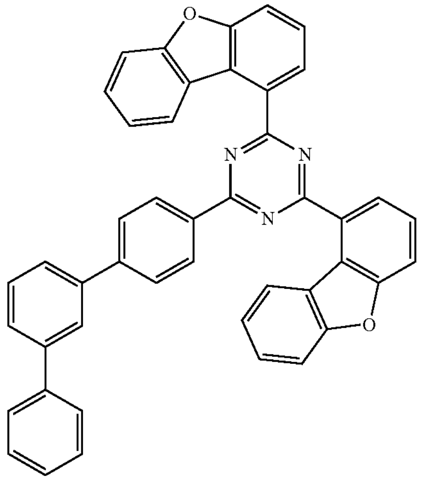
[B-108]
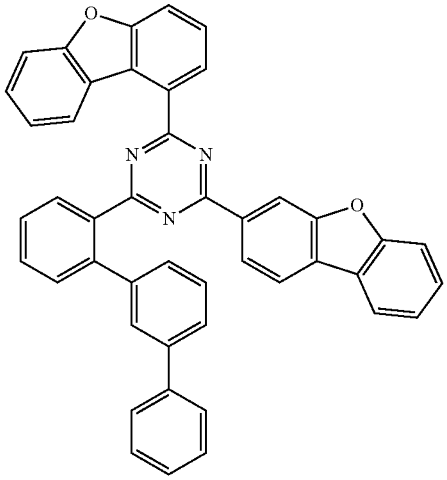
[B-109]
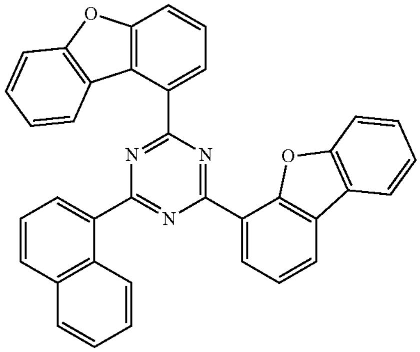
-continued
[B-110]
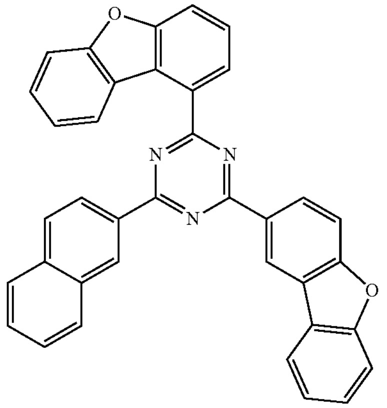
[B-111]
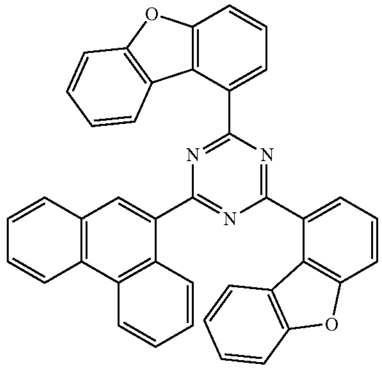
[B-112]
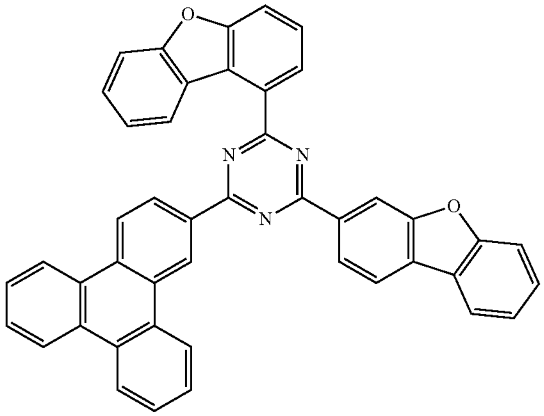
[B-113]
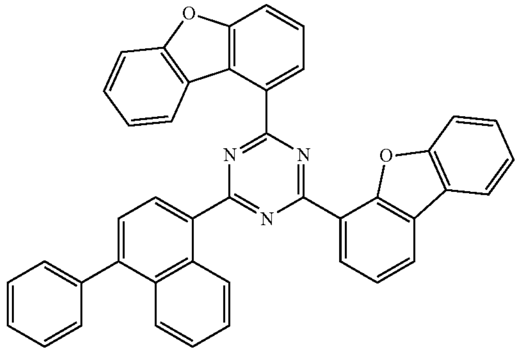

-continued
[B-114]
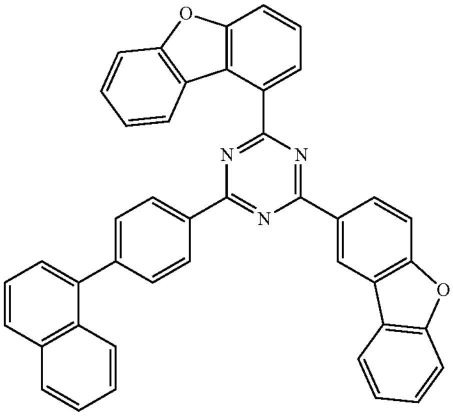
[B-115]
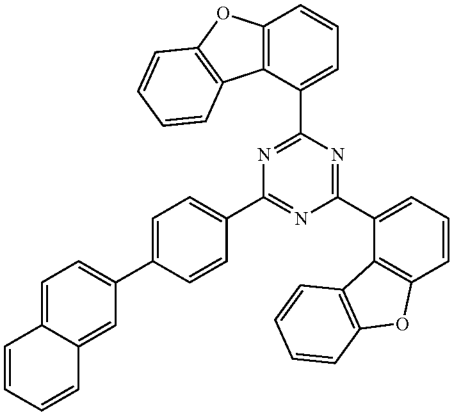
[B-116]
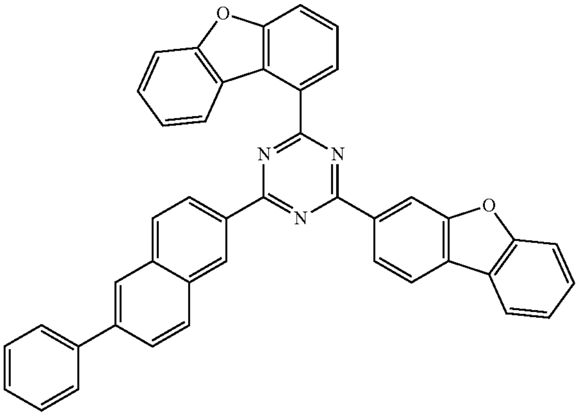
[B-117]
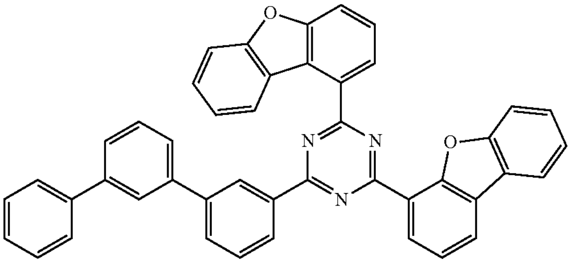
-continued
[B-118]
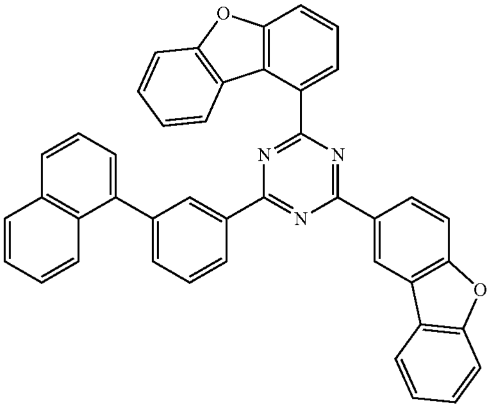
[B-119]
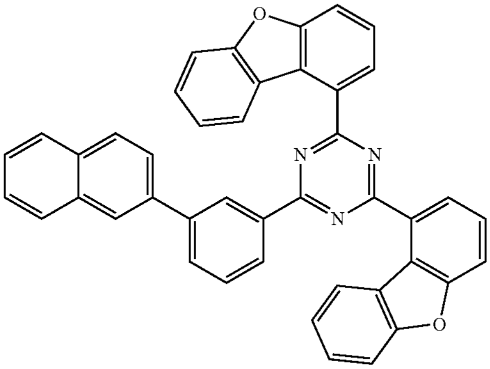
[B-120]
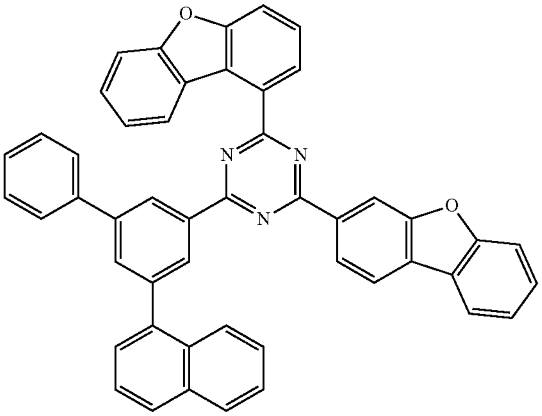

-continued
[B-121]
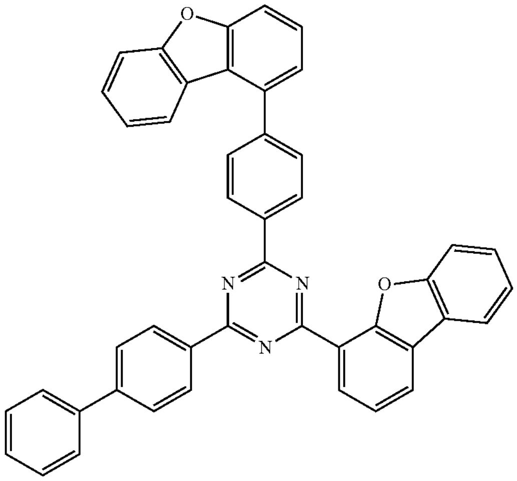
[B-122]
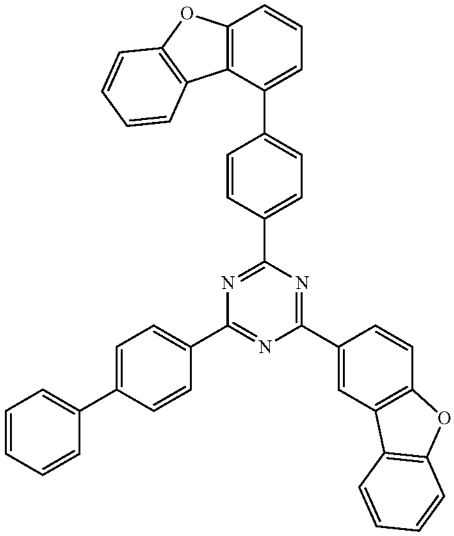
[B-123]
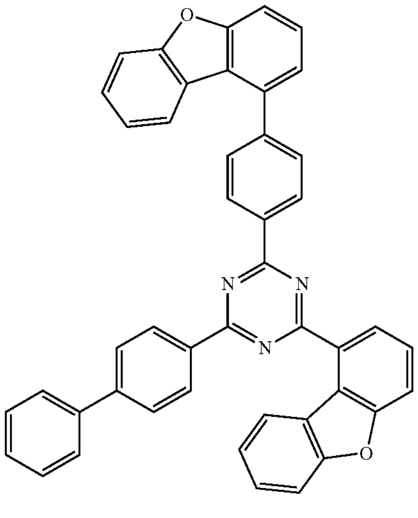
-continued
[B-124]
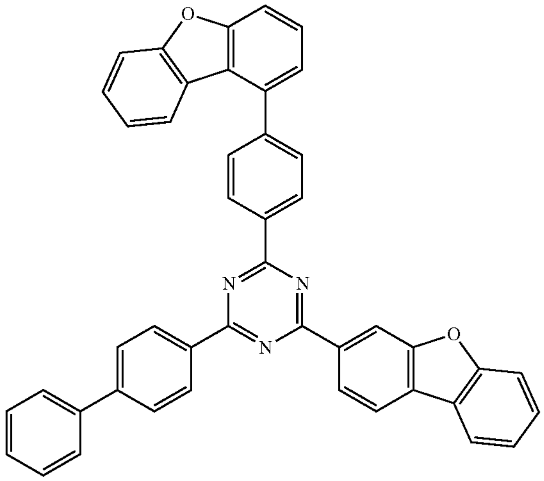
[B-125]
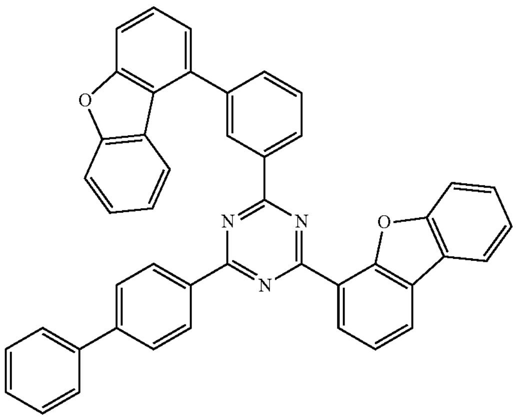
[B-126]
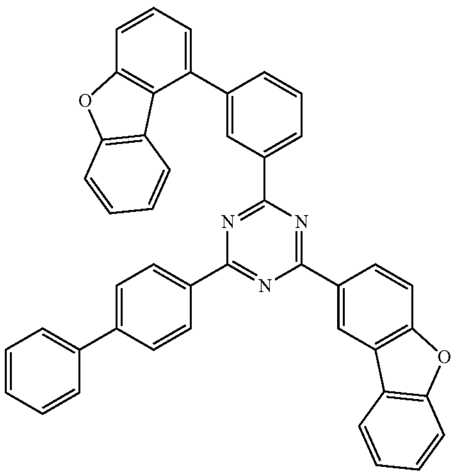

-continued
[B-127]
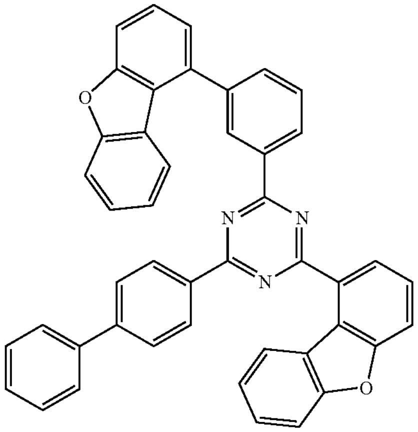
[B-128]
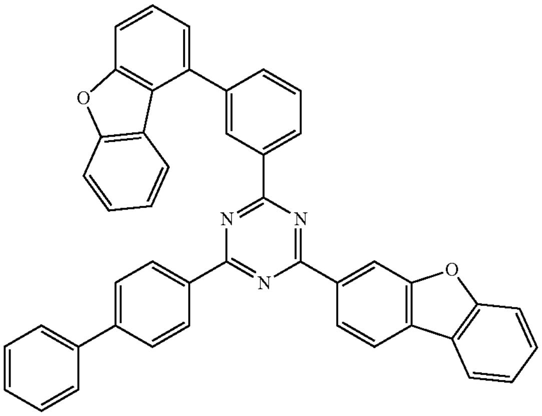
[C-1]
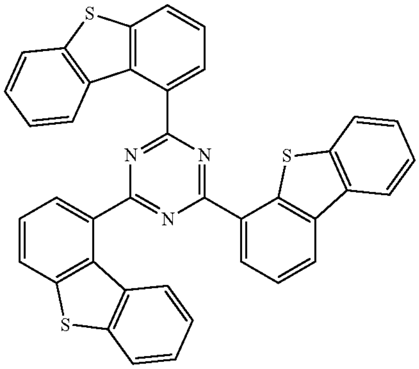
[C-2]
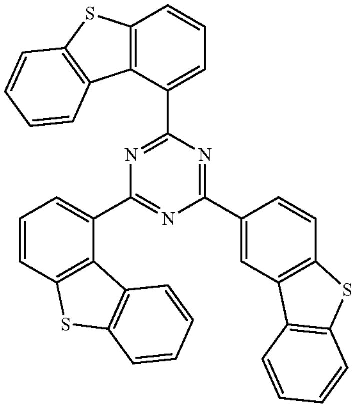
-continued
[C-3]
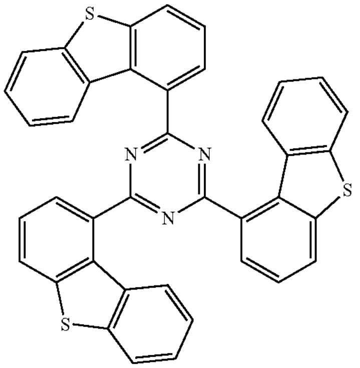
[C-4]
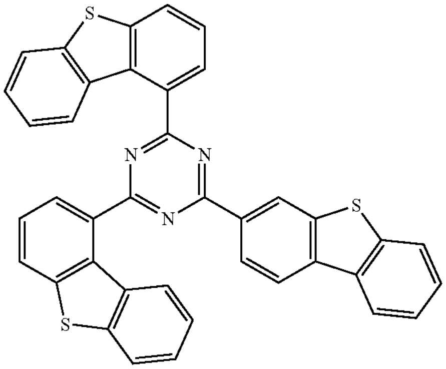
[C-5]
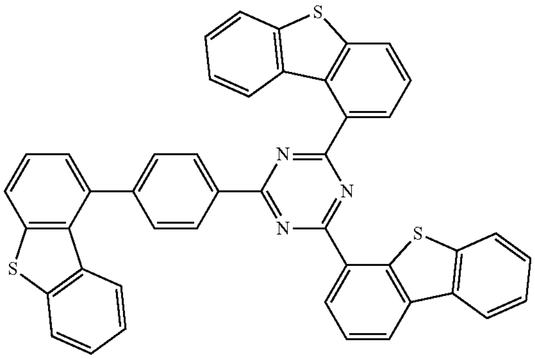
[C-6]
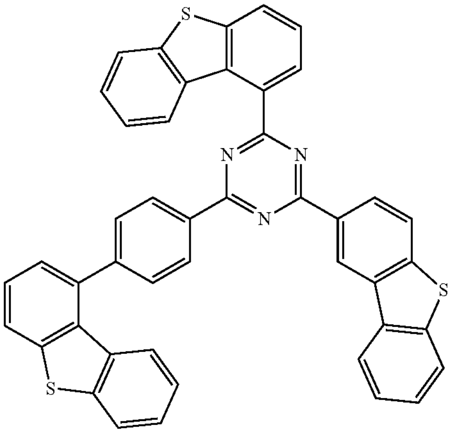

-continued
[C-7]
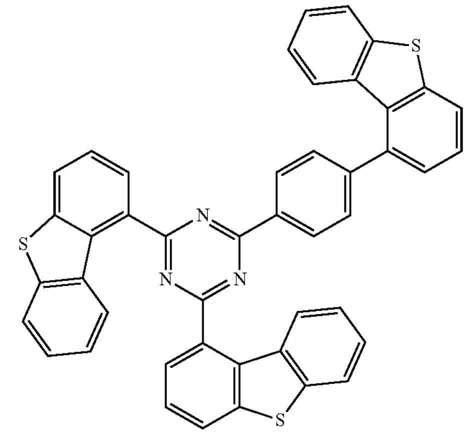
[C-8]
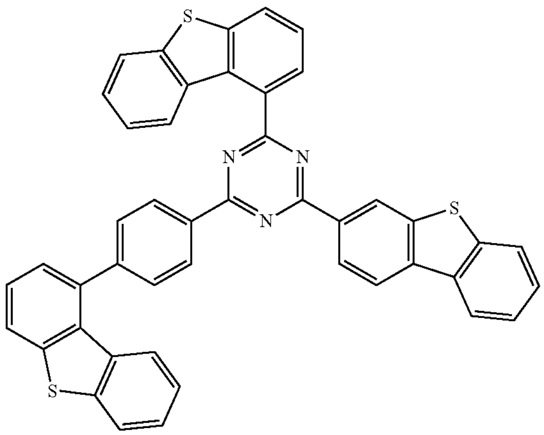
[C-9]
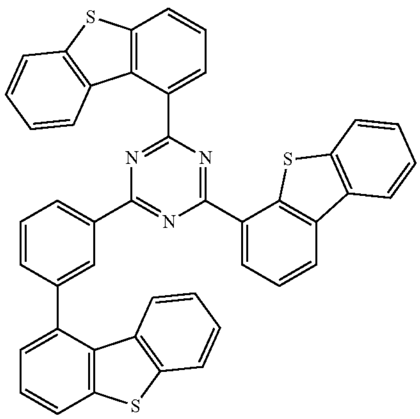
-continued
[C-10]
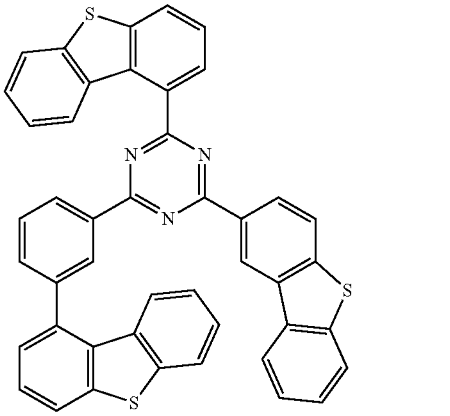
[C-11]
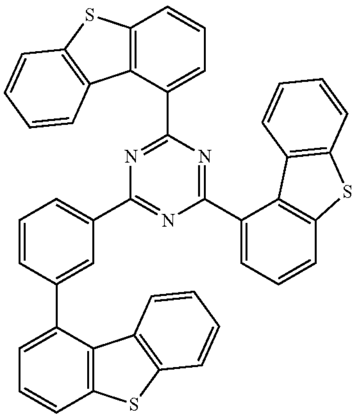
[C-12]
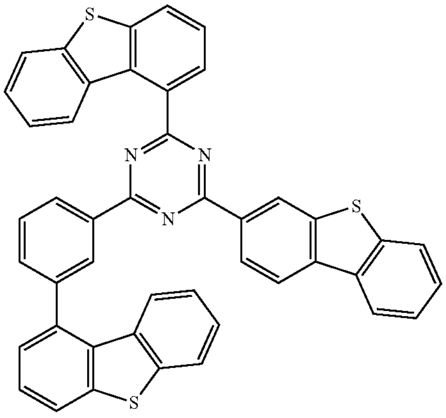

-continued
[C-13]
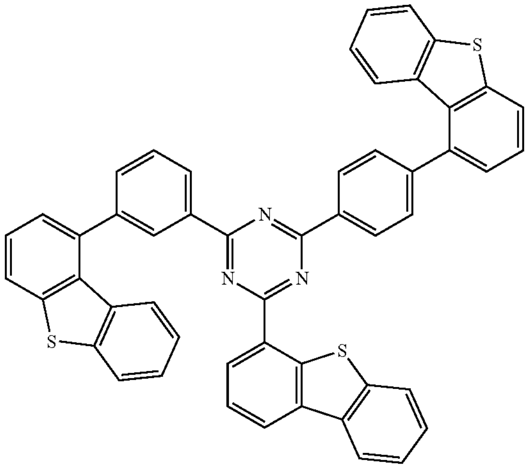
[C-14]
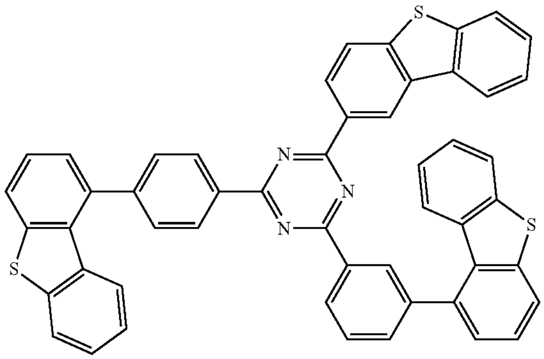
[C-15]
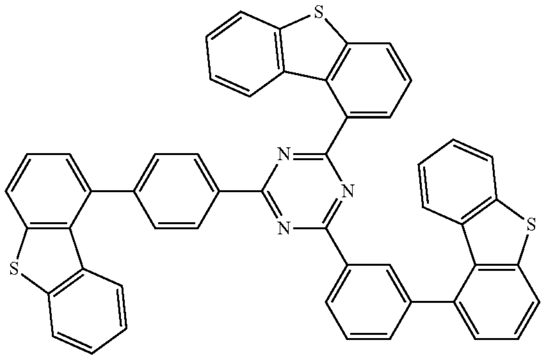
-continued
[C-16]
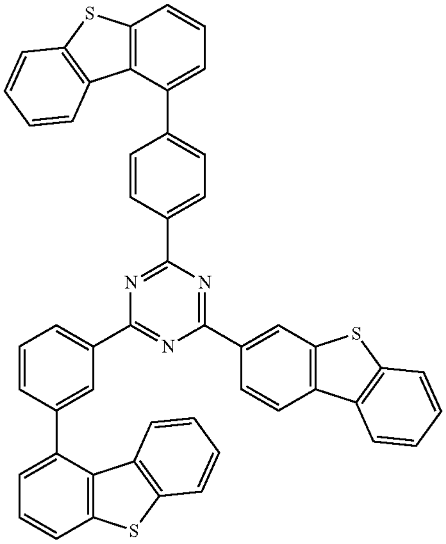
[C-17]
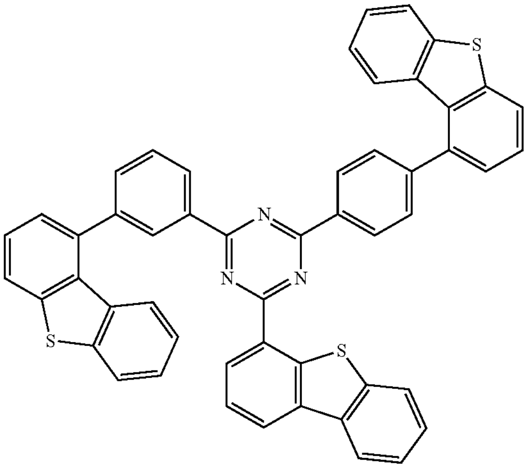
[C-18]
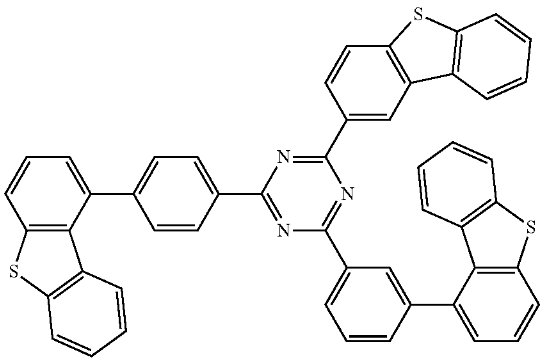

-continued
[C-19]
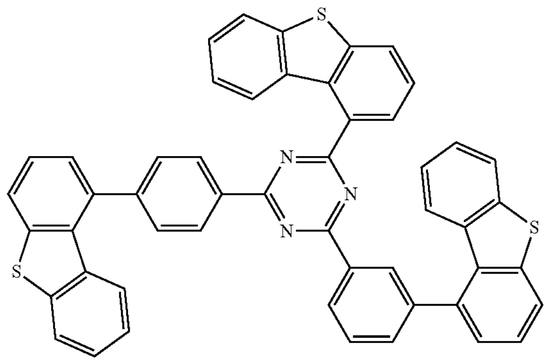
[C-20]
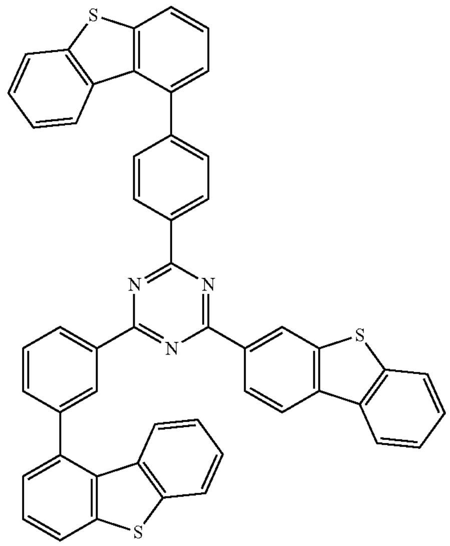
[C-21]
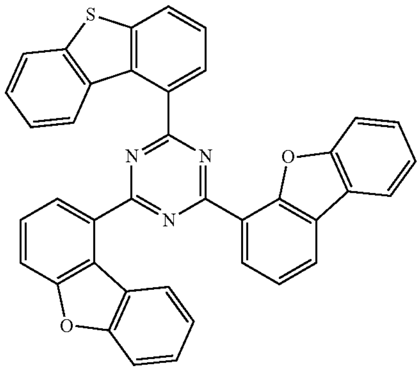
-continued
[C-22]
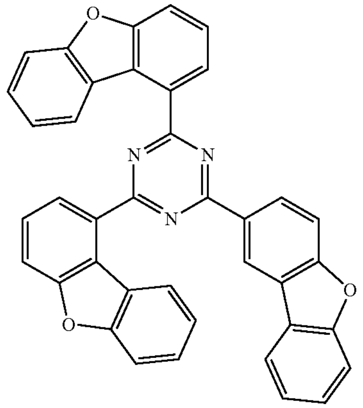
[C-23]
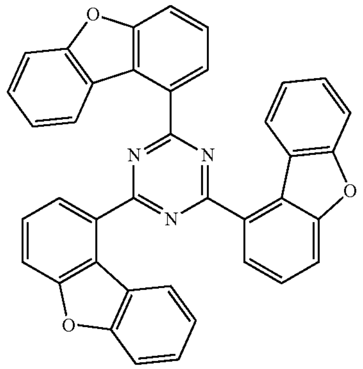
[C-24]
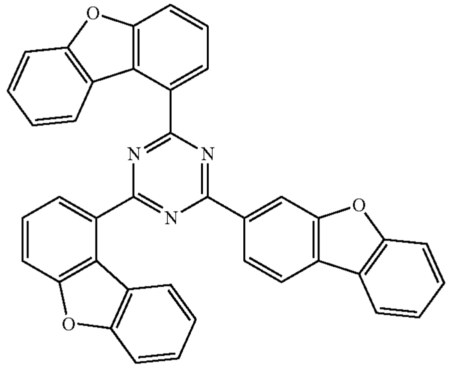
[C-25]
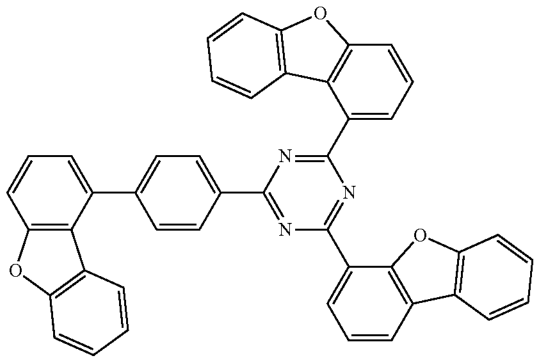

-continued
[C-26]
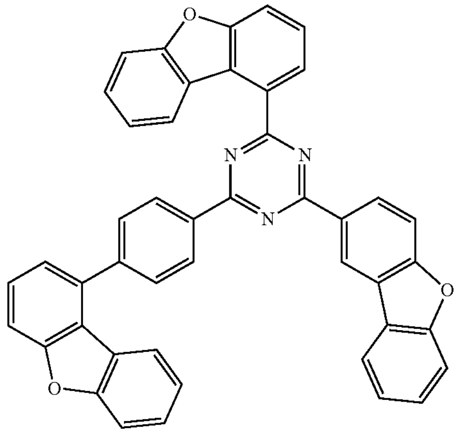
[C-27]
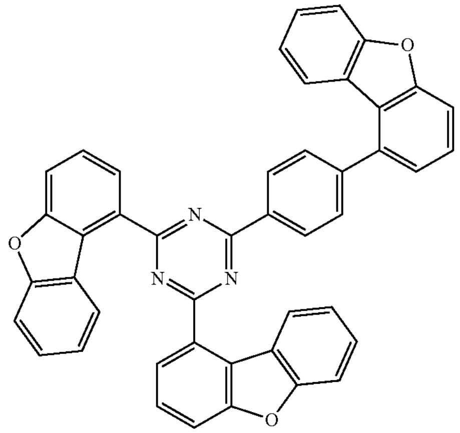
[C-28]
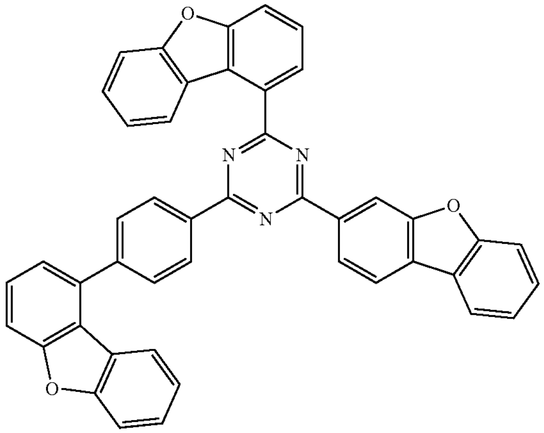
-continued
[C-29]
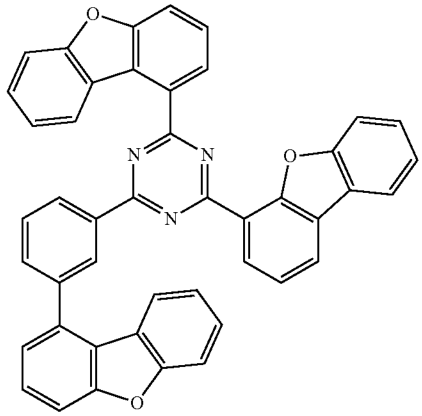
[C-30]
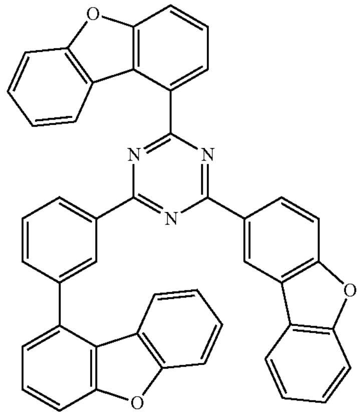
[C-31]
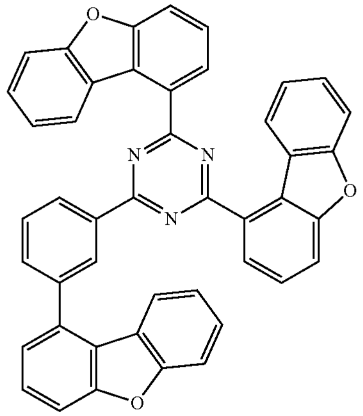

[C-32]
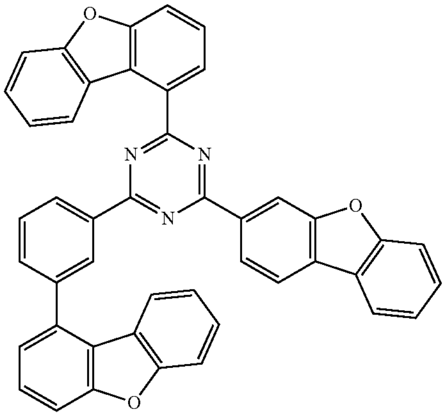
[C-33]
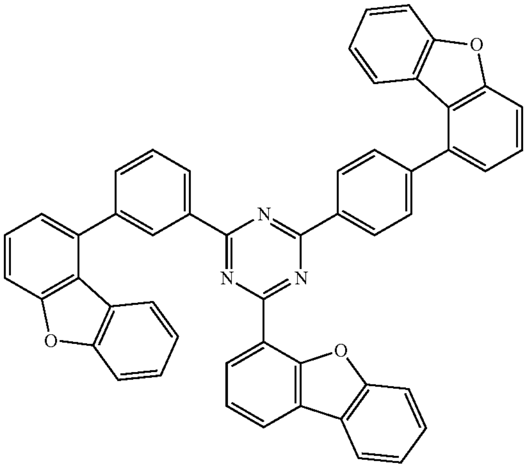
[C-34]
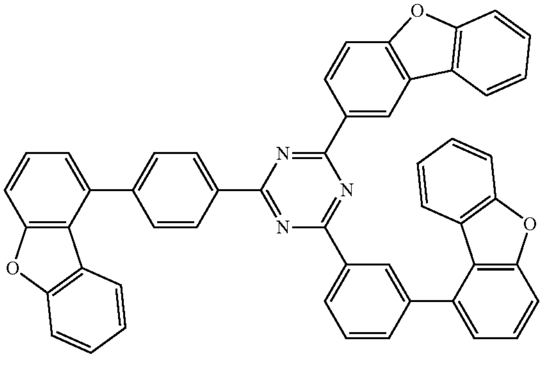
[C-35]
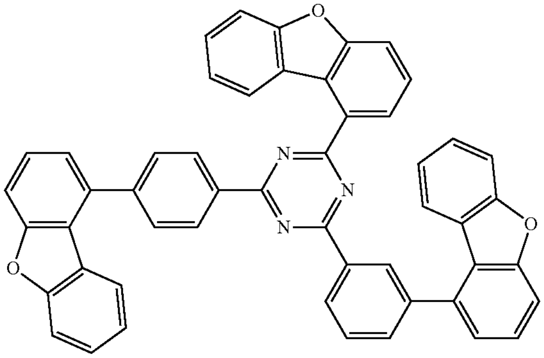
[C-36]
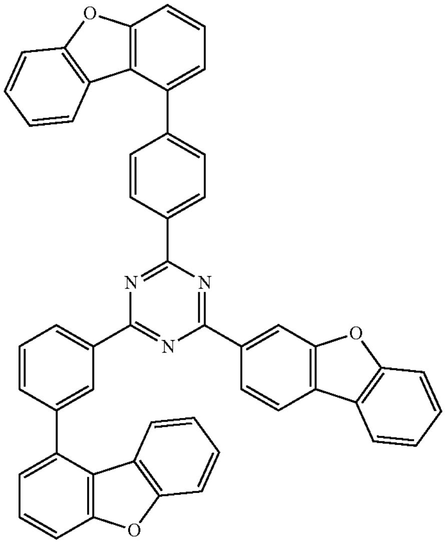
[C-37]
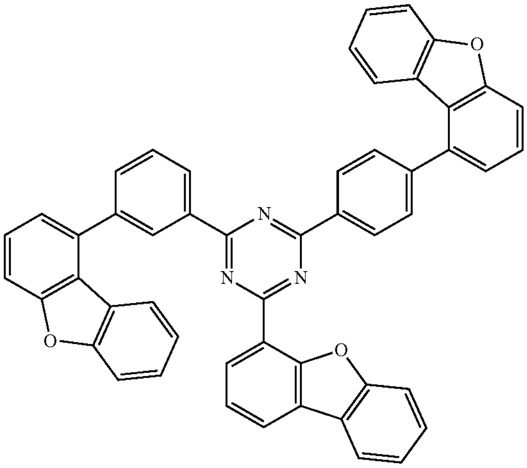

-continued
[C-38]
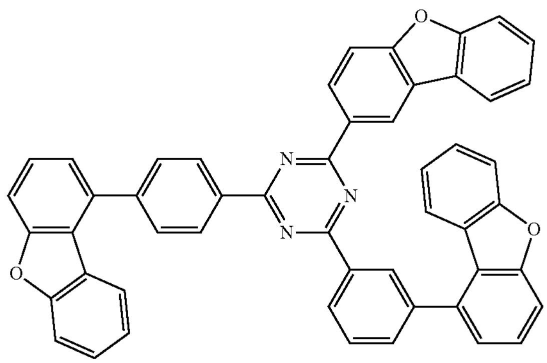
[C-39]
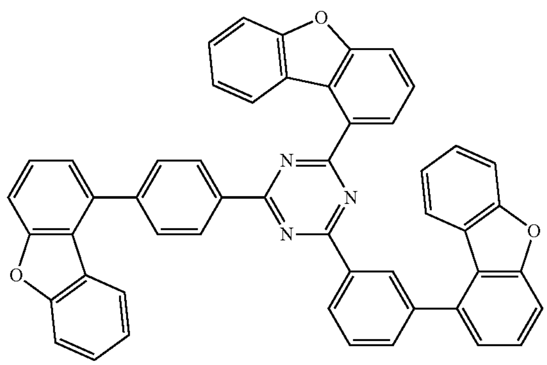
[C-40]
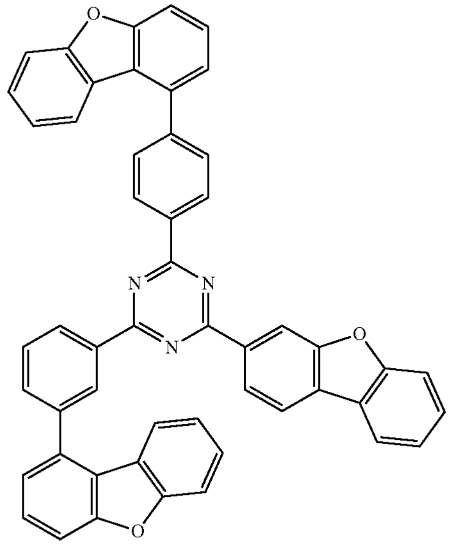
-continued
[D-1]
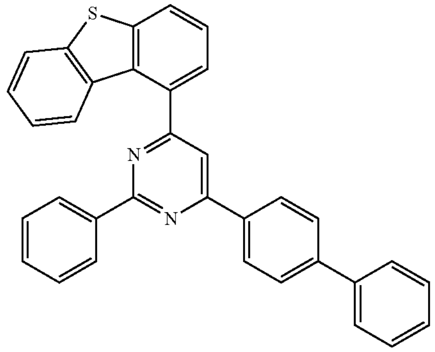
[D-2]
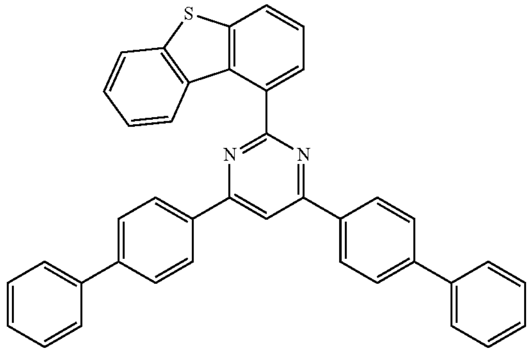
[D-3]
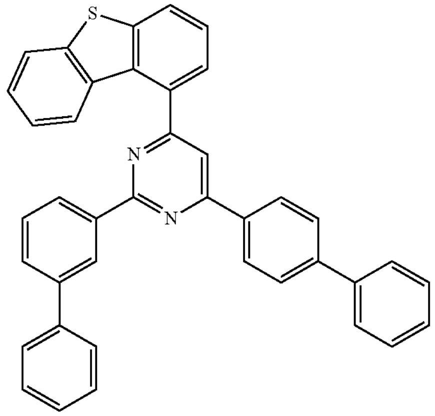
[D-4]
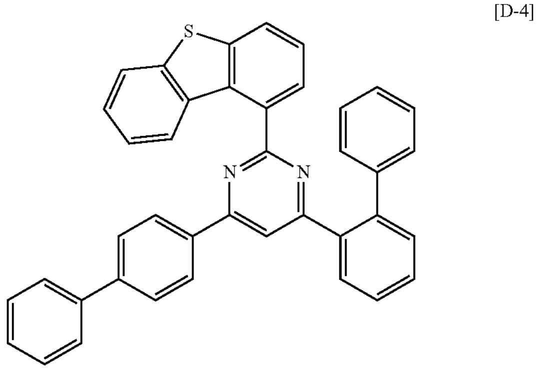

-continued
[D-5]
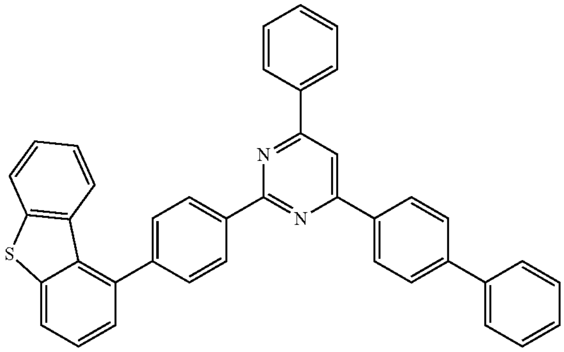
[D-6]
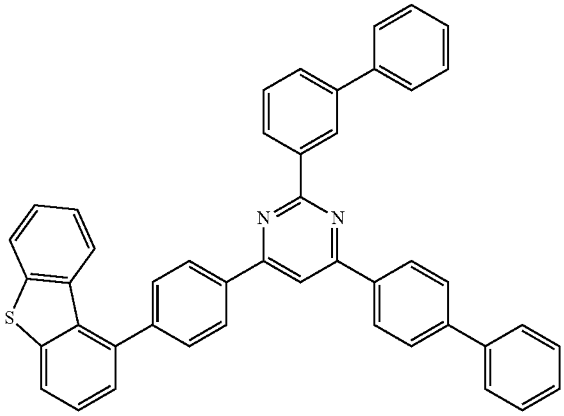
[D-7]
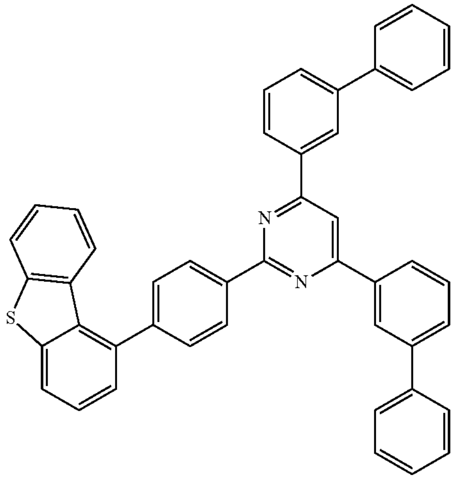
-continued
[D-8]
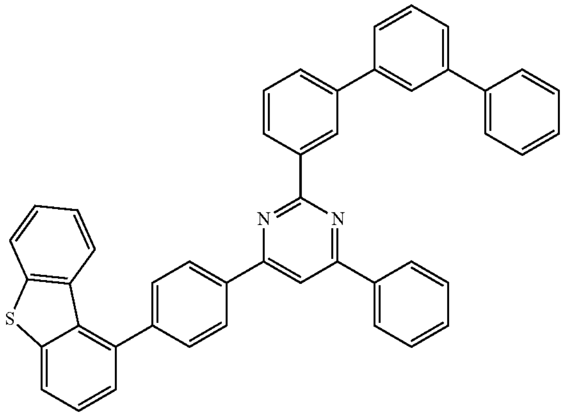
[D-9]
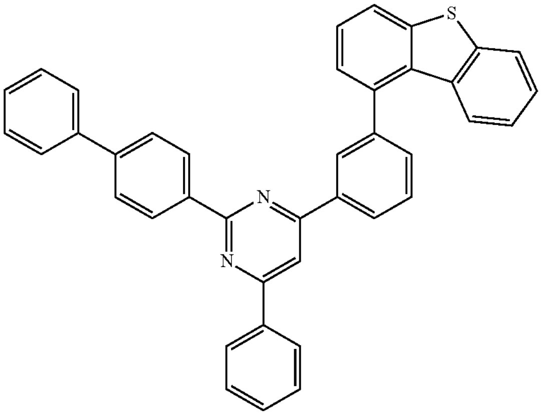
[D-10]
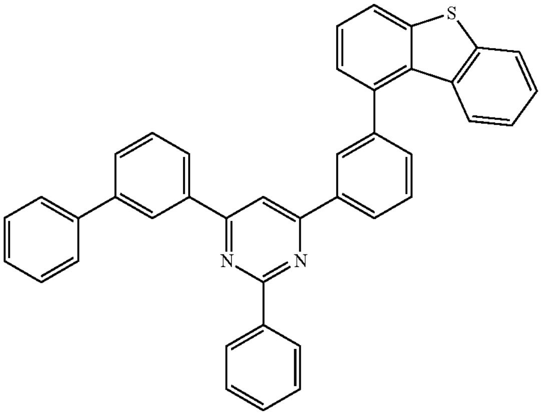

-continued
[D-11]
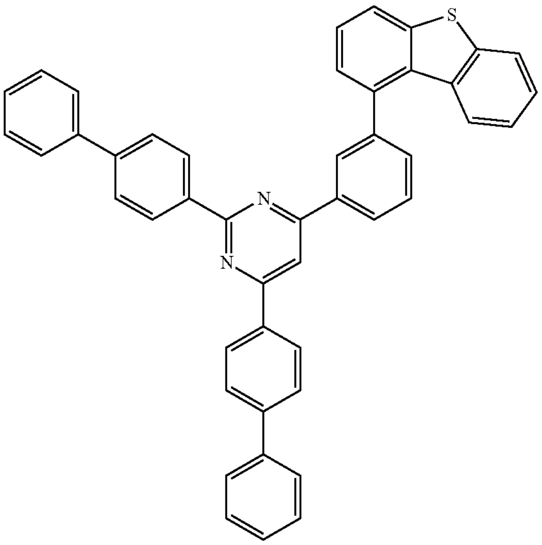
[D-12]
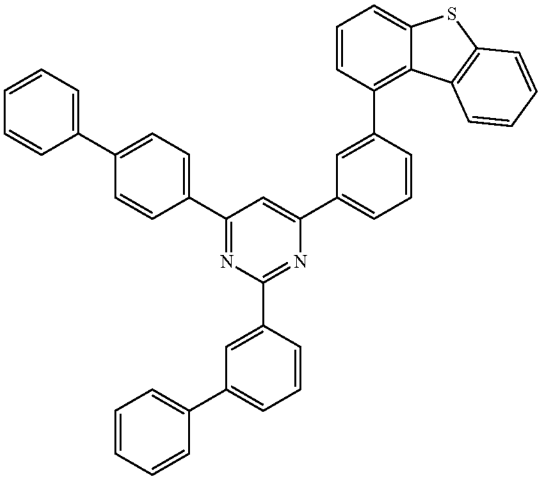
[D-13]
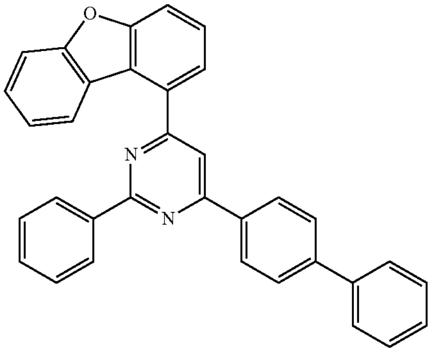
-continued
[D-14]
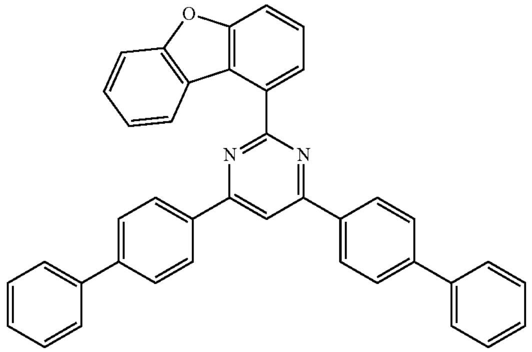
[D-15]
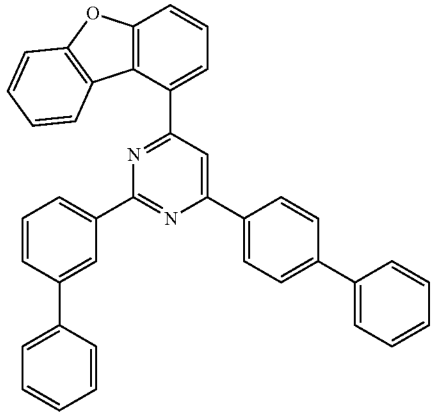
[D-16]
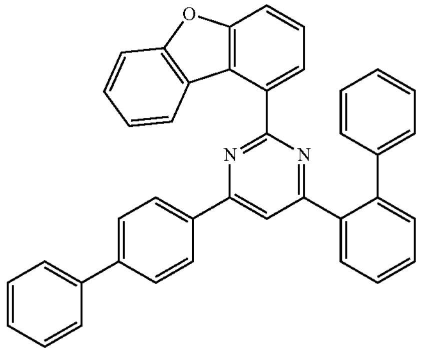
[D-17]
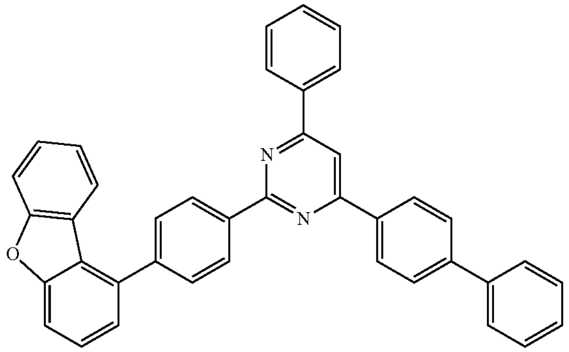

-continued
[D-18]
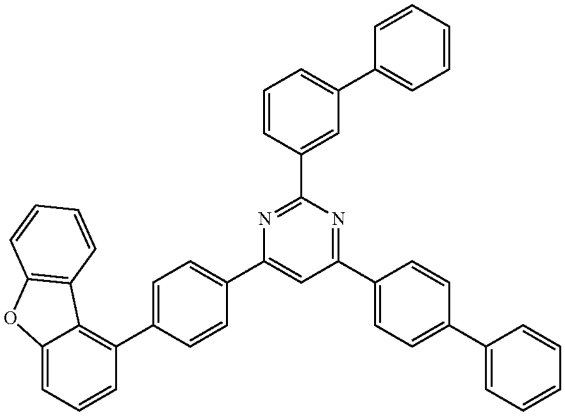
[D-19]
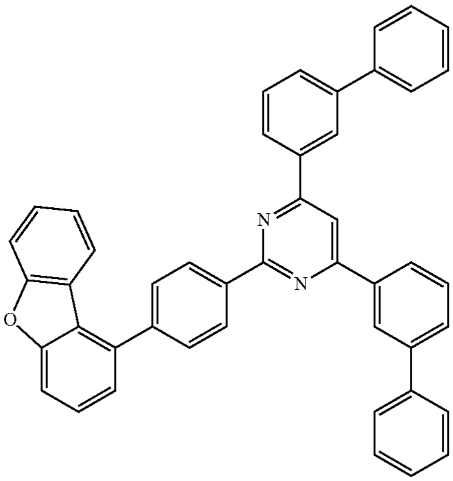
[D-20]
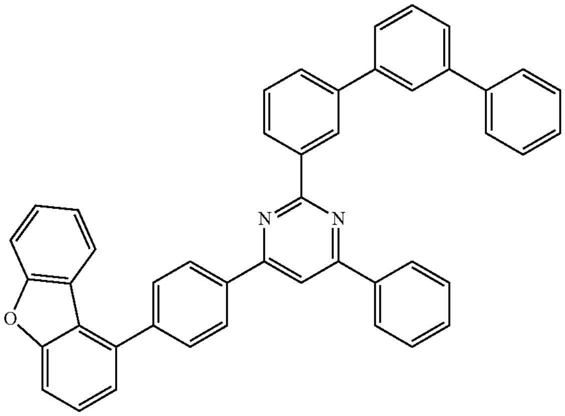
-continued
[D-21]
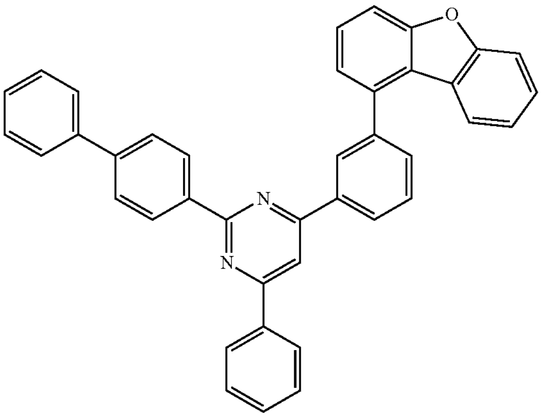
[D-22]
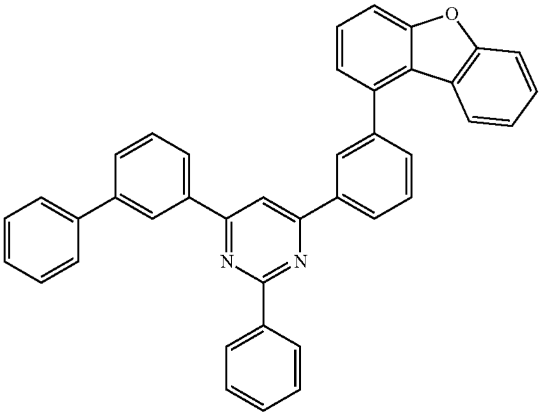
[D-23]
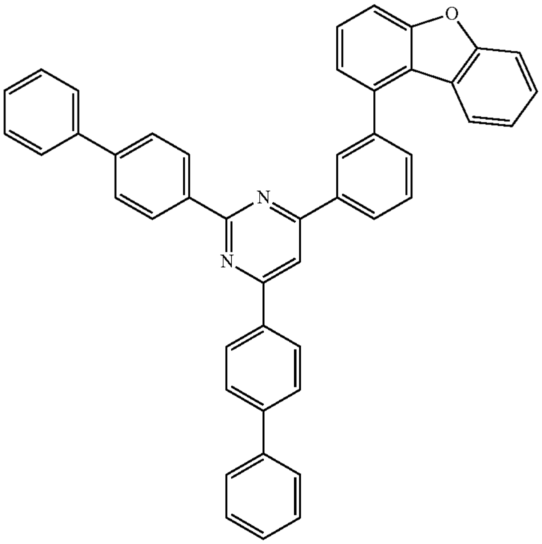

-continued
[D-24]
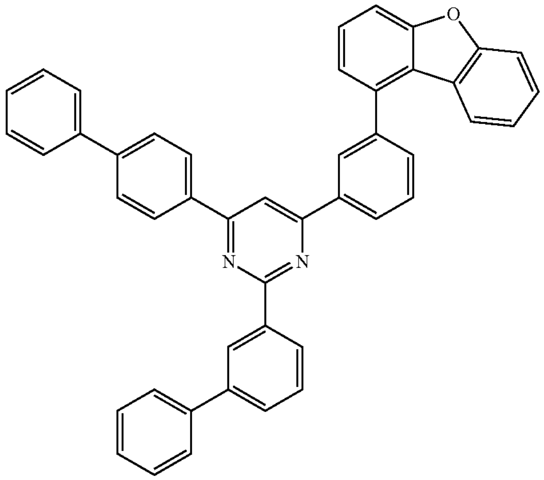
[E-1]
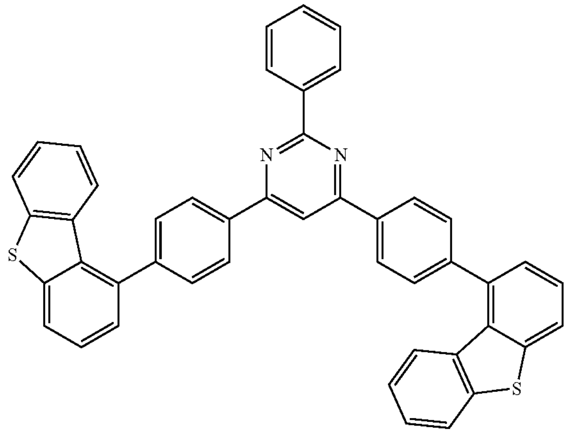
[E-2]
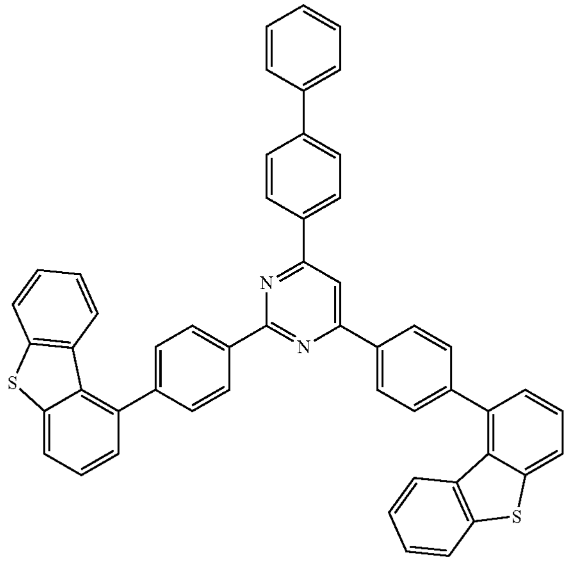
-continued
[E-3]
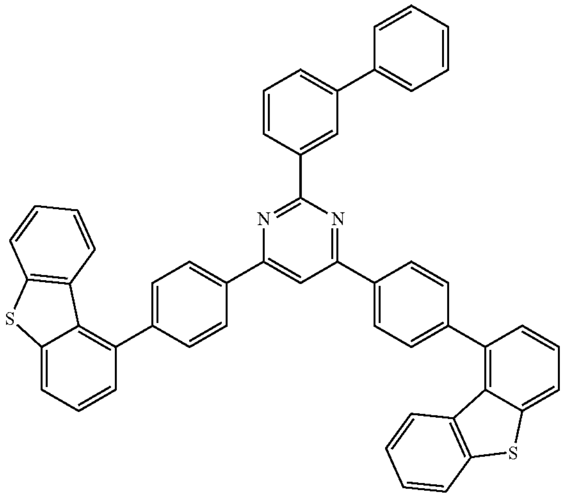
[E-4]
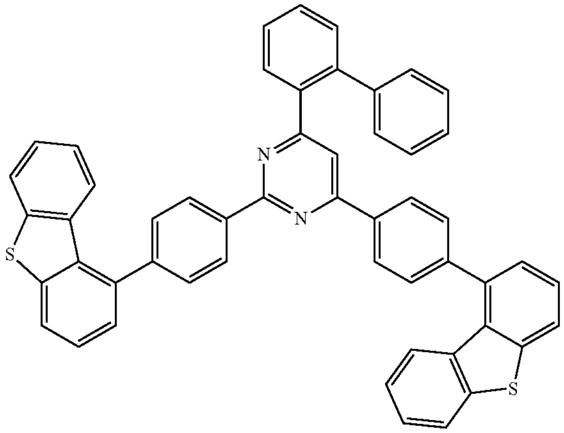
[E-5]
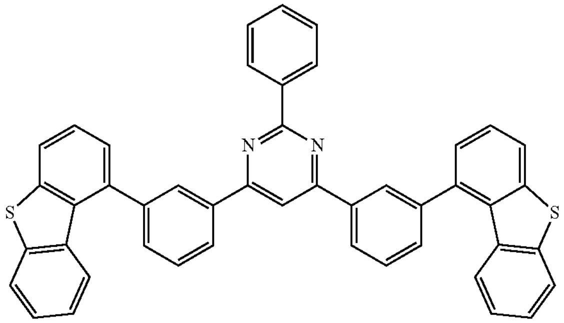

-continued
[E-6]
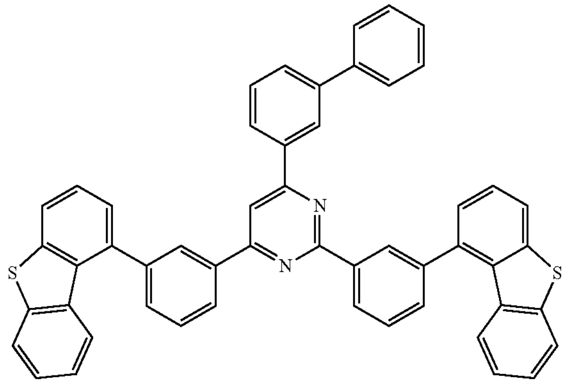
[E-7]
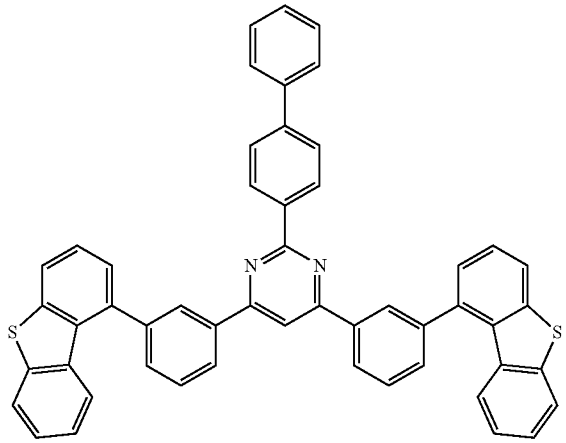
[E-8]
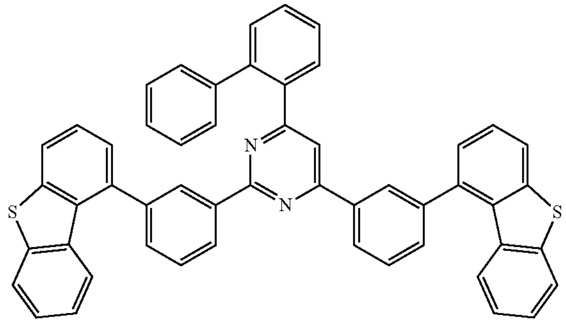
[E-9]
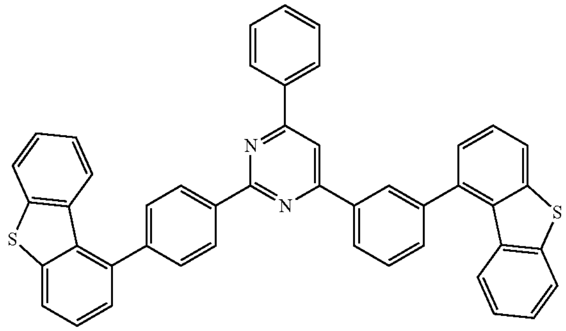
-continued
[E-10]
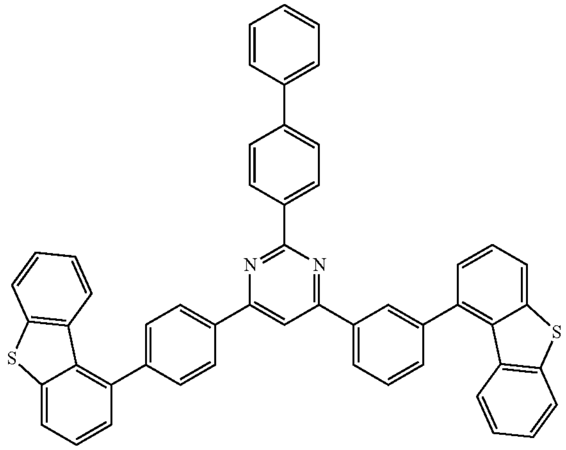
[E-11]
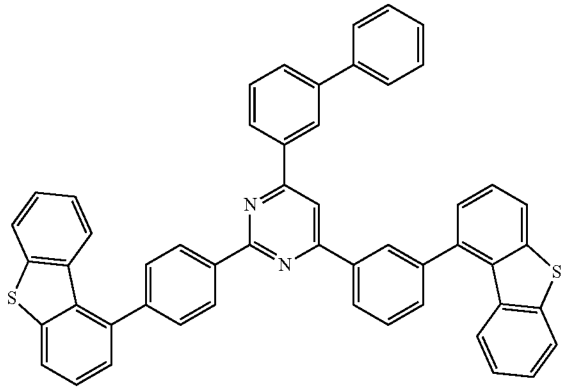
[E-12]
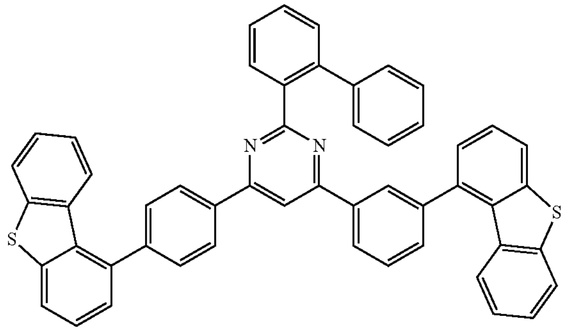
[E-13]
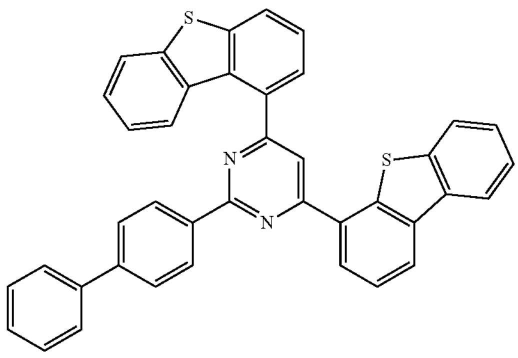

-continued
[E-14]
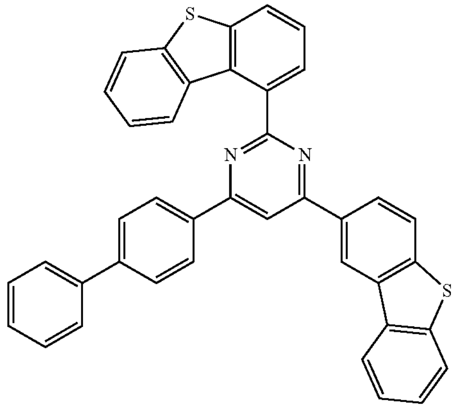
[E-15]
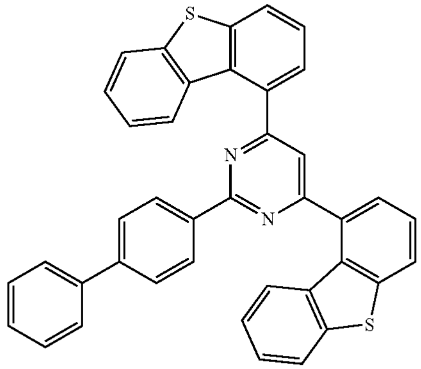
[E-16]
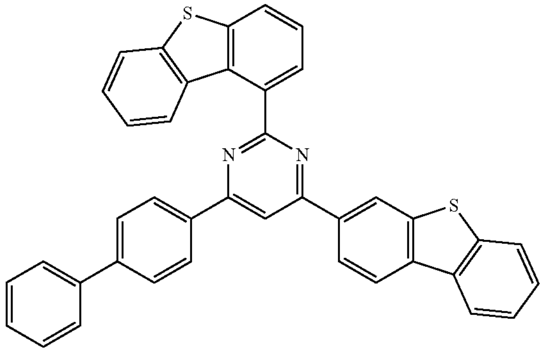
[E-17]
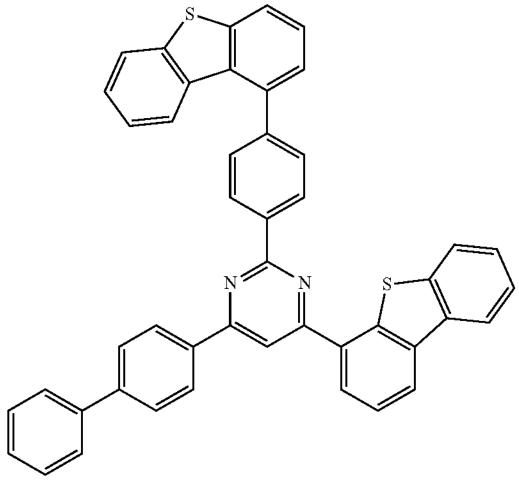
-continued
[E-18]
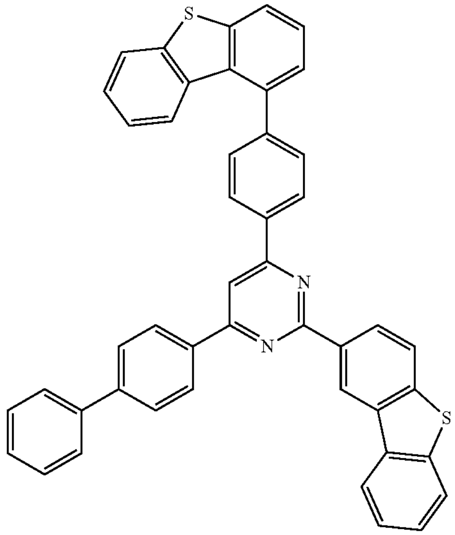
[E-19]
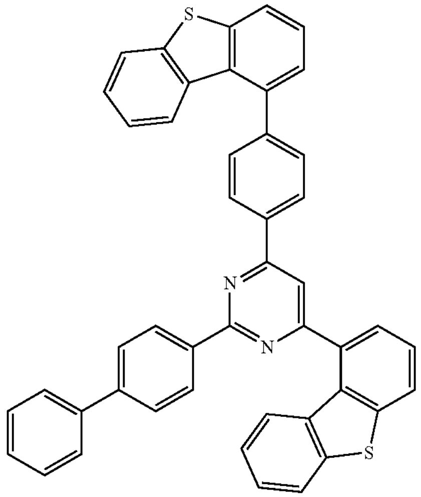
[E-20]
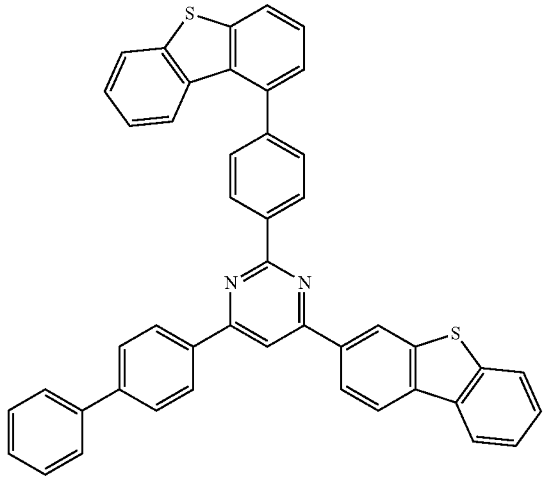

-continued
[E-21]
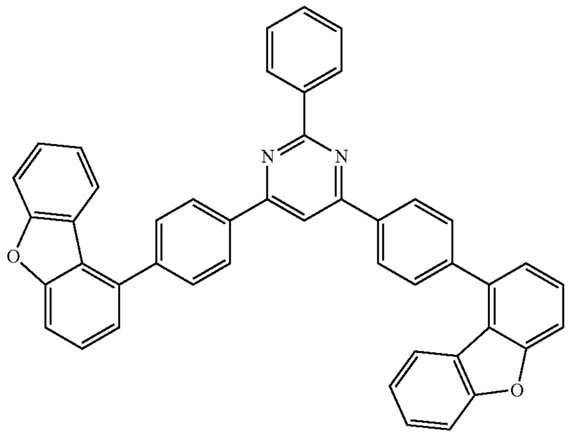
[E-22]
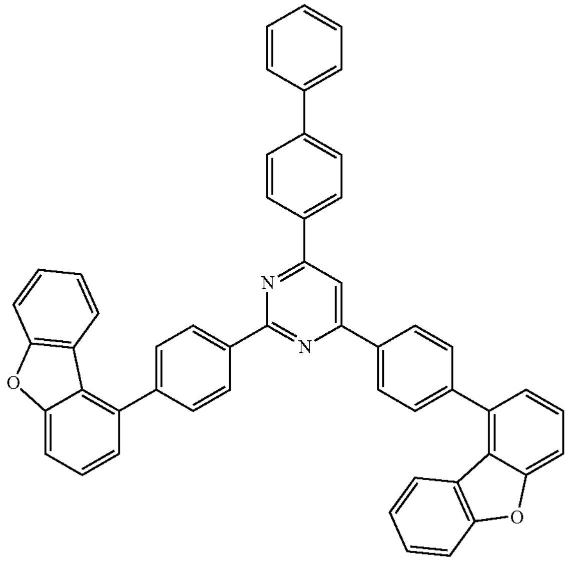
[E-23]
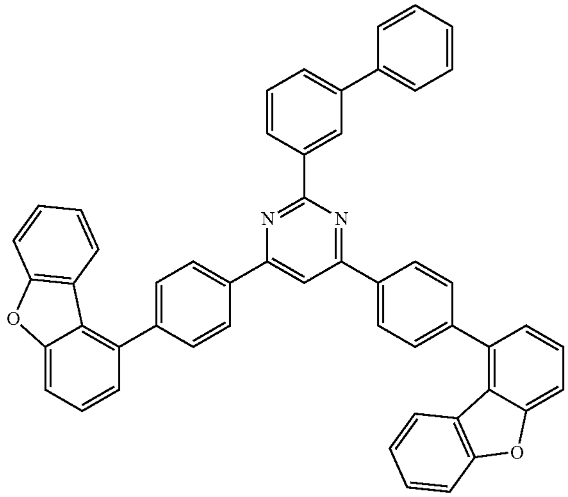
-continued
[E-24]
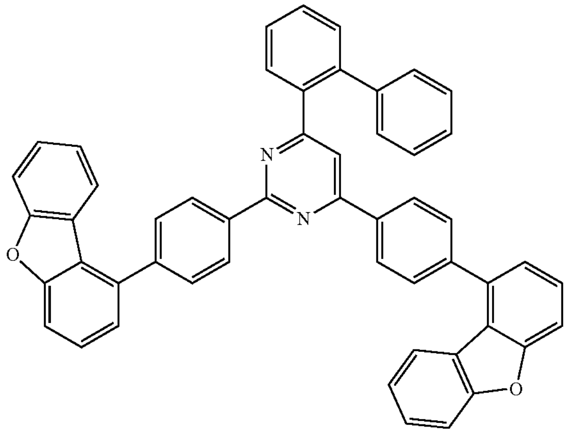
[E-25]
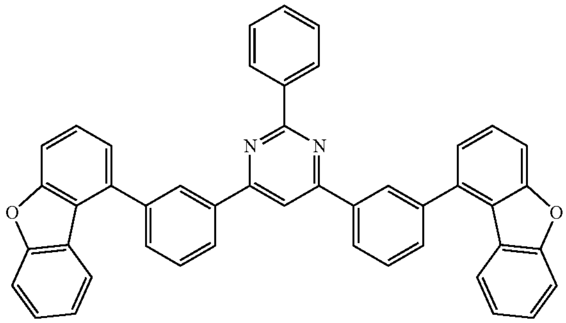
[E-26]
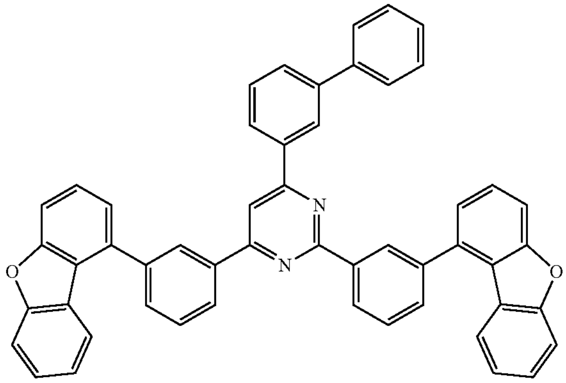

-continued
[E-27]
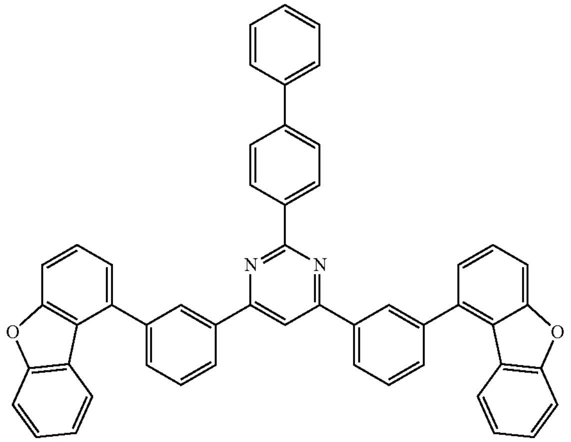
[E-28]
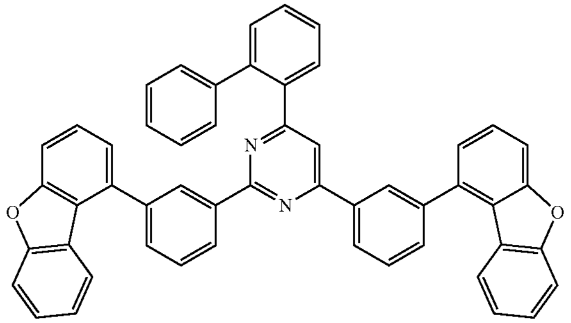
[E-29]
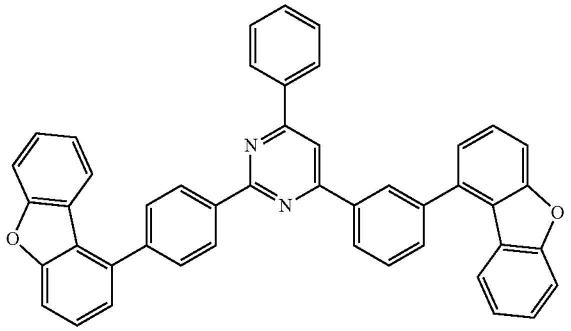
[E-30]
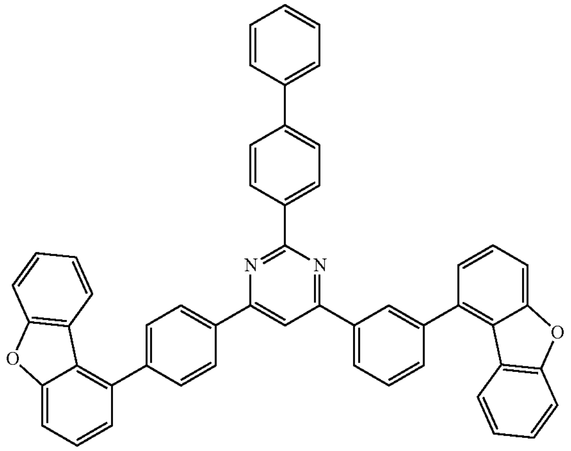
-continued
[E-31]
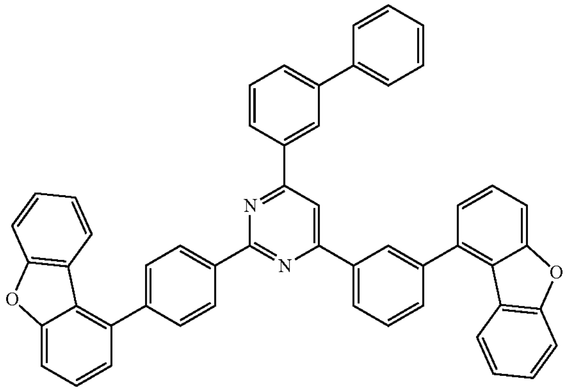
[E-32]
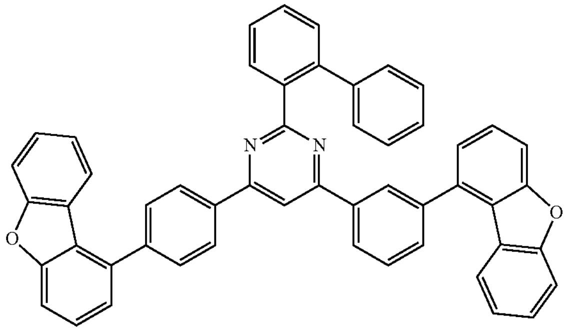
[E-33]
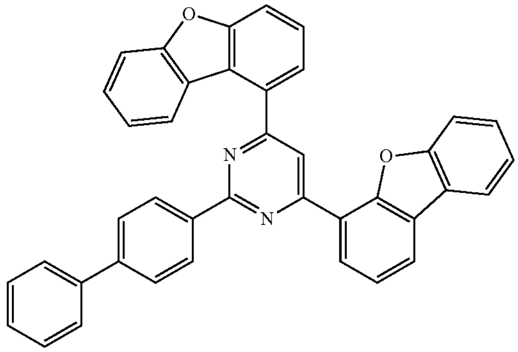
[E-34]
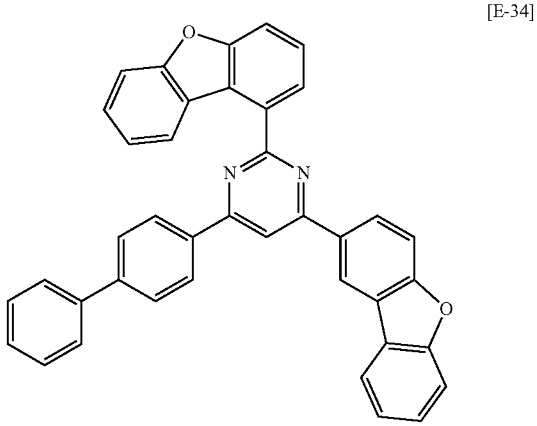

-continued
[E-35]
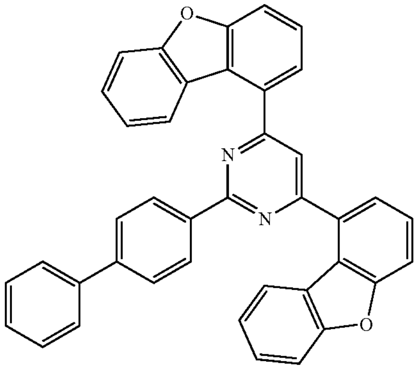
[E-36]
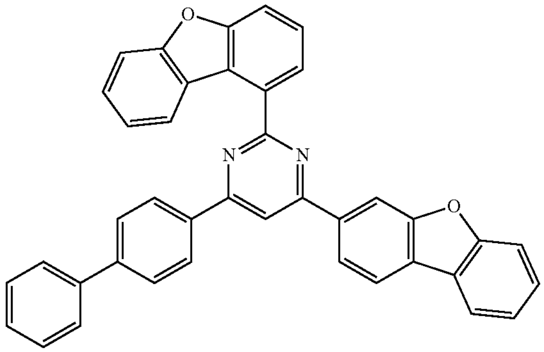
[E-37]
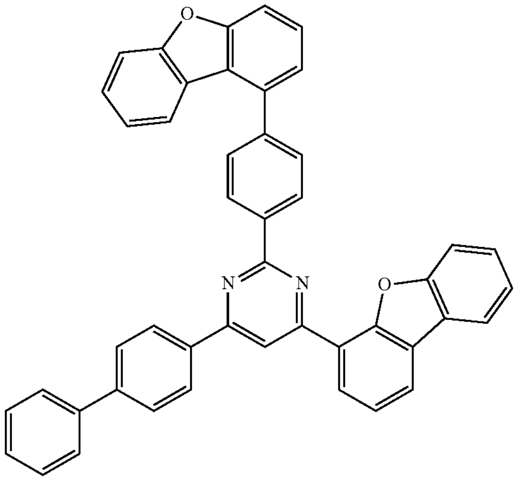
-continued
[E-38]
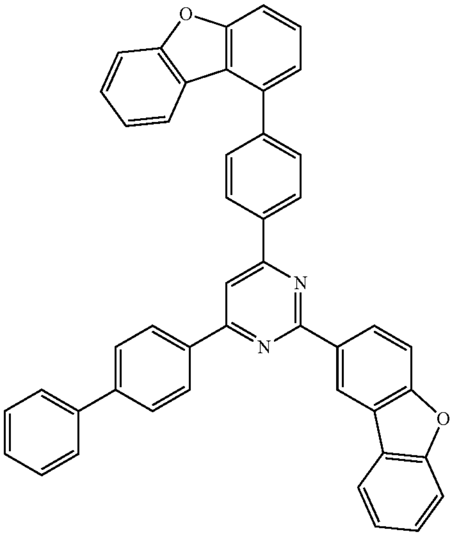
[E-39]
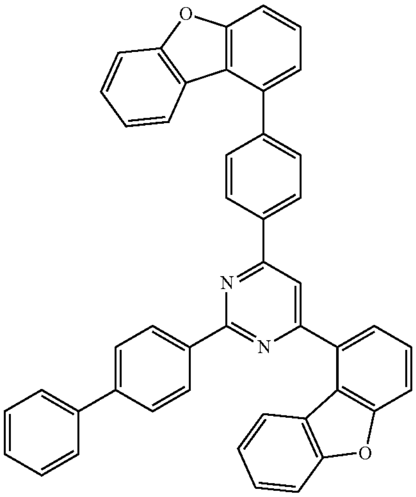
[E-40]
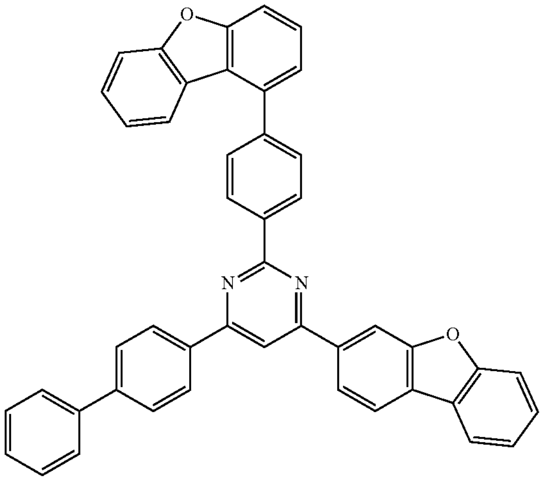

-continued
[F-1]
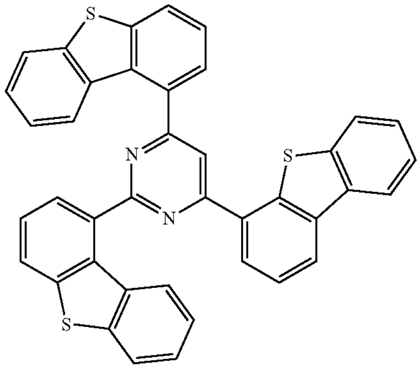
[F-2]
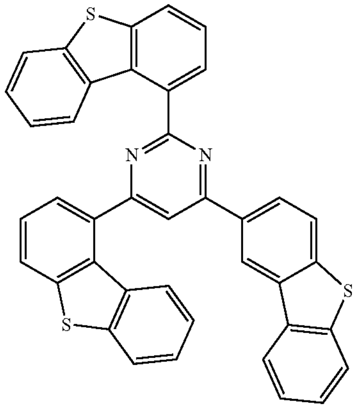
[F-3]
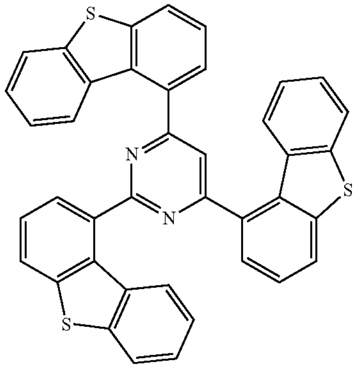
[F-4]
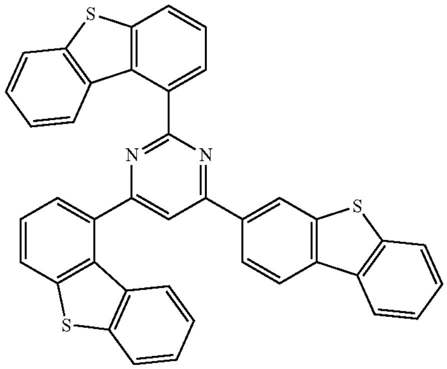
-continued
[F-5]
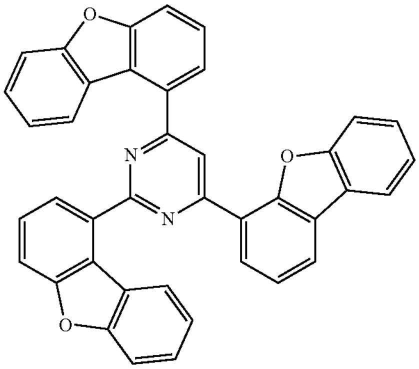
[F-6]
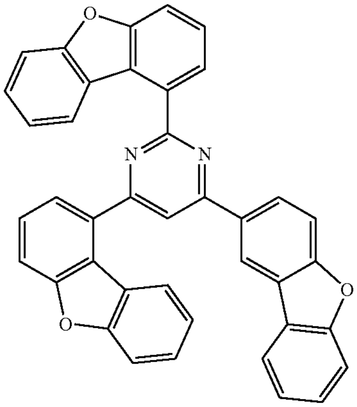
[F-7]
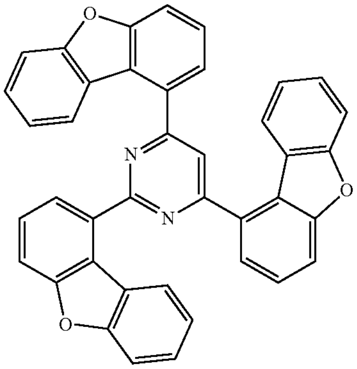
[F-8]
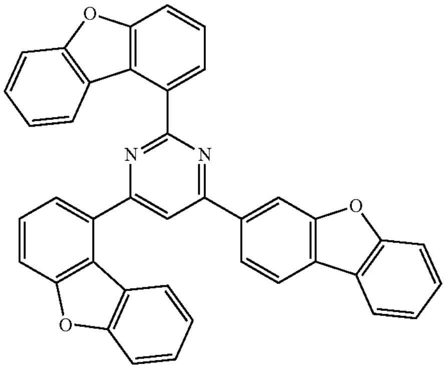
The second host compound that is applied in the form of a composition together with the aforementioned first host compound may be represented by Chemical Formula 2.

[Chemical Formula 2]

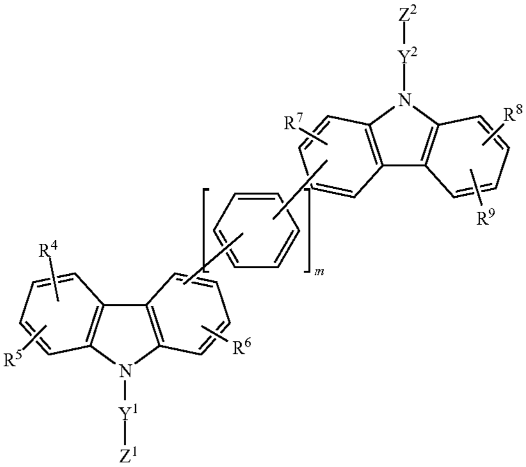

In Chemical Formula 2, $Y^1$ and $Y^2$ are independently a single bond, a substituted or unsubstituted C6 to C30 arylene group, a substituted or unsubstituted C2 to C30 heteroarylene group, or a combination thereof, $Z^1$ and $Z^2$ are independently a substituted or unsubstituted C6 to C30 aryl group, a substituted or unsubstituted C2 to C30 heterocyclic group, or a combination thereof, $R^4$ to $R^9$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, and m is one of integers of 0 to 2, wherein "substituted" of Chemical Formula 2 refers to replacement of at least one hydrogen by deuterium, a C1 to C4 alkyl group, a C6 to C18 aryl group, or a C2 to C30 heteroaryl group.

In an embodiment of the present invention, $Y^1$ and $Y^2$ of Chemical Formula 2 may independently be a single bond, or a substituted or unsubstituted C6 to C18 arylene group. In an embodiment of the present invention, $Z^1$ and $Z^2$ of Chemical Formula 2 may independently be a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted triphenylenyl group, a substituted or unsubstituted pyridinyl group, a substituted or unsubstituted pyrimidinyl group, a substituted or unsubstituted quinazolyl group, a substituted or unsubstituted dibenzothiophenyl group, a substituted or unsubstituted dibenzofuranyl group, a substituted or unsubstituted triazinyl group, a substituted or unsubstituted quinolinyl group, a substituted or unsubstituted isoquinolinyl group, a substituted or unsubstituted carbazolyl group, a substituted or unsubstituted fluorenyl group, or a combination thereof.

Specifically, $Z^1$ and $Z^2$ of Chemical Formula 2 may independently be a substituted or unsubstituted phenyl group, a substituted or unsubstituted biphenyl group, a substituted or unsubstituted terphenyl group, a substituted or unsubstituted naphthyl group, a substituted or unsubstituted triphenylenyl group, a substituted or unsubstituted pyridinyl group, a substituted or unsubstituted pyrimidinyl group, a substituted or unsubstituted dibenzothiophenyl group, a substituted or unsubstituted dibenzofuranyl group, a substituted or unsubstituted carbazolyl group, a substituted or unsubstituted fluorenyl group, or a combination thereof, for example a phenyl group, a biphenyl group, a dibenzofuranyl group, or a dibenzothiophenyl group.

In an embodiment of the present invention, $R^4$ to $R^9$ of Chemical Formula 2 may independently be hydrogen, deuterium, or a substituted or unsubstituted C6 to C12 aryl group.

In an embodiment of the present invention, m of Chemical Formula 2 may be 0 or 1.

In a specific embodiment of the present invention, Chemical Formula 2 may be one of structures of Group II and $*—Y^1—Z^1$ and $*—Y^2—Z^2$ may be one of substituents of Group IV.

[Group III]

C-1

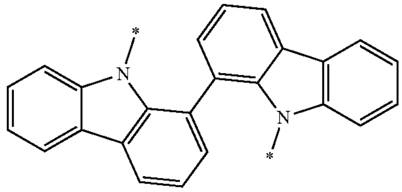

C-2

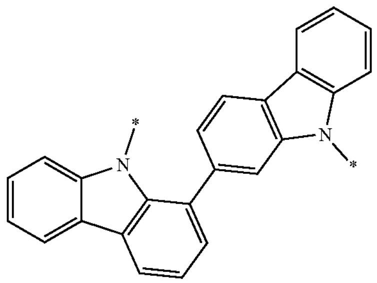

C-3

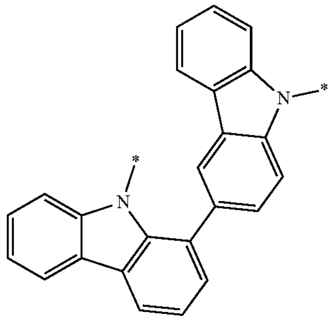

C-4

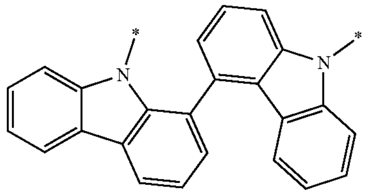

C-5

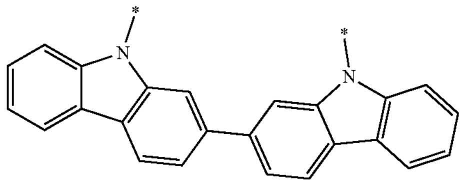

-continued
C-6
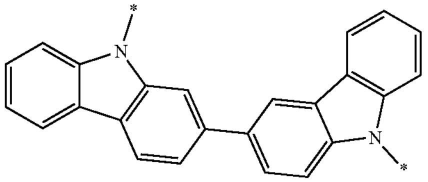
C-7
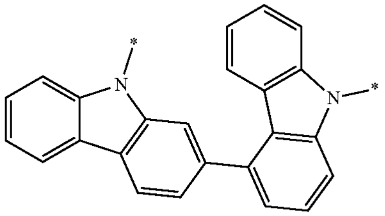
C-8
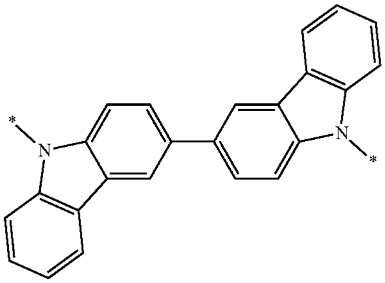
C-9
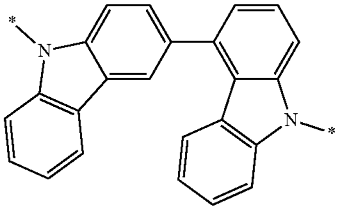
C-10
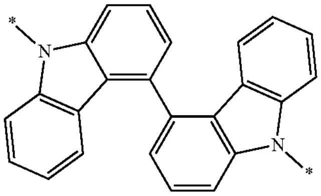
C-11
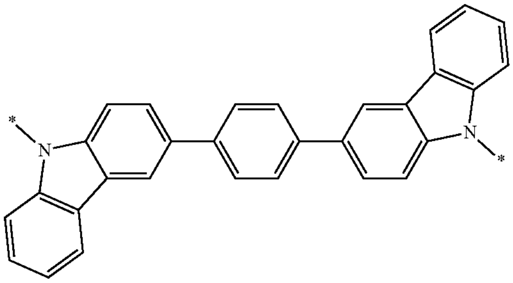
-continued
C-12
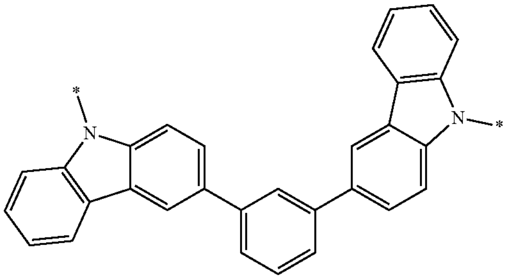
C-13
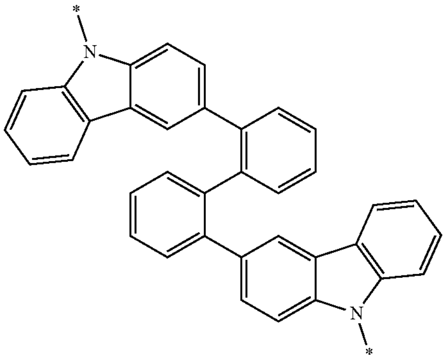
C-14
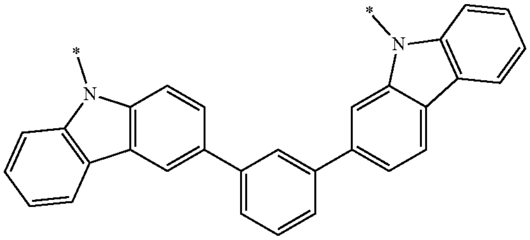
C-15
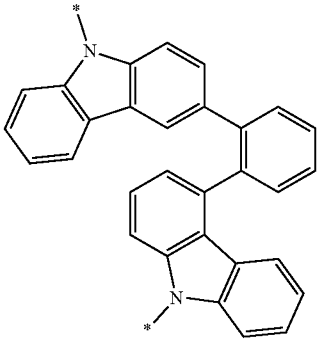
C-16
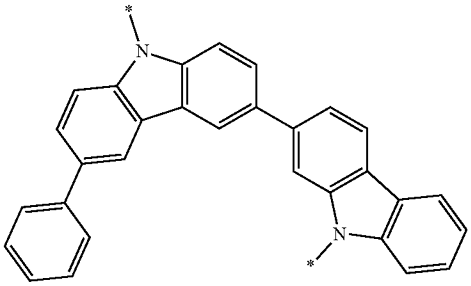

-continued
C-17
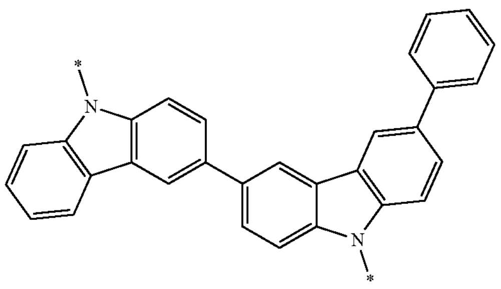
C-18
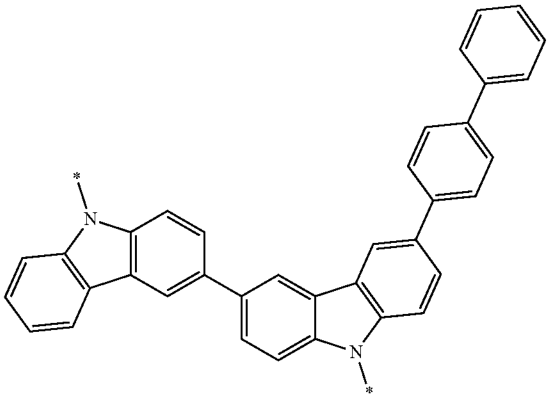
[Group IV]
B-1
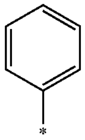
B-2
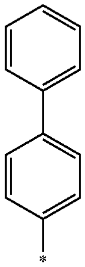
B-3
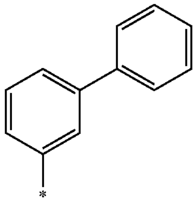
B-4
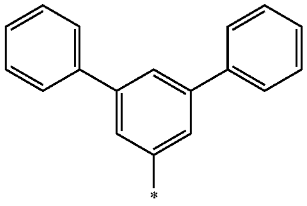
-continued
B-5
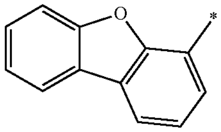
B-6
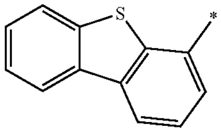
B-7
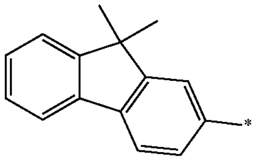
B-8
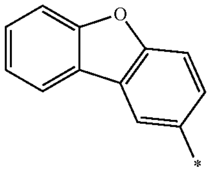
B-9
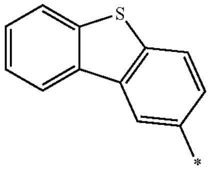
B-10
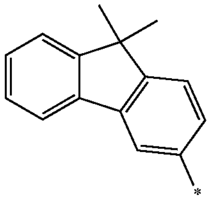
B-11
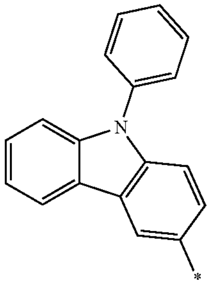
B-12
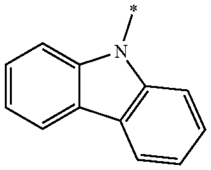

-continued
B-13
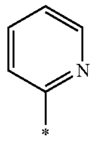
B-14
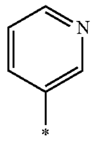
B-15
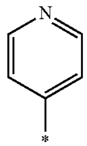
B-16
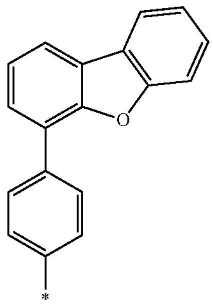
B-17
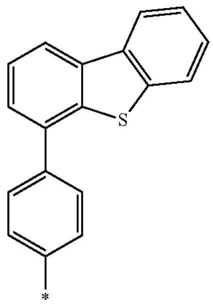
B-18
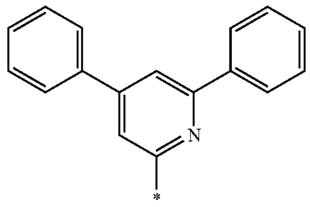
B-19
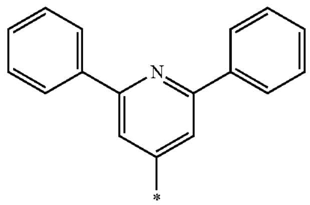
-continued
B-20
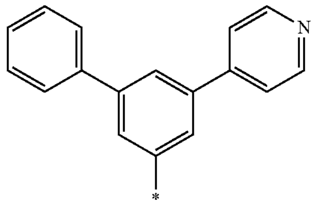
B-21
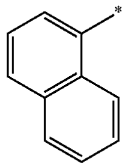
B-22
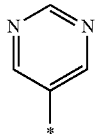
B-23
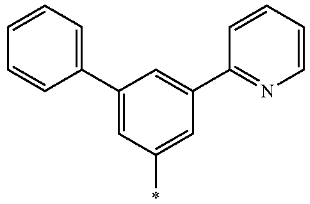
B-24
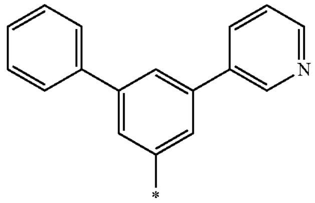
B-25
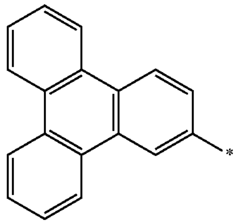
B-26
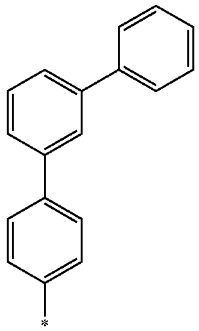
B-27
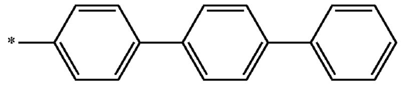

-continued

B-28

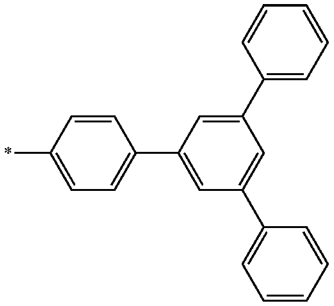

In Groups III and IV, * is a linking point.

On the other hand, "substituted" of Chemical Formula 2 refers to replacement of at least one hydrogen by deuterium, a C1 to C4 alkyl group, a C6 to C18 aryl group, or a C2 to C30 heteroaryl group. In a specific embodiment of the present invention, the "substituted" refers to replacement of at least one hydrogen by deuterium, a phenyl group, an ortho-biphenyl group, a meta-biphenyl group, a para-biphenyl group, a terphenyl group, a naphthyl group, a triphenylene group, a pyridinyl group, a dibenzofuranyl group, or a dibenzothiophenyl group.

In the most specific embodiment of the present invention, Chemical Formula 2 may be represented by C-8 or C-17 of Group III and $*—Y^1—Z^1$ and $*—Y^2—Z^2$ may independently be selected from B-1 to B-6 of Group IV.

The second host compound represented by Chemical Formula 2 may be for example selected from compounds of Group 2, but is not limited thereto.

[Group 2]

[HT-1]

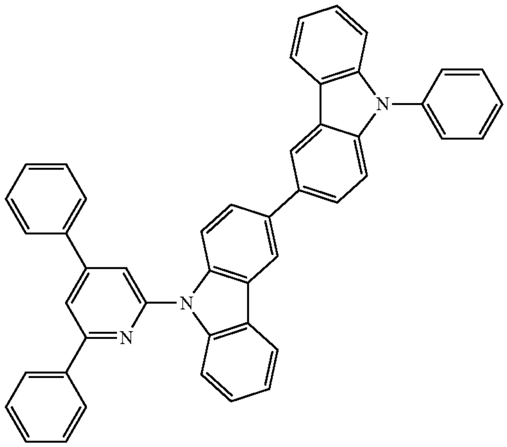

[HT-2]

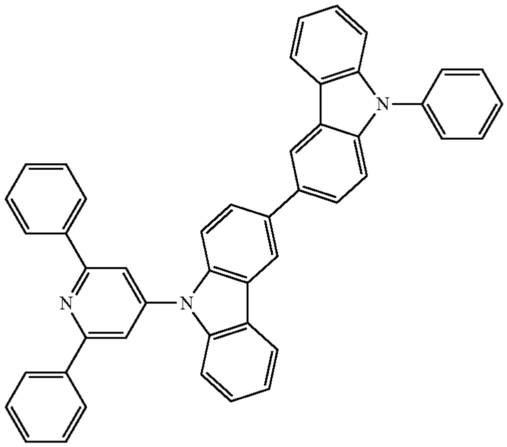

[HT-3]

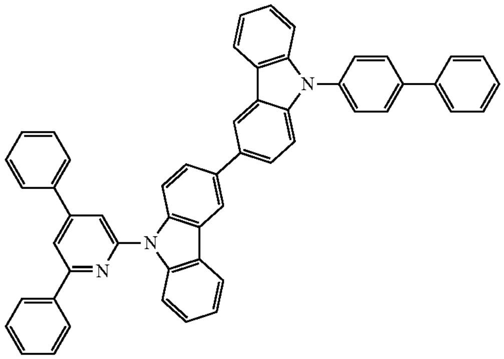

[HT-4]

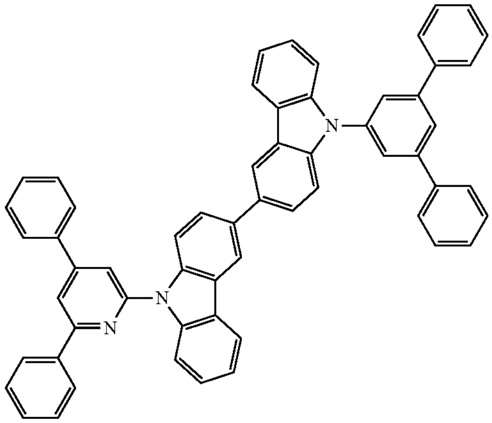

-continued
[HT-5]
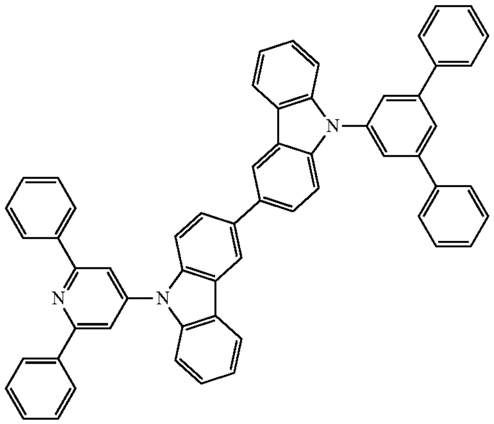
[HT-6]
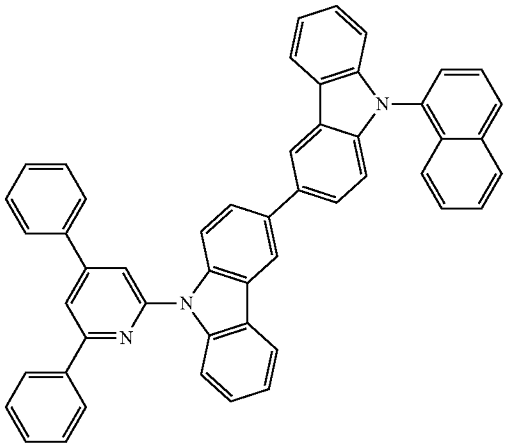
[HT-7]
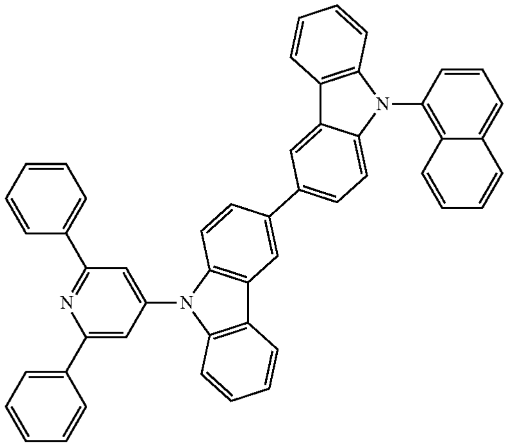
[HT-8]
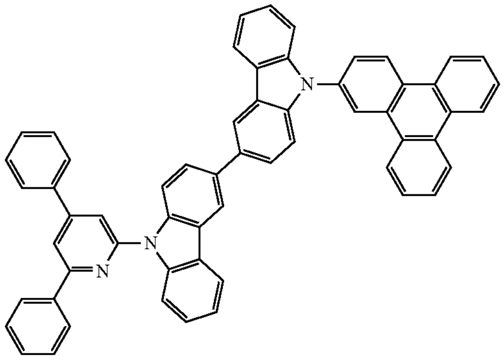
[HT-9]
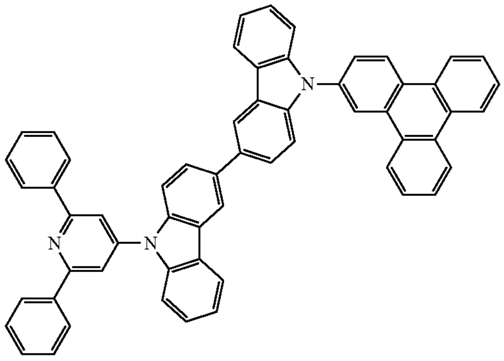
[HT-10]
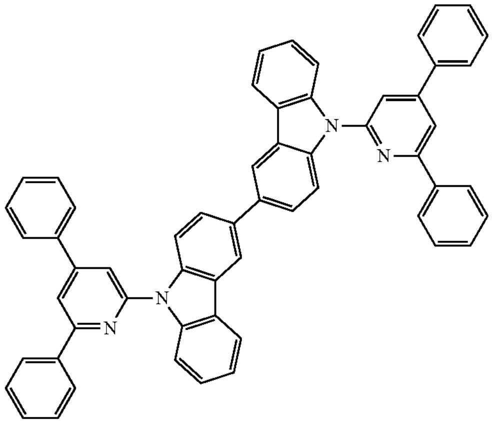

-continued
[HT-11]
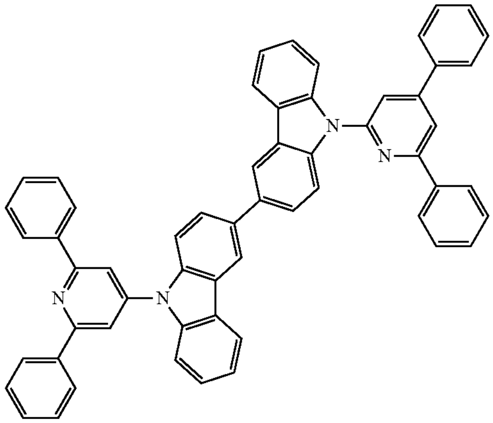
[HT-12]
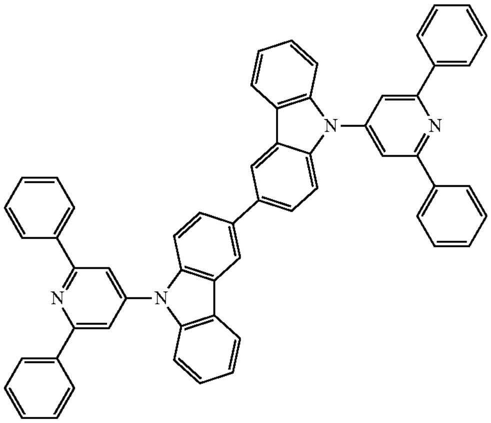
[HT-13]
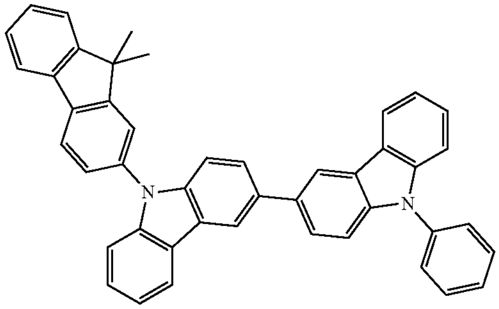
[HT-14]
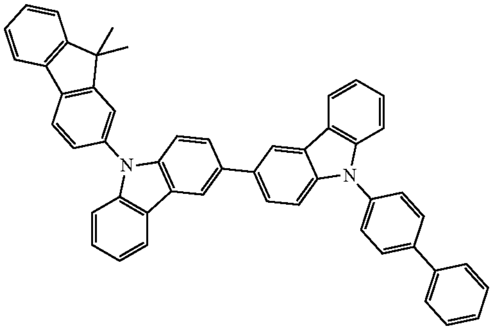
[HT-15]
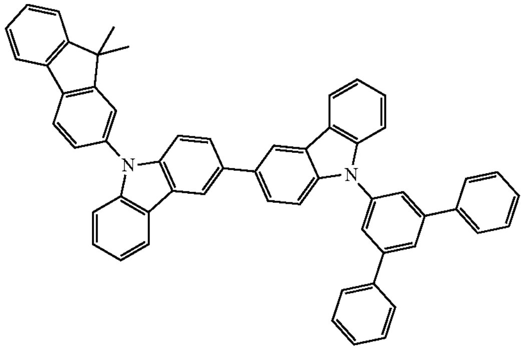
[HT-16]
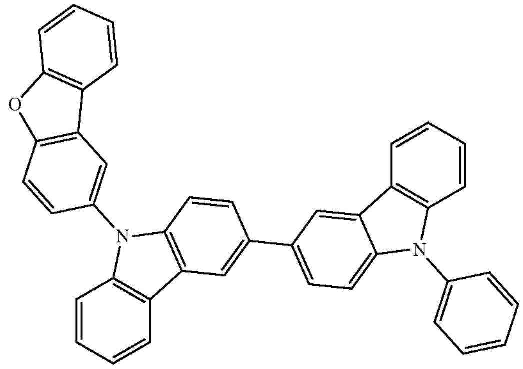
[HT-17]
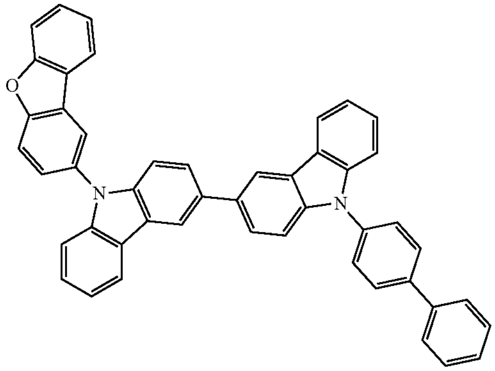
[HT-18]
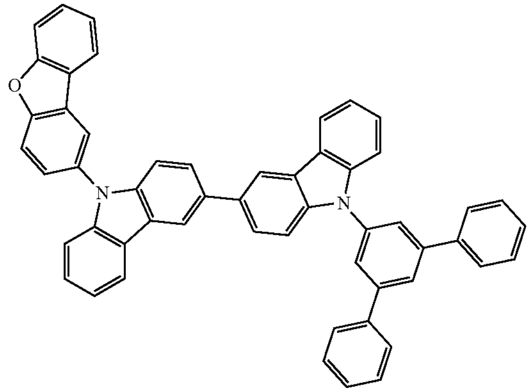

-continued
[HT-19]
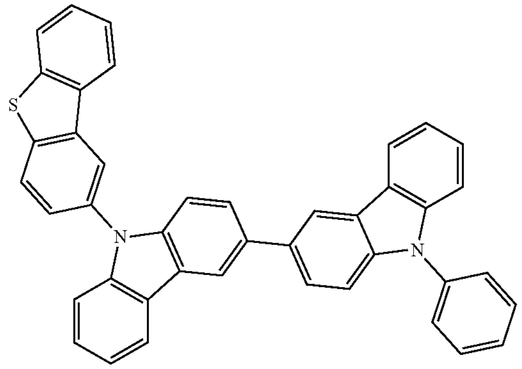
[HT-20]
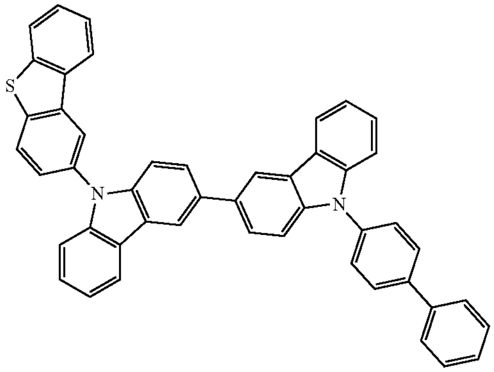
[HT-21]
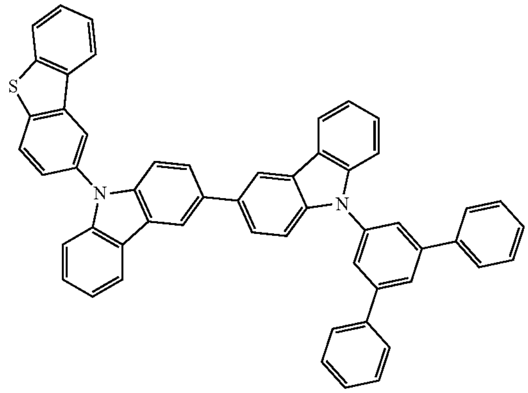
[HT-22]
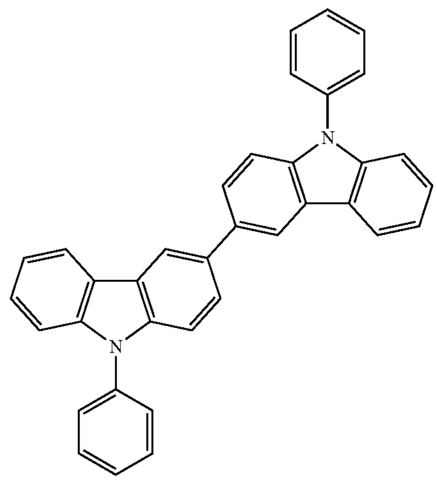
[HT-23]
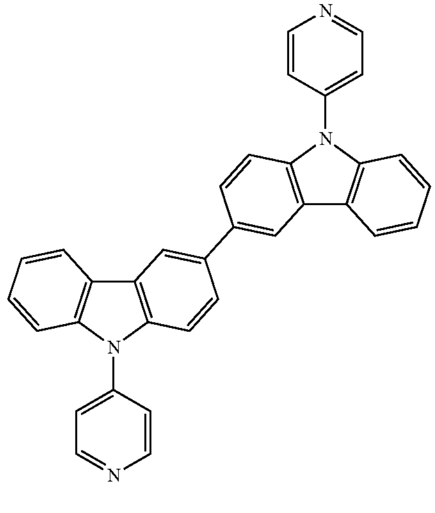
[HT-24]
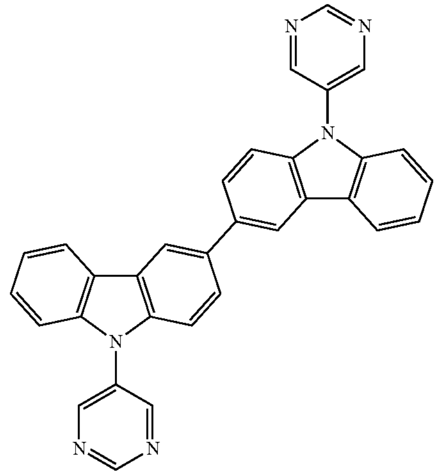

-continued
[HT-25]
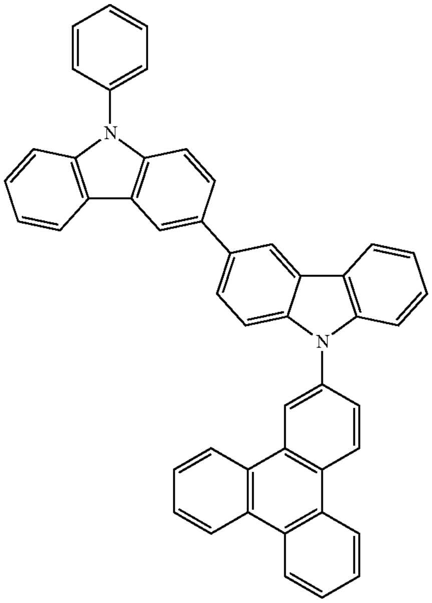
[HT-26]
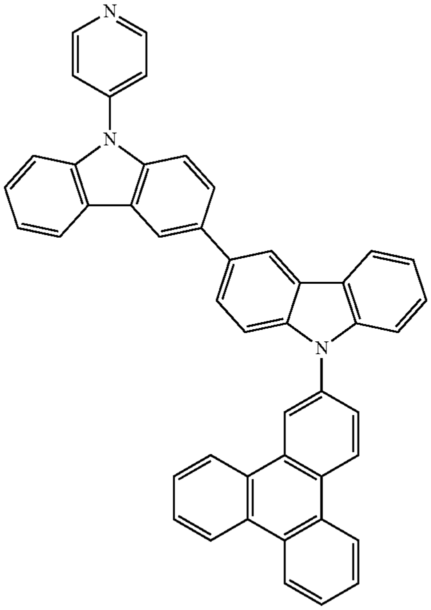
[HT-27]
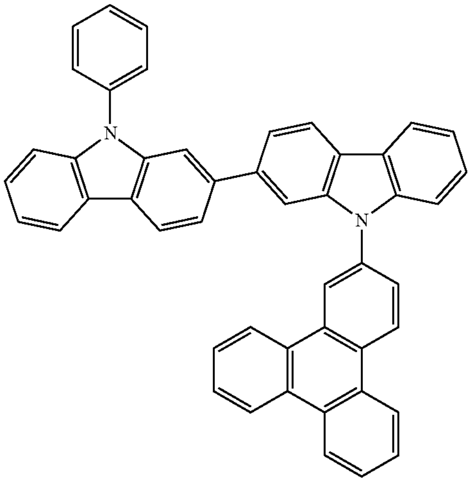
[HT-28]
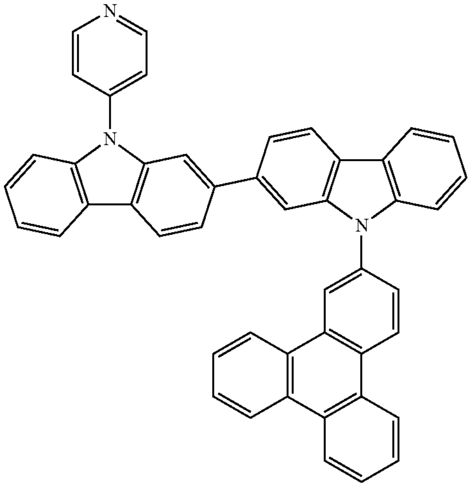
[HT-29]
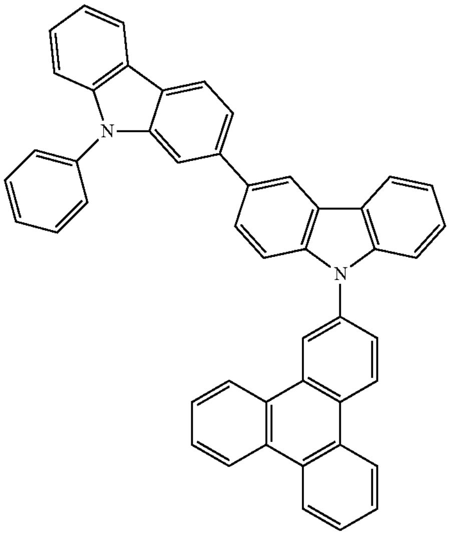
[HT-30]
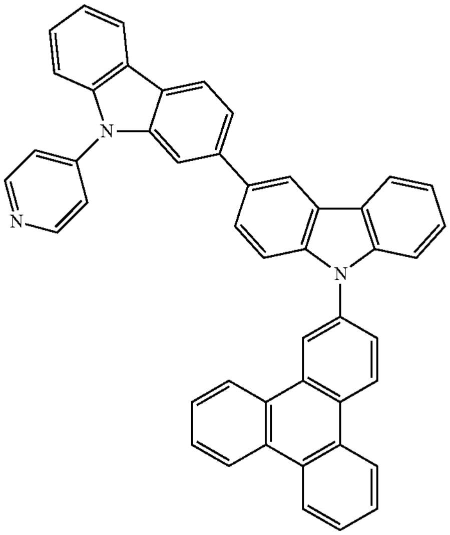

-continued
[HT-31]
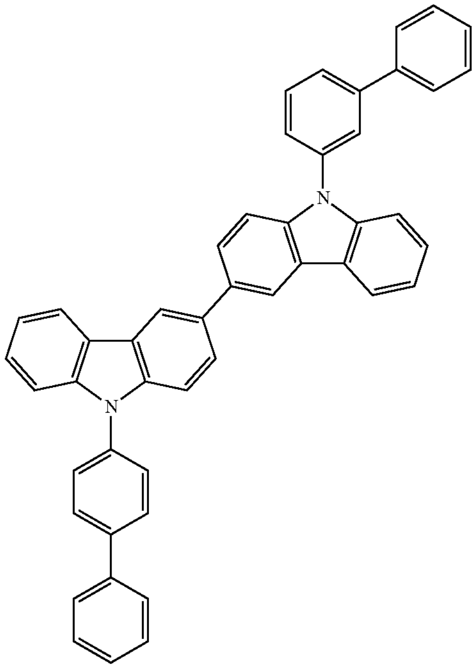
[HT-32]
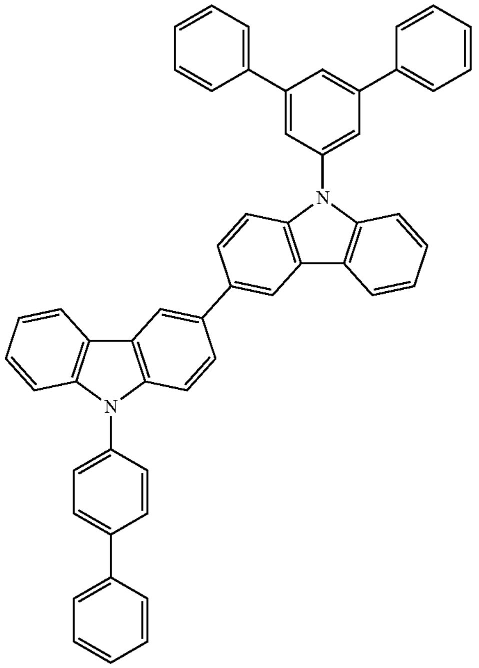
[HT-33]
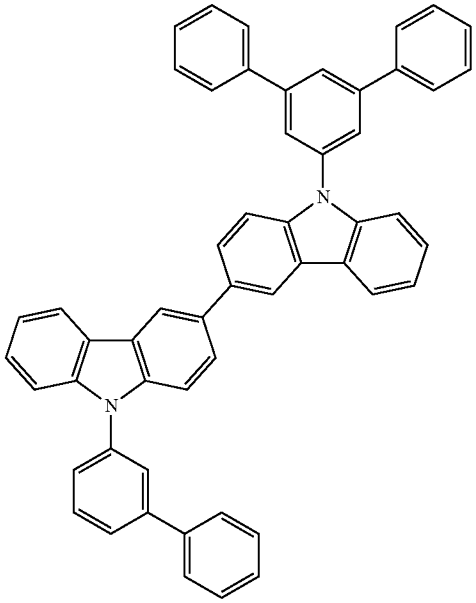
[HT-34]
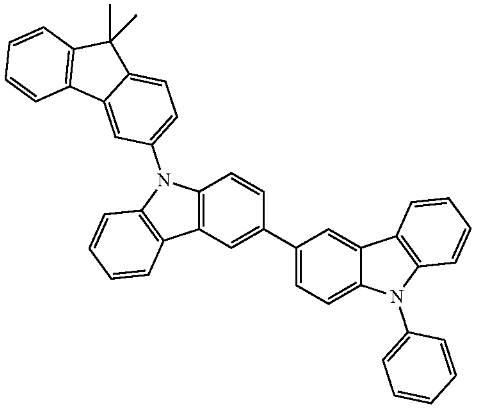

-continued
[HT-35]
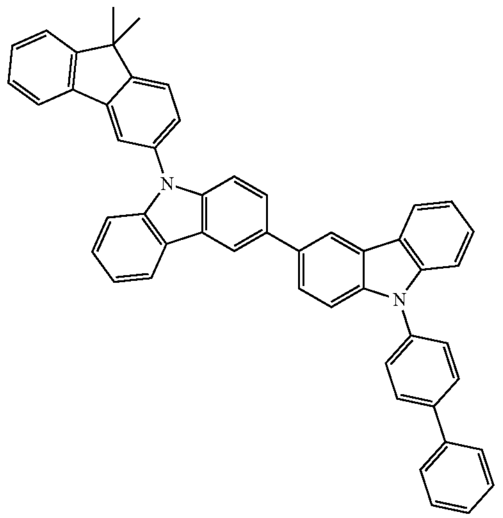
[HT-36]
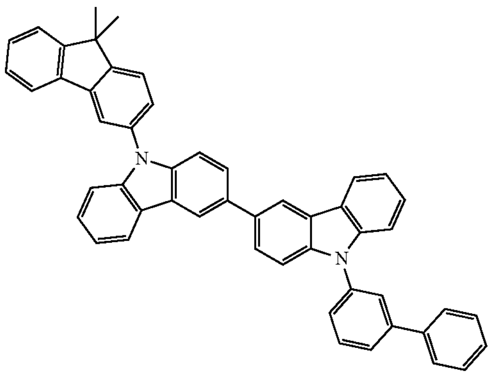
[HT-37]
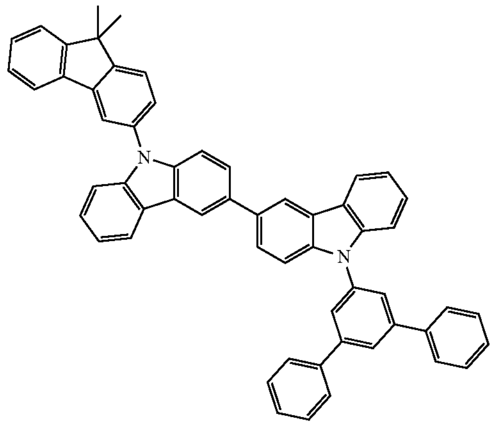
[HT-38]
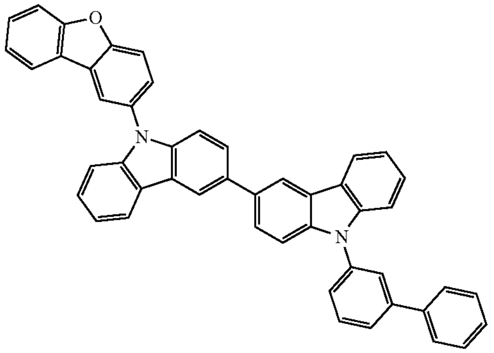
[HT-39]
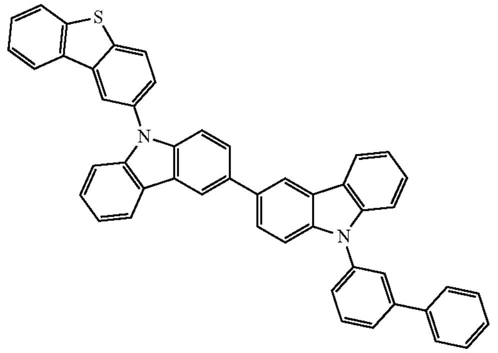
[HT-40]
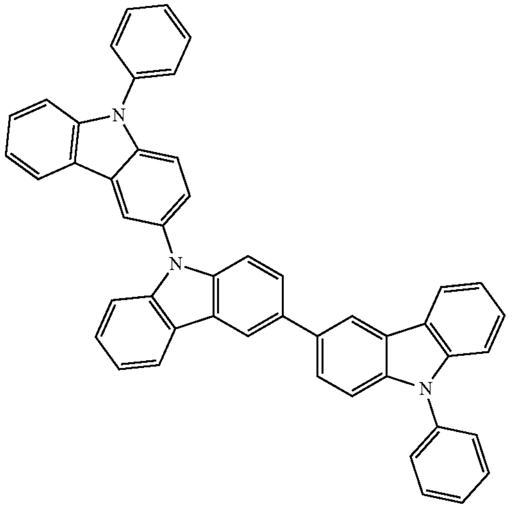

-continued
[HT-41]
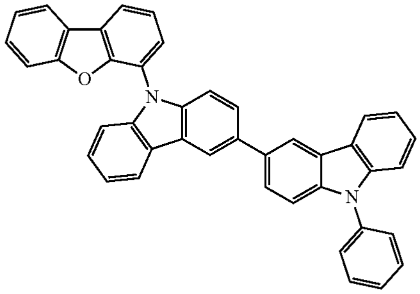
[HT-42]
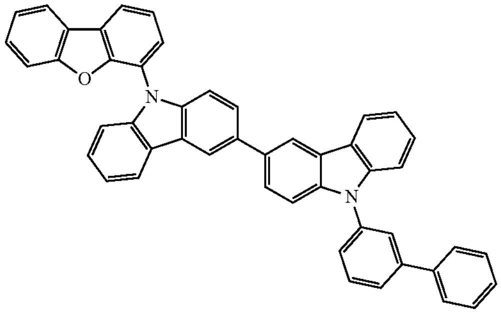
[HT-43]
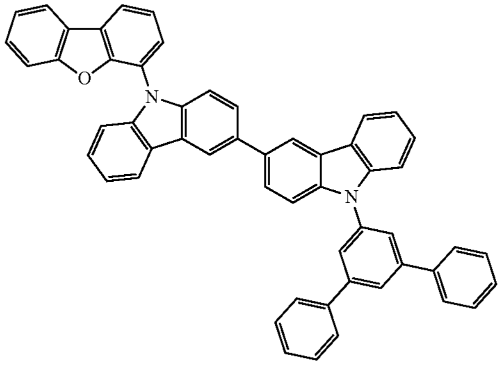
[HT-44]
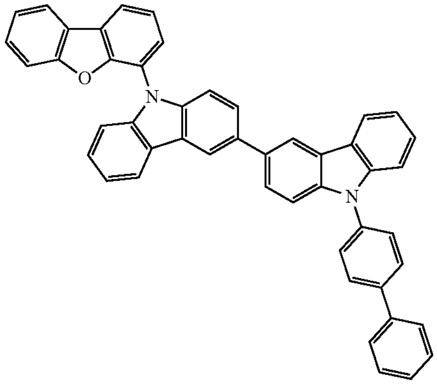
[HT-45]
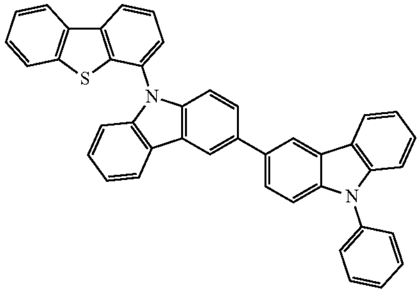
[HT-46]
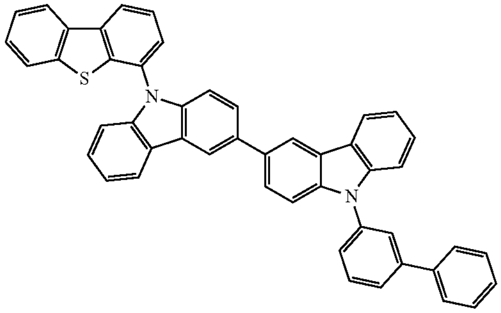
[HT-47]
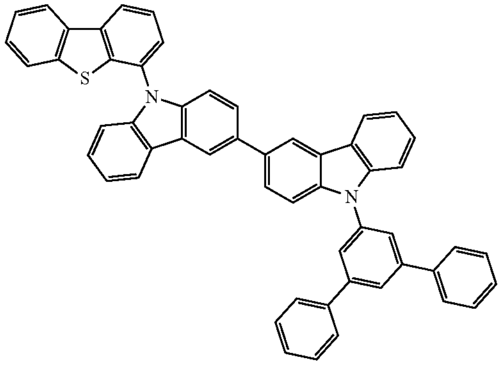
[HT-48]
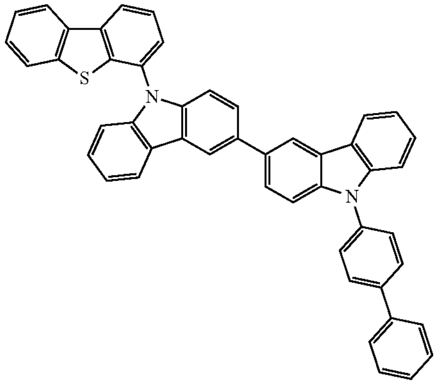

-continued
[HT-49]
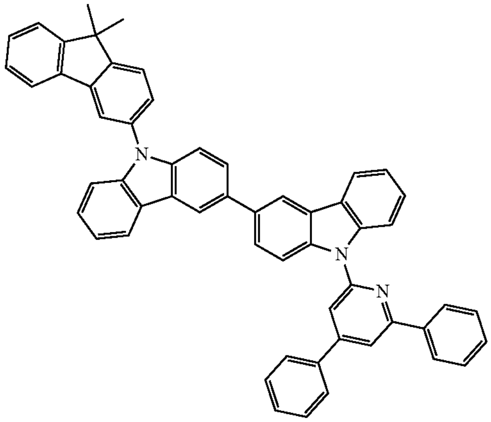
[HT-50]
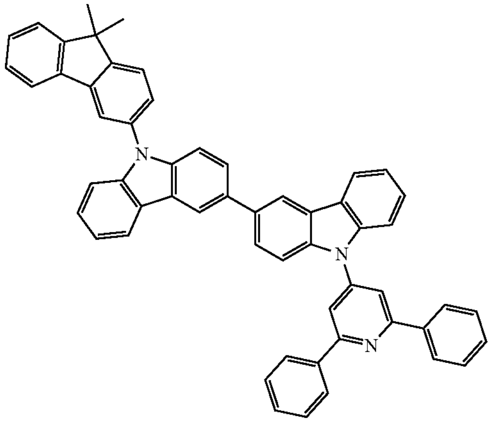
[HT-51]
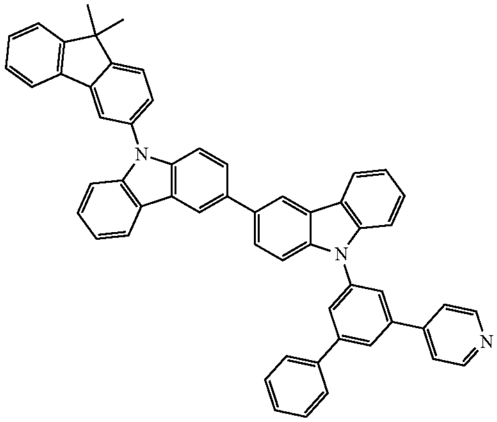
[HT-52]
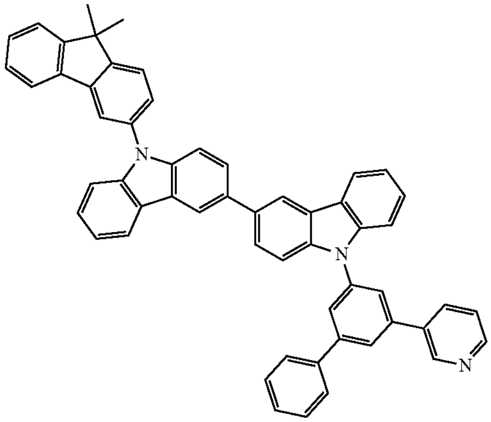
[HT-53]
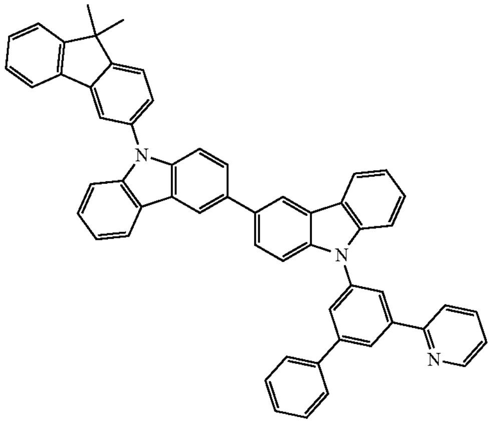
[HT-54]
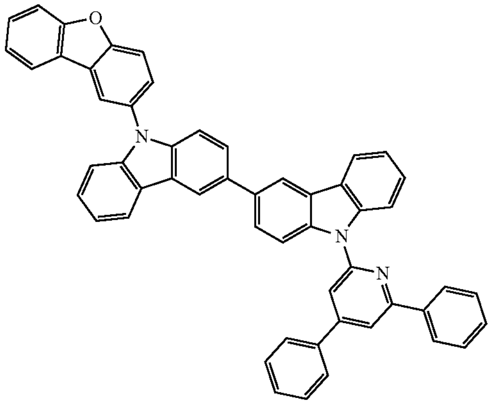

-continued
[HT-55]
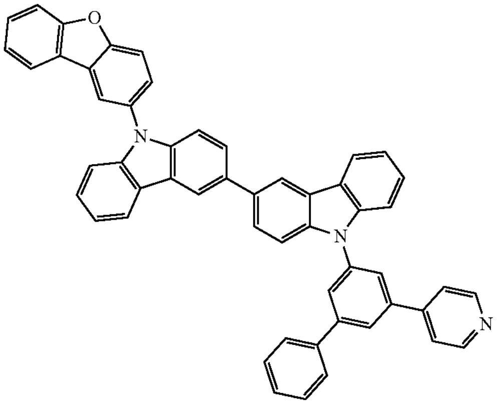
[HT-56]
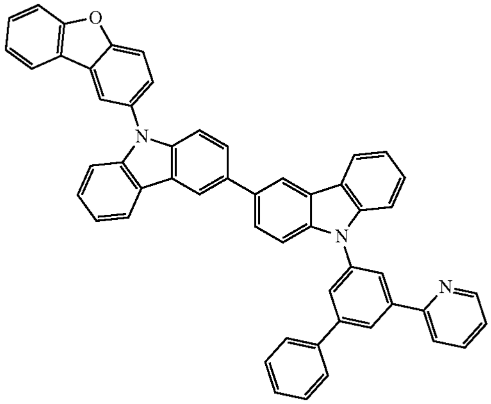
[HT-57]
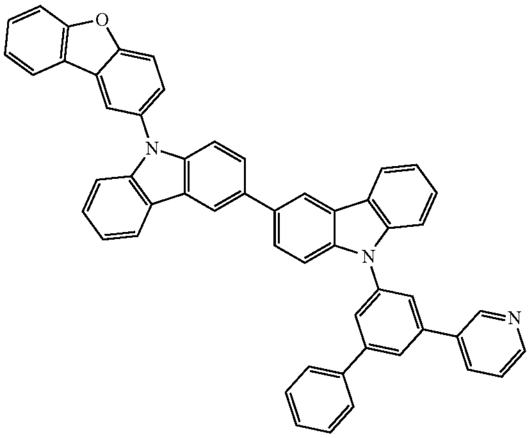
[HT-58]
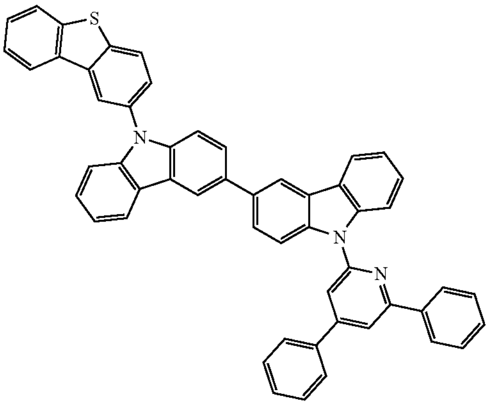
[HT-59]
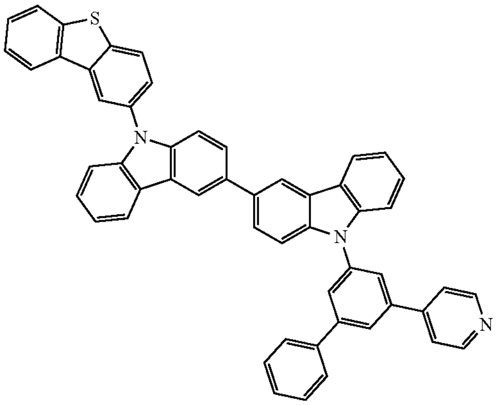
[HT-60]
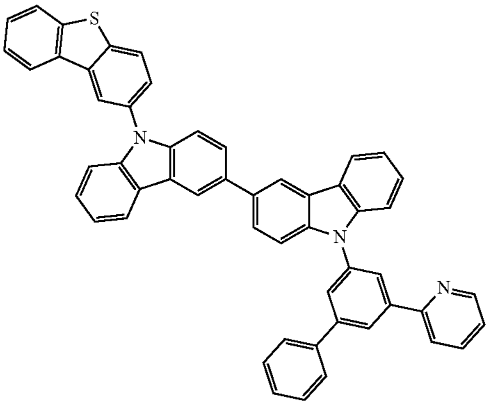

-continued
[HT-61]
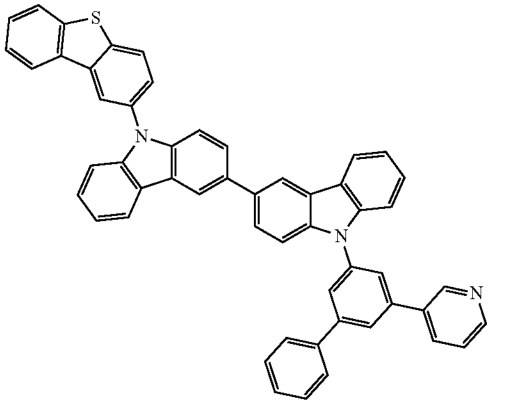
[HT-62]
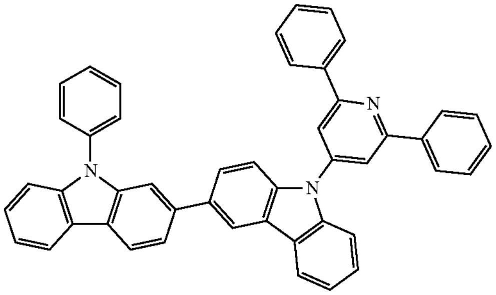
[HT-63]
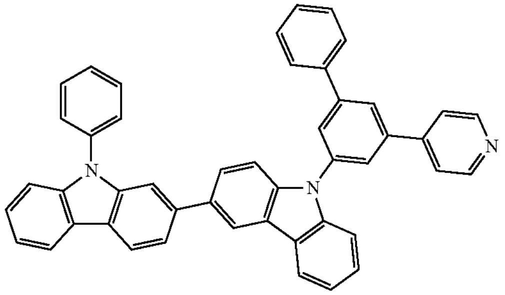
[HT-64]
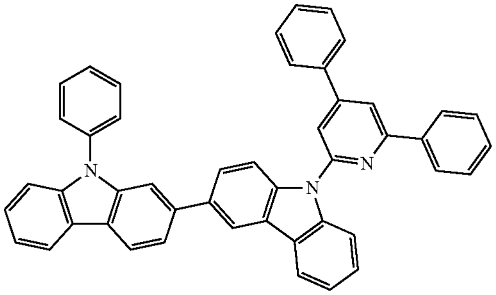
[HT-65]
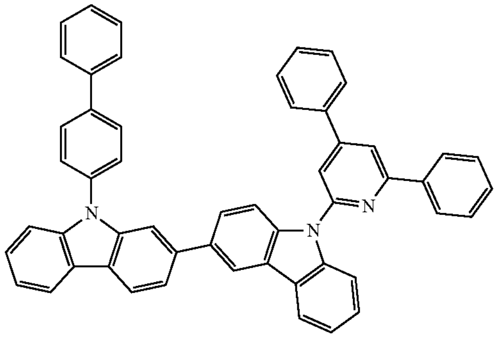
[HT-66]
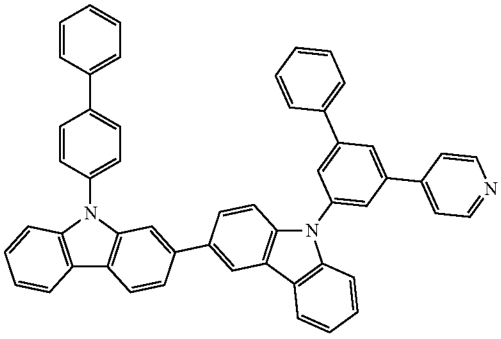
[HT-67]
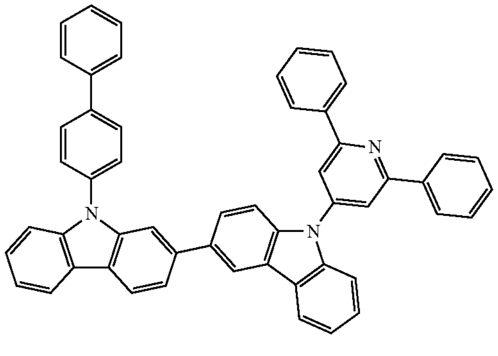
[HT-68]
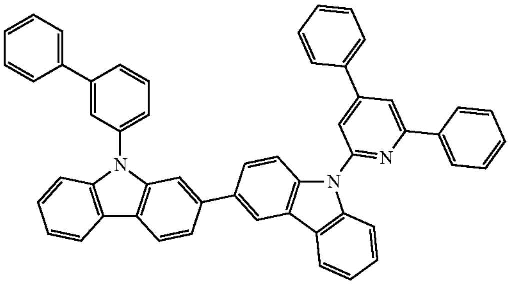

-continued
[HT-69]
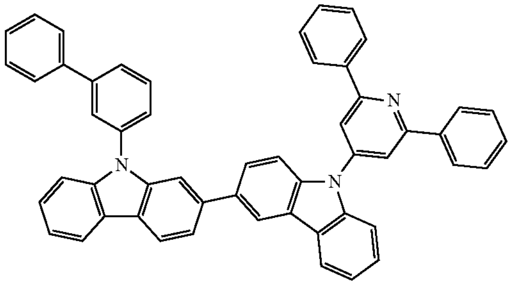
[HT-70]
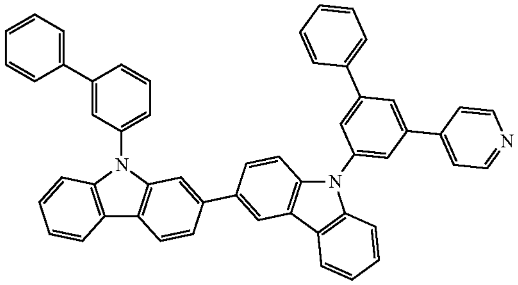
[HT-71]
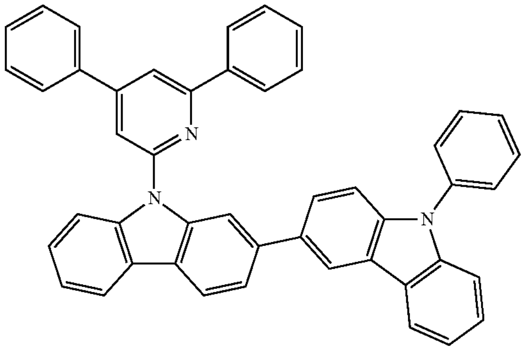
[HT-72]
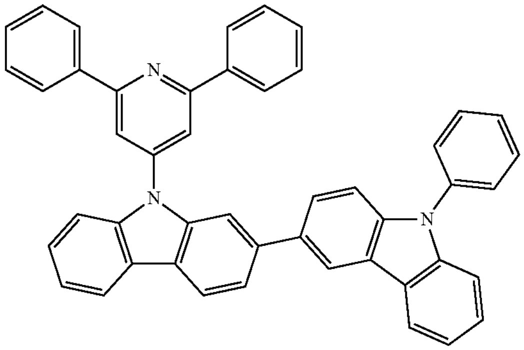
[HT-73]
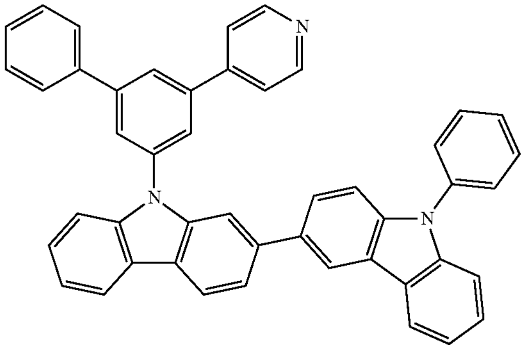
[HT-74]
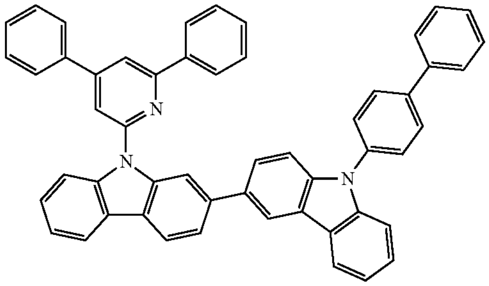
[HT-75]
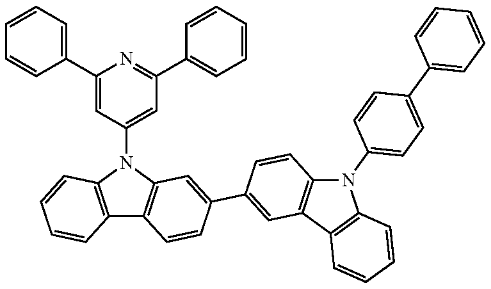
[HT-76]
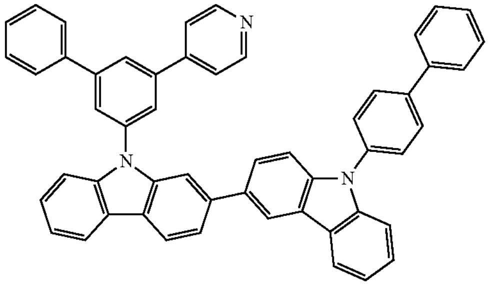
[HT-77]
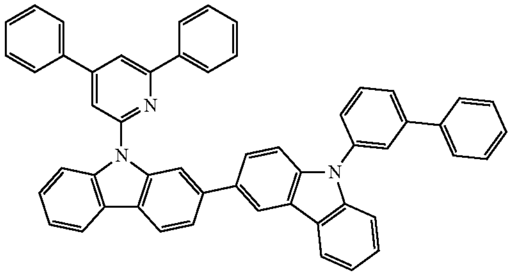
[HT-78]
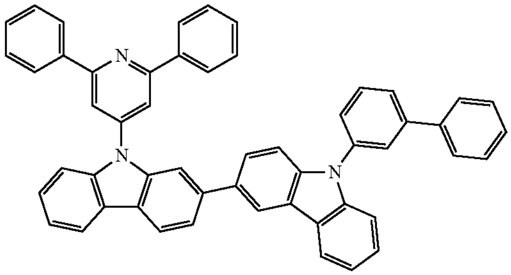

-continued
[HT-79]
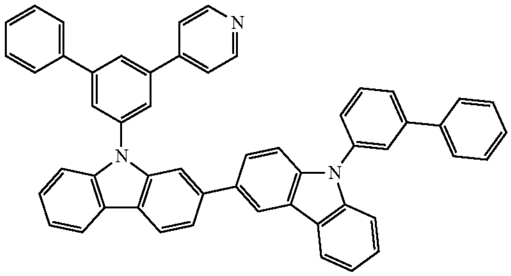
[HT-80]
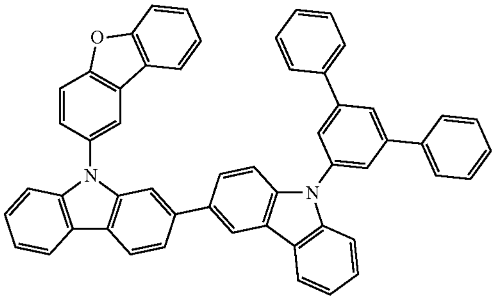
[HT-81]
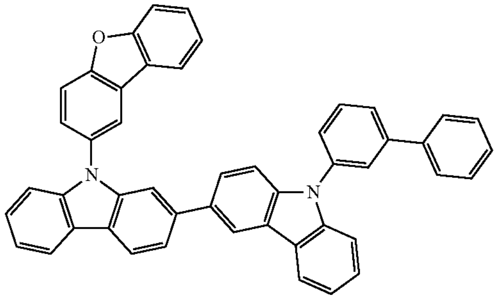
[HT-82]
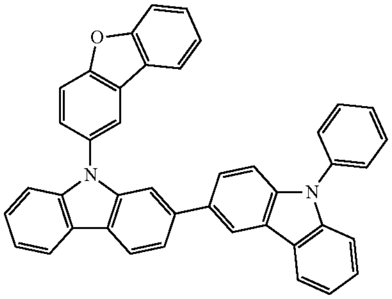
[HT-83]
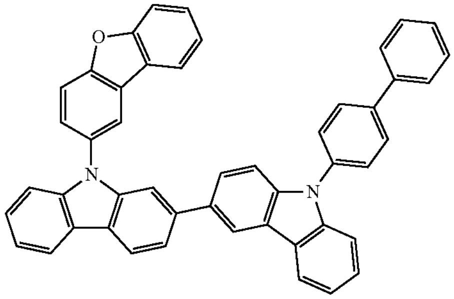
[HT-84]
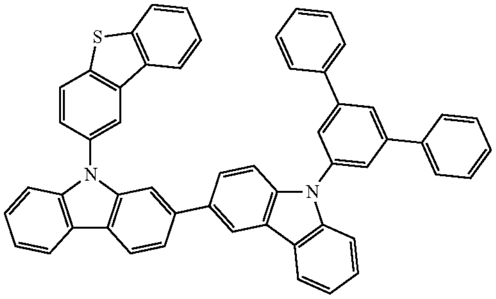
[HT-85]
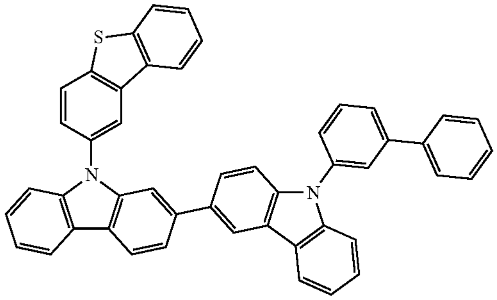
[HT-86]
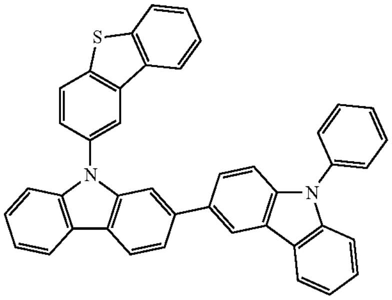

-continued
[HT-87]
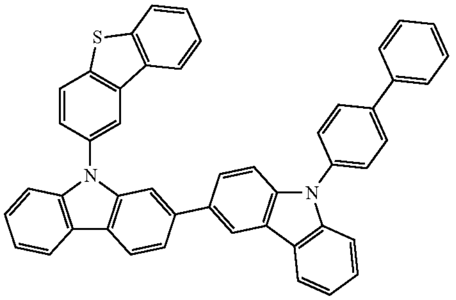
[HT-88]
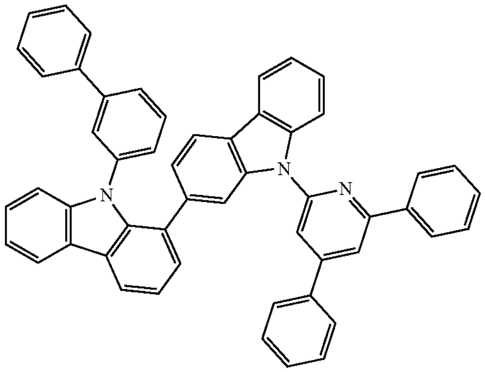
[HT-89]
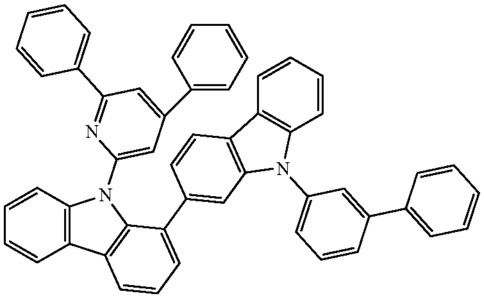
[HT-90]
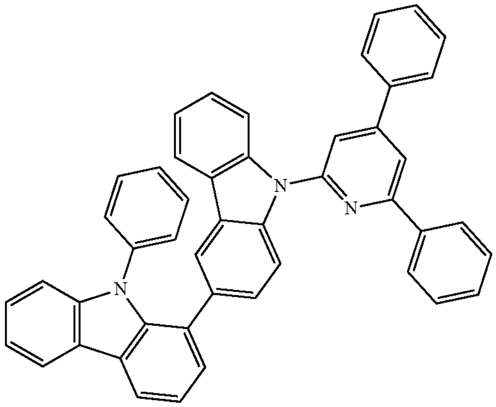
[HT-91]
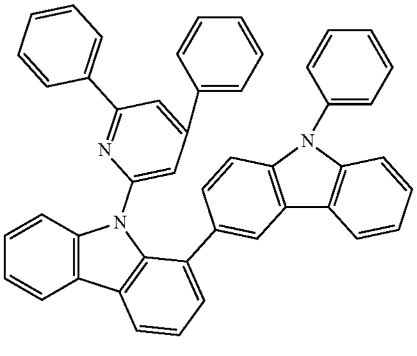
[HT-92]
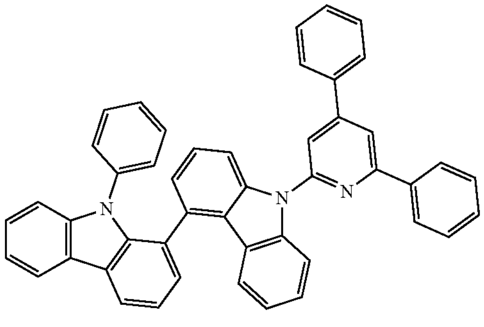
[HT-93]
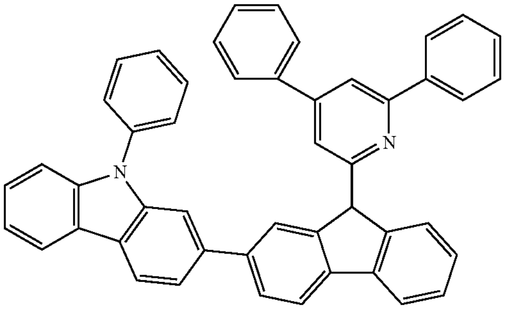
[HT-94]
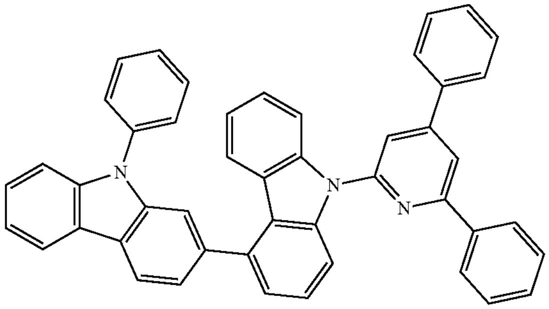

-continued
[HT-95]
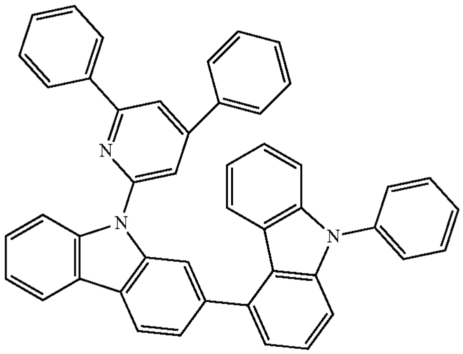
[HT-96]
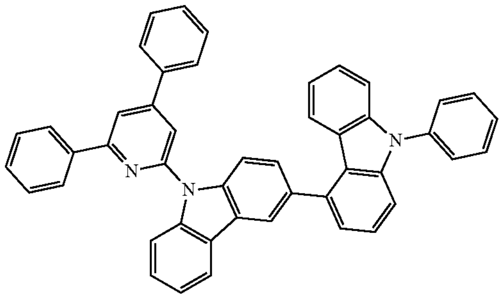
[HT-97]
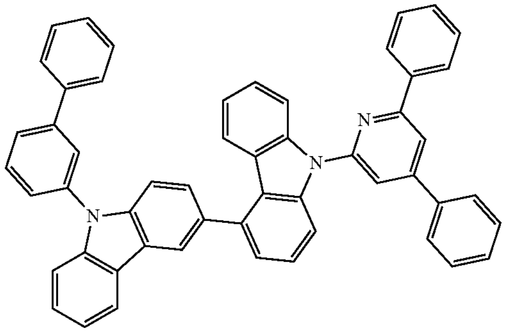
[HT-98]
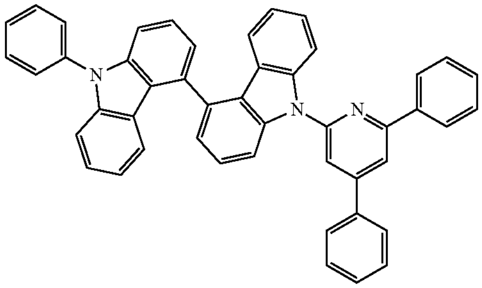
[HT-99]
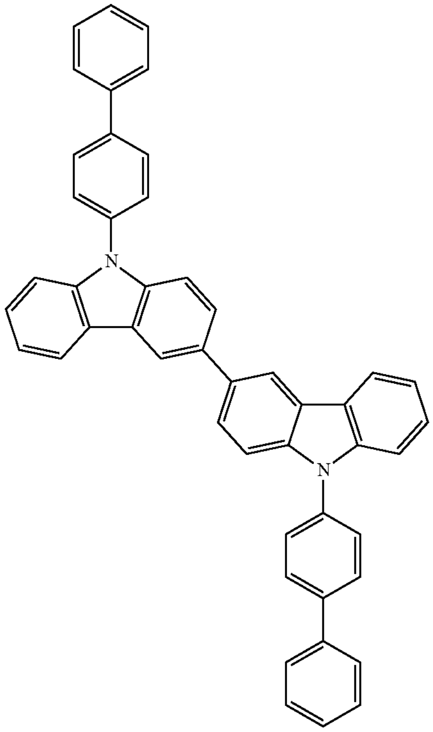
[HT-100]
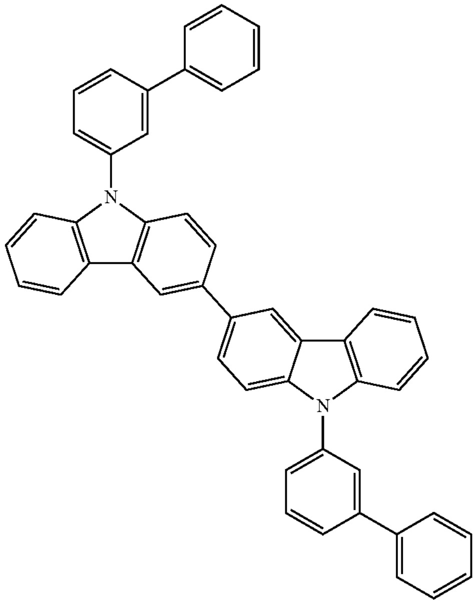

-continued
[HT-101]
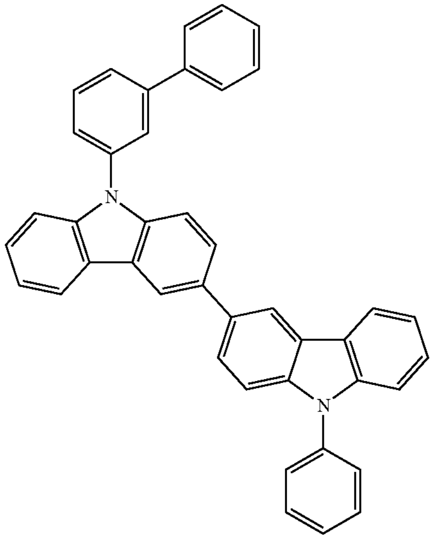
[HT-102]
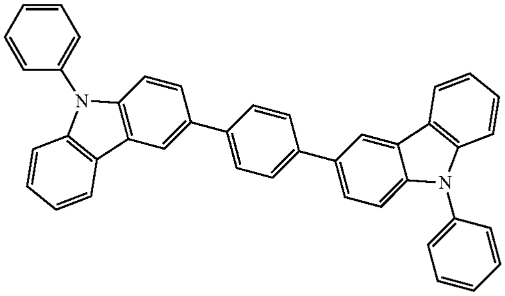
[HT-103]
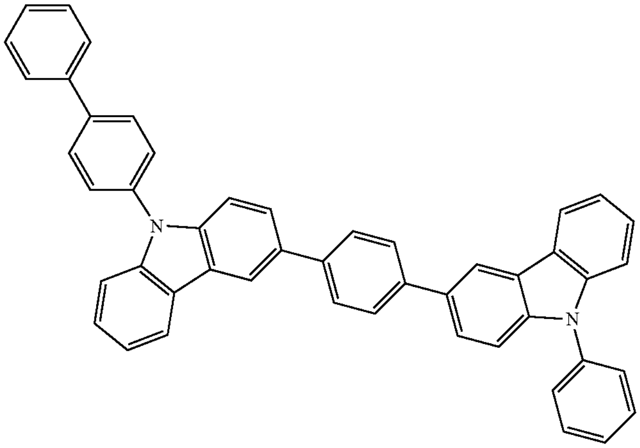
[HT-104]
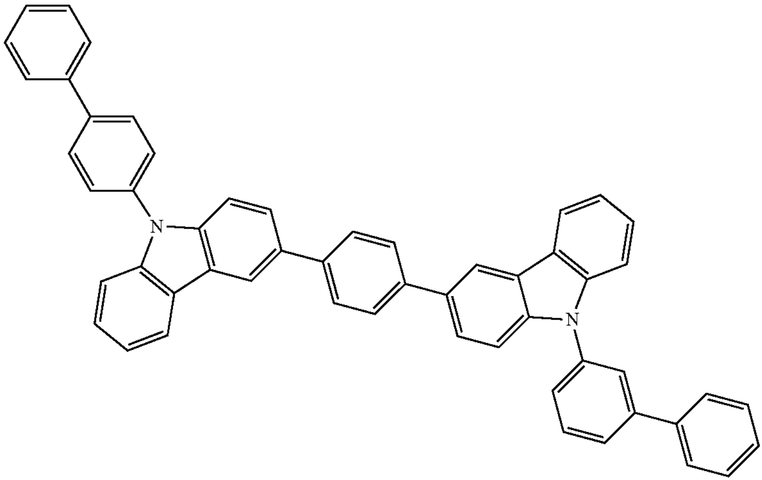

-continued
[HT-105]
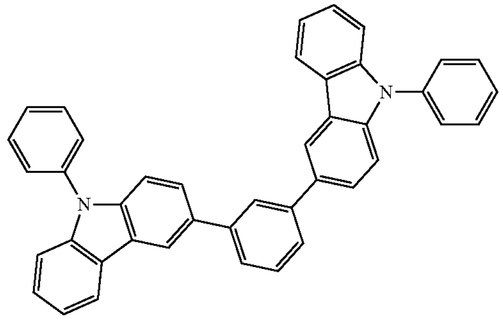
[HT-106]
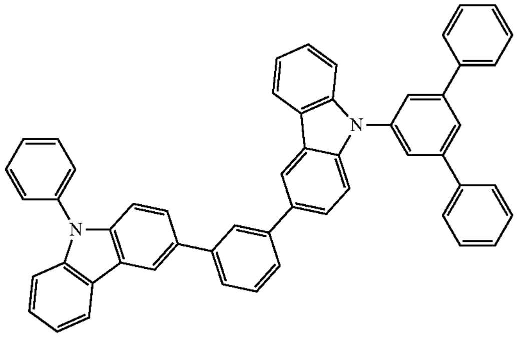
[HT-107]
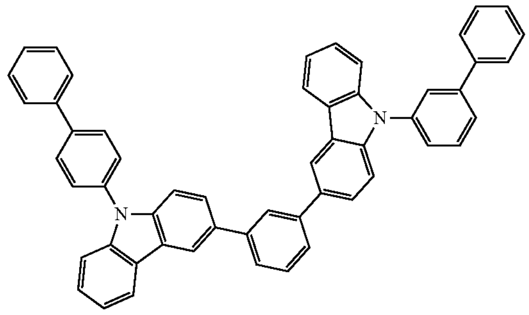
[HT-108]
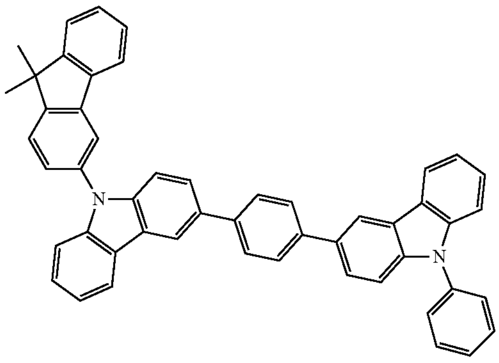
[HT-109]
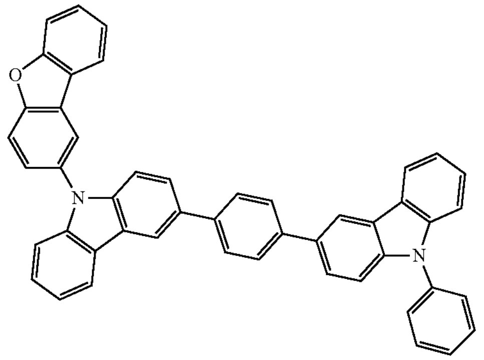
[HT-110]
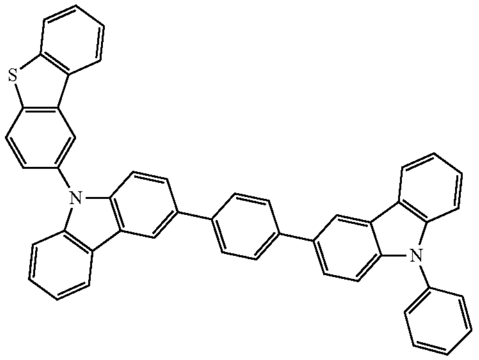
[HT-111]
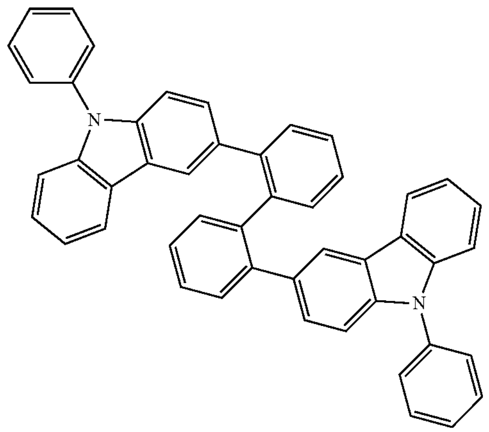
[HT-112]
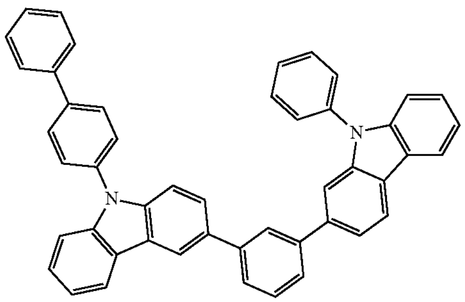

-continued
[HT-113]
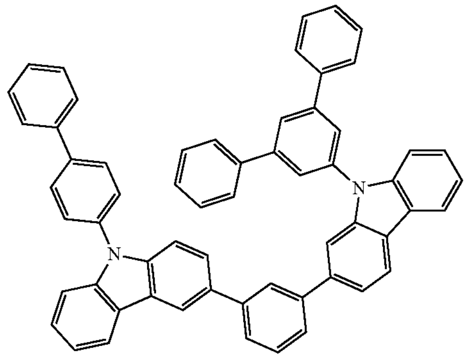
[HT-114]
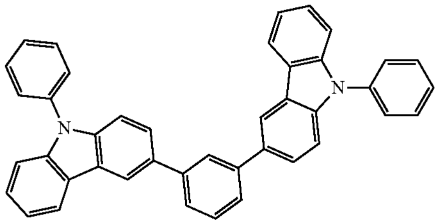
[HT-115]
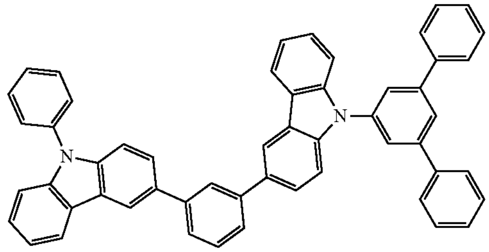
[HT-116]
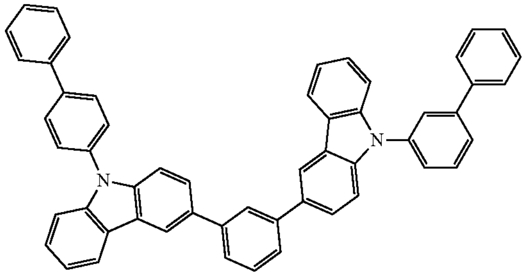
[HT-117]
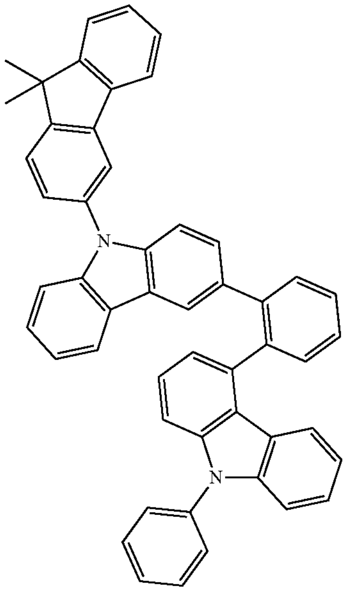
[HT-118]
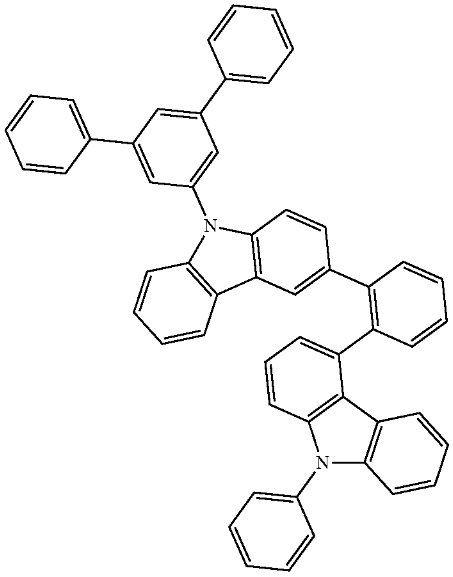

-continued
[HT-119]
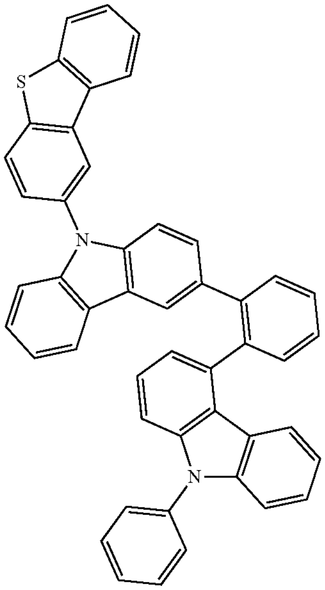
[HT-120]
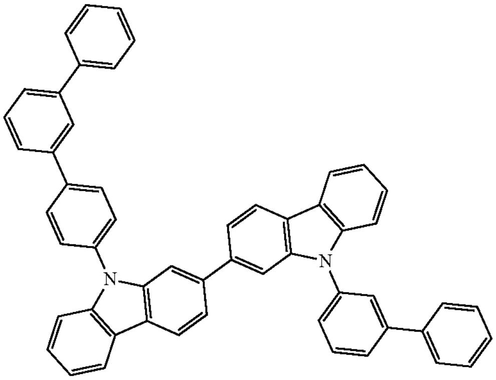
[HT-121]
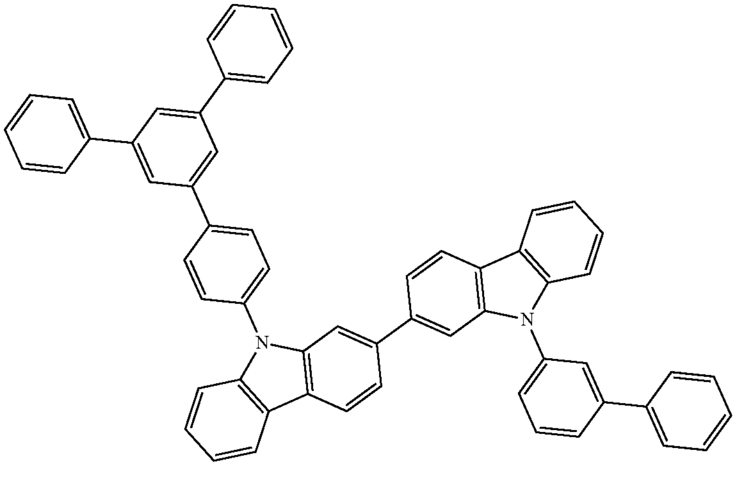

-continued
[HT-122]
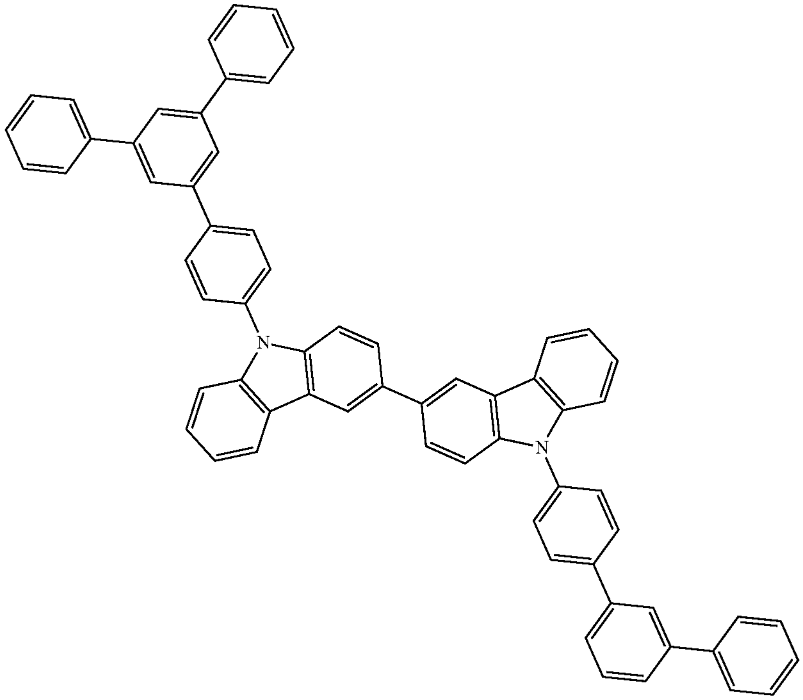
[HT-123]
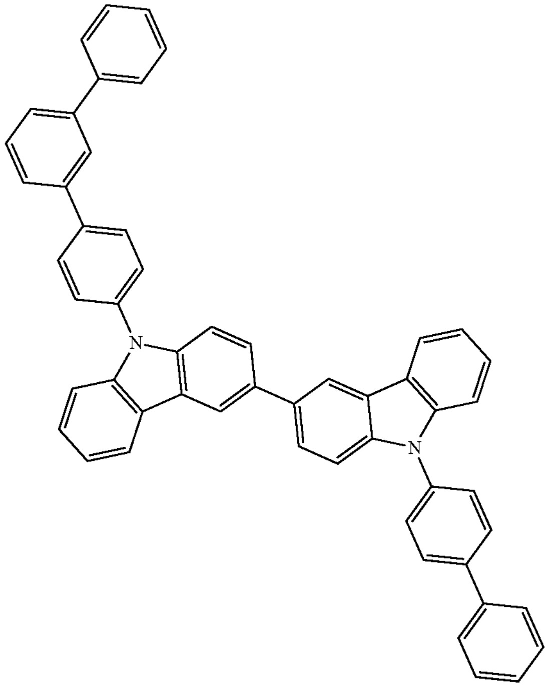

-continued
[HT-124]
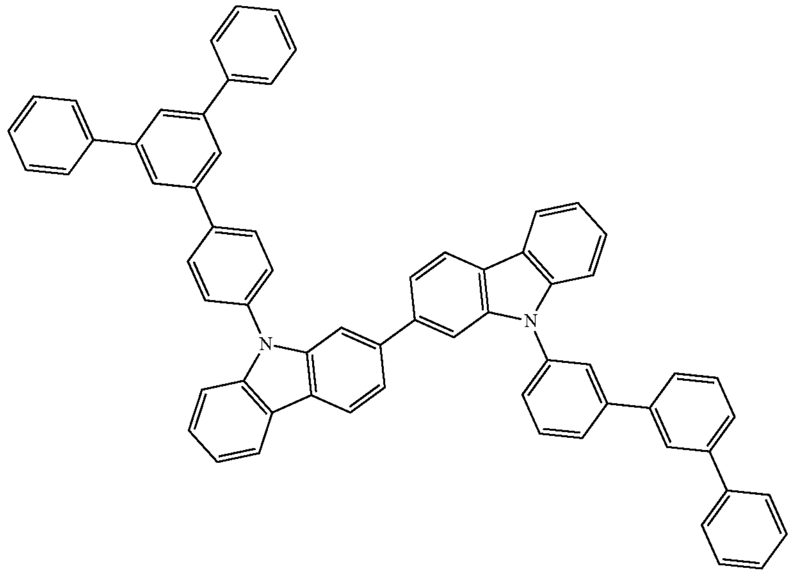
[HT-125]
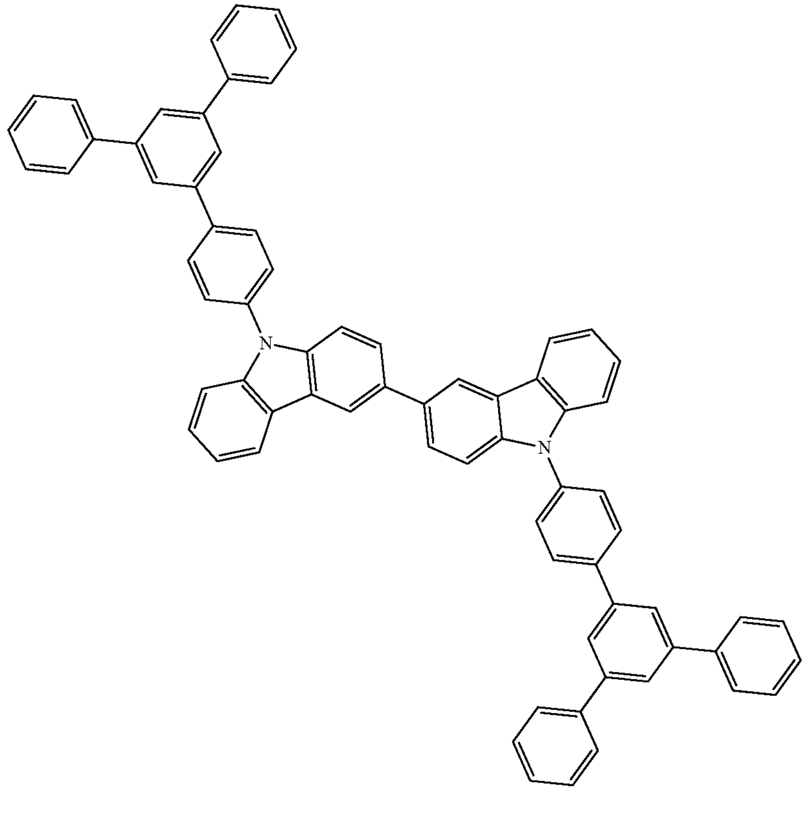

-continued
[HT-126]
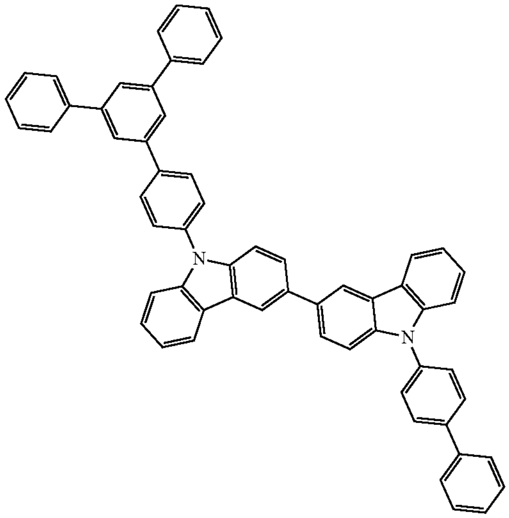
[HT-127]
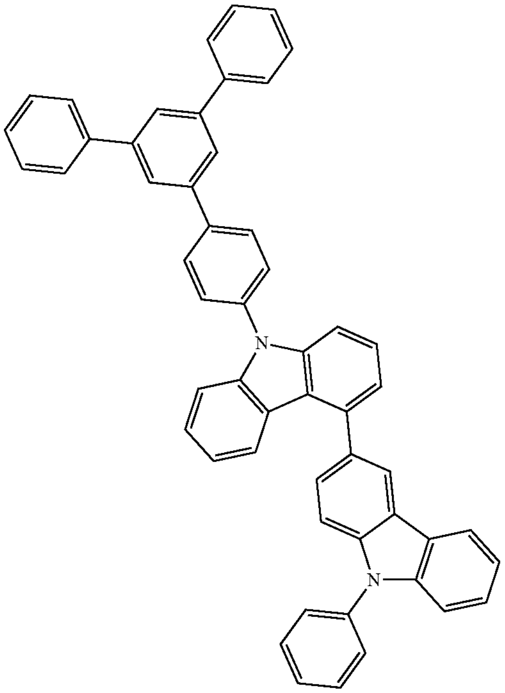
[HT-128]
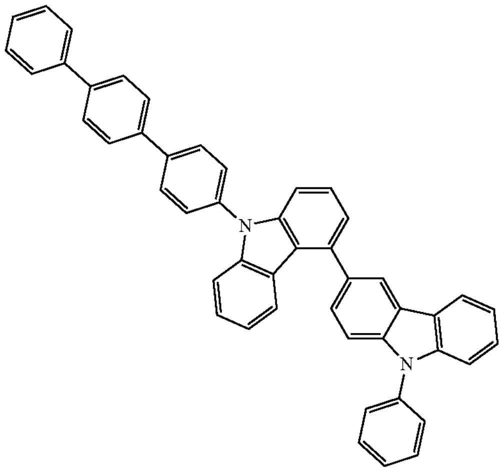
[HT-129]
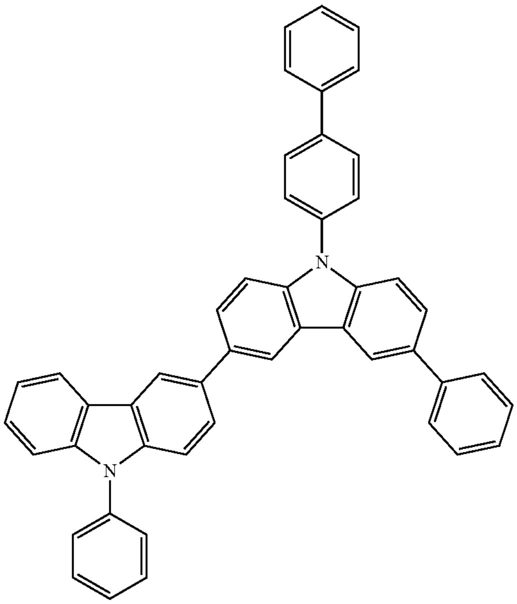

-continued
[HT-130]
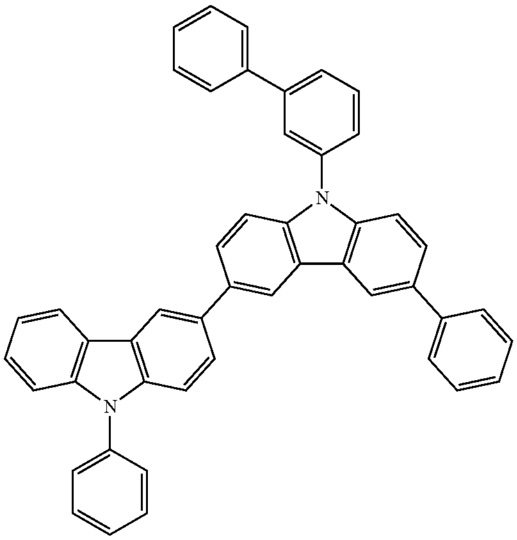
[HT-131]
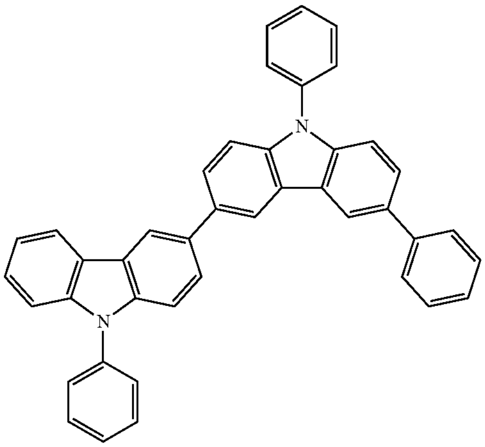
[HT-132]
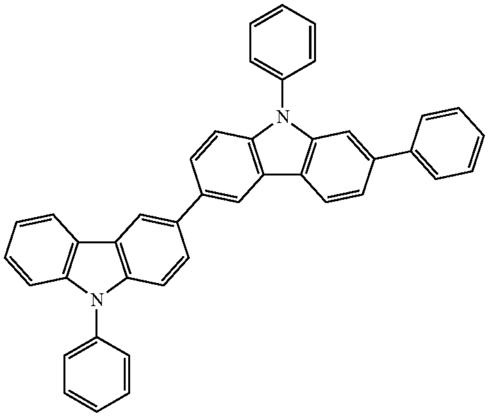
[HT-133]
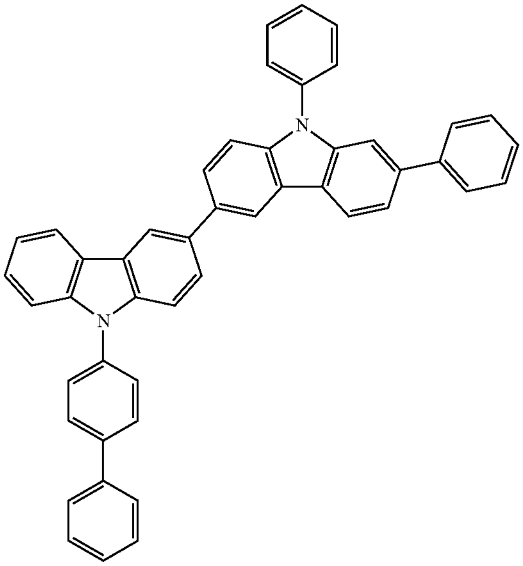
[HT-134]
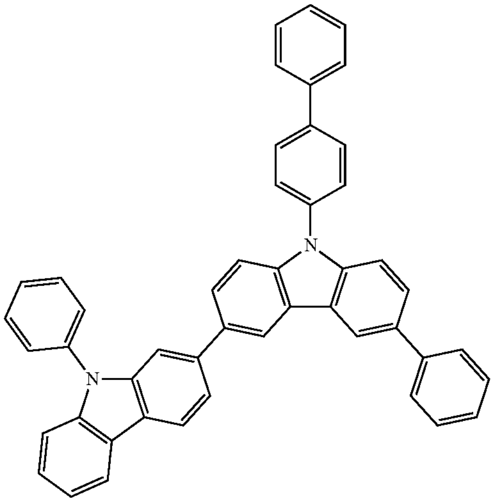
[HT-135]
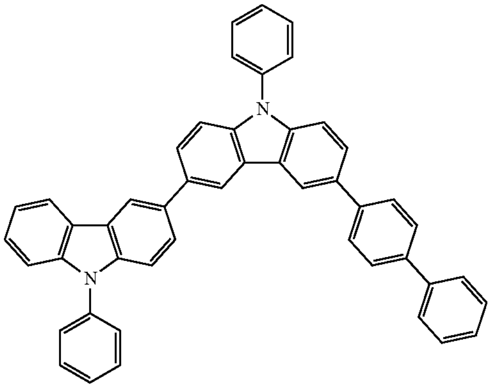

-continued

[HT-136]

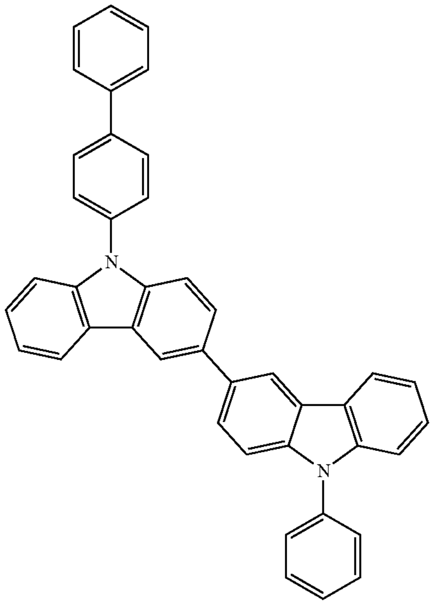

[HT-137]

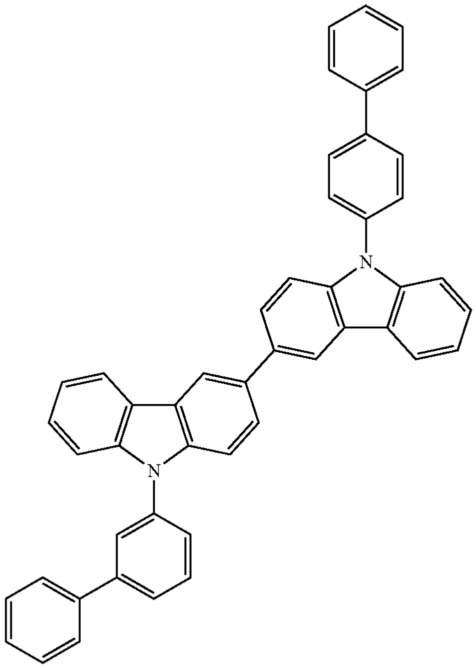

[HT-138]

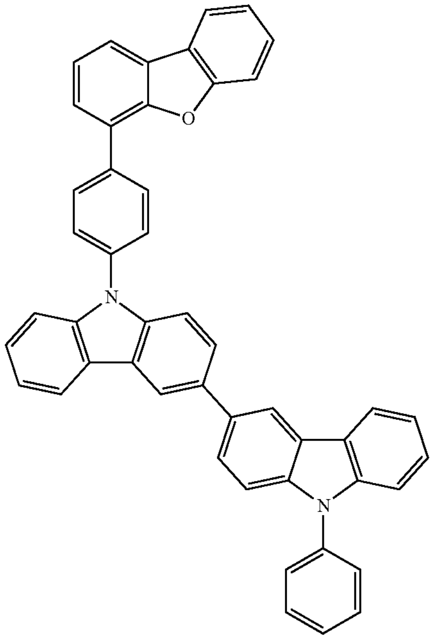

[HT-139]

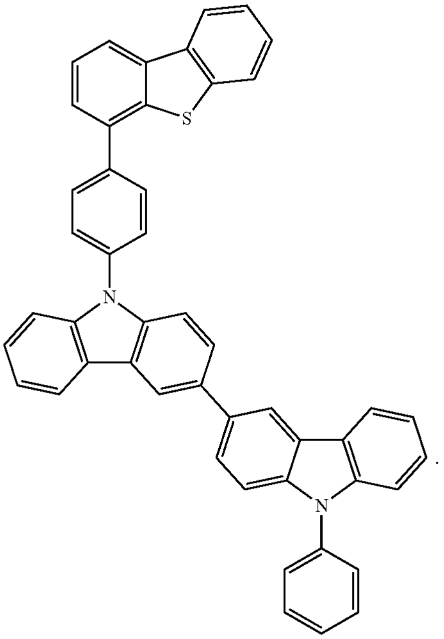

The aforementioned first host compound and second host compound may variously be combined to prepare various compositions.

The composition according to an embodiment of the present invention may include the compound represented by Chemical Formula 1-A or Chemical Formula 1-B as a first host and the compound represented by Chemical Formula C-8 or Chemical Formula C-17 of Group III as a second host.

For example, $*—Y^1—Z^1$ and $*—Y^2—Z^2$ of Chemical Formula 2 may independently be B-1 to B-6 of Group IV.

In a specific embodiment of the present invention, $L^1$ to $L^3$ of Chemical Formula 1-A and Chemical Formula 1-B may independently be a single bond, a para-phenylene group, a meta-phenylene group, or a biphenylene group, $R^1$ to $R^3$ may independently be hydrogen, $R^a$ may be hydrogen or a phenyl group, $R^b$ and $R^c$ may independently be a phenyl group, a meta-biphenyl group, a para-biphenyl group, a triphenylene group, a dibenzofuranyl group, or a dibenzothiophenyl group, and $*—Y^1—Z^1$ and $*—Y^2—Z^2$ of Chemical Formula 2 may independently be selected from B-1, B-2, B-3, B-5, and B-6 of Group IV.

The second host compound is used with the first host compound in the light emitting layer and increases charge mobility and stability, and thereby luminous efficiency and life-span characteristics may be improved. In addition, a ratio of the second host compound and the first host compound may be adjusted and thereby charge mobility may be controlled. When the composition of the present invention is used as a host, a combination ratio thereof may be different according to types and properties of a used dopant.

A combination ratio of the compounds in the composition of the present invention in the composition may be for example a weight ratio of about 1:9 to 9:1, specifically 1:9 to 8:2, 1:9 to 7:3, 1:9 to 6:4, 1:9 to 5:5, 2:8 to 8:2, 2:8 to 7:3, 2:8 to 6:4, or 2:8 to 5:5.

In addition, when the composition of the present invention is used as a host, the first compound for an organic optoelectronic device and the second compound for an organic optoelectronic device may be included in a weight ratio of 1:9 to 5:5, 2:8 to 5:5, or 3:7 to 5:5. For example, the first compound for an organic optoelectronic device and the second compound for an organic optoelectronic device may be included in a weight ratio of 5:5 or 3:7. Within the ranges, efficiency and life-span may be simultaneously improved.

The composition may further include at least one organic compound in addition to the aforementioned first host compound and second host compound.

The composition for an organic optoelectronic device may further include a dopant. The dopant may be a red, green, or blue dopant.

The dopant is mixed in a small amount to cause light emission, and may be generally a material such as a metal complex that emits light by multiple excitation into a triplet or more. The dopant may be, for example an inorganic, organic, or organic/inorganic compound, and one or more types thereof may be used.

The dopant may be for example a phosphorescent dopant and examples of the phosphorescent dopant may be an organometallic compound including Ir, Pt, Os, Ti, Zr, Hf, Eu, Tb, Tm, Fe, Co, Ni, Ru, Rh, Pd, or a combination thereof. The phosphorescent dopant may be for example a compound represented by Chemical Formula Z, but is not limited thereto.

[Chemical Formula Z]

$L_2MX$

In Chemical Formula Z, M is a metal, and L and X are the same or different, and are a ligand to form a complex compound with M.

The M may be for example Ir, Pt, Os, Ti, Zr, Hf, Eu, Tb, Tm, Fe, Co, Ni, Ru, Rh, Pd, or a combination thereof and the L and X may be for example a bidendate ligand.

Hereinafter, an organic optoelectronic device including the aforementioned composition for an organic optoelectronic device is described.

An organic optoelectronic device according to another embodiment includes an anode and a cathode facing each other and at least one organic layer disposed between the anode and the cathode, wherein the organic layer includes the aforementioned composition for an organic optoelectronic device.

For example, the organic layer may include a light emitting layer and the light emitting layer may include the composition for an organic optoelectronic device of the present invention.

Specifically, the composition for an organic optoelectronic device may be included as a host, for example a green host of the light emitting layer.

In addition, the organic layer may include a light emitting layer and at least one auxiliary layer selected from a hole injection layer, a hole transport layer, an electron blocking layer, an electron transport layer, an electron injection layer, and a hole blocking layer and the auxiliary layer may include the composition for an organic optoelectronic device.

The organic optoelectronic device may be any element to convert electrical energy into photoenergy and vice versa without particular limitation, and may be, for example an organic photoelectric element, an organic light emitting diode, an organic solar cell, and an organic photo conductor drum.

Herein, an organic light emitting diode as one example of an organic optoelectronic device is described referring to drawings.

FIGS. 1 and 2 are cross-sectional views of an organic light emitting diode according to embodiments.

Referring to FIG. 1, an organic light emitting diode 100 according to an embodiment includes an anode 120 and a cathode 110 facing each other and an organic layer 105 interposed between the anode 120 and cathode 110.

The anode 120 may be made of a conductor having a large work function to help hole injection, and may be for example a metal, a metal oxide and/or a conductive polymer. The anode 120 may be, for example a metal such as nickel, platinum, vanadium, chromium, copper, zinc, gold, and the like or an alloy thereof; a metal oxide such as zinc oxide, indium oxide, indium tin oxide (ITO), indium zinc oxide (IZO), and the like; a combination of a metal and an oxide such as ZnO and Al or $SnO_2$ and Sb; a conductive polymer such as poly(3-methylthiophene), poly(3,4-(ethylene-1,2-dioxy)thiophene) (PEDT), polypyrrole, and polyaniline, but is not limited thereto.

The cathode 110 may be made of a conductor having a small work function to help electron injection, and may be for example a metal, a metal oxide, and/or a conductive polymer. The cathode 110 may be for example a metal such as magnesium, calcium, sodium, potassium, titanium, indium, yttrium, lithium, gadolinium, aluminum silver, tin, lead, cesium, barium, and the like or an alloy thereof; a multi-layer structure material such as LiF/Al, $LiO_2$/Al, LiF/Ca, LiF/Al, and $BaF_2$/Ca, but is not limited thereto.

The organic layer 105 includes a light emitting layer 130 including the aforementioned compound for an organic optoelectronic device.

FIG. 2 is a cross-sectional view showing an organic light emitting diode according to another embodiment.

Referring to FIG. 2, an organic light emitting diode 200 further includes a hole auxiliary layer 140 in addition to the light emitting layer 130. The hole auxiliary layer 140 may further increase hole injection and/or hole mobility and block electrons between the anode 120 and the light emitting layer 130. The hole auxiliary layer 140 may be, for example a hole transport layer, a hole injection layer, and/or an electron blocking layer and may include at least one layer.

The organic layer 105 of FIG. 1 or 2 may further include an electron injection layer, an electron transport layer, an electron transport auxiliary layer, a hole transport layer, a hole transport auxiliary layer, a hole injection layer, or a combination thereof even if they are not shown. The compound for an organic optoelectronic device of the present invention may be included in the organic layer. The organic light emitting diodes 100 and 200 may be manufactured by forming an anode or a cathode on a substrate, forming an organic layer using a dry film formation method such as a vacuum deposition method (evaporation), sputtering, plasma plating, and ion plating or a wet coating method such as spin coating, dipping, and flow coating, and forming a cathode or an anode thereon.

The organic light emitting diode may be applied to an organic light emitting diode (OLED) display.

Hereinafter, the embodiments are illustrated in more detail with reference to examples. These examples, however, are not in any sense to be interpreted as limiting the scope of the invention.

Hereinafter, starting materials and reactants used in Examples and Synthesis Examples were purchased from Sigma-Aldrich Co. Ltd. or TCI Inc. as far as there are no particular descriptions or were synthesized by known methods.

(Preparation of Compound for Organic Optoelectronic Device)

The compound as one specific examples of the present invention was synthesized through the following steps.

(First Compound for Organic Optoelectronic Device)

(Reaction Scheme 1)

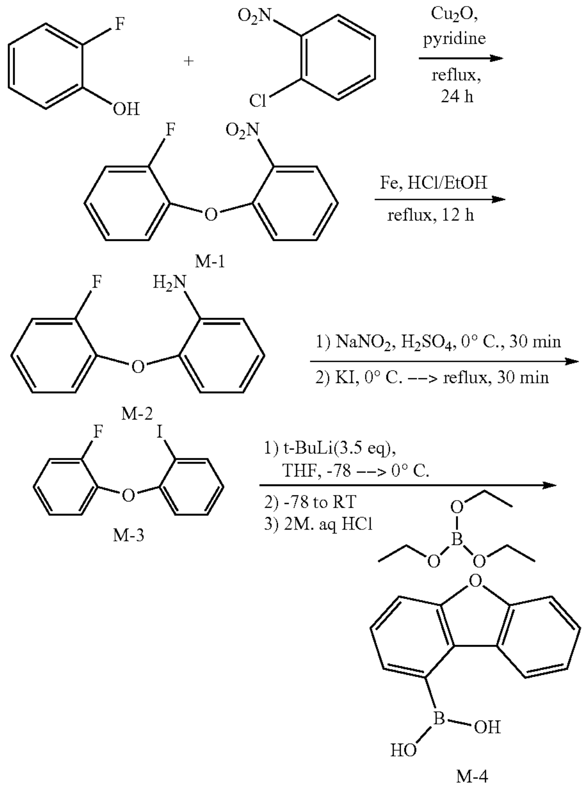

M-1

M-2

M-3

M-4

Synthesis Example 1: Synthesis of Intermediate M-1

25 g (223 mmol) of 2-fluorophenol, 52.7 g (335 mmol) of 2-chloronitrobenzene, and 32 g (223 mol) of copper oxide (I) were put in a 500 mL flask, 223 mL of pyridine was added thereto, and the obtained mixture was refluxed for 24 hours under a nitrogen flow. When a reaction was complete, the pyridine was concentrated under a reduced pressure, and a product therein was dissolved in toluene, and then, insoluble materials remaining therein were filtered with a filter paper. A filtrate thereof was extracted with a 2 M HCl aqueous solution, and an organic layer obtained therefrom was neutralized with a sodium carbonate aqueous solution and washed. The organic layer obtained through the extraction was treated by using magnesium sulfate to remove moisture, and a product therefrom was filtered, concentrated, and purified through silica gel column chromatography with n-hexane/dichloromethane (a volume ratio of 8:2) to obtain Intermediate M-1 as light yellow liquid (37 g, a yield of 71%).

GC-Mass (theoretical value: 233.05 g/mol, measured value: M+1=234 g/mol)

Synthesis Example 2: Synthesis of Intermediate M-2

37 g (159 mmol) of Intermediate M-1 and 320 ml of ethanol were put in a 1 L flask, and an atmosphere thereof was substituted with a nitrogen atmosphere. Herein, 26.6 g (335 mmol) of an iron (Fe) powder was added thereto, the reaction solution was cooled down to 0° C., 66 ml (795 mmol) of concentrated hydrochloric acid (12 M) was added thereto, and the obtained mixture was refluxed and stirred for 12 hours under the nitrogen atmosphere. When a reaction was complete, the reaction solution was added to a sodium hydroxide aqueous solution for neutralization, and the reactants was filtered with a filter paper and washed with toluene. An organic layer obtained through extraction was treated with magnesium sulfate to remove moisture, filtered, and concentrated, and a product therefrom was purified through silica gel column chromatography with n-hexane/dichloromethane (a volume ratio of 7:3) to obtain Intermediate M-2 as a light beige solid (24 g, a yield of 75%).

GC-Mass (theoretical value: 203.07 g/mol, measured value: M+1=204 g/mol)

Synthesis Example 3: Synthesis of Intermediate M-3

24 g (118 mmol) of Intermediate M-2 was put in a 500 mL flask, 59 ml of a 6 M sulfuric acid aqueous solution was added thereto at 0° C., and the obtained mixture was stirred at 0° C. While the reaction solution was maintained at 0° C., an aqueous solution prepared by dissolving 9 g (130 mmol) of sodium nitrite in 36 ml of distilled water was slowly added thereto. The obtained mixture was stirred at 0° ° C.for 30 minutes. An aqueous solution prepared by dissolving 25 g (153 mmol) of potassium iodide in 63 ml of distilled water was slowly added thereto, 0.11 g (1.77 mmol) of a copper powder was added thereto, and the obtained mixture was refluxed and stirred for 1 hour. When a reaction was complete, the resultant was extracted with dichloromethane, and an organic layer obtained therefrom was washed with a potassium carbonate aqueous solution. Then, the organic layer obtained through the extraction under a reduced pressure was treated with magnesium sulfate to remove moisture was filtered, concentrated, and purified through silica gel column chromatography with n-hexane/dichloromethane (a volume ratio of 9:1) to obtain Intermediate M-3 as colorless liquid (28.5 g, a yield of 77%).

GC-Mass (theoretical value: 313.96 g/mol, measured value: M+1=315 g/mol)

Synthesis Example 4: Synthesis of Intermediate M-4

28 g (89.1 mmol) of Intermediate M-3 was put in a 1 L flask, 268 ml of anhydrous tetrahydrofuran was added thereto, and the obtained mixture was stirred. While the reaction solution was maintained under a nitrogen atmosphere at −78° C., 173 mL of tertiary butyllithium [1.7 M in pentane] was slowly added thereto. The obtained mixture was stirred for 20 minutes and then, for 30 minutes at 0° C.

The reaction solution was cooled down again to −78° C., and 16.9 g (116 mmol) of triethylborate was slowly added thereto. The obtained mixture was stirred for 30 minutes at −78° C. and then, for one hour at room temperature. When a reaction was complete, a small amount of methanol was added thereto. 134 mL of a 2 M HCl aqueous solution was added thereto, and the obtained mixture was stirred at room temperature for 2 hours. The resultant was extracted with diethylether and distilled water, an organic layer therefrom was concentrated under a reduced pressure, the residue thereof was dissolved in ethylacetate and filtered with silica gel, and an appropriate amount of a filtrate therefrom was concentrated, and then, hexane was added thereto for recrystallization. A solid generated therein was filtered, washed with hexane, and dried to obtain Intermediate M-4 as a white solid (13 g, a yield of 70%).

Synthesis Example 5: Synthesis of Intermediate M-5

(Reaction Scheme 2)

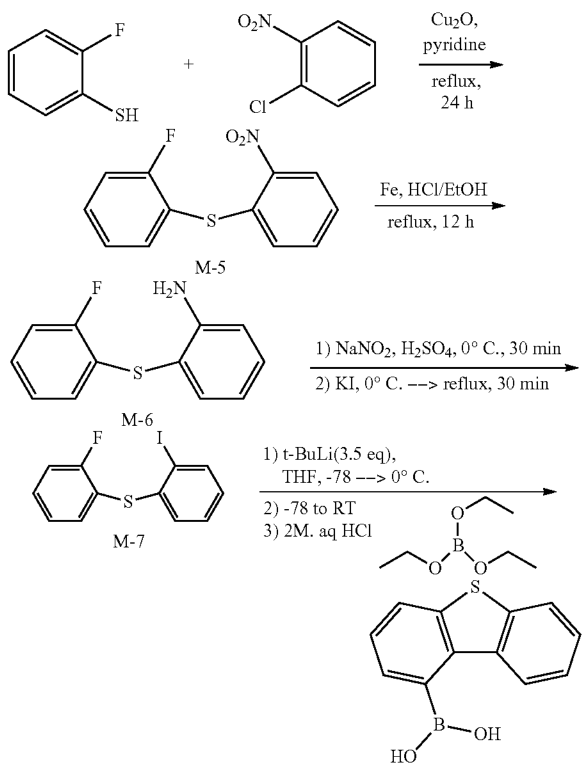

M-8

Intermediate M-5 (50 g, a yield of 90%) as a yellow solid was obtained according to the same method as Synthesis Example 1 except that 39.6 g (223 mmol) of 2-fluorothiophenol was used instead of the 2-fluorophenol.

GC-Mass (theoretical value: 249.03 g/mol, measured value: M+1=250 g/mol)

Synthesis Example 6: Synthesis of Intermediate M-6

Intermediate M-6 (28 g, a yield of 81%) was obtained according to the same method as Synthesis Example 2 except that 28.6 g (159 mmol) of Intermediate M-5 was used instead of Intermediate M-1.

GC-Mass (theoretical value: 219.05 g/mol, measured value: M+1=220 g/mol)

Synthesis Example 7: Synthesis of Intermediate M-7

Intermediate M-7 (28.8 g, a yield of 74%) was obtained according to the same method as Synthesis Example 3 except that 25.9 g (118 mmol) of Intermediate M-6 was used instead of Intermediate M-2.

GC-Mass (theoretical value: 329.94 g/mol, measured value: M+1=331 g/mol)

Synthesis Example 8: Synthesis of Intermediate M-8

Intermediate M-8 (13.4 g, a yield of 66%) was obtained according to the same method as Synthesis Example 4 except that 29.4 g (89.1 mmol) of Intermediate M-7 was used instead of Intermediate M-3.

1H NMR (300 MHz, DMSO-d6) δ8.65 (s, 2H), 8.36 (m, 1H), 8.00 (m, 1H), 7.45-7.51 (m, 4H)

Synthesis Example 9: Synthesis of Intermediate M-9

(Reaction Scheme 3)

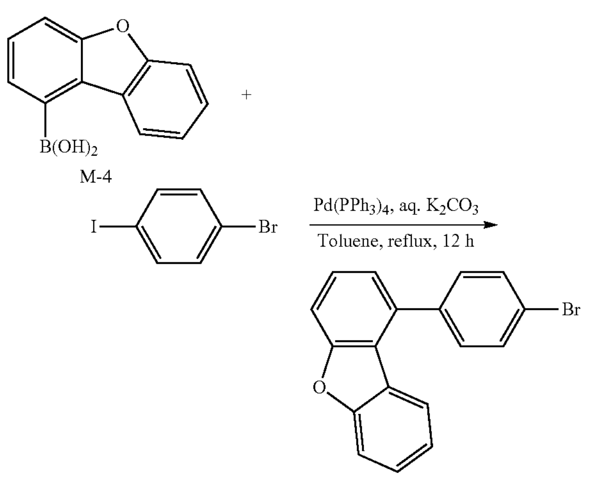

M-9

20 g (94.3 mmol) of Intermediate M-4 and 26.7 g (94.3 mmol) of 1-bromo-4-iodobenzene were put in a round-bottomed flask and dissolved in 313 ml of toluene, 117 ml of an aqueous solution in which 19.5 g (141.5 mmol) of potassium carbonate was dissolved was added thereto, and the obtained mixture was stirred. 1.09 g (0.94 mmol) of tetrakistriphenylphosphine palladium was added thereto, and the obtained mixture was refluxed and stirred under a nitrogen atmosphere for 12 hours. When a reaction was complete, an extract obtained from extraction with ethylacetate was dried with magnesium sulfate, filtered, and concentrated under a reduced pressure. A product therefrom was purified through silica gel column chromatography with n-hexane/dichloromethane (a volume ratio of 9:1) to obtain 27 g (a yield of 89%) of Intermediate M-9 as a white solid.

LC-Mass (theoretical value: 322.00 g/mol, measured value: M+=322.07 g/mol, M+2=324.21 g/mol)

Synthesis Example 10: Synthesis of Intermediate M-10

(Reaction Scheme 4)

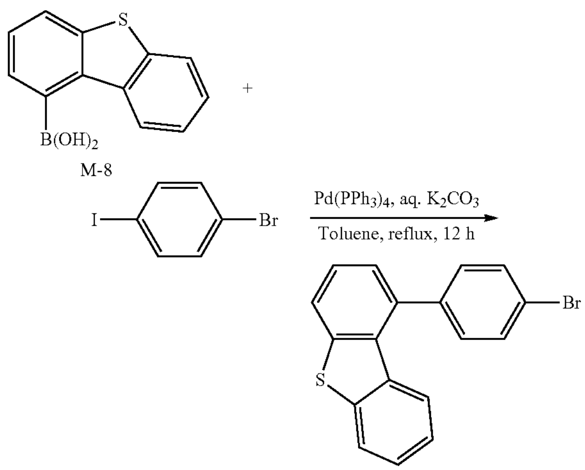

M-8

M-10

Intermediate M-10 (29 g, a yield of 91%) as a white solid was obtained according to the same method as Synthesis Example 9 except that 21.5 g (94.3 mmol) of Intermediate M-8 was used instead of Intermediate M-4.

LC-Mass (theoretical value: 337.98 g/mol, measured value: M+=338.11 g/mol, M+2=340.25 g/mol)

Synthesis Example 11: Synthesis of Intermediate M-11

(Reaction Scheme 5)

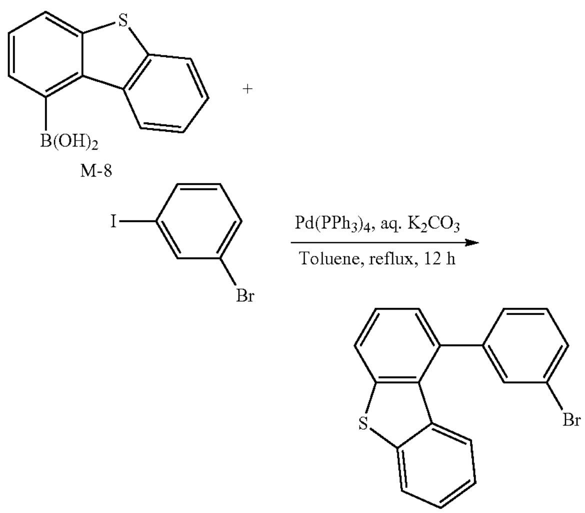

M-8

M-11

Intermediate M-11 (28.5 g, a yield of 89%) as a white solid was obtained according to the same method as Synthesis Example 9 except that 21.5 g (94.3 mmol) of Intermediate M-8 was used instead of Intermediate M-4, and 26.7 g (94.3 mmol) of 1-bromo-3-iodobenzene was used instead of the 1-boromo-4-iodobenzene.

LC-Mass (theoretical value: 337.98 g/mol, measured value: M+=338.15 g/mol, M+2=340.21 g/mol)

Synthesis Example 12: Synthesis of Intermediate M-12

(Reaction Scheme 6)

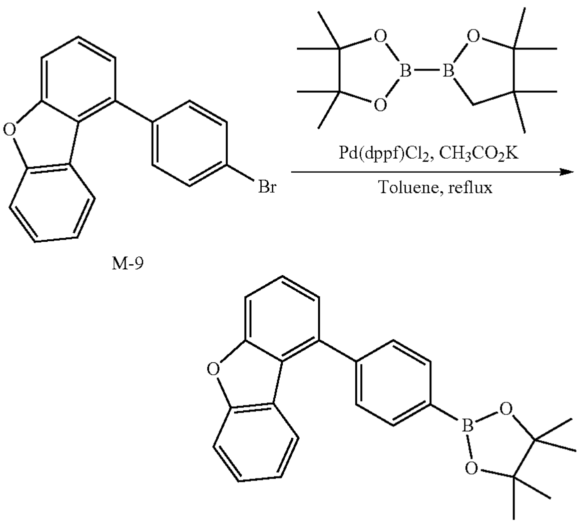

M-9

M-12

Intermediate M-9 (20 g, 61.9 mmol), 4,4,4',4',5,5,5',5'-octamethyl-2,2'-bi(1,3,2-dioxaborolane (18.9 g, 74.3 mmol), potassium acetate (KOAc, 0.505 g, 86.7 mmol), and 1,1'-bis(diphenylphosphino) ferrocene-palladium(II) dichloride (2.53 g, 0.619 mmol) were added to 200 mL of toluene in a 500 mL flask and then, stirred at 110° C. for 12 hours. When a reaction was complete, the reaction solution was extracted with water and toluene, an organic layer obtained therefrom was treated with magnesium sulfate to removed moisture, concentrated, and purified through silica gel column chromatography with n-hexane/ethylacetate (a volume ratio of 9:1) to obtain Intermediate M-12 as a white solid (19.3 g, a yield of 84%).

LC-Mass (theoretical value: 370.17 g/mol, measured value: M+=370.31 g/mol)

Synthesis Example 13: Synthesis of Intermediate M-13

(Reaction Scheme 7)

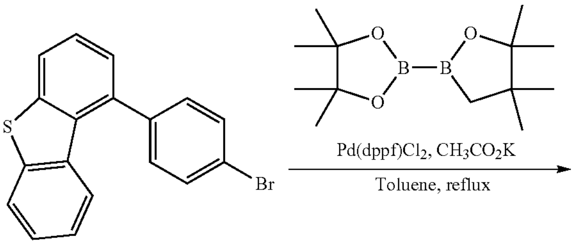

M-10

-continued

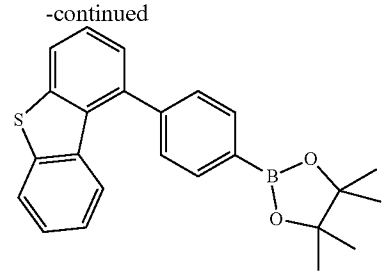

M-13

20.6 g (a yield of 86%) of Intermediate M-13 as a white solid was obtained according to the same method as Synthesis Example 12 except that 21 g (61.9 mmol) of Intermediate M-10 was used instead of Intermediate M-9.

LC-Mass (theoretical value: 386.15 g/mol, measured value: M+=386.29 g/mol)

Synthesis Example 14: Synthesis of Intermediate M-14

(Reaction Scheme 8)

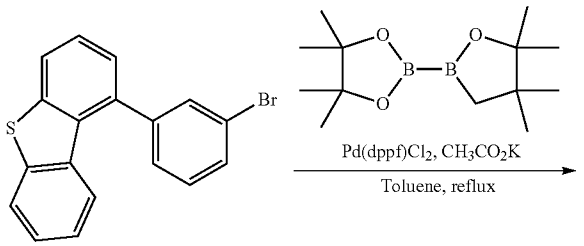

M-11

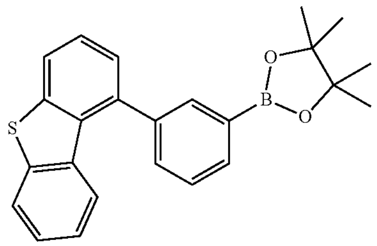

M-14

20.8 g (a yield of 87%) of Intermediate M-14 as a white solid was obtained according to the same method as Synthesis Example 12 except that 21 g (61.9 mmol) of Intermediate M-11 was used instead of Intermediate M-9.

LC-Mass (theoretical value: 386.15 g/mol, measured value: M+=386.29 g/mol)

Synthesis Example 15: Synthesis of Intermediate M-15

(Reaction Scheme 9)

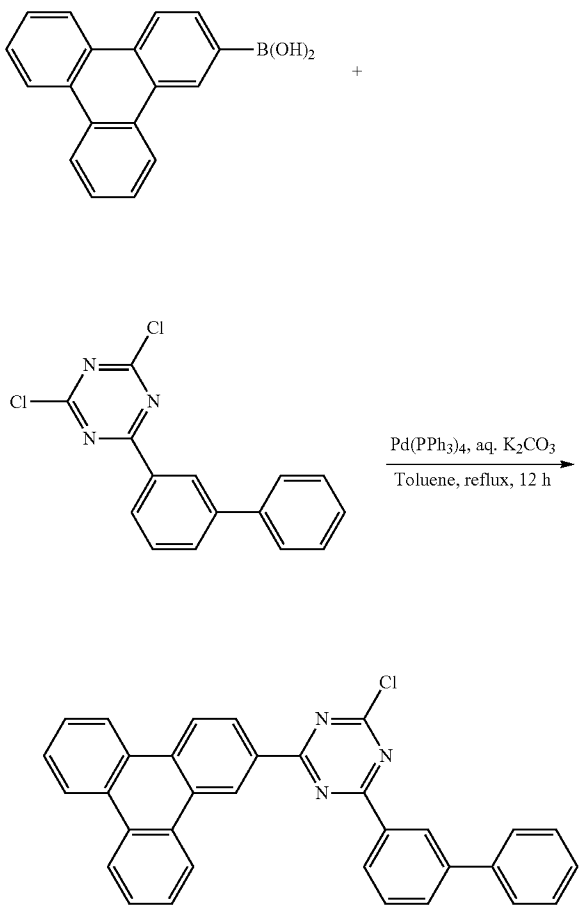

M-15

8.2 g (30 mmol) of triphenylen-2-yl boronic acid and 9.1 g (30 mmol) of 2-([1,1'-biphenyl]-3-yl)-4,6-dichloro-1,3,5-triazine were put in a round-bottomed flask and then, dissolved in 150 ml of tetrahydrofuran, 62 ml of an aqueous solution in which 6.2 g (45 mmol) of potassium carbonate was dissolved was added thereto, and the obtained mixture was stirred. 0.35 g (0.3 mmol) of tetrakistriphenylphosphine palladium was added thereto, and the obtained mixture was refluxed and stirred for 12 hours under a nitrogen atmosphere. When a reaction was complete, the resultant was cooled down, and a solid precipitated therein was filtered under a reduced pressure and washed with toluene and distilled water. The filtered solid was heated and dissolved in toluene and then, filtered with silica gel under a reduced pressure. A filtrate therefrom was concentrated and recrystallized/purified to obtain 12 g (a yield of 81%) of Intermediate M-15 as a white solid.

LC-Mass (theoretical value: 493.13 g/mol, measured value: M+=493.54/mol)

Synthesis Example 16: Synthesis of Intermediate M-16

(Reaction Scheme 10)

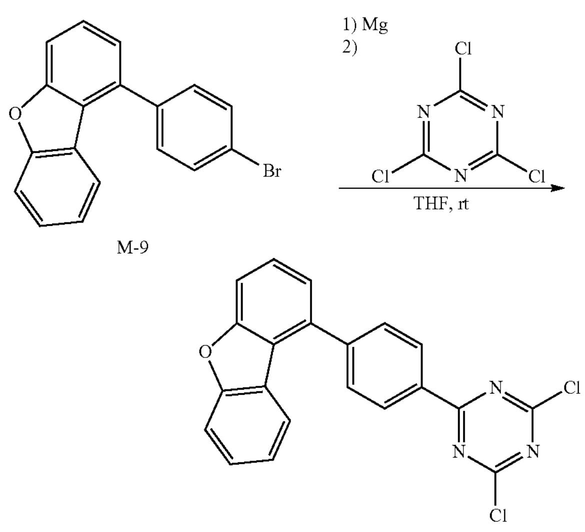

M-9

M-17

0.75 g (30.9 mmol) of a magnesium pellets was put in a 250 mL round-bottomed flask, 10 mL of anhydrous tetrahydrofuran was added thereto, and the obtained mixture was stirred under a nitrogen atmosphere at room temperature. A solution prepared by dissolving 10 g (30.9 mmol) of Intermediate M-9 in 50 ml of anhydrous tetrahydrofuran was slowly added thereto for 30 minutes at room temperature, and the obtained mixture was stirred. The solution was refluxed and stirred under a nitrogen atmosphere for 3 hours and then, cooled down to room temperature to obtain a Grignard reagent solution of Intermediate M-9. On the other hand, 5.7 g (30.9 mmol) of cyanuric chloride was put in a 250 mL round-bottomed flask, 50 ml of anhydrous tetrahydrofuran was added thereto, and the obtained mixture was stirred under a nitrogen atmosphere and cooled down to 0° C. Subsequently, the prepared Grignard reagent solution of Intermediate M-9 was slowly added thereto at 0° C., and then, the obtained mixture was heated up to room temperature and stirred for 12 hours. The reaction solution was slowly added to 100 mL of 1 M HCl ice water, extracted with diethylether and distilled water, an organic layer therefrom was concentrated under a reduced pressure, a residue thereof was dissolved in dichloromethane and filtered with silica gel, and then, an appropriate amount of the filtrate was concentrated, and hexane was added thereto for recrystallization. A solid generated therein was filtered, washed with hexane, and dried to obtain Intermediate M-16 as a white solid (7.9 g, a yield of 65%).

LC-Mass (theoretical value: 391.03 g/mol, measured value: M+=391.39 g/mol)

Examples 1 to 6: Synthesis of Compounds A-2, A-21, A-43, A-63, A-98 and D-14

Compounds A-2, A-21, A-43, A-63, A-98 and D-14 were synthesized according to the same method as Synthesis Example 15 by changing an intermediate respectively corresponding thereto.

The intermediates for synthesizing Compounds A-2, A-21, A-43, A-63, A-98 and D-14 according to Examples 1 to 6, yield amounts, yields, and LC/MS analysis results are shown in Table 1.

Example 7: Synthesis of Compound B-9

11.6 g (30 mmol) of Intermediate M-14 and 3.4 g (15 mmol) of 2,4-dichloro-6-phenyl-1,3,5-triazine were put in a round-bottomed flask and dissolved in 100 ml of tetrahydrofuran, 62 ml of an aqueous solution in which 6.2 g (45 mmol) of potassium carbonate was added thereto, and the obtained mixture was stirred. 0.35 g (0.3 mmol) of tetrakistriphenylphosphine palladium was added thereto, and the obtained mixture was refluxed and stirred for 12 hours under a nitrogen atmosphere. When a reaction was complete, the resultant was cooled down, and a solid precipitated therein was filtered under a reduced pressure and washed with toluene and distilled water. The filtered solid was heated and dissolved in toluene, and the solution was filtered with silica gel under a reduced pressure. The filtered solution was concentrated and then, recrystallized and purified to obtain 8.9 g (a yield of 87%) of Compound B-9 as a white solid.

LC-Mass (theoretical value: 684.18 g/mol, measured value: M+1=685.21/mol)

Example 8 to 10: Synthesis of Compounds B-107, C-27 and E-21

Compounds B-107, C-27, and E-21 were synthesized according to the same method as Example 7 by changing intermediates respectively corresponding thereto.

The intermediates for synthesizing Compounds B-107, C-27, and E-21 according to Examples 8 to 10, yield amounts, yields, and LC/MS analysis results were shown in Table 1.

TABLE 1

| | Used intermediates (Amounts) | | Structure | | |
|---|---|---|---|---|---|
| Examples | Boron intermediate | Halogen intermediate | of products structure | Amount (yield) | LC/MS M + 1 = g/mol |
| Example 1 | M-8 (6.8 g) | M-18 (12.6 g) | A-2 | 15.5 g 91% | 568.32 |
| Example 2 | M-13 (11.6 g) | M-21 (10.3 g) | A-21 | 15.2 g 89% | 568.25 |
| Example 3 | M-14 (11.6 g) | M-18 (12.6 g) | A-43 | 17.8 g 92% | 644.28 |
| Example 4 | M-4 (6.4 g) | M-20 (12.6 g) | A-63 | 14.6 g 88% | 552.19 |
| Example 5 | M-12 (11.1 g) | M-15 (14.8 g) | A-98 | 18.3 g 87% | 702.29 |

TABLE 1-continued

| | Used intermediates (Amounts) | | Structure | | |
|---|---|---|---|---|---|
| Examples | Boron intermediate | Halogen intermediate | of products structure | Amount (yield) | LC/MS M + 1 = g/mol |
| Example 6 | M-4 (6.4 g) | M-19 (12.6 g) | D-14 | 14.0 g 85% | 551.31 |
| Example 7 | M-14 (11.6 g) | 2,4-dichloro-6-phenyl-1,3,5-triazine (3.4 g) | B-9 | 8.9 g 87% | 685.21 |
| Example 8 | M-4 (6.4 g) | M-22 (5.7 g) | B-107 | 8.7 g 90% | 642.22 |
| Example 9 | M-4 (6.4 g) | M-17 (5.9 g) | C-27 | 8.1 g 82% | 656.30 |
| Example 10 | M-12 (11.1 g) | 4,6-dichloro-2-phenylpyrimidine (3.4 g) | E-21 | 8.0 g 83% | 641.20 |

Chemical structures of intermediates not described in the above synthesis examples among the intermediates used in Examples 1 to 10 are shown as follows.

[M-18]

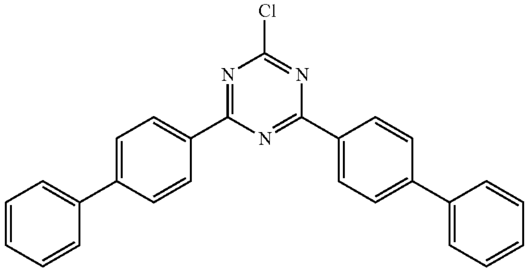

[M-19]

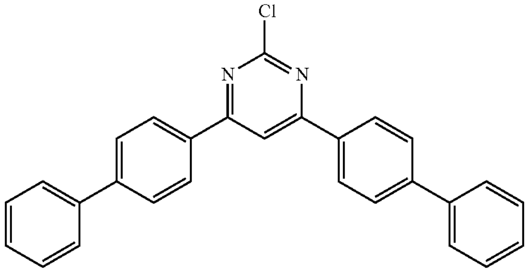

[M-20]

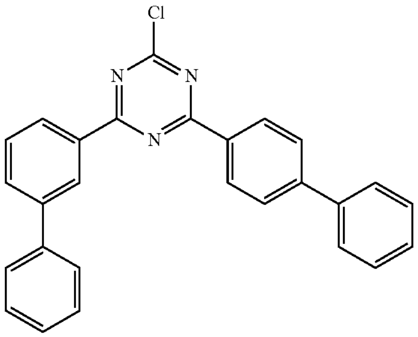

-continued

[M-21]

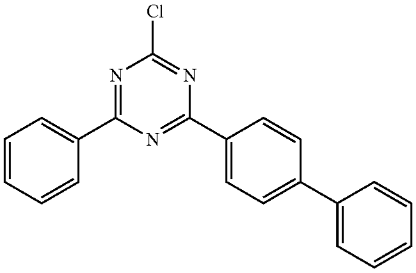

[M-22]

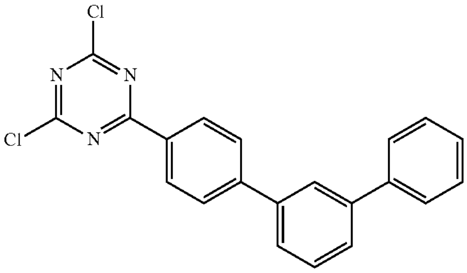

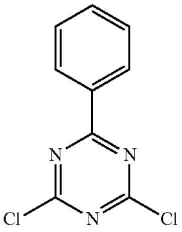

2,4-dichloro-6-phenyl-1,3,5-triazine

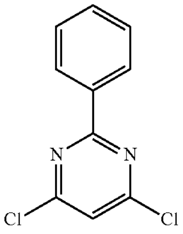

4,6-dichloro-2-phenylpyrimidine (Synthesis of Second Compound for Organic Optoelectronic Device)

Example 11: Synthesis of Compound HT-130

(Reaction Scheme 11)

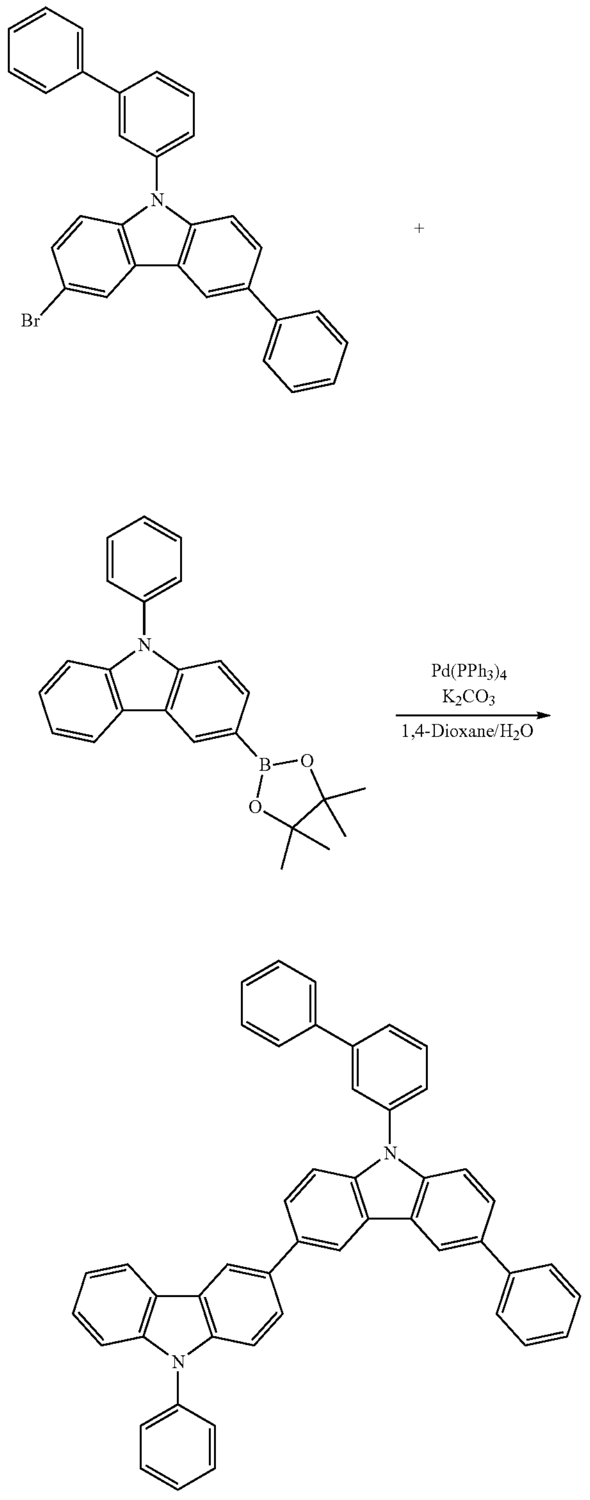

HT-130

20.00 g (42.16 mmol) of 3-bromo-6-phenyl-N-metabiphenylcarbazole and 17.12 g (46.38 mmol) of N-phenylcarbazole-3-boronic ester were mixed with 175 mL of tetrahydrofuran:toluene mixed in a ratio of 1:1 and 75 mL of a 2 M-potassium carbonate aqueous solution under a nitrogen atmosphere in a 500 mL round-bottomed flask equipped with a stirrer, 1.46 g (1.26 mmol) of tetrakistriphenylphosphinepalladium (0) was added thereto, and the obtained mixture was heated and refluxed under a nitrogen flow for 12 hours. When a reaction was complete, the reactants were poured into methanol, a solid generated therein was filtered, sufficiently washed with water and methanol, and dried. A resulting material obtained therefrom was heated and dissolved in 700 mL of chlorobenzene, silica gel filtered, then, after removing a solvent therefrom, heated and dissolved in 400 mL of chlorobenzene, and recrystallized to obtain 18.52 g (a yield of 69%) of Compound HT-130.

calcd. C42H32N2: C, 90.54; H, 5.07; N, 4.40; found: C, 90.54; H, 5.07; N, 4.40

Example 12: Synthesis of Compound HT-138

(Reaction Scheme 12)

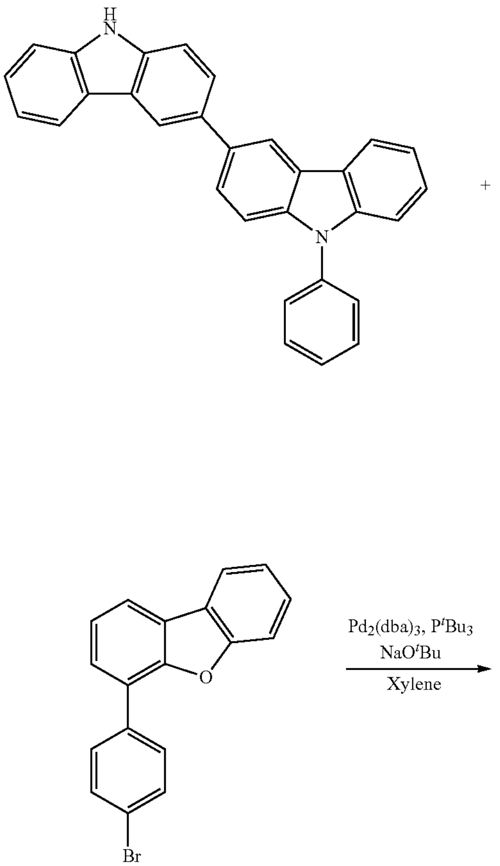

-continued

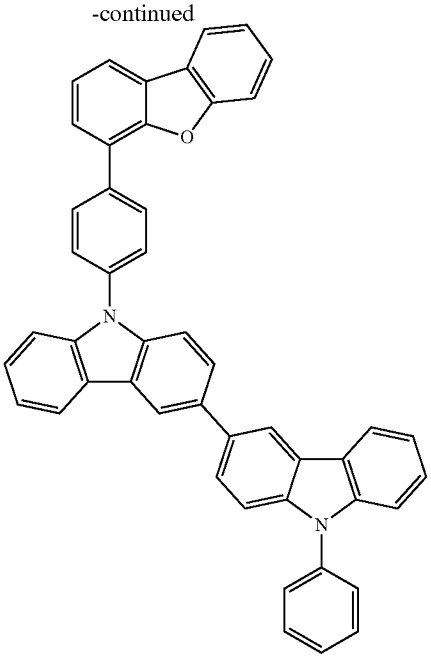

HT-138

6.3 g (15.4 mmol) of N-phenyl-3,3-bicarbazole, 5.0 g (15.4 mmol) of 4-(4-bromophenyl)dibenzo[b,d]furan, 3.0 g (30.7 mmol) of sodium t-butoxide, 0.9 g (1.5 mmol) of tris(dibenzylideneacetone)dipalladium, and 1.2 mL of tri t-butylphosphine (50% in toluene) were mixed with 100 mL of xylene in a 250 mL round flask and then, heated and refluxed under a nitrogen flow for 15 hours. The obtained mixture was added to 300 mL of methanol, a solid crystallized therein was filtered, dissolved in dichlorobenzene, filtered with silica gel/Celite, and then, after removing an appropriate amount of an organic solvent, recrystallized with methanol to obtain Compound HT-138 (7.3 g, a yield of 73%).

calcd. C48H30N2O : C, 88.59; H, 4.65; N, 4.30; 0, 2.46; found : C, 88.56; H, 4.62; N, 4.20; O, 2.43

(Manufacture of Organic Light Emitting Diode)

Device Example 1

A glass substrate coated with ITO (indium tin oxide) as a 1500 Å-thick thin film was ultrasonic wave-washed with distilled water. After washing with the distilled water, the glass substrate was ultrasonic wave-washed with a solvent such as isopropyl alcohol, acetone, methanol, and the like and dried and then, moved to a plasma cleaner, cleaned by using oxygen plasma for 10 minutes, and moved to a vacuum depositor. This obtained ITO transparent electrode was used as an anode, a 700 Å-thick hole injection layer was formed on the ITO substrate by vacuum depositing Compound A, and a hole transport layer was formed on the injection layer by depositing Compound B to be 50 Å thick and Compound C to be 1020 Å thick. On the hole transport layer, a 400 Å-thick light emitting layer was formed by simultaneously vacuum-depositing Compound A-43 of Synthesis Example 3 and Compound HT-130 of Synthesis Example 11 as a host and being doped with 10 wt % of tris(2-phenylpyridine)iridium(III) [Ir(ppy)3] (Cas No. 94928-86-6) as a dopant. Herein, Compound A-43 and Compound HT-130 were used in a ratio of 3:7 and the ratios were separately in the following examples. Subsequently, Compound D and Liq were vacuum-deposited simultaneously at a 1:1 ratio on the light emitting layer to form a 300 Å-thick electron transport layer and a cathode was formed by sequentially vacuum-depositing Liq to be 15 Å thick and Al to be 1200 Å thick on the electron transport layer, manufacturing an organic light emitting diode.

The organic light emitting diode had a five-layered organic thin layer structure as follows:

A structure of ITO/Compound A (700 Å)/Compound B (50 Å)/Compound C (1020 Å)/EML [Compound A-43: HT-130:Ir(ppy)3=27 wt %:63 wt %:10 wt %] (400 Å)/ Compound D : Liq (300 Å)/Liq (15 Å)/Al (1200 Å).

Compound A: N4,N4'-diphenyl-N4,N4'-bis(9-phenyl-9H-carbazol-3-yl)biphenyl-4,4'-diamine Compound B: 1,4,5,8,9,11-hexaazatriphenylene-hexacarbonitrile (HAT-CN), Compound C: N-(biphenyl-4-yl)-9,9-dimethyl-N-(4-(9-phenyl-9H-carbazol-3-yl)phenyl)-9H-fluoren-2-amine Compound D: 8-(4-(4,6-di(naphthalen-2-yl)-1,3,5-triazin-2-yl)phenyl)quinoline Device Examples 2 to 14

Organic light emitting diodes according to Device Examples 2 to 14 were respectively manufactured according to the same method as Device Example 1 except that host shown in Tables 2 and 3 were used instead of Compound A-43 and Compound HT--130 for forming a light emitting layer.

Device Examples 15 and 16

Organic light emitting diodes according to Device Examples 15 to 16 were manufactured according to the same method as Device Example 1 except that Compound B-9 and Compound A-98 were used respectively alone as a host for a light emitting layer.

Comparative Device Examples 1 to 3

Organic light emitting diodes according to Comparative Device Examples 1 to 3 were manufactured according to the same method as Device Example 1 except that Comparative Compounds ET-1 to ET-3 were used respectively alone as a host for a light emitting layer. po Chemical structures of Compounds ET-1 to ET-3 used in Comparative Examples 1 to 3 as an electron transport host were shown as follows.

ET-1

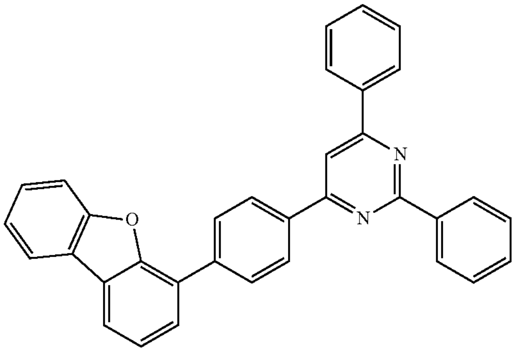

-continued

ET-2

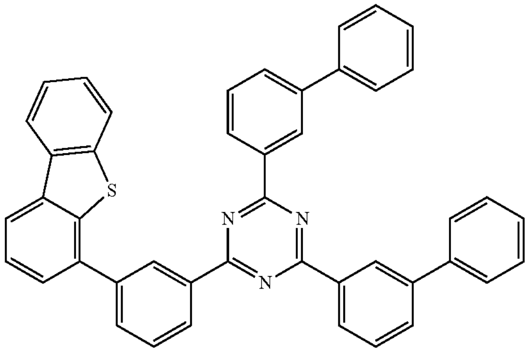

ET-3

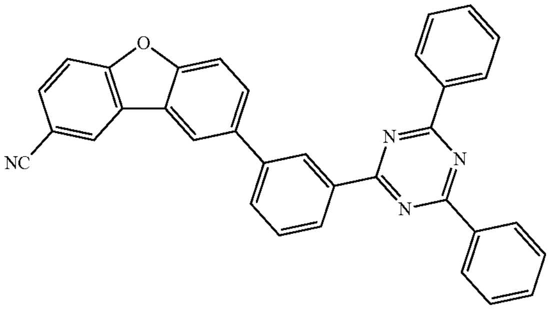

Comparative Device Examples 4 to 7

Organic light emitting diodes according to Comparative Device Examples 4 to 7 were manufactured according to the same method as Device Example 1 except that Comparative Compounds ET-1 to ET-3 were used respectively instead of Compound A-43.

Evaluation 1: Synergic Effect of Luminous efficiency and Life-span

Luminous efficiency and life-span characteristics of the organic light emitting diodes according to Device Examples 1 to 16 and Comparative Device Examples 1 to 7 were evaluated. Specific measurement methods are as follows, and the results are shown in Table 2, Table 3, and Table 4.

(1) Measurement of Current Density Change Depending on Voltage Change

The obtained organic light emitting diodes were measured regarding a current value flowing in the unit element, while increasing the voltage from 0 V to 10 V using a current-voltage meter (Keithley 2400), and the measured current value was divided by area to provide the results.

(2) Measurement of Luminance Change Depending on Voltage Change Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 $mA/cm^2$) were calculated by using the luminance, current density, and voltages (V) from the items (1) and (2).

(4) Measurement of Life-span

T95 life-spans of the organic light emitting diodes according to Examples 1 to 16 and Comparative Example 1 to Comparative Example 7 were measured as a time when their luminance decreased down to 95% relative to the initial luminance after emitting light with 5000 $cd/m^2$ as the initial luminance ($cd/m^2$) and measuring their luminance decrease depending on a time with a Polanonix life-span measurement system.

(5) Measurement of Driving Voltage

A driving voltage of each diode was measured using a current-voltage meter (Keithley 2400) at 15 $mA/cm^2$.

TABLE 2

In the case of triazine

| Device Example | First host | Second host | First host:Second host (wt/wt) | Driving voltage (V) | Luminous efficiency (cd/A) | Color | Life-span T95 (h) |
|---|---|---|---|---|---|---|---|
| Device Example 1 | A-43 | HT-130 | 3:7 | 4.85 | 41.5 | green | 395 |
| Device Example 2 | A-63 | HT-130 | 3:7 | 4.94 | 45.6 | green | 424 |
| Device Example 3 | A-98 | HT-130 | 3:7 | 4.68 | 47.8 | green | 585 |
| Device Example 5 | B-9 | HT-130 | 3:7 | 4.98 | 49.0 | green | 405 |
| Device Example 6 | C-27 | HT-31 | 3:7 | 4.70 | 48.7 | green | 480 |
| Device Example 7 | A-98 | HT-31 | 1:1 | 4.45 | 46.2 | green | 505 |
| Device Example 8 | A-43 | HT-138 | 3:7 | 4.88 | 42.5 | green | 400 |
| Device Example 9 | A-63 | HT-138 | 3:7 | 4.90 | 46.9 | green | 420 |
| Device Example 10 | A-98 | HT-138 | 3:7 | 4.70 | 49.8 | green | 580 |
| Device Example 12 | B-9 | HT-138 | 3:7 | 5.00 | 50.0 | green | 415 |
| Device Example 13 | C-27 | HT-138 | 3:7 | 4.69 | 49.9 | green | 470 |
| Device Example 14 | A-98 | HT-138 | 1:1 | 4.50 | 46.7 | green | 510 |
| Comparative Device Example 5 | ET-2 | HT-130 | 3:7 | 5.45 | 45.0 | green | 360 |
| Comparative Device Example 6 | ET-3 | HT-130 | 3:7 | 5.37 | 44.2 | green | 290 |
| Comparative Device Example 7 | ET-2 | HT-130 | 1:1 | 5.25 | 44.0 | green | 330 |

TABLE 3

In the case of pyrimidine

| Device Example | First host | Second host | First host:Second host (wt/wt) | Driving voltage (V) | Luminous efficiency (cd/A) | Color | Life-span T95 (h) |
|---|---|---|---|---|---|---|---|
| Device Example 4 | D-14 | HT-130 | 3:7 | 5.10 | 46.9 | green | 365 |
| Device Example 11 | D-14 | HT-138 | 3:7 | 5.15 | 47.5 | green | 370 |
| Comparative Device Example 1 | ET-1 | — | — | 5.85 | 24.8 | green | 55 |
| Comparative Device Example 4 | ET-1 | HT-130 | 3:7 | 5.95 | 39.5 | green | 125 |

TABLE 4

In the case of single host

| Device Example | First host | Second host | First host:Second host (wt/wt) | Driving voltage (V) | Luminous efficiency (cd/A) | Color | Life-span T95 (h) |
|---|---|---|---|---|---|---|---|
| Device Example 15 | B-9 | — | — | 4.25 | 26.9 | green | 180 |
| Device Example 16 | A-98 | — | — | 4.15 | 29.1 | green | 210 |
| Comparative Device Example 1 | ET-1 | — | — | 5.85 | 24.8 | green | 55 |
| Comparative Device Example 2 | ET-2 | — | — | 5.25 | 25.5 | green | 160 |
| Comparative Device Example 3 | ET-3 | — | — | 5.15 | 24.0 | green | 115 |

Referring to Tables 2 to 4, the organic light emitting diodes using a first host having excellent electron transport characteristics and a second host having excellent hole transport characteristics according to Device Examples 1 to 14 exhibited a low driving voltage, high efficiency, and long life-span characteristics compared with those of Comparative Device Examples 4 to 7. Accordingly, since the first hosts A-43, A-63, A-98, B-9, and C-27 of the present invention had excellent electron transport characteristics compared with the fist hosts ET-1 to ET-3 of Comparative Device Examples, in addition, the organic light emitting diodes using the hosts alone according to Device Examples 15 and 16 showed a low driving voltage and high efficiency compared with those of Comparative Device Examples 1 to 3, the first host of the present invention showed excellent electron transport characteristics. Particularly, the organic light emitting diode using the first host for electron transportation according to the present invention with a second host for hole transportation such as a bicarbazole derivative of the present invention for forming a phosphorescent light emitting layer showed remarkably improved luminous efficiency and life-span characteristics simultaneously compared with the organic light emitting diodes using the first host for electron transportation alone.

While this invention has been described in connection with what is presently considered to be practical example embodiments, it is to be understood that the invention is not limited to the disclosed embodiments. On the contrary, it is intended to cover various modifications and equivalent arrangements included within the spirit and scope of the appended claims.

Therefore, the aforementioned embodiments should be understood to be exemplary but not limiting the present invention in any way.

DESCRIPTION OF SYMBOLS

100, 200: organic light emitting diode
105: organic layer
110: cathode
120: anode
130: light emitting layer
140: hole auxiliary layer

What is claimed is:

1. A composition for an organic optoelectronic device, the composition comprising:

a first host compound, the first host compound being a compound of Group 3; and a second host compound represented by Chemical Formula 2,

[Group 3]

[G-1]

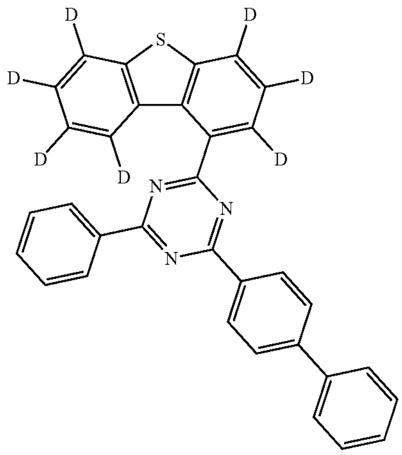

-continued
[G-2]
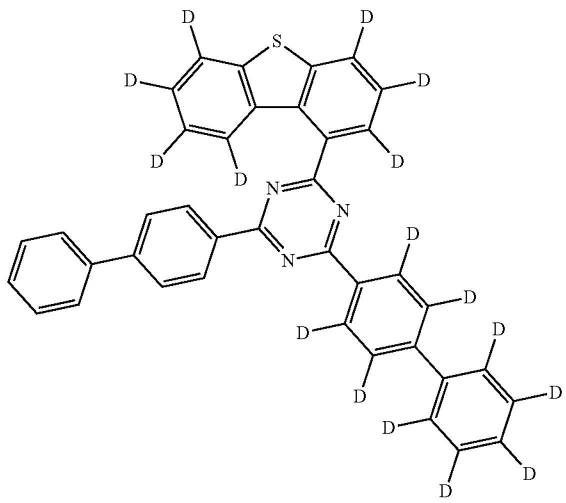
[G-3]
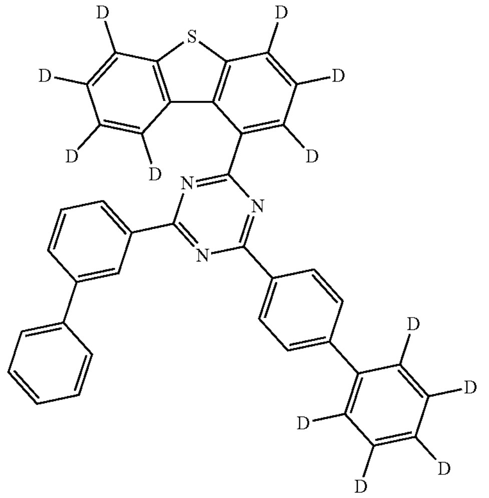
[G-4]
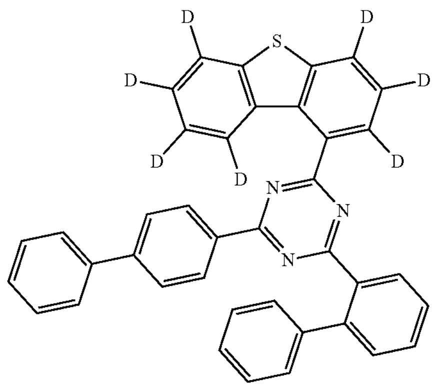
-continued
[G-5]
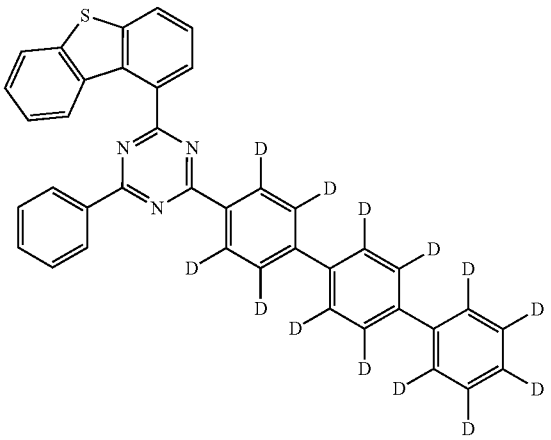
[G-6]
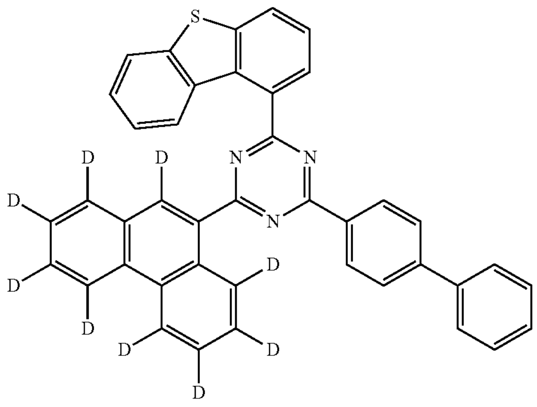
[G-7]
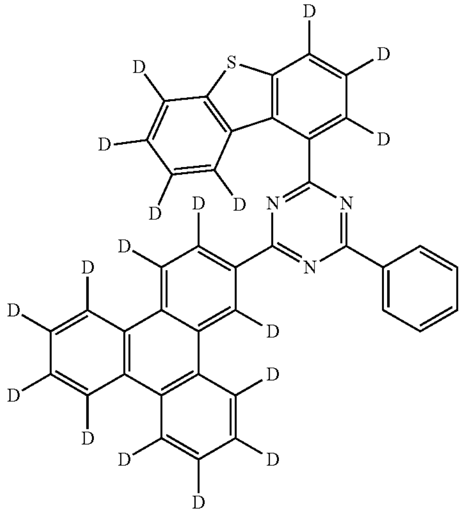

-continued
[G-8]
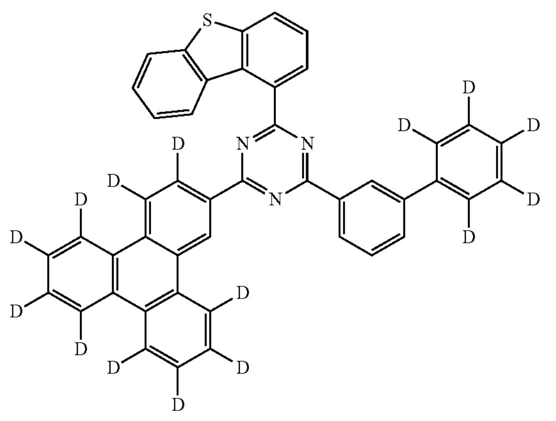
[G-9]
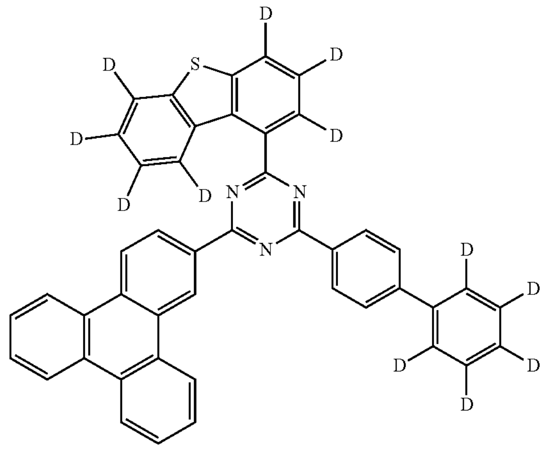
[G-10]
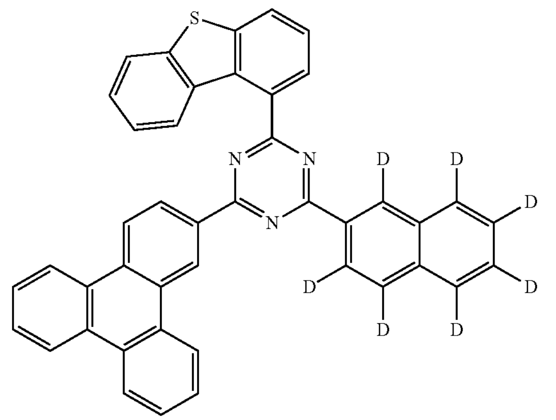
-continued
[G-11]
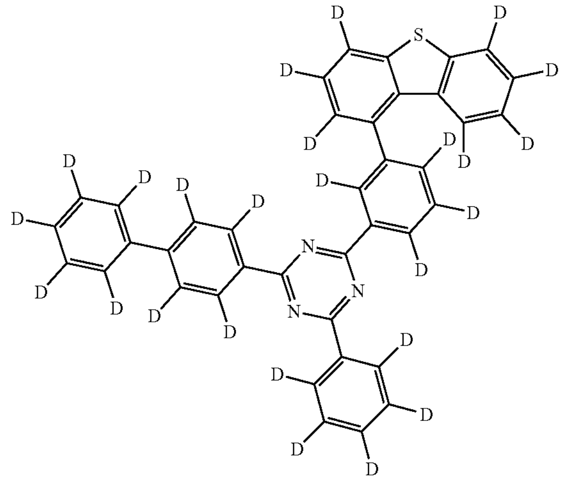
[G-12]
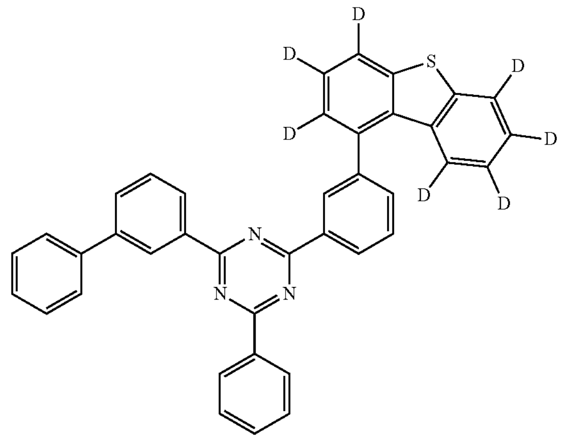
[G-13]
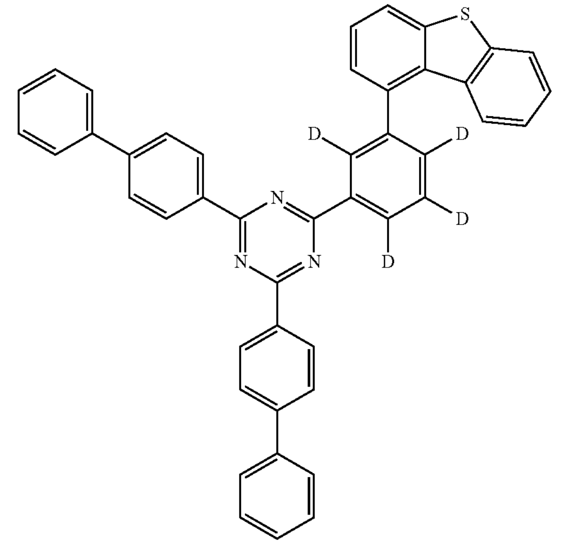

-continued
[G-14]
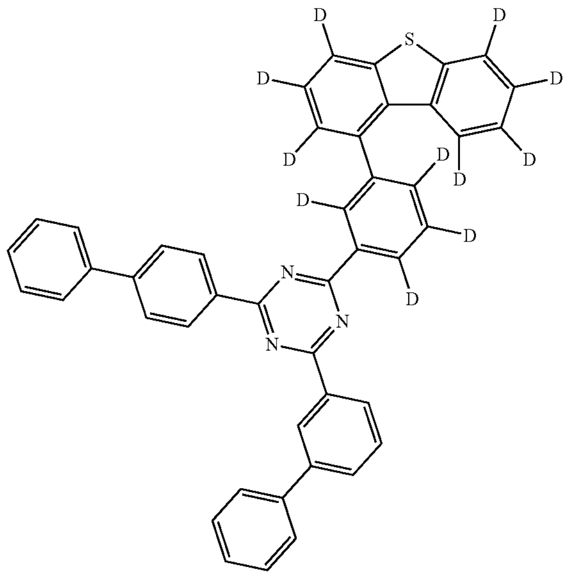
[G-15]
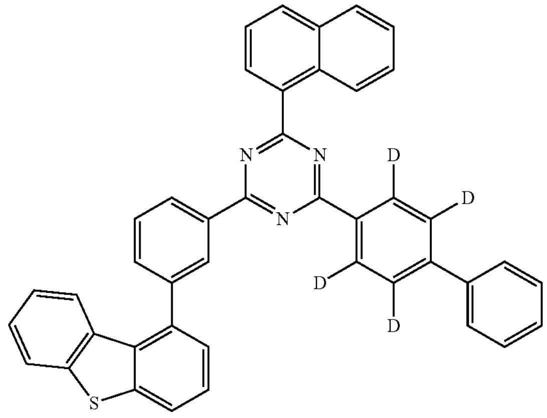
[G-16]
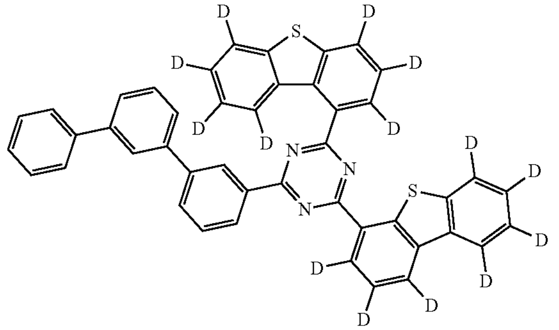
-continued
[G-17]
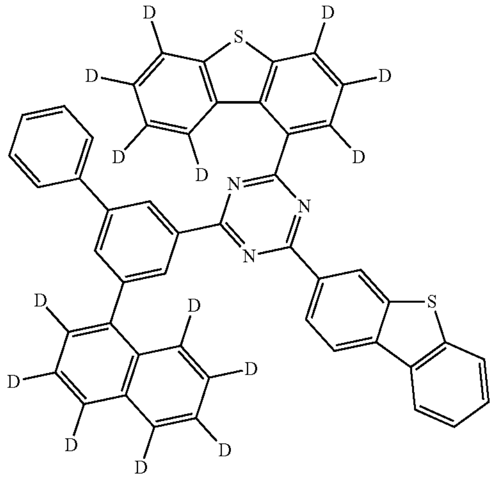
[G-18]
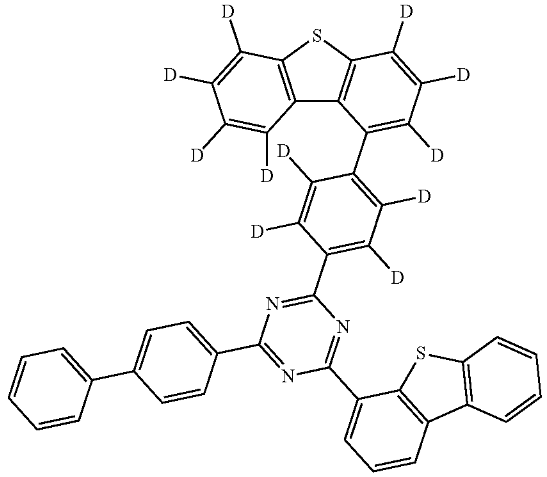
[G-19]
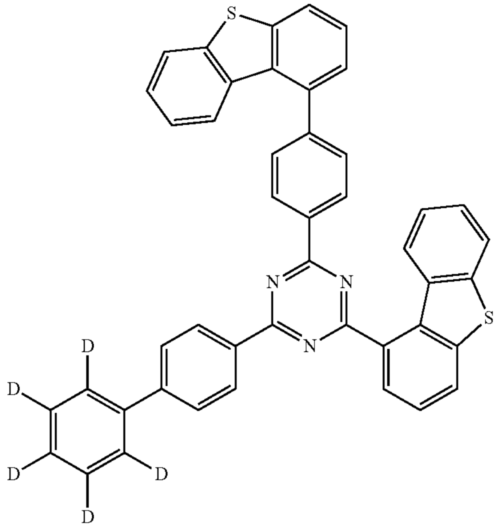

-continued
[G-20]
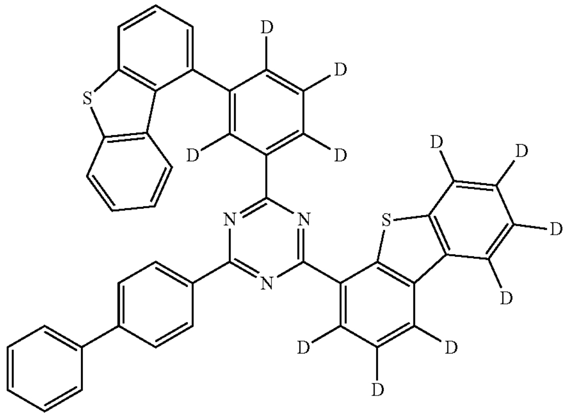
[G-21]
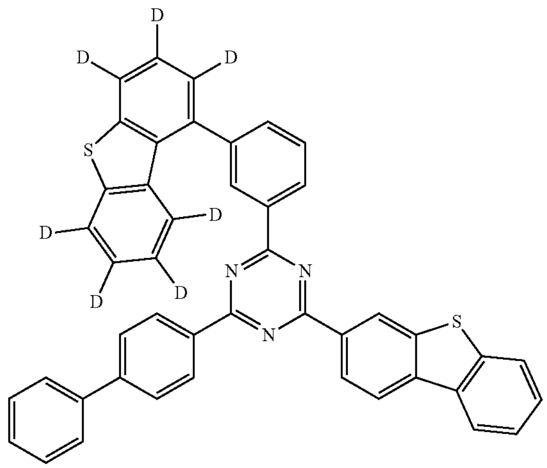
[G-22]
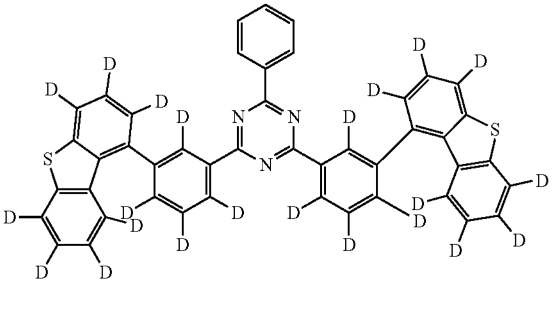
-continued
[G-23]
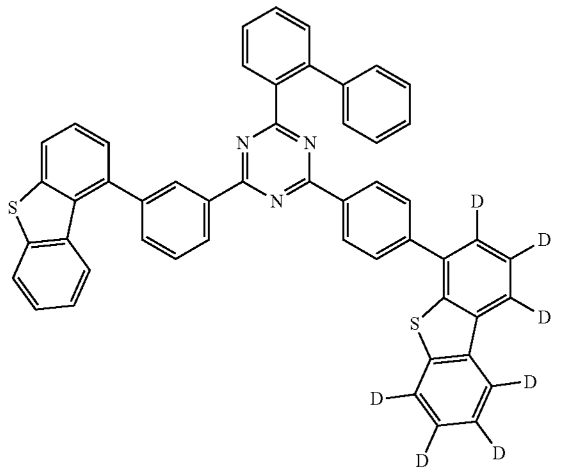
[G-24]
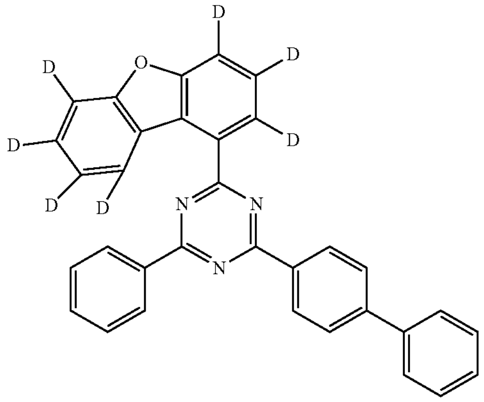
[G-25]
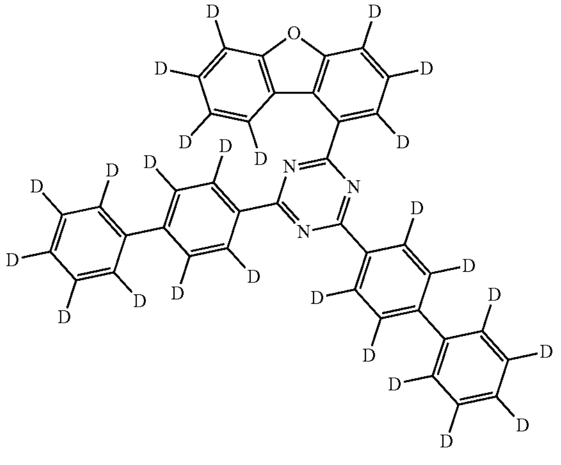

-continued
[G-26]
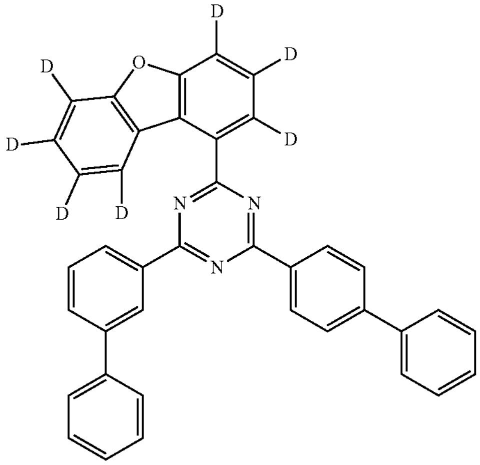
[G-27]
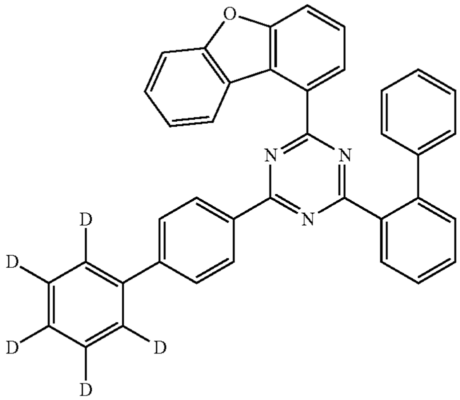
[G-28]
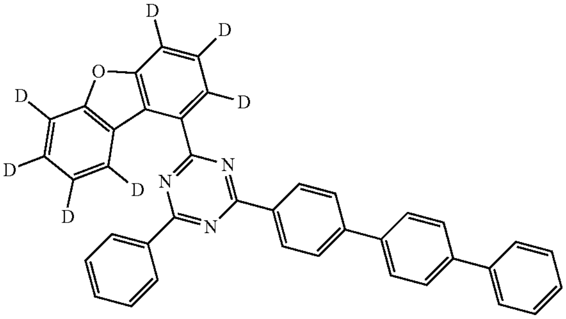
[G-29]
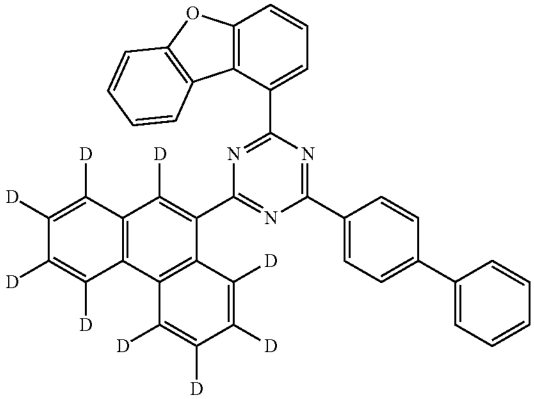
-continued
[G-30]
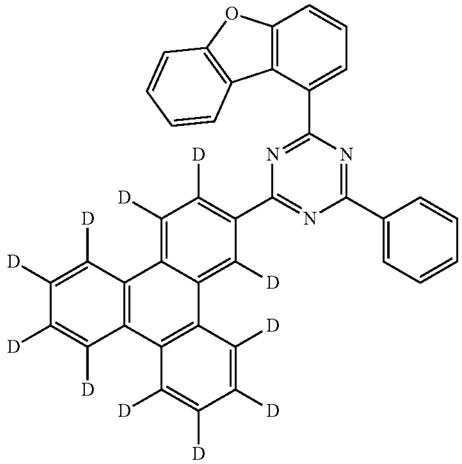
[G-31]
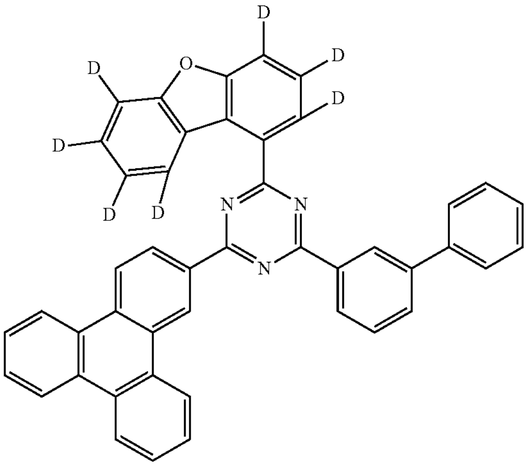
[G-32]
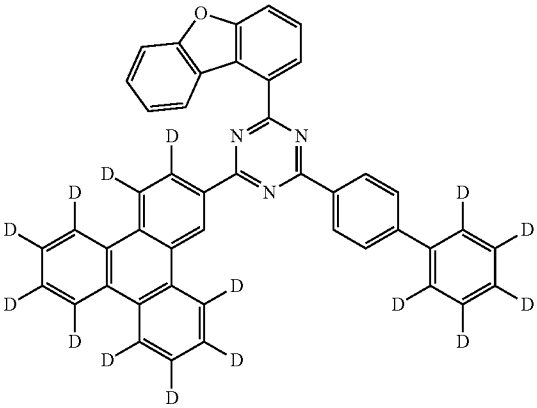

-continued
[G-33]
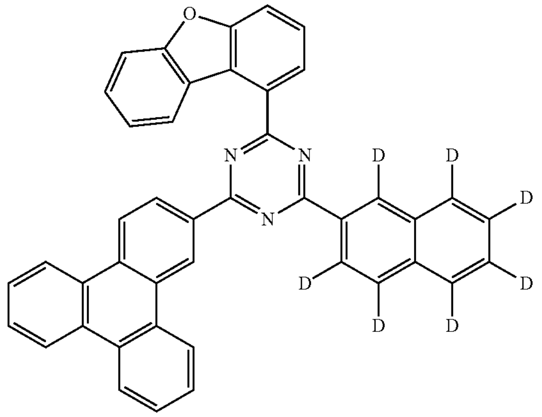
[G-34]
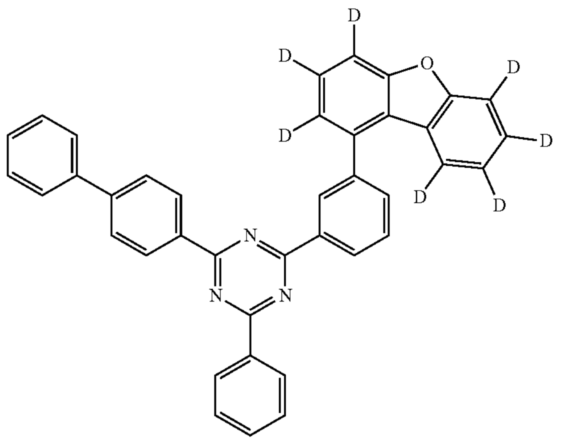
[G-35]
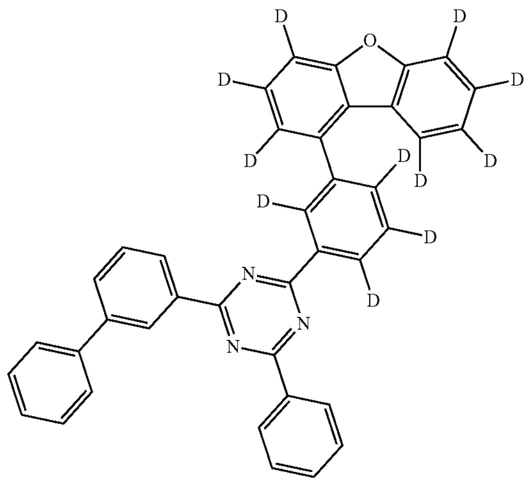
-continued
[G-36]
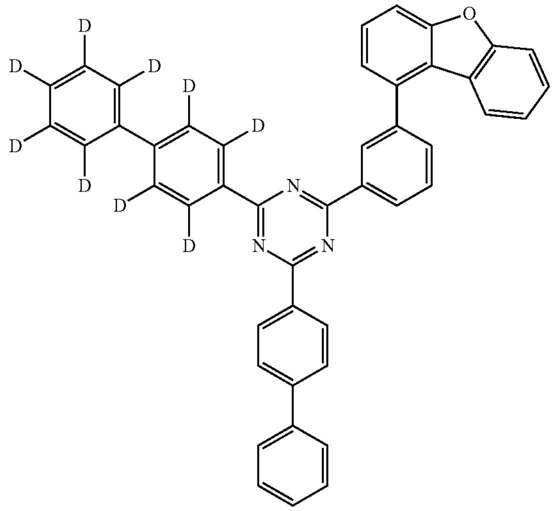
[G-37]
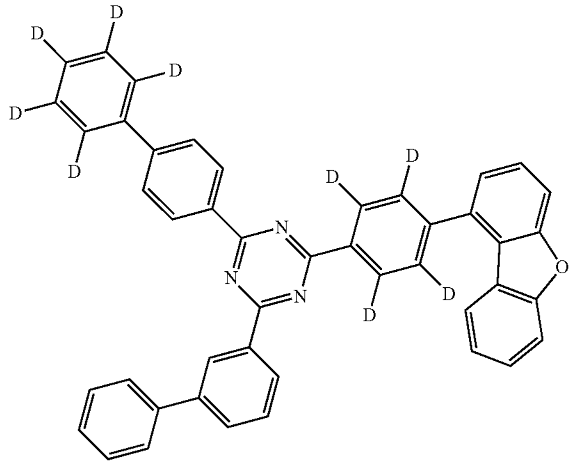
[G-38]
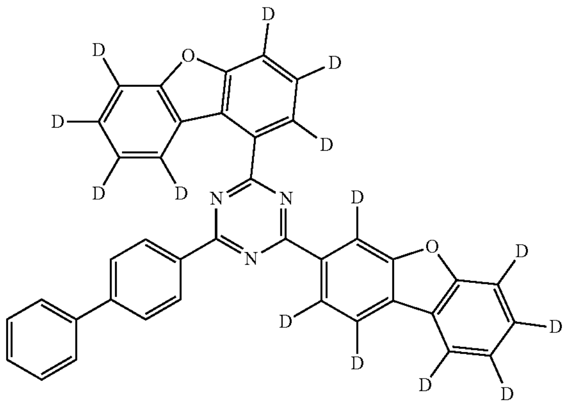

-continued
[G-39]
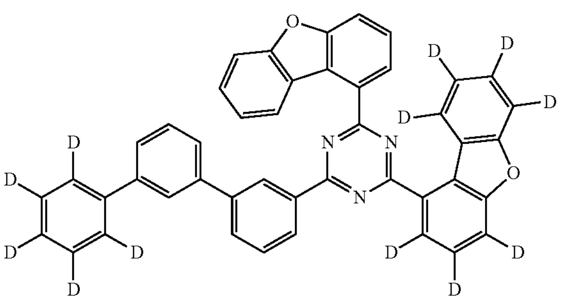
[G-40]
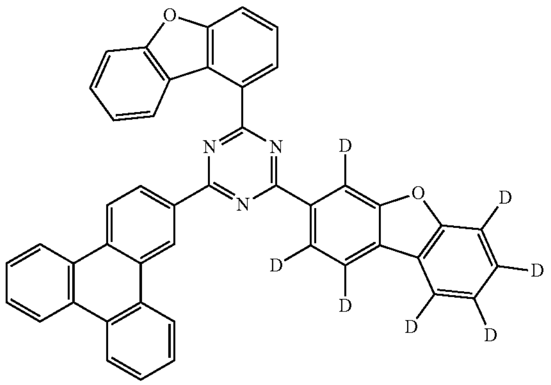
[G-41]
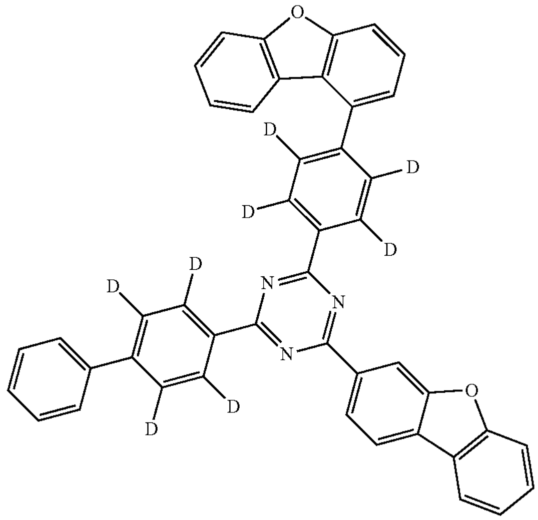
-continued
[G-42]
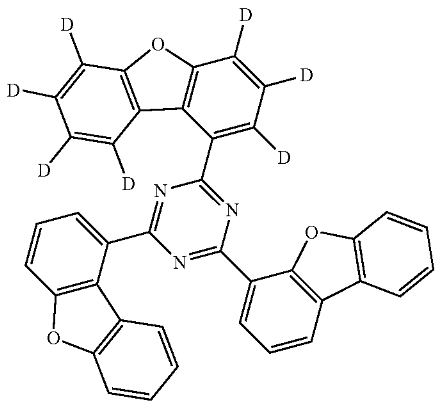
[G-43]
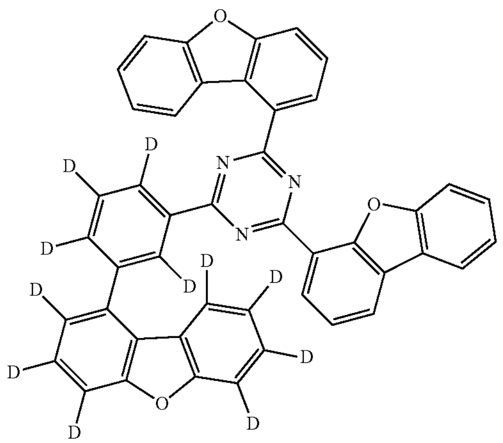
[G-44]
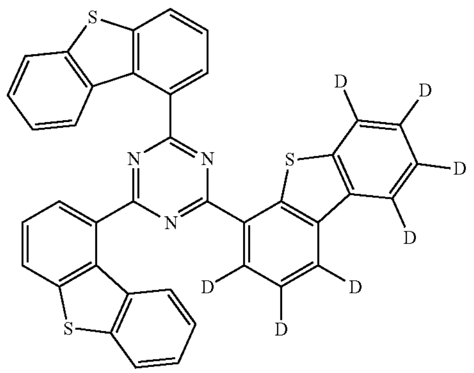

-continued

[G-45]

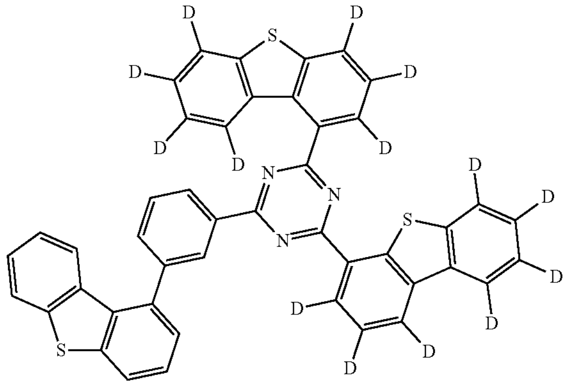

[Chemical Formula 2]

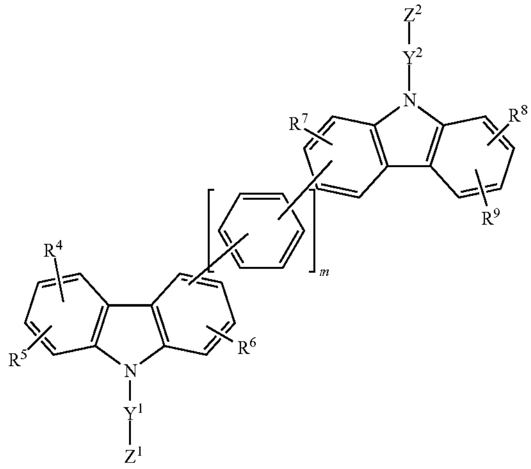

wherein, in Chemical Formula 2, $Y^1$ and $Y^2$ are each independently a single bond, a substituted or unsubstituted C6 to C30 arylene group, a substituted or unsubstituted C2 to C30 heteroarylene group, or a combination thereof, $Z^1$ and $Z^2$ are independently a substituted or unsubstituted C6 to C30 aryl group, a substituted or unsubstituted C2 to C30 heterocyclic group, or a combination thereof, $R^4$ to $R^9$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, and m is an integer of 0 to 2; and wherein "substituted" of Chemical Formula 2 refers to replacement of at least one hydrogen by deuterium, a C1 to C4 alkyl group, a C6 to C18 aryl group, or a C2 to C30 heteroaryl group.

2. The composition for an organic optoelectronic device of claim 1, wherein $Z^1$ and $Z^2$ of Chemical Formula 2 are each independently a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted triphenylene group, a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted quinazolyl group, a substituted or unsubstituted dibenzothiophenyl group, a substituted or unsubstituted dibenzofuranyl group, a substituted or unsubstituted carbazolyl group, a substituted or unsubstituted fluorenyl group, or a combination thereof.

3. The composition for an organic optoelectronic device of claim 1, wherein:

Chemical Formula 2 includes a moiety of Group III, and moieties *—$Y^1$—$Z^1$ and *—$Y^2$—$Z^2$ of Chemical Formula 2 are each independently a moiety of Group IV,

[Group III]

C-1

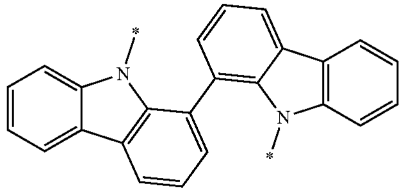

C-2

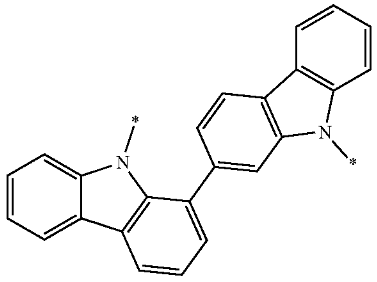

C-3

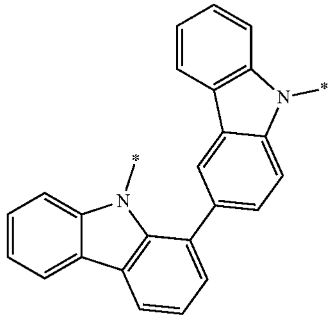

C-4

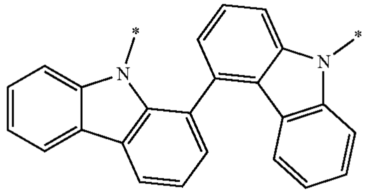

C-5

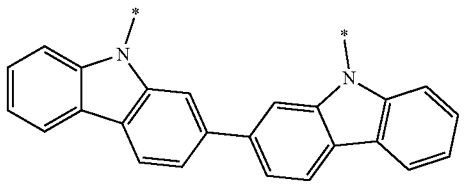

-continued
C-6
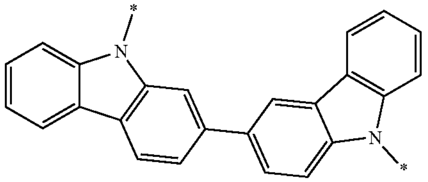
C-7
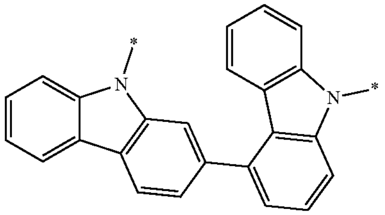
C-8
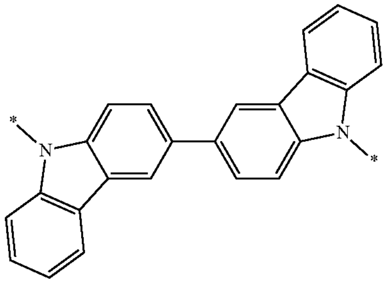
C-9
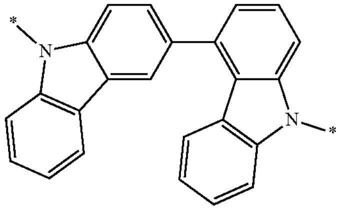
C-10
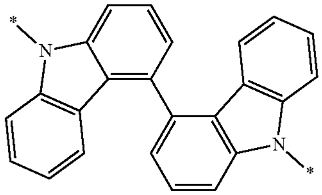
C-11
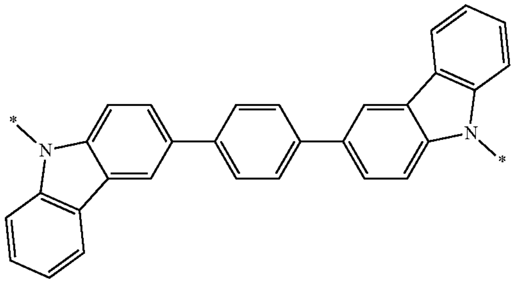
-continued
C-12
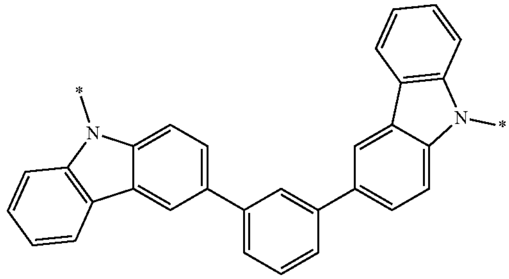
C-13
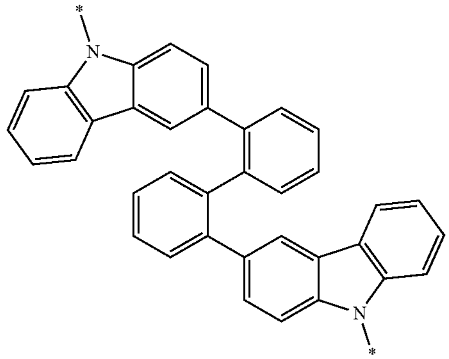
C-14
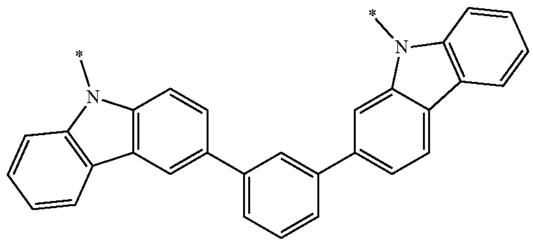
C-15
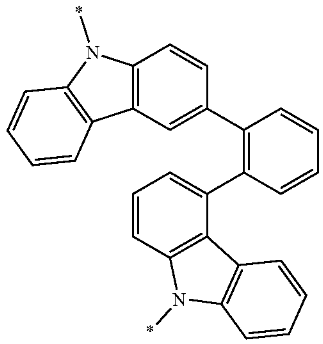
C-16
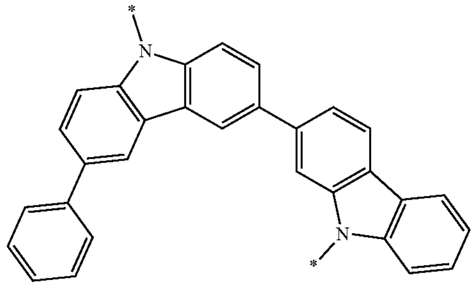

-continued
C-17
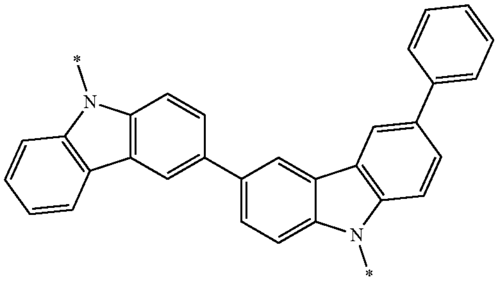
C-18
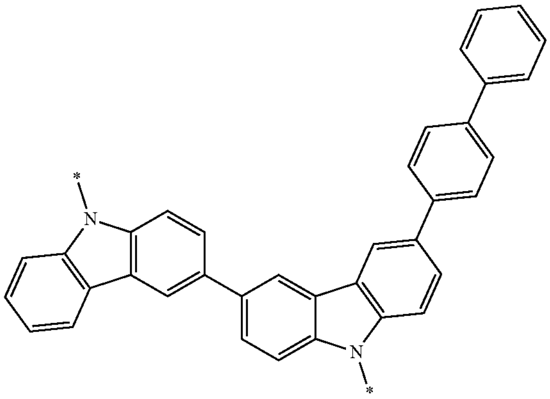
[Group IV]
B-1
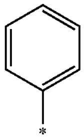
B-2
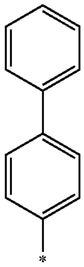
B-3
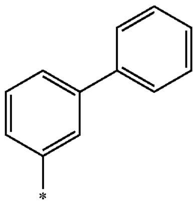
B-4
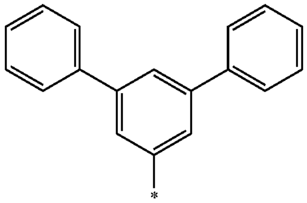
-continued
B-5
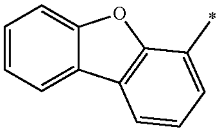
B-6
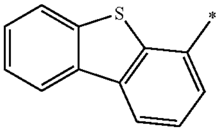
B-7
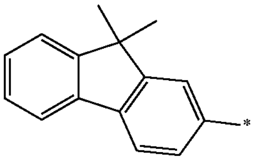
B-8
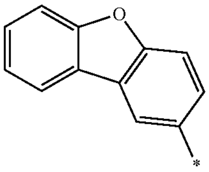
B-9
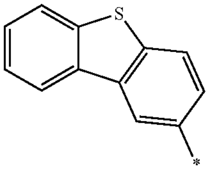
B-10
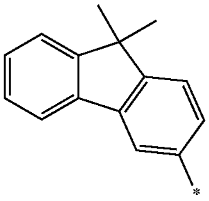
B-11
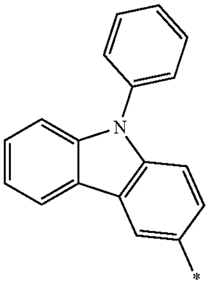
B-12
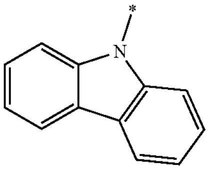

-continued
B-13
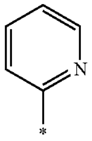
B-14
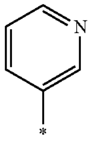
B-15
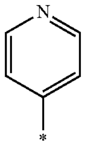
B-16
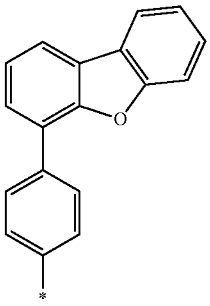
B-17
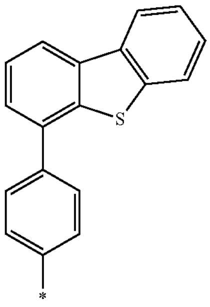
B-18
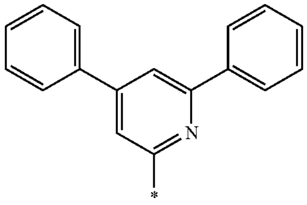
B-19
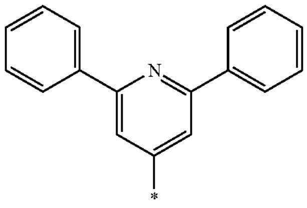
-continued
B-20
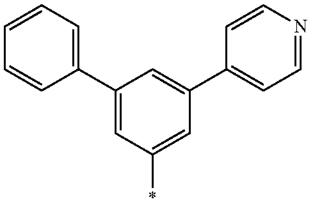
B-21
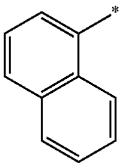
B-22
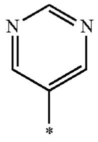
B-23
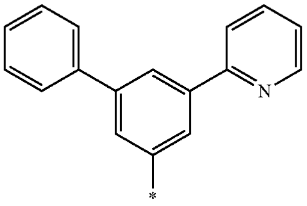
B-24
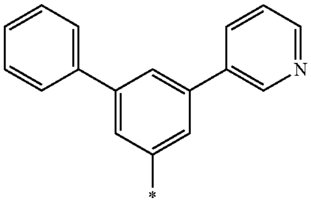
B-25
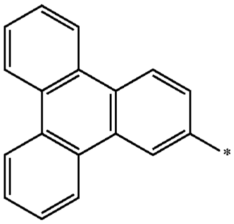
B-26
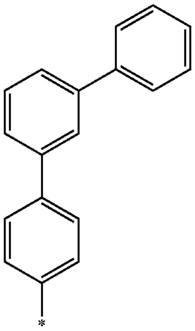
B-27
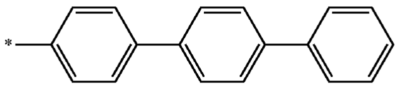

-continued

B-28

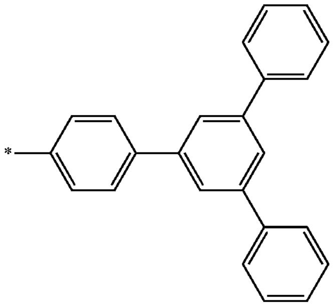

in Groups III and IV, * is a linking point with adjacent atoms.

4. The composition for an organic optoelectronic device of claim 3, wherein:

Chemical Formula 2 includes moiety C-8 or moiety C-17 of Group III, and moieties *—$Y^1$—$Z^1$ and *—$Y^2$—$Z^2$ of Chemical Formula 2 are independently one of moieties B-1 to B-6 of Group IV.

5. The composition for an organic optoelectronic device of claim 4, wherein moieties *—$Y^1$—$Z^1$ and *—$Y^2$—$Z^2$ of Chemical Formula 2 are each independently one of moieties B-1, B-2, B-3, B-5, and B-6:

B-1

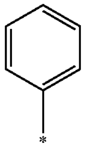

B-2

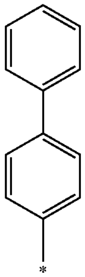

-continued

B-3

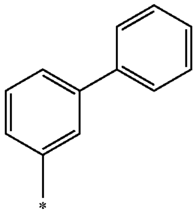

B-5

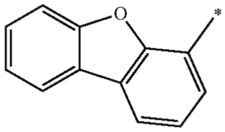

B-6

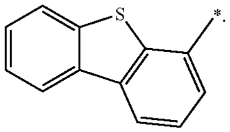

6. An organic optoelectronic device, comprising:

an anode and a cathode facing each other, and at least one organic layer between the anode and the cathode, wherein the at least one organic layer includes the composition for an organic optoelectronic device of claim 1.

7. The organic optoelectronic device of claim 6, wherein:

the at least one organic layer includes a light emitting layer, and the composition for an organic optoelectronic device is a host of the light emitting layer.

8. A display device comprising the organic optoelectronic device of claim 6.

* * * * *